(12) United States Patent
Soon-Shiong et al.

(10) Patent No.: US 12,576,141 B2
(45) Date of Patent: *Mar. 17, 2026

(54) ALBUMIN BOUND MACROMOLECULE TRI-AGONIST ACTIVATING GLP-1/GIP/GLUCAGON RECEPTORS

(71) Applicant: AlbuNext, LLC, El Segundo, CA (US)

(72) Inventors: Patrick Soon-Shiong, Culver City, CA (US); Martin Robitaille, Saint-Colomban (CA); Bing Song, El Segundo, CA (US)

(73) Assignee: AlbuNext, LLC, El Segundo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/753,823

(22) Filed: Jun. 25, 2024

(65) Prior Publication Data

US 2024/0425557 A1 Dec. 26, 2024

Related U.S. Application Data

(60) Provisional application No. 63/650,095, filed on May 21, 2024, provisional application No. 63/641,782, filed on May 2, 2024, provisional application No. 63/631,777, filed on Apr. 30, 2024, provisional application No. 63/634,379, filed on Apr. 15, 2024, provisional application No. 63/568,988, filed on Mar. 22, 2024, provisional application No. 63/567,402, filed on Mar. 19, 2024, provisional application No. 63/566,870, filed on Mar. 18, 2024, provisional application No. 63/564,941, filed on Mar. 13, 2024, provisional application No. 63/564,426, filed on Mar. 12, 2024, provisional application No. 63/561,187, filed on Mar. 4, 2024, provisional application No. 63/551,334, filed on Feb. 8, 2024, provisional application No. 63/551,370, filed on Feb. 8, 2024, provisional application No. 63/551,315, filed on Feb. 8, 2024, provisional application No. 63/625,169, filed on Jan. 25, 2024, provisional application No. 63/624,692, filed on Jan. 24, 2024, provisional application No. 63/619,584, filed on Jan. 10, 2024, provisional application No. 63/523,324, filed on Jun. 26, 2023.

(51) Int. Cl.

| | |
|---|---|
| A61K 39/00 | (2006.01) |
| A61K 38/00 | (2006.01) |
| A61K 38/38 | (2006.01) |
| A61P 3/10 | (2006.01) |
| C07K 14/47 | (2006.01) |
| C07K 14/765 | (2006.01) |
| C07K 16/28 | (2006.01) |

(52) U.S. Cl.
CPC ........ *A61K 39/0005* (2013.01); *A61K 38/385* (2013.01); *A61P 3/10* (2018.01); *C07K 14/4722* (2013.01); *C07K 14/765* (2013.01); *C07K 16/28* (2013.01); *A61K 38/00* (2013.01); *A61K 2039/505* (2013.01); *C07K 2317/75* (2013.01); *C07K 2317/92* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 6,514,500 B1 | 2/2003 | Bridon et al. | |
| 6,528,486 B1 | 3/2003 | Larsen et al. | |
| 2007/0269863 A1* | 11/2007 | Bridon | C07K 14/60 |
| | | | 435/71.1 |
| 2009/0186819 A1 | 7/2009 | Carrier et al. | |
| 2016/0015838 A1* | 1/2016 | Li | A61K 51/04 |
| | | | 530/330 |

(Continued)

FOREIGN PATENT DOCUMENTS

| | | |
|---|---|---|
| CA | 2501421 A1 | 11/2000 |
| CA | 2550050 A1 | 6/2005 |

(Continued)

OTHER PUBLICATIONS

Ma et al. "Conformational flexibility of fatty acid-free bovine serum albumin proteins enables superior antifouling coatings", Communications Materials, 2020, 01-45 Pages.

(Continued)

*Primary Examiner* — Marianne P Allen
(74) *Attorney, Agent, or Firm* — Umberg Zipser LLP; Martin Fessenmaier; Priti Phukan

(57) ABSTRACT

A pharmaceutical composition comprises a GPCR agonist fusion protein in which a GPCR agonist peptide is covalently coupled to albumin via a linker in a manner that is resistant to a retro-Michael addition. Advantageously, compositions presented herein avoid decoupling of the agonist form the albumin while retaining the agonist in a steric relationship to the albumin that allows for effective binding and activation of the GPCR while also enabling gp60-mediated transcytosis and FcRn-mediated albumin recycling. These properties enable ultra-low dosages for the GPCR agonist fusion protein to give a therapeutic effect while substantially reducing or even entirely avoiding adverse effects otherwise commonly associated with unbound agonists. Such retro-Michael resistant composition is generally achieved by conformational modification of the albumin, resulting in stereoselective coupling of the linker to the albumin.

11 Claims, 44 Drawing Sheets

Specification includes a Sequence Listing.

(56) References Cited

U.S. PATENT DOCUMENTS

| | | | | |
|---|---|---|---|---|
| 2017/0296684 A1* | 10/2017 | Driver | ............... | A61K 51/0497 |
| 2022/0106361 A1* | 4/2022 | Fuhrmann | ............... | C07K 7/06 |
| 2024/0197894 A1 | 6/2024 | Dong et al. | | |

FOREIGN PATENT DOCUMENTS

| | | | |
|---|---|---|---|
| CA | 2434237 C | 5/2012 | |
| WO | 2007053946 A1 | 5/2007 | |
| WO | 2009075859 A2 | 6/2009 | |
| WO | 2011109784 A1 | 9/2011 | |
| WO | 2011109787 A1 | 9/2011 | |

OTHER PUBLICATIONS

Sun et al. "Small-molecule albumin ligand modification to enhance the anti-diabetic ability of GLP-1 derivatives", Elsevier Masson SAS, Feb. 11, 2022, 01-12 Pages.

Scheider et al. "An effective method for defatting albumin using resin columns", Biochim Biophys Acta, Nov. 17, 1970; 221(2); 376-8.

International Search Report and Written Opinion received for International PCT Application Serial No. PCT/US2024/035475 dated Jan. 10, 2025, 25 pages.

Kim. "Development and Characterization of a Glucagon-Like Peptide 1-Albumin Conjugate" 751-759. Diabetes. Web. Mar. 31, 2003; <Figure 1; abstract; pp. 751, 752, 757>; <DOI:10.2337/diabetes. 52.3.751>.

Lim. "Evaluation of In Vivo Prepared Albumin-Drug Conjugate Using Immunoprecipitation Linked LC-MS Assay and Its Application to Mouse Pharmacokinetic Study" 2-12. Molecules. Web. Apr. 4, 2023; <pp. 2 and 6>; <DOI:10.3390/molecules28073223>.

Zyl. "Diagnosis and treatment of diabetic ketoacidosis" 35-39. Taylor and Francis. Web. Aug. 15, 2014; <p. 37; Table III>; <DOI:10.1080/20786204.2008.10873664>.

Bahne. "Metformin-induced glucagon-like peptide-1 secretion contributes to the actions of metformin in type 2 diabetes" 1-15. JCL Insight. Web. Dec. 6, 2018; ; <DOI: 10.1172/jci.insight. 93936>.

International Search Report and Written Opinion received for International PCT Application Serial No. PCT/US2024/035478 dated Dec. 18, 2024, 22 pages.

International Preliminary Report on Patentability received in PCT Application No. PCT/US2024/035475 dated Sep. 10, 2025, 11 pages.

International Preliminary Report on Patentability received in International Application No. PCT/US24/35478 dated Aug. 7, 2025, 14 pages.

Notice of Allowance received in U.S. Appl. No. 18/753,928 dated Nov. 19, 2025, 16 pages.

* cited by examiner

SEQ ID NO:2

Ser-Pro-Pro-Pro-Ala-Gly-Ser-Ser-Ser-Pro-Gly-Gly

Glu-Glu-Glu-Ala-Val-Arg-Leu-Phe-Ile-Glu-Trp-Leu-Lys-Asn

Arg-Gln-Lys-Ser-Leu-Asp-Ser-Thr-Phe-Thr-Gly-Glu-Gly-his

[Exendin-4(1-39)-Lys-(aminoethoxy-ethoxy-acetyl-N-propionylsuccinimide)-NH2] [Recombinant Human Albumin]

625 Amino Acids (C203 H311 N55 O66 S + rHA)

GLP-1 AGONISTS

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| AB-496 | H | a | E | G | T | F | T | S | D | Y | A | K | Y | L | D | A | R | R | A | K | E | F | V | Q | W | L | V | N | G | G | P | S | S | G | A | P | P | P | S | K |
| AB-497 | H | a | E | G | T | F | T | S | D | Y | A | K | Y | L | D | A | R | R | A | K | E | F | I | A | W | L | L | Q | G | G | P | S | S | G | A | P | P | S | K |
| AB-498 | H | a | E | G | T | F | T | S | D | Y | A | K | Y | L | D | A | R | R | A | K | E | F | I | E | Y | L | Y | N | G | G | P | S | S | G | A | P | P | P | S | K |
| AB-499 | H | a | E | G | T | F | T | S | D | Y | A | K | Y | L | D | A | R | R | A | K | E | F | I | A | Y | L | L | E | G | G | P | S | S | G | A | P | P | P | S | K |
| AB-500 | H | a | E | G | T | F | T | S | D | Y | A | K | Y | L | D | A | R | R | A | K | E | F | I | E | W | L | Y | R | G | G | P | S | S | G | A | P | P | P | S | K |
| AB-501 | H | a | E | G | T | F | T | S | D | Y | A | K | Y | L | * | A | R | R | A | K | E | F | V | Q | W | L | K | A | G | G | P | P | G | G | A | P | P | P | S | K |

SEQ ID NO:460
SEQ ID NO:461
SEQ ID NO:462
SEQ ID NO:463
SEQ ID NO:464
SEQ ID NO:465

K*-AEEA-MPA
K*-(AEEA)²-MPA

FIG.4

GLP-1/GIP DUAL-AGONISTS

GLP-1/GcG DUAL-AGONISTS

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| AB-436 | SEQ ID NO:404 | H | S | Q | G | T | F | T | S | D | L | S | K | Q | L | E | S | K | A | A | Q | D | F | I | E | W | L | K | A | G | G | P | S | S | G | A | P | P | P | S | K* |
| AB-437 | SEQ ID NO:405 | H | S | Q | G | T | F | T | S | D | Y | S | K | Y | L | D | A | R | R | A | K | E | E | I | E | W | L | K | A | G | G | P | S | S | G | A | P | P | P | S | K* |
| AB-438 | SEQ ID NO:406 | H | S | Q | G | T | F | T | S | D | Y | S | K | Y | L | D | A | R | R | A | K | E | E | I | E | W | L | K | A | G | G | P | S | S | G | A | P | P | P | S | K* |
| AB-439 | SEQ ID NO:407 | H | S | Q | G | T | F | T | S | D | Y | S | K | Y | L | D | S | R | R | A | K | E | E | I | E | W | L | K | A | G | G | P | S | S | G | A | P | P | P | S | K* |
| AB-440 | SEQ ID NO:408 | H | S | Q | G | T | F | T | S | D | Y | S | K | Y | L | D | S | R | R | A | K | E | E | I | E | W | L | K | A | G | G | P | S | S | G | A | P | P | P | S | K* |
| AB-441 | SEQ ID NO:409 | H | S | Q | G | T | F | T | S | D | Y | S | K | Y | L | D | A | R | R | A | K | E | E | I | E | W | L | K | N | G | G | P | S | S | G | A | P | P | P | S | K* |
| AB-442 | SEQ ID NO:410 | H | S | Q | G | T | F | T | S | D | L | S | K | Q | L | D | S | K | A | A | Q | D | F | I | A | W | L | Y | A | G | G | P | S | S | G | A | P | P | P | S | K* |
| AB-443 | SEQ ID NO:411 | H | S | Q | G | T | F | T | S | D | Y | S | K | Y | L | D | A | R | R | A | K | E | E | I | E | W | L | K | A | G | G | P | S | S | G | A | P | P | P | S | K* |
| AB-444 | SEQ ID NO:412 | H | S | Q | G | T | F | T | S | D | Y | S | K | Y | L | D | A | R | R | A | Q | E | E | I | E | W | L | K | A | G | G | P | S | S | G | A | P | P | P | S | K* |
| AB-445 | SEQ ID NO:413 | H | S | Q | G | T | F | T | S | D | Y | S | K | Y | L | D | S | K | A | A | K | E | E | I | E | W | L | K | A | G | G | P | S | S | G | A | P | P | P | S | K* |
| AB-446 | SEQ ID NO:414 | H | S | Q | G | T | F | T | S | D | Y | S | K | Y | L | D | S | K | R | A | K | E | E | I | E | W | L | K | A | G | G | P | S | S | G | A | P | P | P | S | K* |
| AB-447 | SEQ ID NO:415 | H | S | Q | G | T | F | T | S | D | Y | S | K | Y | L | D | S | R | R | A | K | E | E | I | E | W | L | K | A | G | G | P | S | S | G | A | P | P | P | S | K* |
| AB-448 | SEQ ID NO:409 | H | S | Q | G | T | F | T | S | D | Y | S | K | Y | L | E | A | R | R | A | K | E | E | I | E | W | L | K | A | G | G | P | S | S | G | A | P | P | P | S | K* |
| AB-449 | SEQ ID NO:416 | H | S | Q | G | T | F | T | S | D | Y | S | K | Y | L | D | A | R | R | A | K | E | E | I | E | W | L | K | A | G | G | P | S | S | G | A | P | P | P | S | K* |
| AB-450 | SEQ ID NO:417 | H | S | Q | G | T | F | T | S | D | Y | S | K | Y | L | E | A | R | R | A | K | E | E | I | E | W | L | K | A | G | G | P | S | S | G | A | P | P | P | G | K* |

K*:AEEA-MPA
K*:(AEEA)₂-MPA

FIG.6

GLP-1/GIP/GcG TRI-AGONISTS

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | SEQ ID NO. |
|---|---|---|---|---|---|---|---|---|---|---|---|---|---|---|---|---|---|---|---|---|---|---|---|---|---|---|---|---|---|---|---|---|---|---|---|---|---|---|---|---|---|
| AB-651 | H | a | Q | G | T | F | T | S | D | Y | S | K | Y | L | D | E | R | A | A | Q | A | F | I | E | Y | L | L | E | G | G | P | S | S | G | A | P | P | P | S | K* | 418 |
| AB-652 | H | a | Q | G | T | F | T | S | D | Y | S | K | Y | L | D | E | R | A | A | Q | A | F | I | E | Y | L | L | D | G | G | P | S | S | G | A | P | P | P | S | K* | 419 |
| AB-653 | H | a | Q | G | T | F | T | S | D | Y | S | K | Y | L | D | E | R | A | A | Q | A | F | I | E | Y | L | L | D | G | G | P | S | S | G | A | P | P | P | S | K* | 420 |
| AB-654 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 421 |
| AB-655 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 422 |
| AB-656 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 423 |
| AB-657 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 390 |
| AB-658 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 424 |
| AB-659 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 425 |
| AB-660 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 426 |
| AB-661 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 426 |
| AB-662 | H | a | Q | G | T | F | T | S | D | Y | S | K | Y | L | D | E | R | A | A | Q | A | F | I | V | Q | W | L | L | D | G | G | P | S | S | G | A | P | P | P | S | K* | 427 |
| AB-663 | H | a | Q | G | T | F | T | S | D | Y | S | K | Y | L | D | E | R | A | A | Q | A | F | I | V | Q | W | L | L | D | G | G | P | S | S | G | A | P | P | P | S | K* | 428 |
| AB-664 | H | a | Q | G | T | F | T | S | D | Y | S | K | Y | L | D | E | R | A | A | Q | A | F | I | V | Q | W | L | L | D | G | G | P | S | S | G | A | P | P | P | S | K* | 429 |
| AB-665 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 430 |
| AB-666 | H | a | Q | G | T | F | T | S | D | Y | S | K | Y | L | D | A | R | R | A | K | E | F | I | V | Q | Y | L | L | D | G | G | P | S | S | G | A | P | P | P | S | K* | 431 |
| AB-667 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 432 |
| AB-668 | H | a | Q | G | T | F | T | S | D | Y | A | K | Y | L | D | A | R | R | A | K | E | F | I | V | Q | Y | L | L | D | G | G | P | S | S | G | A | P | P | P | S | K* | 433 |
| AB-669 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 434 |
| AB-670 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 435 |
| AB-671 | H | a | Q | G | T | F | T | S | D | Y | S | K | Y | L | D | A | R | R | A | K | E | F | I | V | Q | Y | L | L | D | G | G | P | S | S | G | A | P | P | P | S | K* | 436 |
| AB-672 | H | a | Q | G | T | F | T | S | D | Y | A | K | Y | L | D | A | R | R | A | K | E | F | I | V | Q | Y | L | L | D | G | G | P | S | S | G | A | P | P | P | S | K* | 437 |
| AB-673 | H | a | Q | G | T | F | T | S | D | Y | S | K | Y | L | D | E | R | A | A | Q | A | F | I | V | Q | W | L | L | D | G | G | P | S | S | G | A | P | P | P | S | K* | 438 |
| AB-674 | H | a | Q | G | T | F | T | S | D | Y | S | K | Y | L | D | E | R | A | A | Q | A | F | I | V | Q | Y | L | L | D | G | G | P | S | S | G | A | P | P | P | S | K* | 439 |
| AB-675 | H | a | Q | G | T | F | T | S | D | Y | S | K | Y | L | D | E | R | A | A | Q | A | F | I | V | Q | W | L | L | D | G | G | P | S | S | G | A | P | P | P | S | K* | 440 |
| AB-676 | H | a | Q | G | T | F | T | S | D | Y | S | K | Y | L | D | A | R | R | A | K | E | F | I | V | Q | Y | L | L | D | G | G | P | S | S | G | A | P | P | P | S | K* | 441 |
| AB-677 | H | a | Q | G | T | F | T | S | D | Y | S | K | Y | L | D | A | R | R | A | K | E | F | I | I | Q | W | L | L | D | G | G | P | S | S | G | A | P | P | P | S | K* | 442 |
| AB-678 | H | a | Q | G | T | F | T | S | D | Y | A | K | Y | L | D | A | R | R | A | A | E | F | I | V | Q | Y | L | L | D | G | G | P | S | S | G | A | P | P | P | S | K* | 443 |
| AB-679 | H | a | Q | G | T | F | T | S | D | Y | A | K | Y | L | D | A | R | R | A | K | E | F | I | V | W | L | L | D | G | G | P | S | S | G | A | P | P | P | S | K* | | 444 |
| AB-680 | H | a | Q | G | T | F | T | S | D | Y | S | K | Y | L | D | A | R | R | A | A | E | F | I | V | Q | Y | L | L | D | G | G | P | S | S | G | A | P | P | P | S | K* | 445 |
| AB-681 | H | a | Q | G | T | F | T | S | D | Y | A | K | Y | L | D | A | R | R | A | K | E | F | I | V | Q | Y | L | L | D | G | G | P | S | S | G | A | P | P | P | S | K* | 446 |
| AB-682 | H | a | Q | G | T | F | T | S | D | Y | A | K | Y | L | D | A | R | R | A | K | E | F | I | V | F | W | L | L | D | G | G | P | S | S | G | A | P | P | P | S | K* | 447 |
| AB-683 | H | a | Q | G | T | F | T | S | D | Y | A | K | Y | L | D | A | R | R | A | K | E | F | I | V | Q | Y | L | L | D | G | G | P | S | S | G | A | P | P | P | S | K* | 448 |
| AB-684 | H | a | Q | G | T | F | T | S | D | Y | S | K | Y | L | D | E | R | A | A | Q | A | F | I | V | Q | W | L | L | D | G | G | P | S | S | G | A | P | P | P | S | K* | 449 |
| AB-685 | H | a | Q | G | T | F | T | S | D | Y | S | K | Y | L | D | E | R | A | A | Q | A | F | I | V | F | W | L | L | D | G | G | P | S | S | G | A | P | P | P | S | K* | 450 |
| AB-686 | H | a | Q | G | T | F | T | S | D | Y | S | K | Y | L | D | E | R | A | A | Q | A | F | I | V | F | W | L | L | D | G | G | P | S | S | G | A | P | P | P | S | K* | 451 |
| AB-687 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 452 |
| AB-688 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 453 |
| AB-689 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 454 |
| AB-690 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 455 |
| AB-691 | H | a | Q | G | T | F | T | S | D | Y | S | K | Y | L | D | A | R | R | A | K | E | F | I | V | Q | W | L | L | D | G | G | P | S | S | G | A | P | P | P | S | K* | 456 |
| AB-692 | H | a | Q | G | T | F | T | S | D | Y | A | K | Y | L | D | A | R | R | A | K | E | F | I | V | Q | W | L | L | D | G | G | P | S | S | G | A | P | P | P | S | K* | 457 |
| AB-693 | H | a | Q | G | T | F | T | S | D | Y | S | K | Y | L | D | A | R | R | A | K | E | F | I | V | Q | Y | L | L | F | G | G | P | S | S | G | A | P | P | P | S | K* | 458 |
| AB-694 | H | a | Q | G | T | F | T | S | D | Y | A | K | Y | L | D | A | R | R | A | K | E | F | I | V | Q | Y | L | L | F | G | G | P | S | S | G | A | P | P | P | S | K* | 459 |

K*: AEEA-MPA
K*:(AEEA)2-MPA

FIG.7

GLP-1/GIP/GcG TRI-AGONISTS

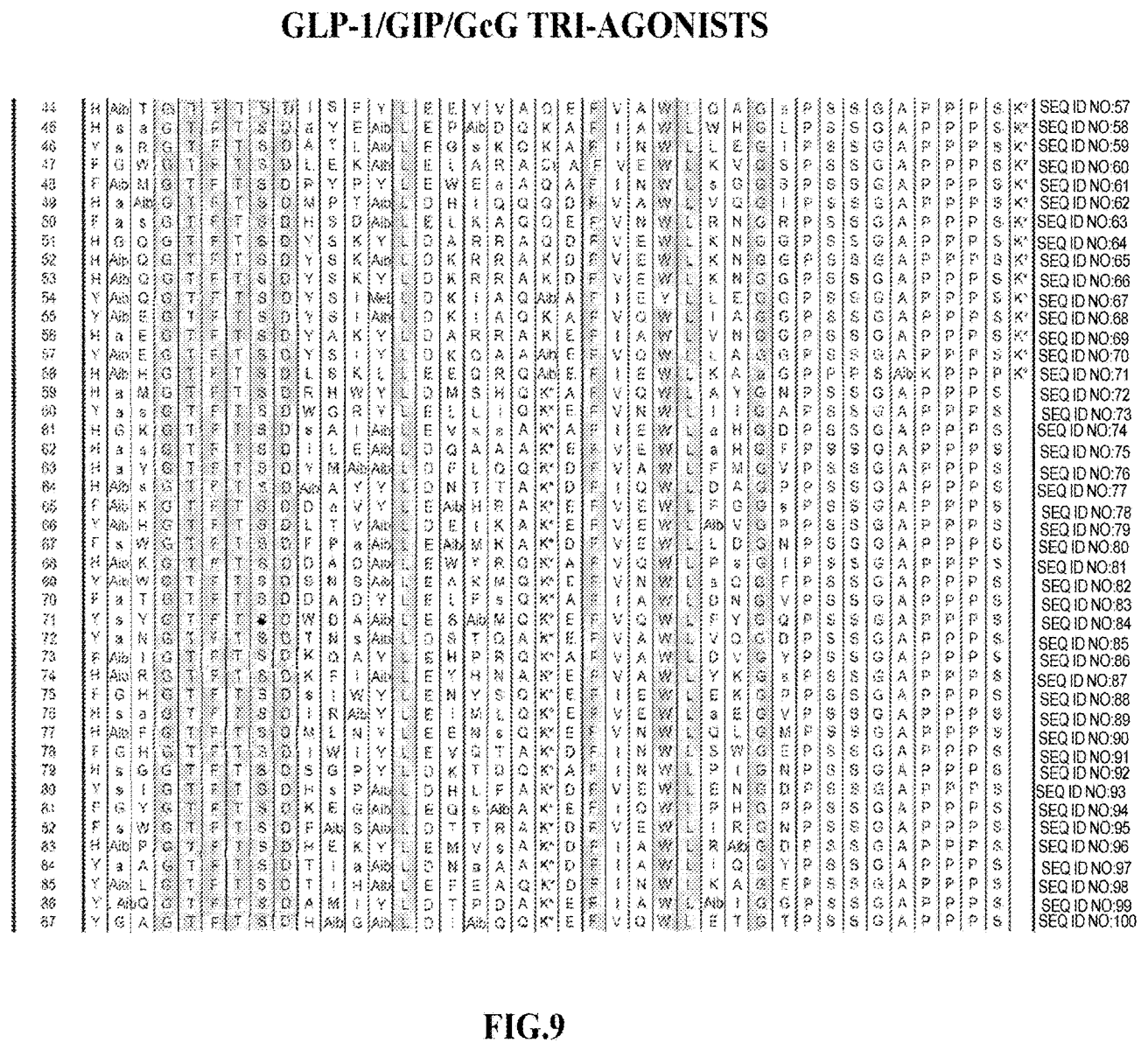

GLP-1/GIP/GcG TRI-AGONISTS

SEQ ID NO:57
SEQ ID NO:58
SEQ ID NO:59
SEQ ID NO:60
SEQ ID NO:61
SEQ ID NO:62
SEQ ID NO:63
SEQ ID NO:64
SEQ ID NO:65
SEQ ID NO:66
SEQ ID NO:67
SEQ ID NO:68
SEQ ID NO:69
SEQ ID NO:70
SEQ ID NO:71
SEQ ID NO:72
SEQ ID NO:73
SEQ ID NO:74
SEQ ID NO:75
SEQ ID NO:76
SEQ ID NO:77
SEQ ID NO:78
SEQ ID NO:79
SEQ ID NO:80
SEQ ID NO:81
SEQ ID NO:82
SEQ ID NO:83
SEQ ID NO:84
SEQ ID NO:85
SEQ ID NO:86
SEQ ID NO:87
SEQ ID NO:88
SEQ ID NO:89
SEQ ID NO:90
SEQ ID NO:91
SEQ ID NO:92
SEQ ID NO:93
SEQ ID NO:94
SEQ ID NO:95
SEQ ID NO:96
SEQ ID NO:97
SEQ ID NO:98
SEQ ID NO:99
SEQ ID NO:100

FIG.9

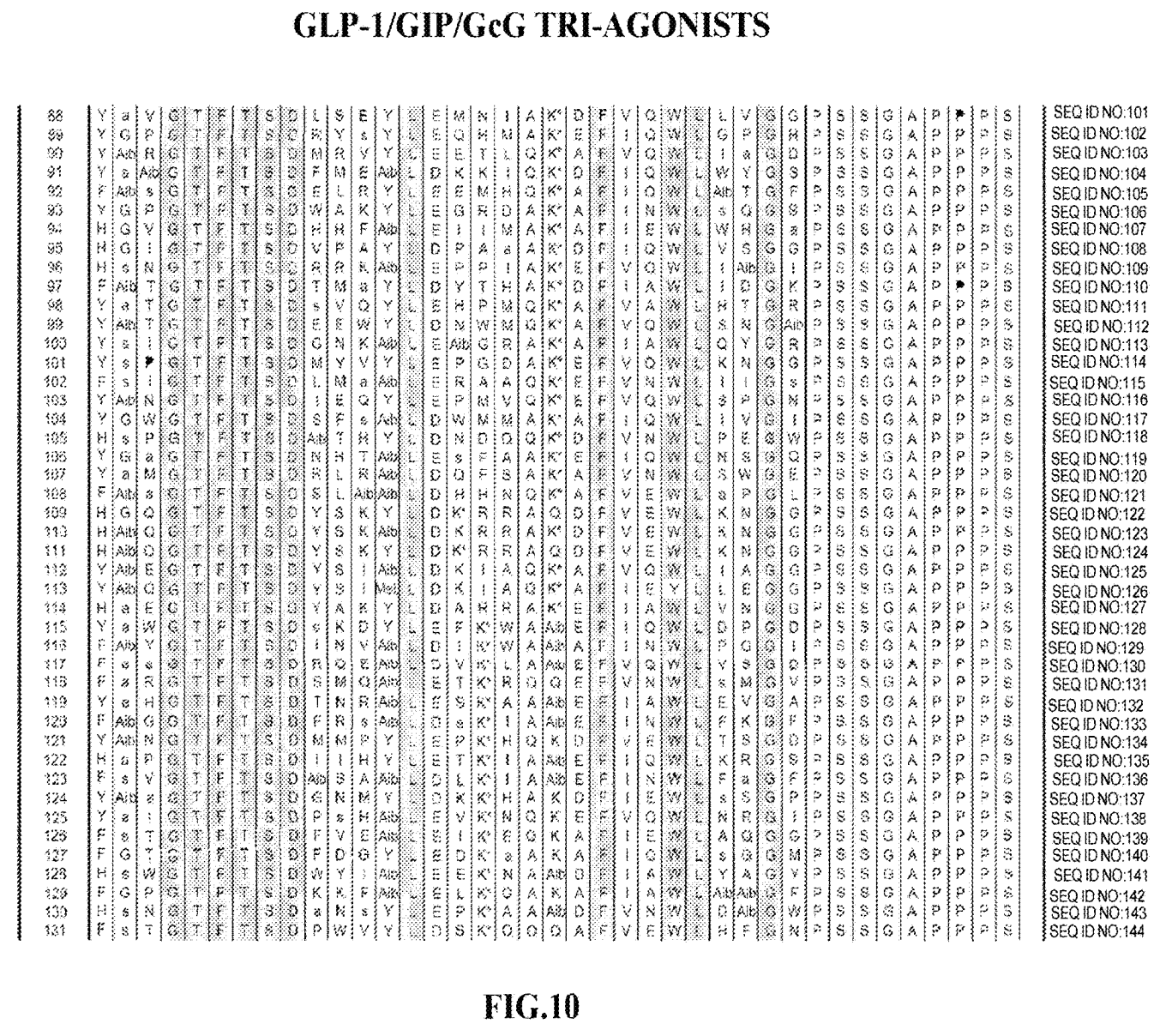

GLP-1/GIP/GcG TRI-AGONISTS

SEQ ID NO:101
SEQ ID NO:102
SEQ ID NO:103
SEQ ID NO:104
SEQ ID NO:105
SEQ ID NO:106
SEQ ID NO:107
SEQ ID NO:108
SEQ ID NO:109
SEQ ID NO:110
SEQ ID NO:111
SEQ ID NO:112
SEQ ID NO:113
SEQ ID NO:114
SEQ ID NO:115
SEQ ID NO:116
SEQ ID NO:117
SEQ ID NO:118
SEQ ID NO:119
SEQ ID NO:120
SEQ ID NO:121
SEQ ID NO:122
SEQ ID NO:123
SEQ ID NO:124
SEQ ID NO:125
SEQ ID NO:126
SEQ ID NO:127
SEQ ID NO:128
SEQ ID NO:129
SEQ ID NO:130
SEQ ID NO:131
SEQ ID NO:132
SEQ ID NO:133
SEQ ID NO:134
SEQ ID NO:135
SEQ ID NO:136
SEQ ID NO:137
SEQ ID NO:138
SEQ ID NO:139
SEQ ID NO:140
SEQ ID NO:141
SEQ ID NO:142
SEQ ID NO:143
SEQ ID NO:144

FIG.10

GLP-1/GIP/GcG TRI-AGONISTS

FIG.11

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Group 1 | AB-674 | Y | Aib | E | G | T | F | T | S | D | Y | S | I | Y | L | D | K | Q | A | A | Aib | E | F | V | Q | W | L | L | A | G | G | P | S | S | G | A | P | P | P | S | K* | 238 |
| | AB-804-2 | Y | a | E | G | T | F | T | S | D | Y | A | I | Y | L | D | A | Q | A | Q | G | D | F | V | Q | W | L | L | A | G | G | P | S | S | G | A | P | P | P | S | K* | 468 |
| | AB-804-3 | Y | a | E | G | T | F | T | S | D | Y | S | I | Y | L | D | K | I | A | Q | Q | D | F | V | Q | W | L | L | A | G | G | P | S | S | G | A | P | P | P | S | K* | 470 |
| | AB-670 | Y | Aib | E | G | T | F | T | S | D | Y | S | I | Aib | L | D | K | I | A | Q | K* | A | F | V | Q | W | L | I | A | G | G | P | S | S | G | A | P | P | P | S | | 237 |
| | AB-671 | Y | Aib | E | G | T | F | T | S | D | Y | S | I | Aib | L | D | K | I | A | Q | K | A | F | V | Q | W | L | L | A | G | G | P | S | S | G | A | P | P | P | S | K* | 68 |
| Group 2 | AB-495 | H | Aib | Q | G | T | F | T | S | D | Y | S | K | Y | L | D | E | R | A | A | Q | D | F | V | Q | W | L | I | L | D | G | G | P | S | S | G | A | P | P | P | S | K* | 468 |
| | AB-804-6 | H | Aib | Q | G | T | F | T | S | D | Y | S | K | Y | L | D | K | I | A | Q | D | D | F | V | A | Y | L | L | D | G | G | P | S | S | G | A | P | P | P | S | K* | 469 |
| | AB-804-4 | H | Aib | Q | G | T | F | T | S | D | L | S | K | Y | L | D | E | I | A | V | Q | D | F | I | E | W | L | L | Q | G | G | P | S | S | G | A | P | P | P | S | K* | 356 |
| | AB-492 | Y | Aib | Q | G | T | F | T | S | D | Y | S | I | MeL | L | D | K | K* | A | Q | Aib | A | F | I | E | Y | L | L | E | G | G | P | S | S | G | A | P | P | P | S | | 179 |
| | AB-496 | Y | Aib | Q | G | T | F | T | S | D | Y | S | I | MeL | L | D | K | I | A | Q | Aib | A | F | I | E | Y | L | L | E | C | G | P | S | S | G | A | P | P | P | S | K* | 67 |
| | AB-444 | H | a | Q | G | T | F | T | S | D | Y | A | K | Y | L | D | A | R | R | A | K | E | F | I | A | W | L | V | N | G | G | P | S | S | G | A | P | P | P | S | K* | 223 |

| | | |
|---|---|---|
| | K*: AEEA-MPA | |
| | K*: (AEEEA)-MPA | |
| | a: D-ala | |
| | Aib: Aminoisobutyric Acid | |
| | MeL: α-Methyl-L-leucine | |

FIG. 12A

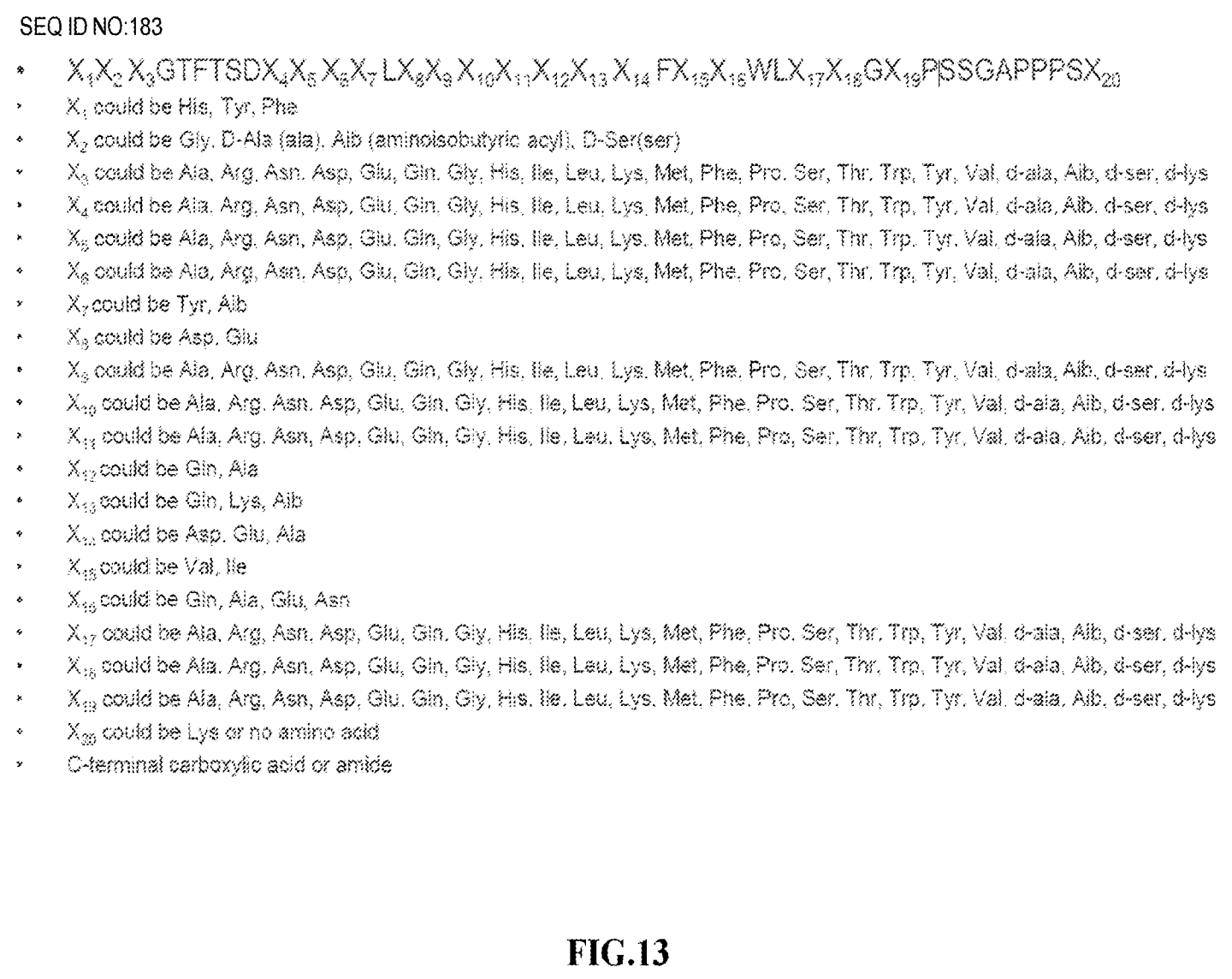

SEQ ID NO:183

X₁X₂X₃GTFTSDX₄X₅X₆X₇LX₈X₉X₁₀X₁₁X₁₂X₁₃X₁₄FX₁₅WLX₁₇X₁₆GX₁₈PISSCAPPPSX₂₀

* X₁ could be His, Tyr, Phe

* X₂ could be Gly, D-Ala (ala), Aib (aminoisobutyric acyl). D-Ser(ser)

* X₃ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₄ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₅ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₆ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₇ could be Tyr, Aib

* X₈ could be Asp, Glu

* X₉ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₁₀ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₁₁ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₁₂ could be Gln, Ala

* X₁₃ could be Gln, Lys, Aib

* X₁₄ could be Asp, Glu, Ala

* X₁₅ could be Val, Ile

* X₁₆ could be Gln, Ala, Glu, Asn

* X₁₇ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₁₈ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₁₉ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys

* X₂₀ could be Lys or no amino acid

* C-terminal carboxylic acid or amide

FIG.13

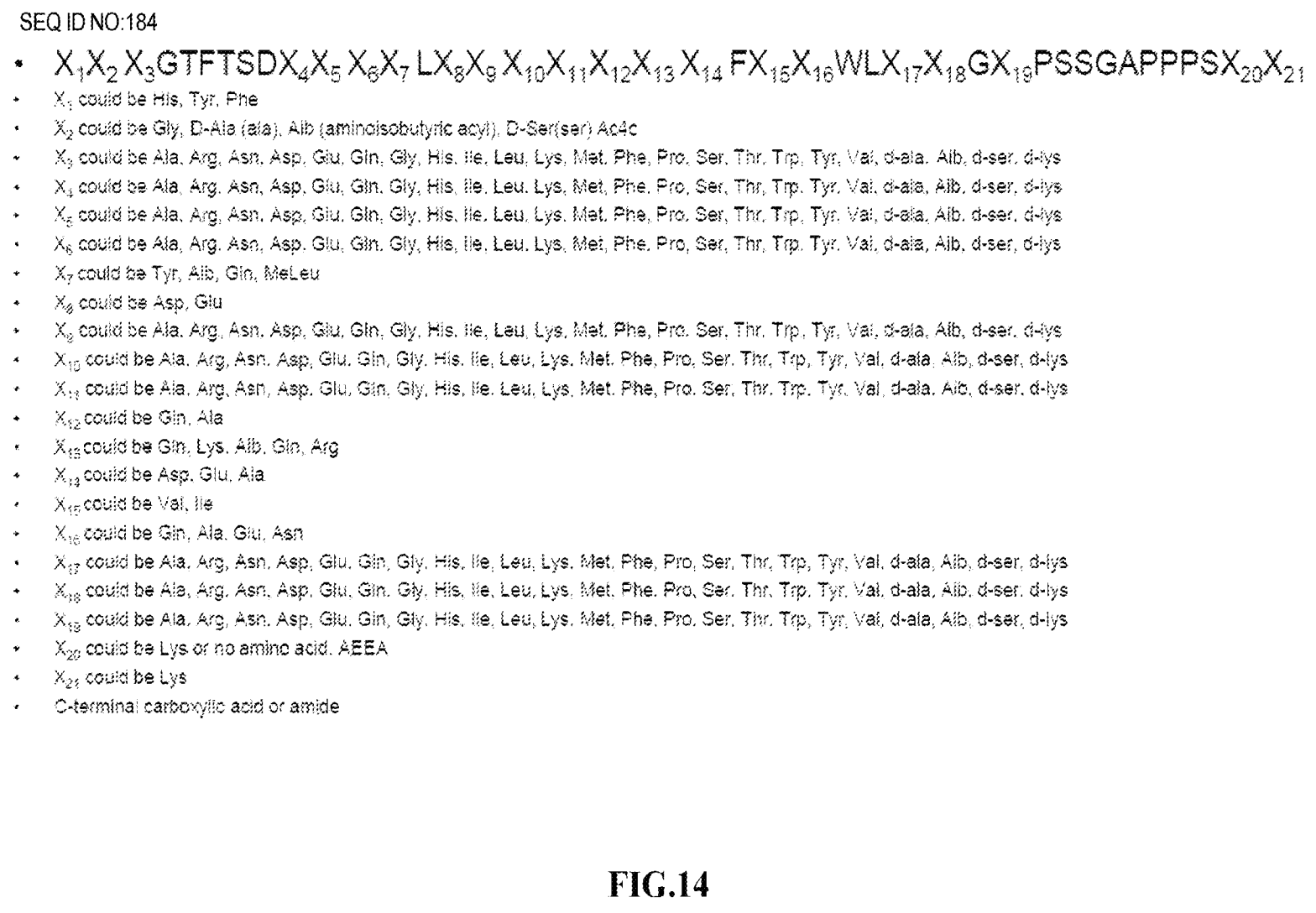

SEQ ID NO:184

X₁X₂X₃GTFTSDX₄X₅X₆X₇LX₈X₉X₁₀X₁₁X₁₂X₁₃X₁₄FX₁₅X₁₆WLX₁₇X₁₈GX₁₉PSSGAPPPSX₂₀X₂₁

- X₁ could be His, Tyr, Phe
- X₂ could be Gly, D-Ala (a:a), Aib (aminoisobutyric acyl), D-Ser/ser) Ac4c
- X₃ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₄ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₅ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₆ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₇ could be Tyr, Aib, Gln, MeLeu
- X₈ could be Asp, Glu
- X₉ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₁₀ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₁₁ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₁₂ could be Gln, Ala
- X₁₃ could be Gln, Lys, Aib, Gln, Arg
- X₁₄ could be Asp, Glu, Ala
- X₁₅ could be Val, Ile
- X₁₆ could be Gln, Ala, Glu, Asn
- X₁₇ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₁₈ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₁₉ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- X₂₀ could be Lys or no amino acid, AEEA
- X₂₁ could be Lys
- C-terminal carboxylic acid or amide

FIG.14

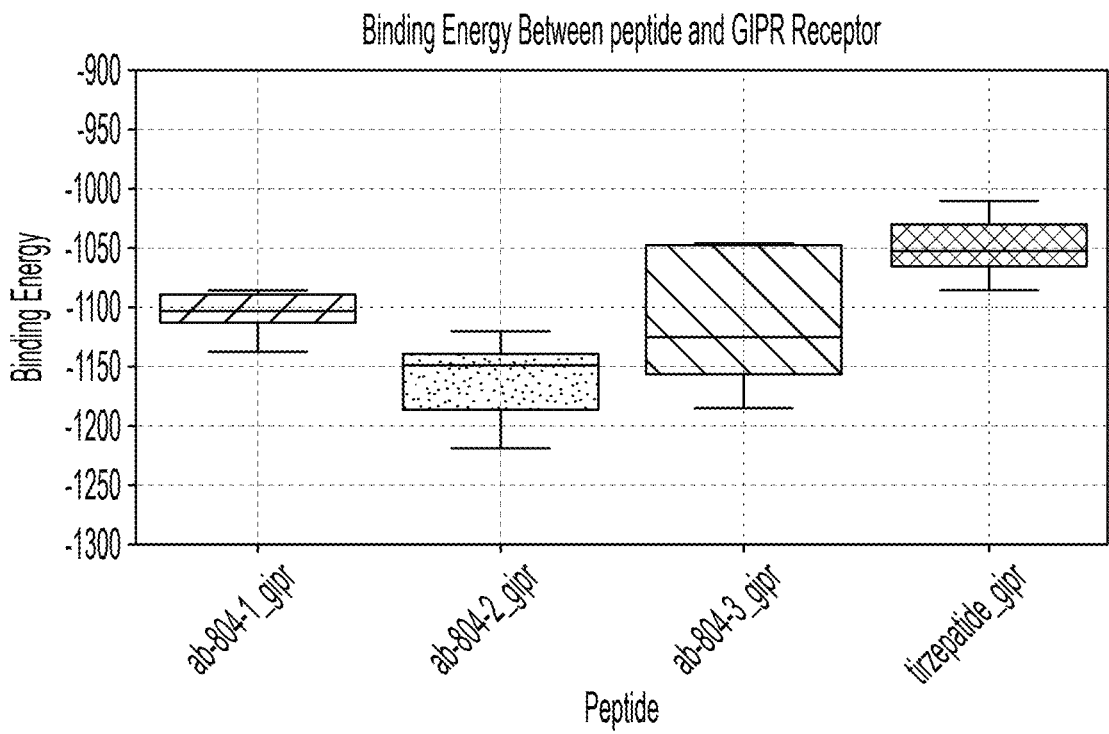
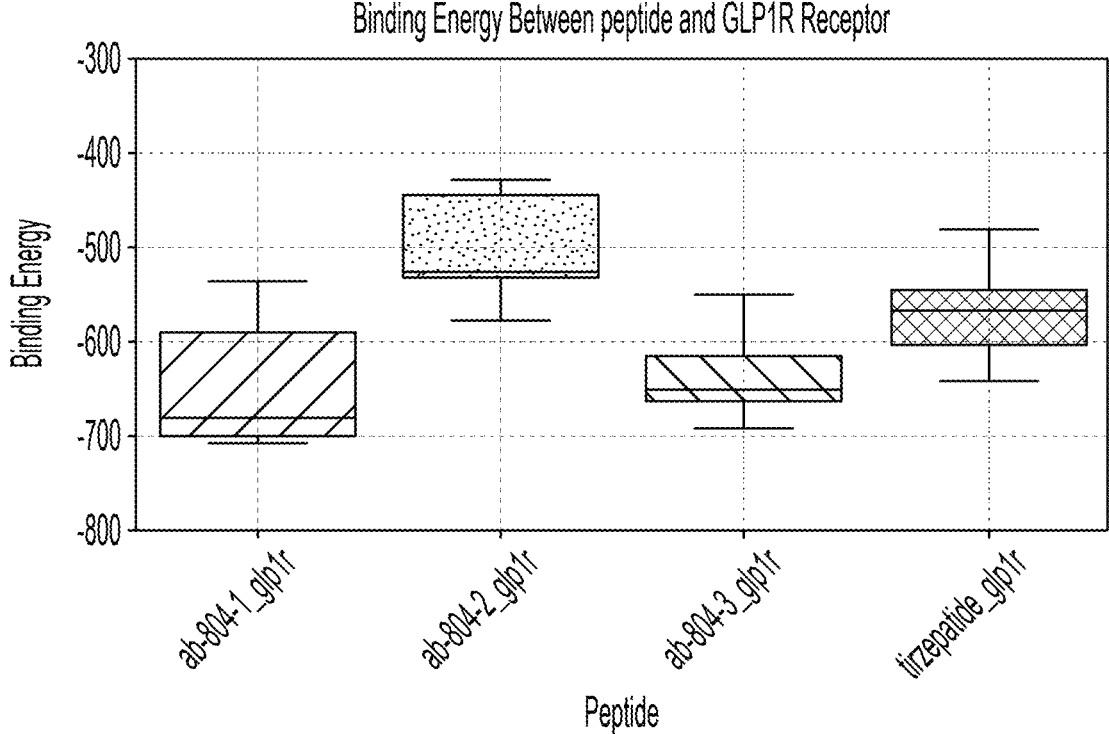
FIG.15

Self Energy

Peptide S1, S2, S3, S4

| | ab-804-1 | ab-804-1_gipr | ab-804-1_glp1r | tirzepatide | tirzepatide_gipr | tirzepatide_glp1r | ab-804-2 | ab-804-2_gipr | ab-804-2_glp1r | ab-804-3 | ab-804-3_gipr | ab-804-3_glp1r |
|---|---|---|---|---|---|---|---|---|---|---|---|---|
| 0 | -327.59 | -10,874.54 | -8,861.01 | -224.19 | -10,718.93 | -8,691.07 | -248.95 | -10,876.32 | -8,652.50 | -265.06 | -10,858.79 | -8,783.04 |
| 1 | -326.25 | -10,849.63 | -8,854.51 | -223.27 | -10,699.18 | -8,654.20 | -242.19 | -10,845.20 | -8,606.07 | -262.23 | -10,829.54 | -8,755.87 |
| 2 | -324.53 | -10,839.88 | -8,832.66 | -220.43 | -10,686.39 | -8,617.81 | -233.49 | -10,805.88 | -8,601.60 | -253.51 | -10,799.72 | -8,743.35 |
| 3 | -317.82 | -10,826.38 | -8,743.24 | -218.14 | -10,663.51 | -8,596.56 | -233.01 | -10,796.37 | -8,518.26 | -241.43 | -10,720.57 | -8,708.13 |
| 4 | -315.31 | -10,822.28 | -8,687.71 | -210.96 | -10,643.37 | -8,532.16 | -228.77 | -10,779.24 | -8,504.18 | -240.91 | -10,718.82 | -8,643.11 |

| | gip | gipr | gip_gipr | glp1 | glp1r | glp1_glp1r |
|---|---|---|---|---|---|---|
| 0 | -530.62 | -9,407.61 | -10,500.46 | -423.81 | -7,826.03 | -8,662.20 |
| 1 | -525.55 | -9,405.50 | -10,494.44 | -423.77 | -7,802.25 | -8,645.32 |
| 2 | -521.51 | -9,376.58 | -10,474.49 | -422.34 | -7,753.47 | -8,577.36 |
| 3 | -520.83 | -9,359.20 | -10,408.53 | -412.02 | -7,748.98 | -8,534.28 |
| 4 | -515.55 | -9,333.01 | -10,405.27 | -406.83 | -7,702.98 | -8,494.71 |

FIG.16

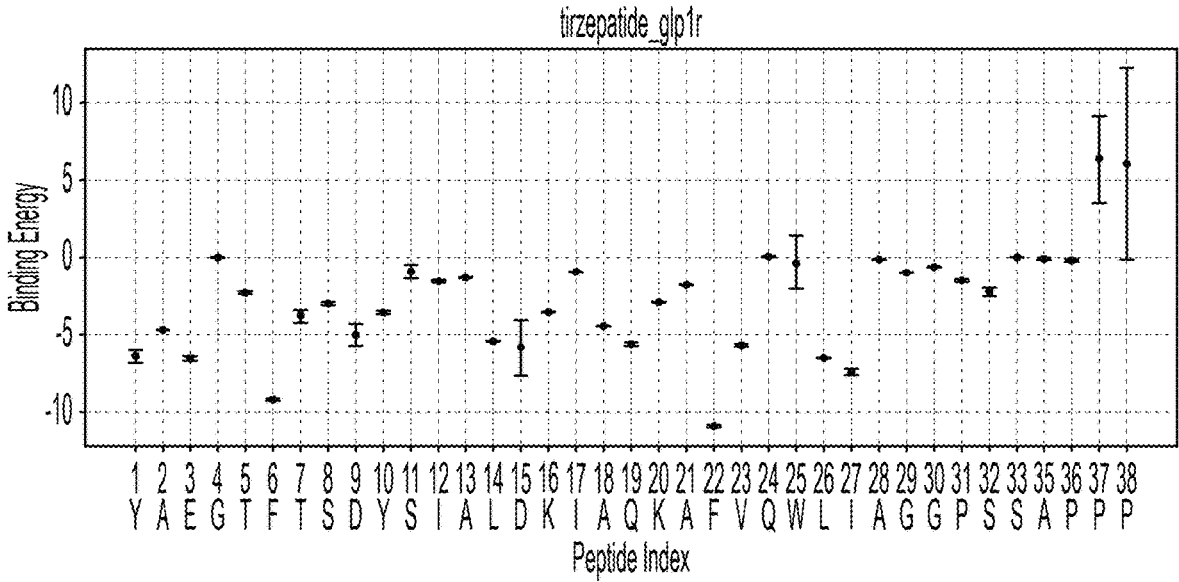
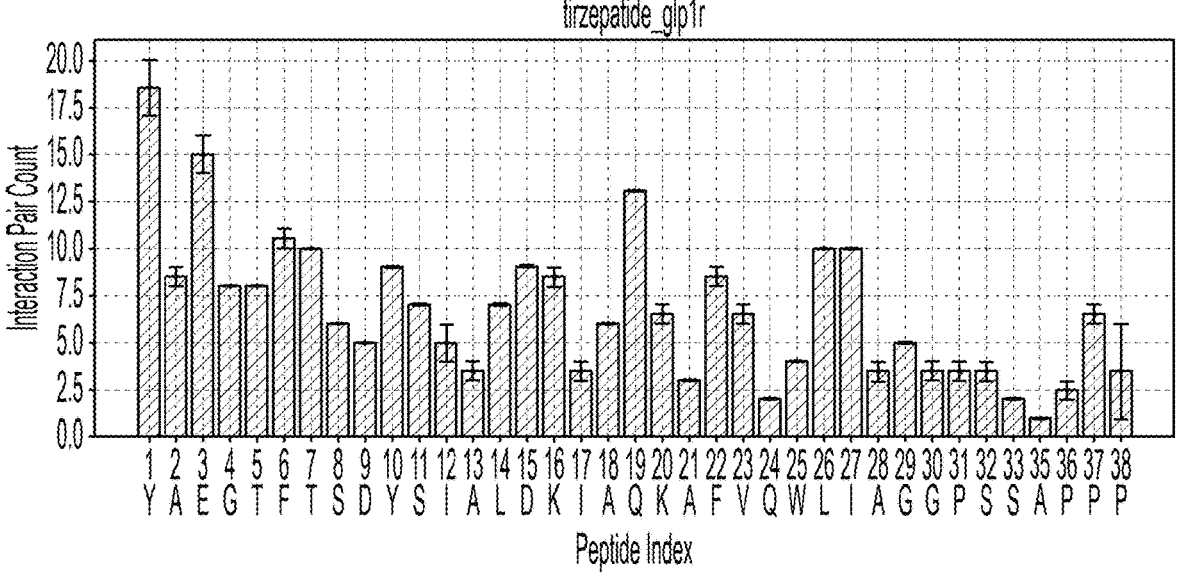
FIG.17

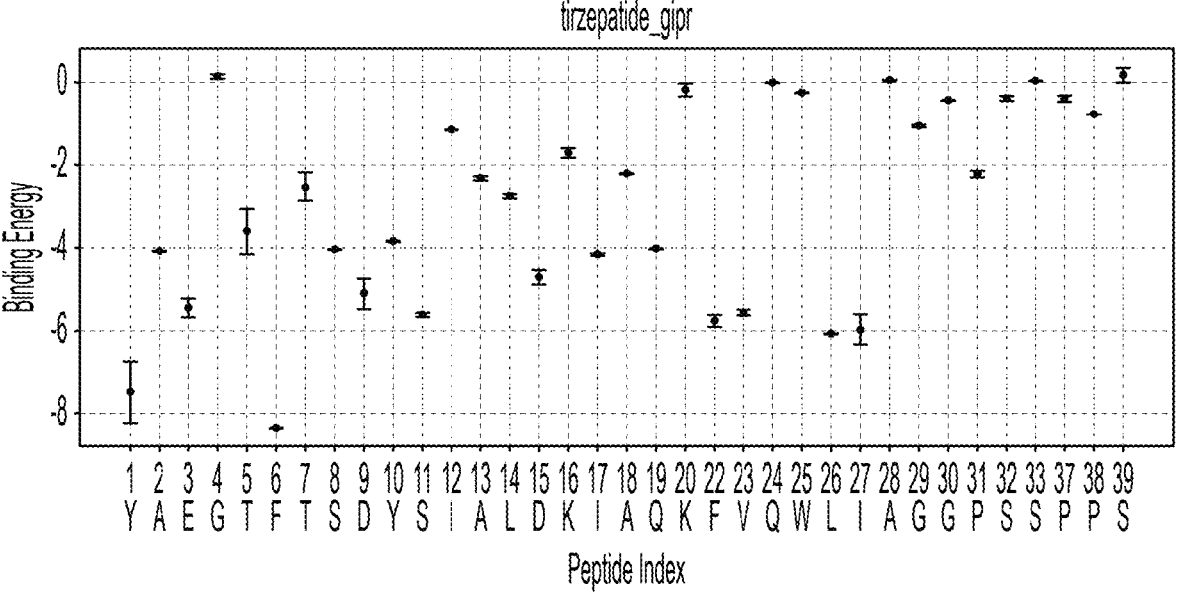
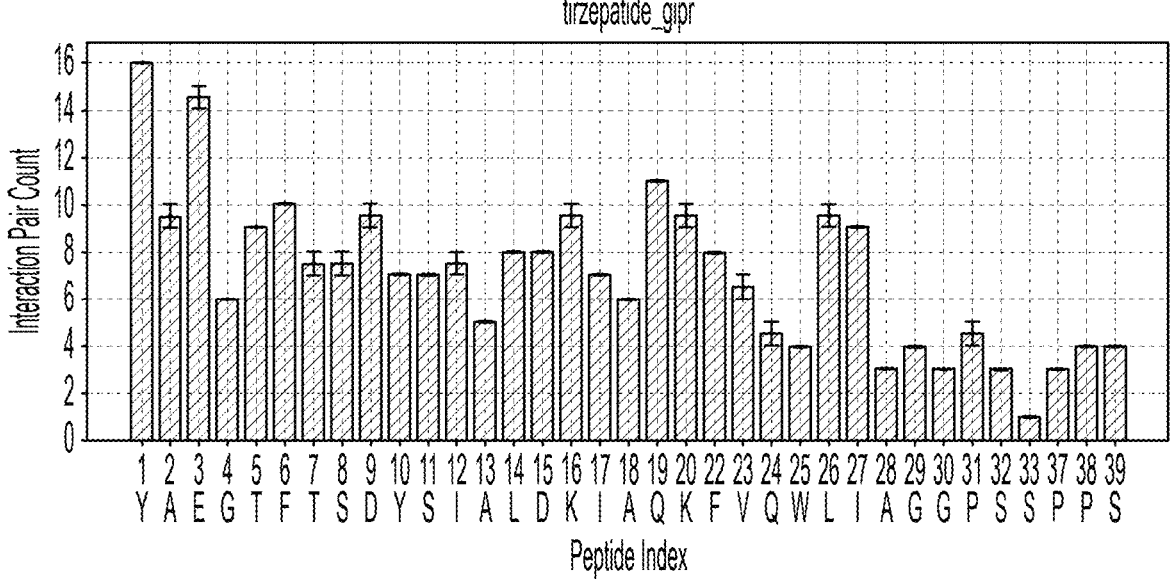
FIG.17 (Continued)

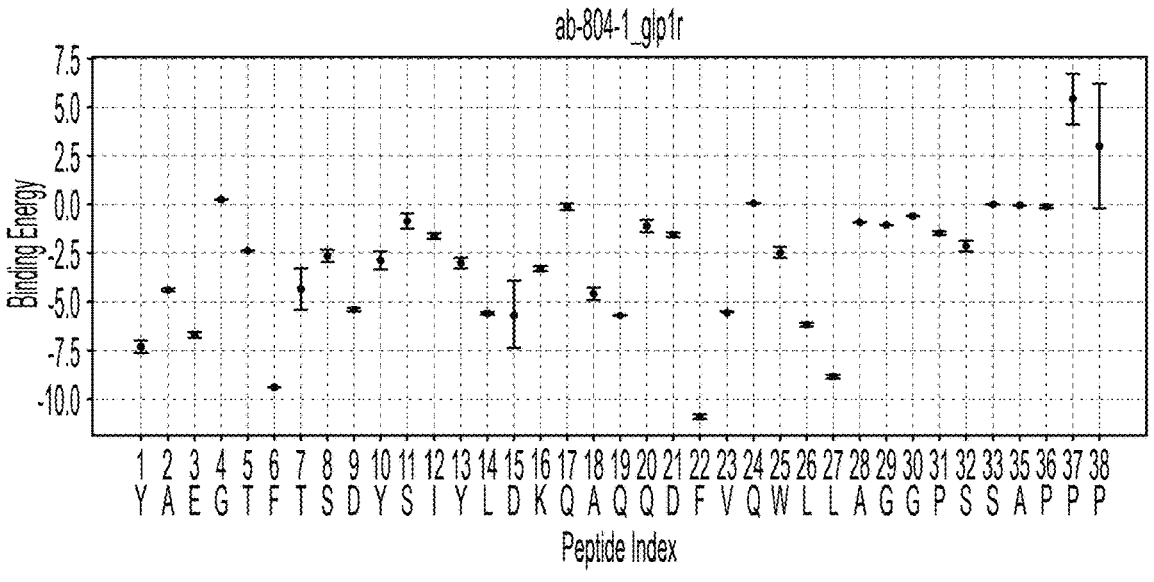
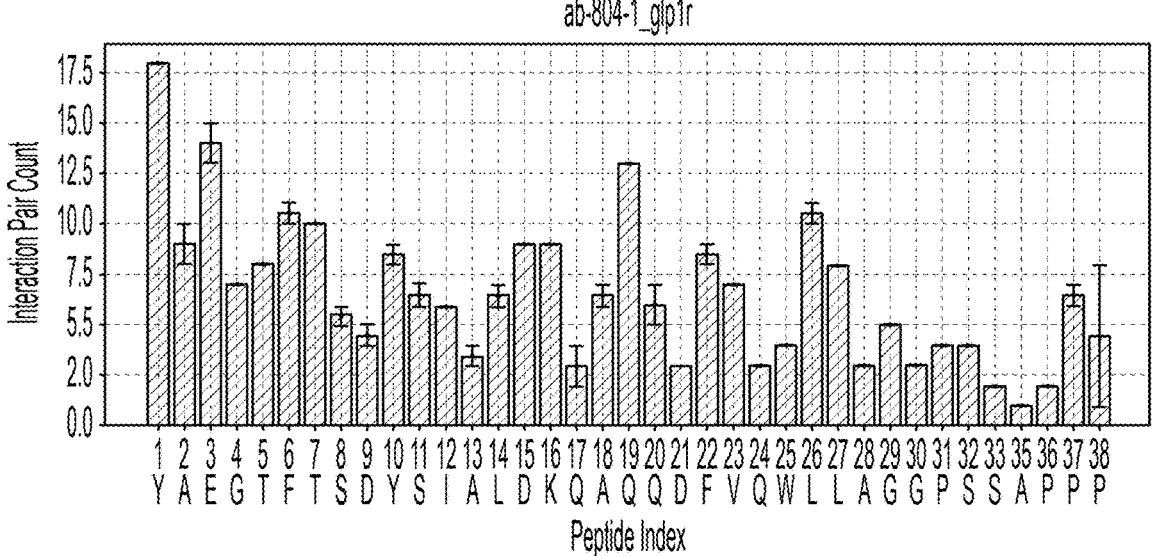
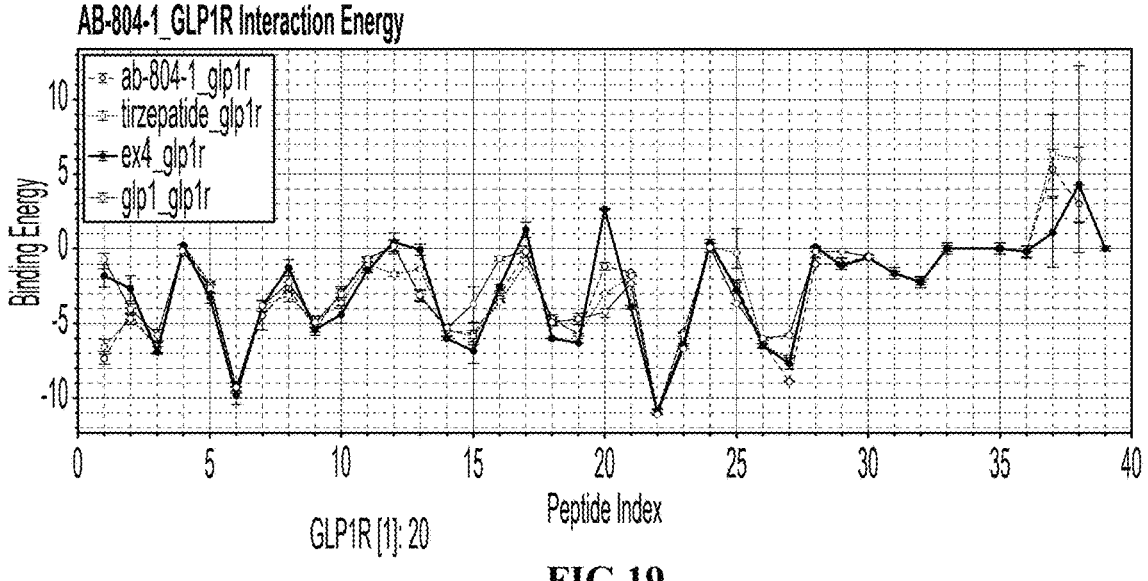
FIG.19

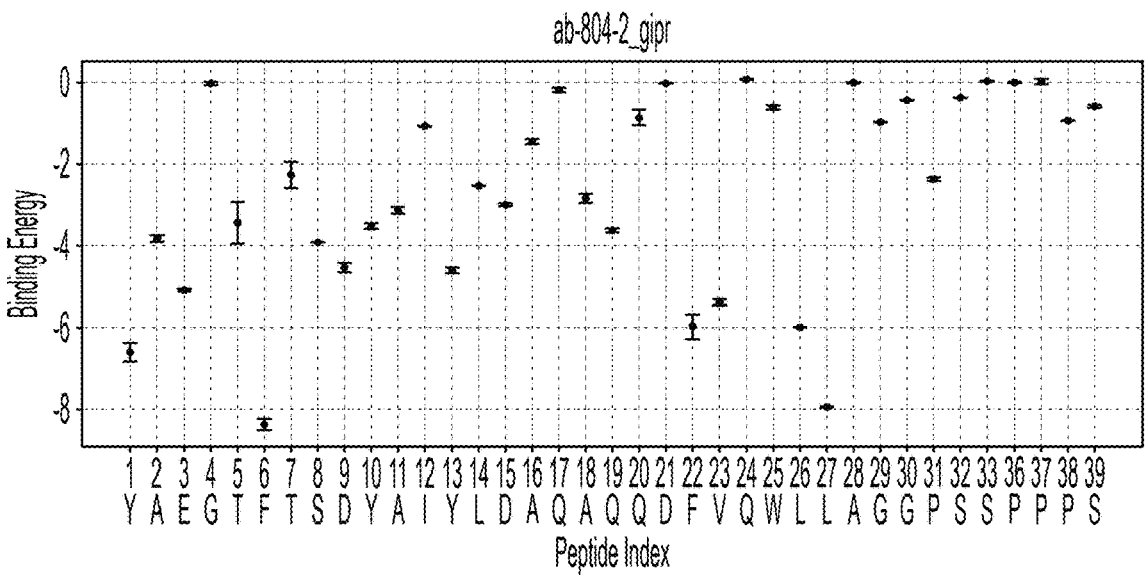
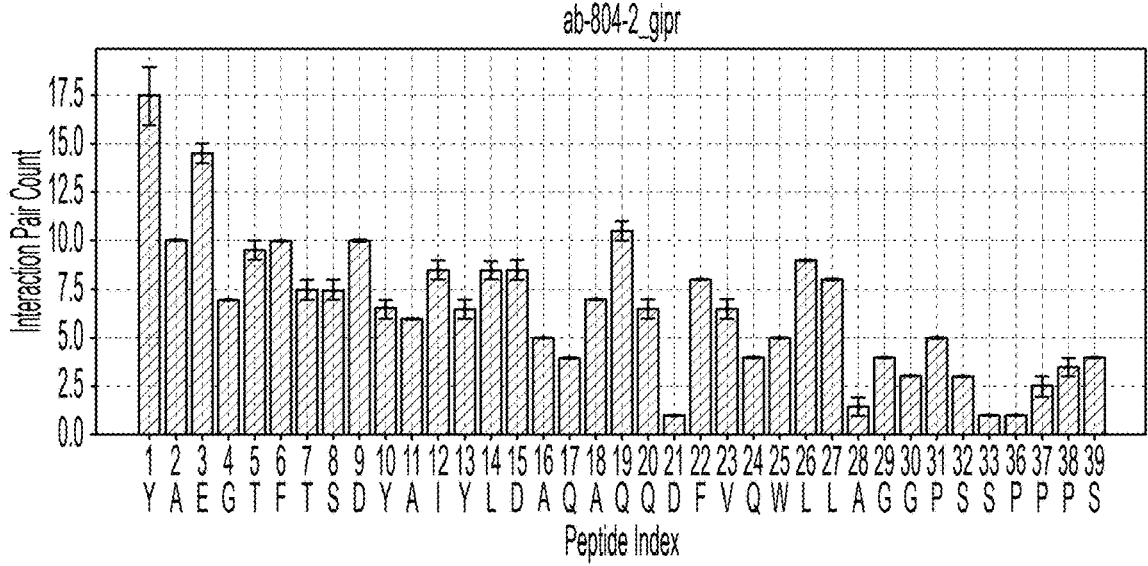
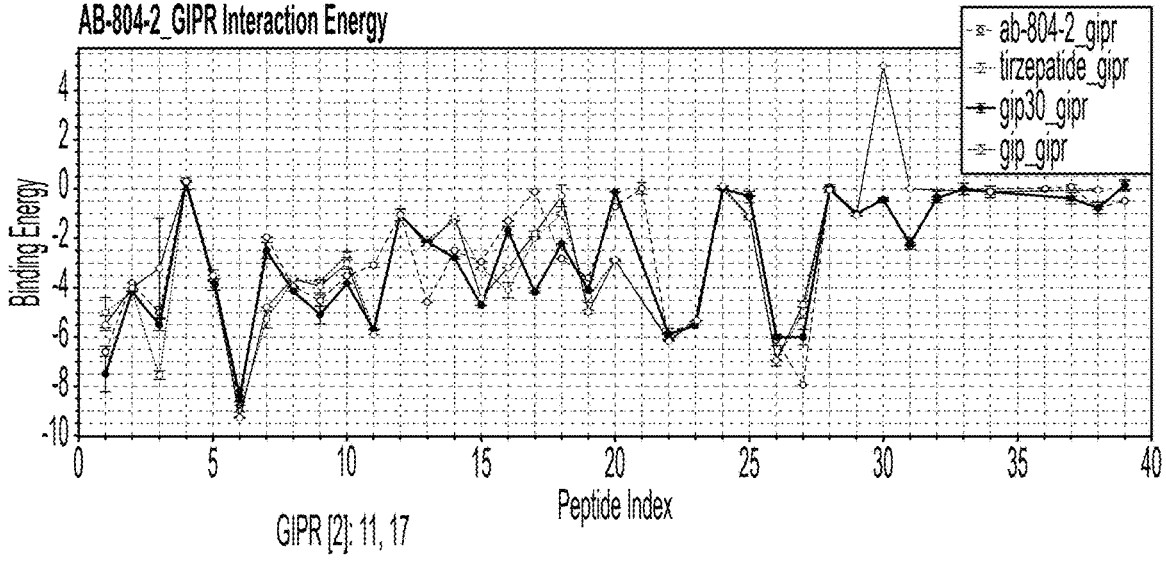
FIG.20

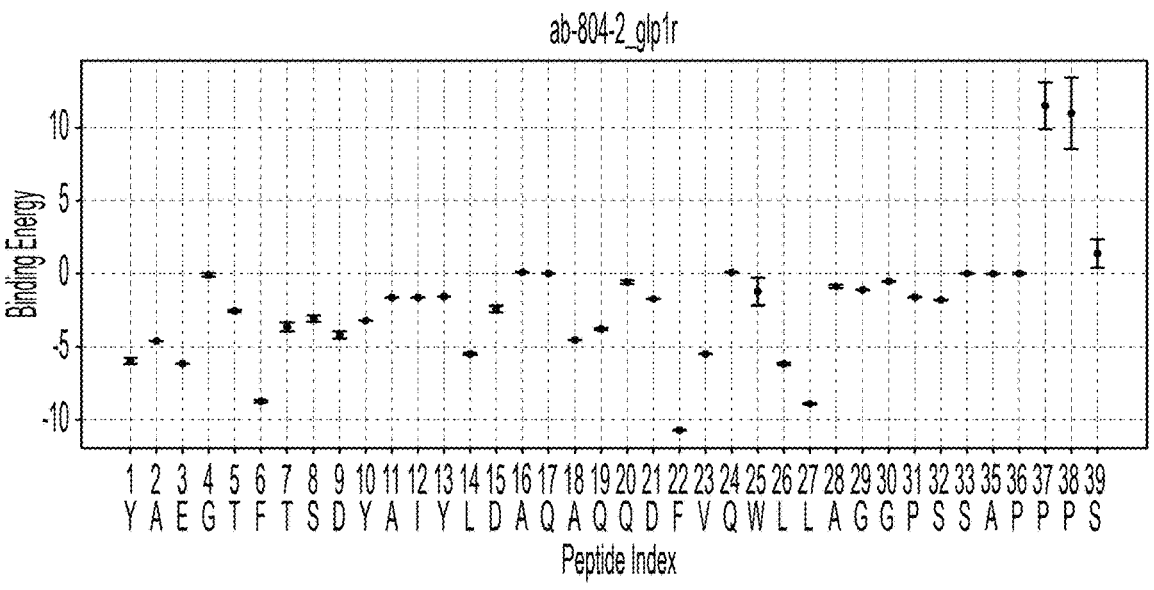
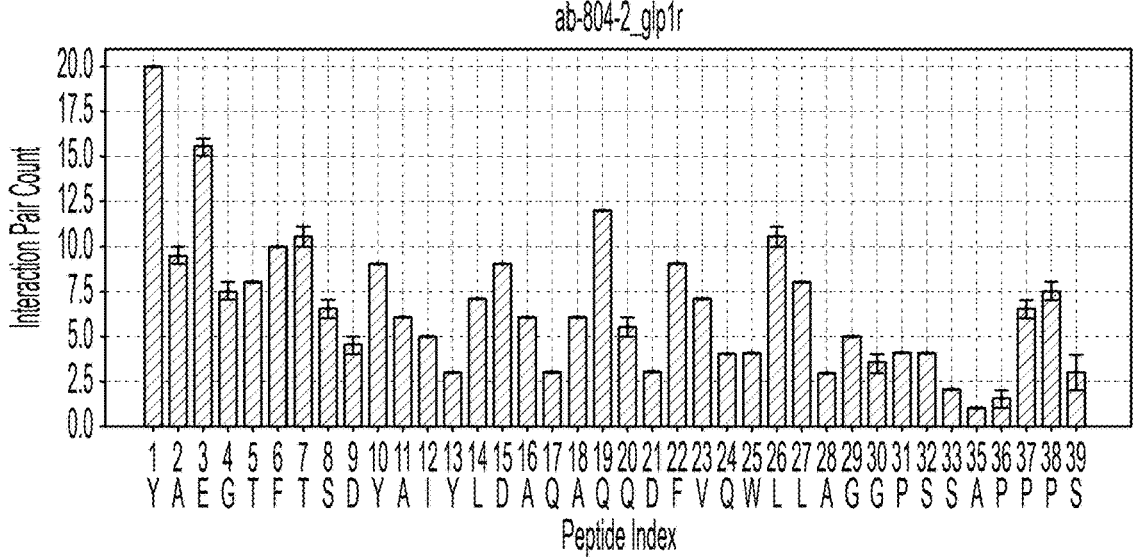
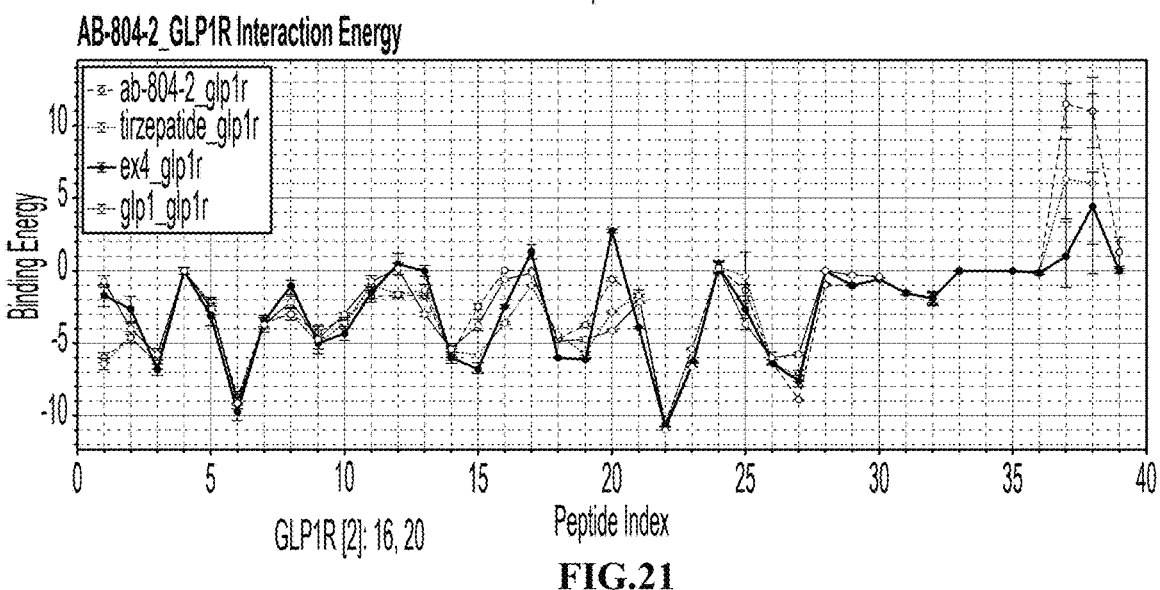
FIG.21

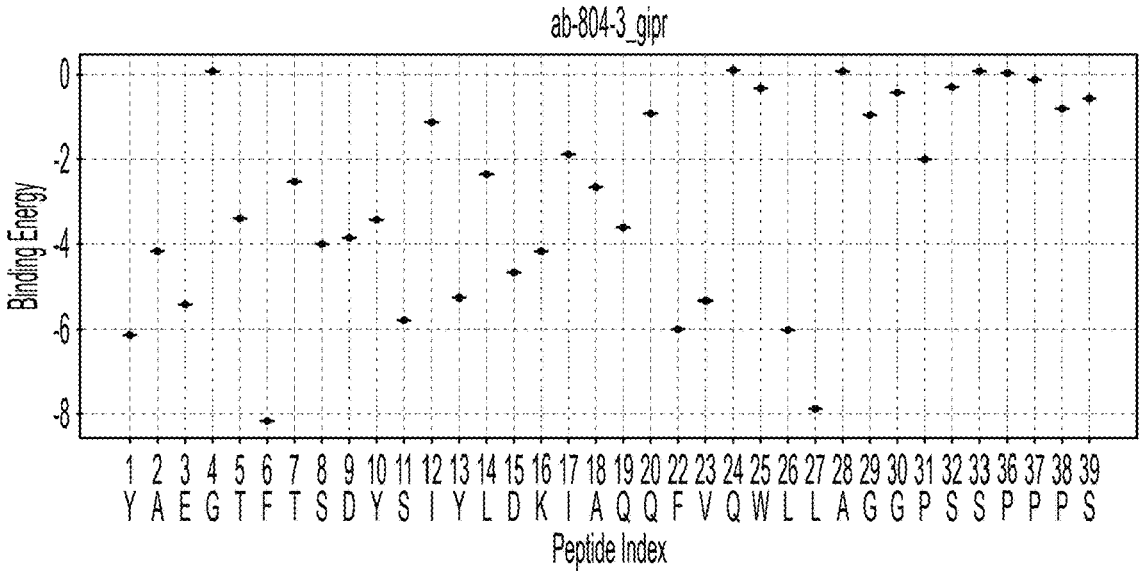
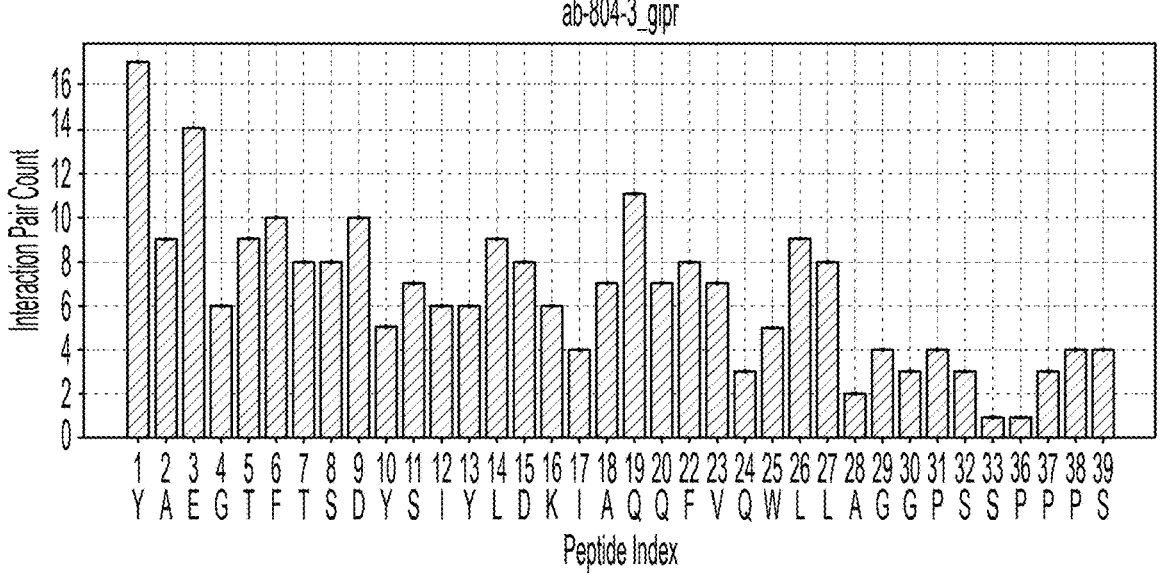
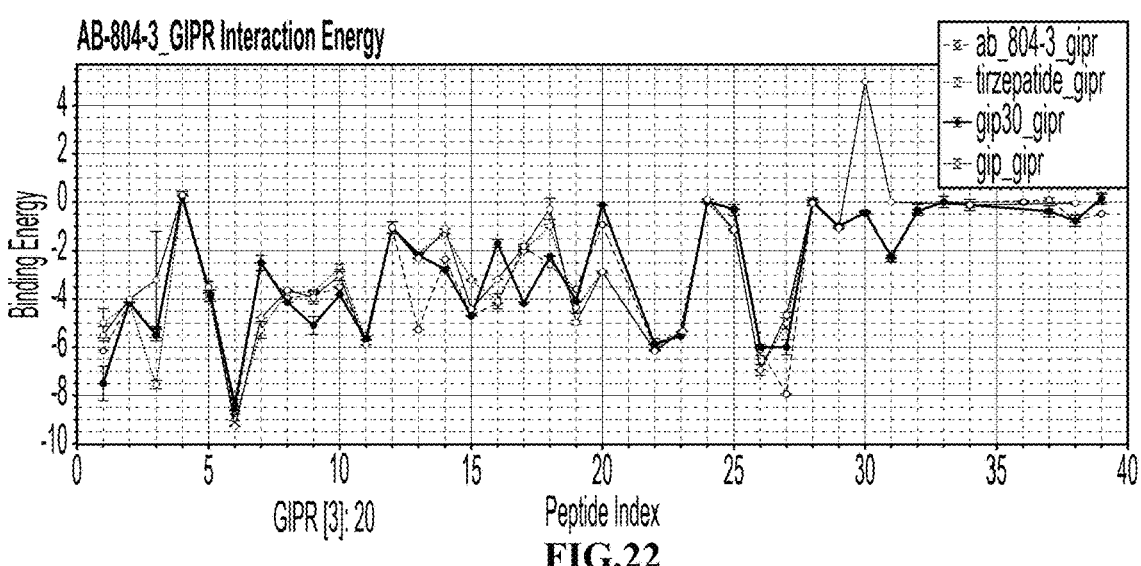
FIG.22

| | glp1_glp1r_energy | gip30_gipr_energy | gcg_gcgr_energy | glp1_glp1r_pair | gip30_gipr_pair | gcg_gcgr_pair |
|---|---|---|---|---|---|---|
| 1 | -0.74 (H) | -5.02 (Y) | -3.36 (H) | 16.0 | 17.5 | 13.5 |
| 2 | -3.94 (A) | -4.14 (A) | -3.27 (S) | 10.0 | 9.5 | 9.5 |
| 3 | -5.70 (E) | -7.51 (E) | -5.22 (Q) | 12.5 | 13.5 | 13 |
| 4 | -0.13 (G) | 0.348 (G) | -0.49 (G) | 6.0 | 5.5 | 7.5 |
| 5 | -2.57 (T) | -3.85 (T) | -3.01 (T) | 8.5 | 8 | 8 |
| 6 | -9.11 (F) | -9.20 (F) | -9.43 (F) | 11.5 | 10 | 9.5 |
| 7 | -3.81 (T) | -5.26 (I) | -4.45 (T) | 9.5 | 10 | 12.5 |
| 8 | -2.26 (S) | -3.65 (S) | -3.24 (S) | 5.5 | 4.5 | 6.5 |
| 9 | -4.81 (D) | -3.76 (D) | -4.28 (D) | 4.5 | 8 | 6 |
| 10 | -3.08 (V) | -2.75 (Y) | -3.60 (Y) | 6.5 | 6 | 8 |
| 11 | -0.65 (S) | -5.66 (S) | -0.82 (S) | 6.0 | 6 | 8 |
| 12 | 0.163 (S) | -1.13 (I) | -3.65 (K) | 5.0 | 5 | 8.5 |
| 13 | -2.93 (Y) | -2.19 (A) | -5.17 (Y) | 3.5 | 4 | 5 |
| 14 | -5.24 (L) | -1.29 (M) | -5.87 (L) | 6.0 | 6 | 4 |
| 15 | -3.69 (E) | -3.19 (D) | -8.09 (D) | 11.5 | 7.5 | 9 |
| 16 | -0.60 (G) | -4.09 (K) | -1.14 (S) | 5.5 | 7 | 7 |
| 17 | -0.23 (Q) | -1.98 (I) | -0.13 (R) | 5.5 | 4.5 | 3.5 |
| 18 | -4.92 (A) | -1.06 (H) | -5.71 (R) | 6.0 | 3.5 | 13 |
| 19 | -4.65 (A) | -4.41 (Q) | -4.83 (A) | 9.0 | 11 | 7 |
| 20 | -4.20 (K) | -2.92 (Q) | -0.03 (Q) | 8.5 | 8 | 9.5 |
| 21 | -2.28 (E) | nan (D) | -1.37 (D) | 6.5 | NaN | 2.5 |
| 22 | -11.0 (F) | -6.08 (F) | -11.6 (F) | 8.0 | 6 | 9 |
| 23 | -6.71 (I) | -5.34 (V) | -6.30 (V) | 7.5 | 8.5 | 9 |
| 24 | 0.008 (A) | 0.129 (N) | 0.036 (Q) | 1.0 | 2 | 2 |
| 25 | -3.60 (W) | -1.21 (W) | -5.80 (W) | 3.5 | 3 | 8 |
| 26 | -5.99 (L) | -6.87 (L) | -6.80 (L) | 9.5 | 9 | 11 |
| 27 | -5.78 (V) | -5.04 (L) | -6.96 (M) | 6.5 | 8.5 | 9.5 |
| 28 | -0.16 (K) | -0.10 (A) | -0.21 (N) | 3.0 | 1 | 3.5 |
| 29 | -0.18 (G) | -0.99 (Q) | -0.47 (T) | 4.5 | 4 | 7 |

FIG.24

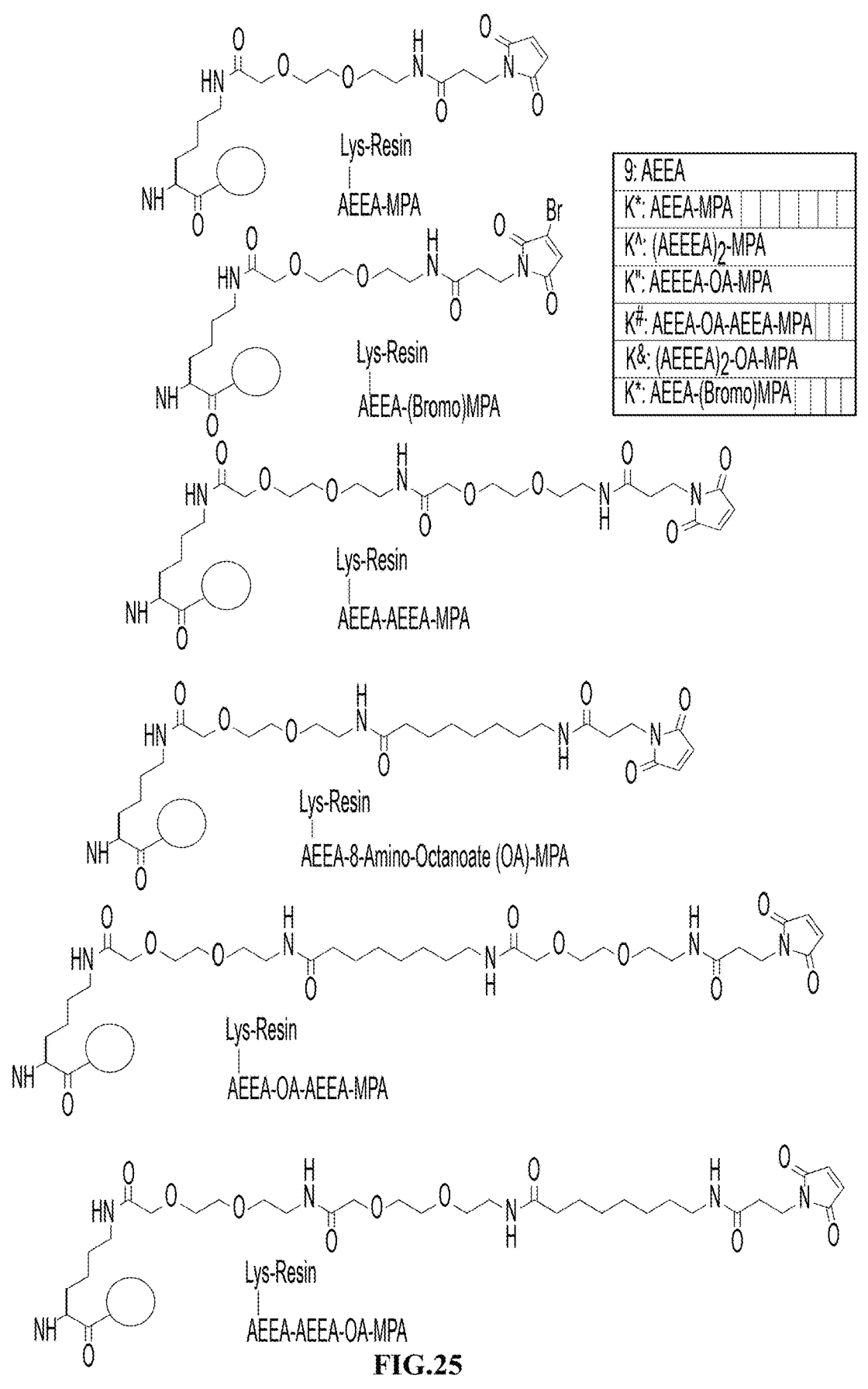

| 9: AEEA |
| --- |
| K*: AEEA-MPA |
| K^: (AEEEA)$_2$-MPA |
| K": AEEEA-OA-MPA |
| K#: AEEA-OA-AEEA-MPA |
| K&: (AEEEA)$_2$-OA-MPA |
| K*: AEEA-(Bromo)MPA |

Lys-Resin

AEEA-MPA

Lys-Resin

AEEA-(Bromo)MPA

Lys-Resin

AEEA-AEEA-MPA

Lys-Resin

AEEA-8-Amino-Octanoate (OA)-MPA

Lys-Resin

AEEA-OA-AEEA-MPA

Lys-Resin

AEEA-AEEA-OA-MPA

FIG.25

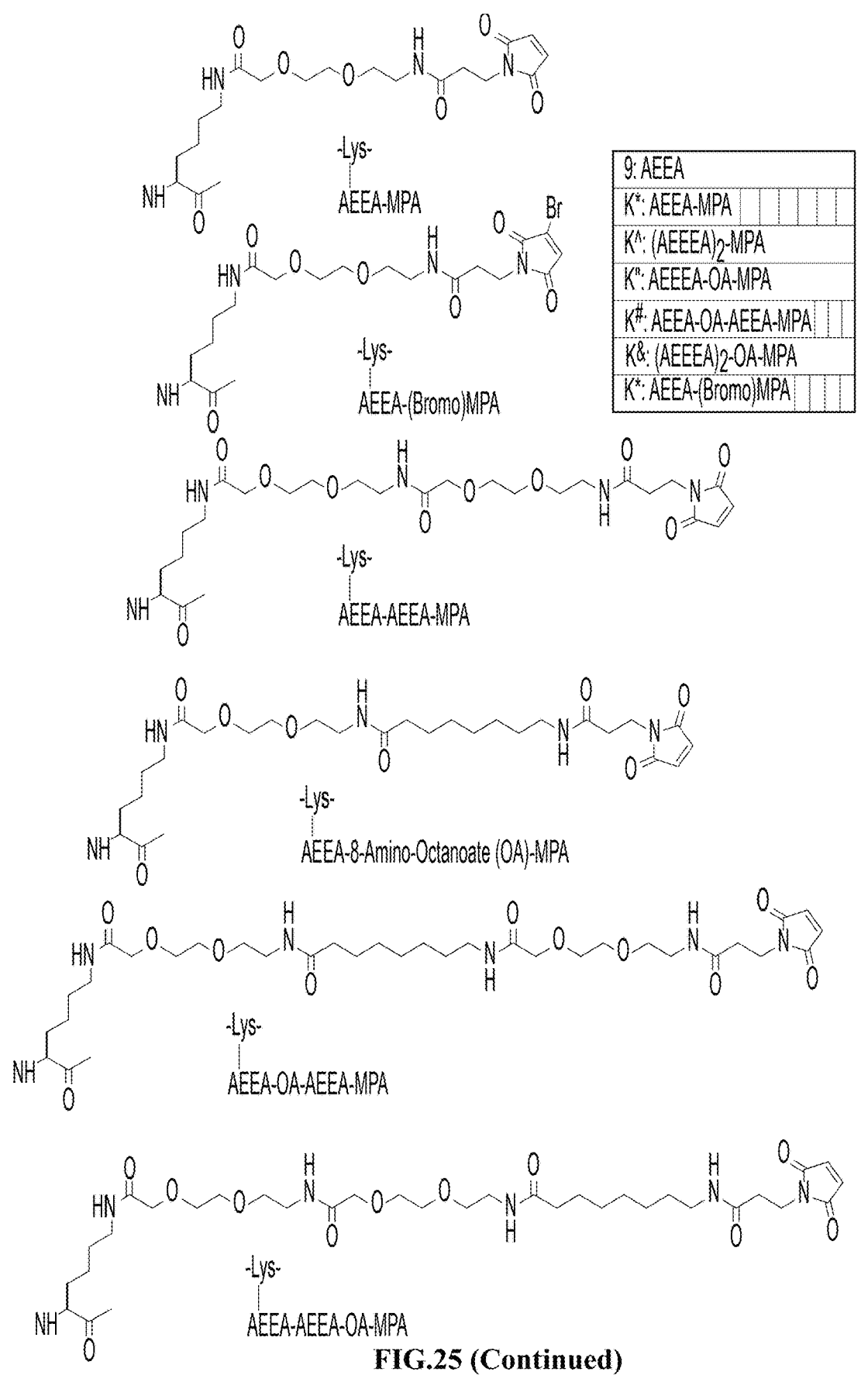

| 9: AEEA |
|---|
| K*: AEEA-MPA |
| K^: (AEEEA)$_2$-MPA |
| K": AEEEA-OA-MPA |
| K#: AEEA-OA-AEEA-MPA |
| K&: (AEEEA)$_2$-OA-MPA |
| K*: AEEA-(Bromo)MPA |

-Lys-
AEEA-MPA

-Lys-
AEEA-(Bromo)MPA

-Lys-
AEEA-AEEA-MPA

-Lys-
AEEA-8-Amino-Octanoate (OA)-MPA

-Lys-
AEEA-OA-AEEA-MPA

-Lys-
AEEA-AEEA-OA-MPA

FIG.25 (Continued)

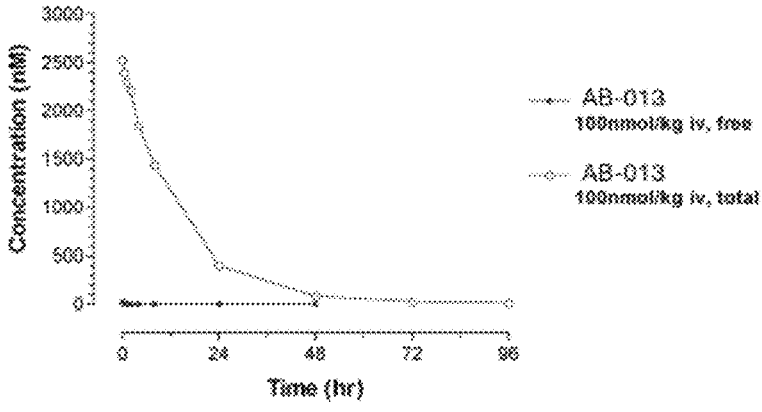
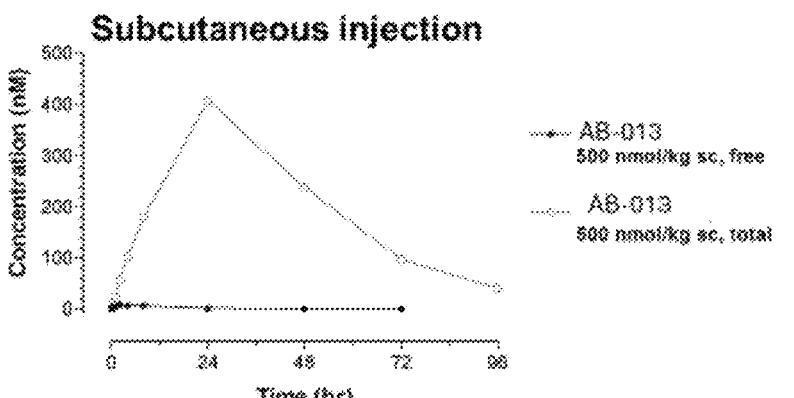
FIG.29
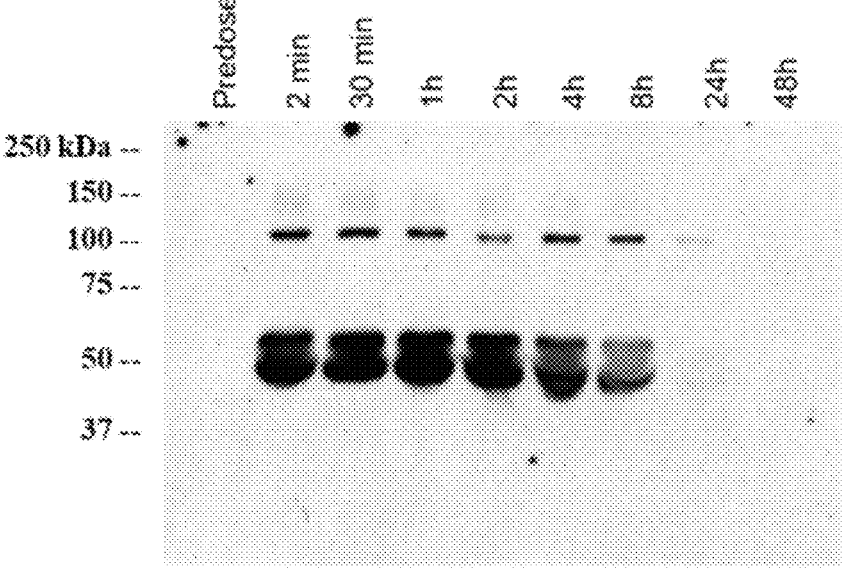
FIG.30

Figure 31A:
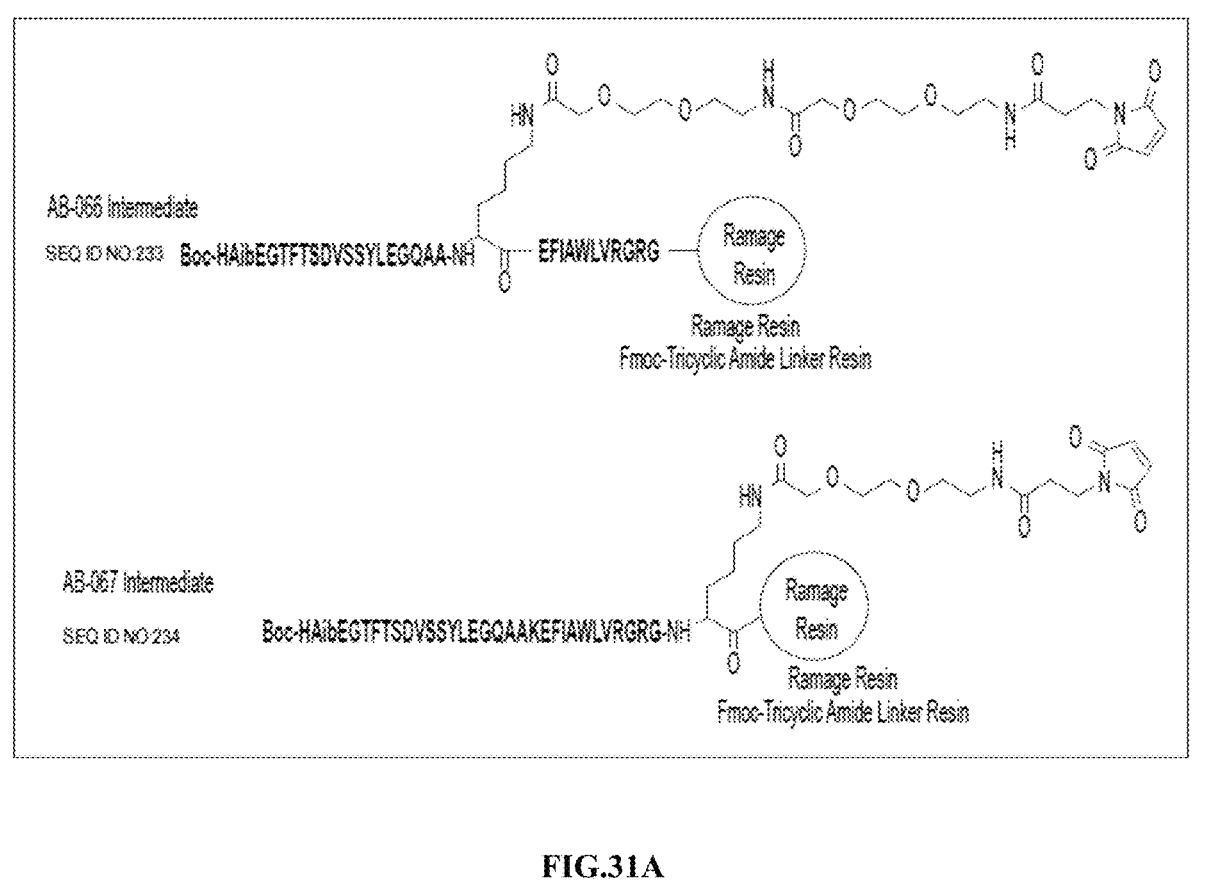

AB-066 Intermediate
SEQ ID NO.233   Boc-HAibEGTFTSDVSSYLEGQAA-NH ——— EFIAWLVRGRG ——— Ramage Resin Ramage Resin
Fmoc-Tricyclic Amide Linker Resin AB-067 Intermediate
SEQ ID NO.234   Boc-HAibEGTFTSDVSSYLEGQAAKEFIAWLVRGRG-NH ——— Ramage Resin Ramage Resin
Fmoc-Tricyclic Amide Linker Resin

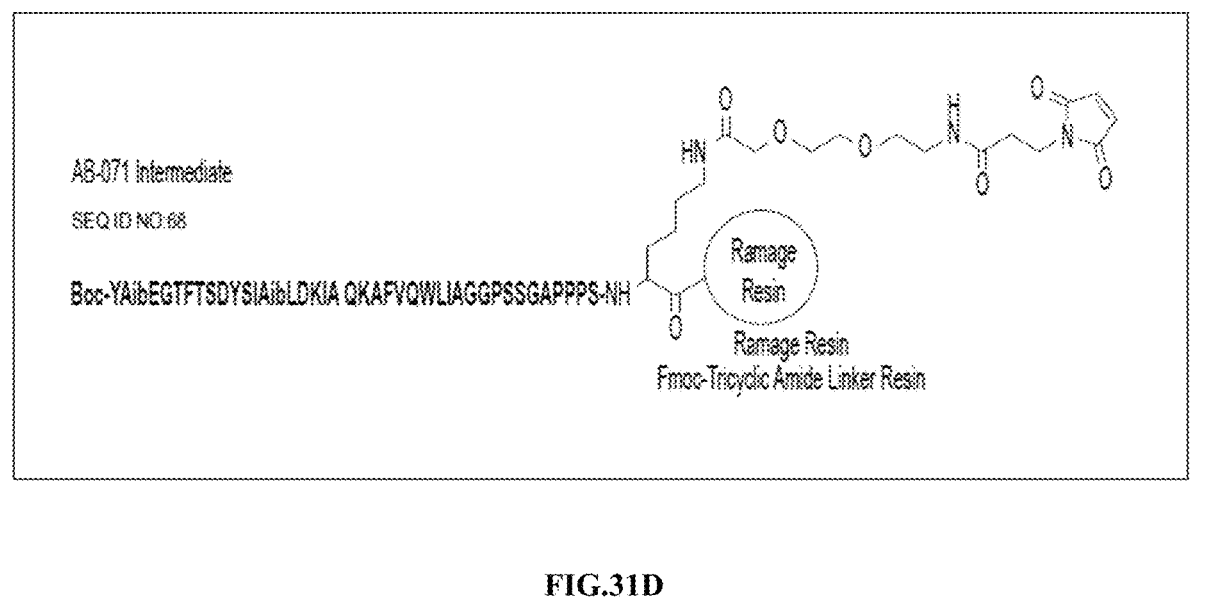

AB-071 Intermediate

SEQ ID NO:68

Boc-YAibEGTFTSDYSIAibLDKIA QKAFVQWLIAGGPSSGAPPPS-NH

Ramage Resin

Ramage Resin
Fmoc-Tricyclic Amide Linker Resin

FIG.31D

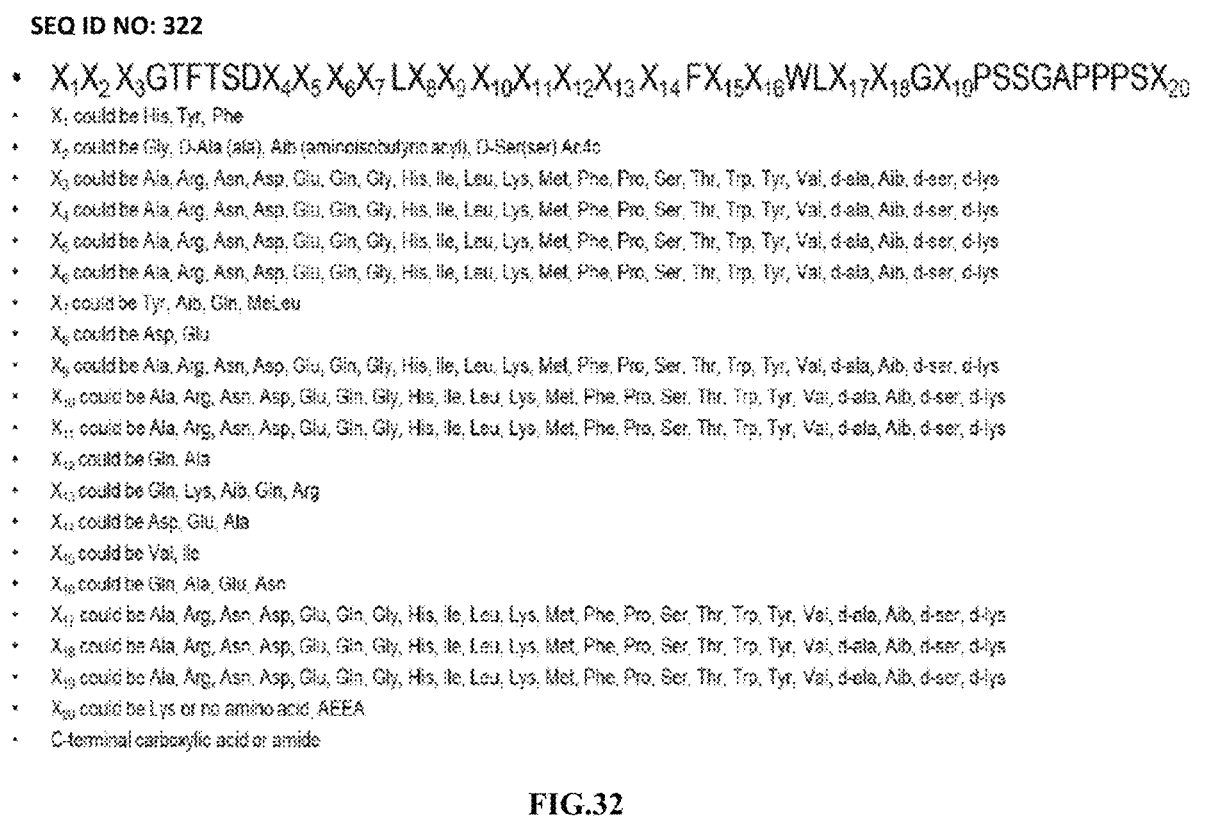

SEQ ID NO: 322

- $X_1X_2X_3GTFTSDX_4X_5X_6X_7LX_8X_9X_{10}X_{11}X_{12}X_{13}X_{14}FX_{15}X_{16}WLX_{17}X_{18}GX_{19}PSSGAPPPSX_{20}$
- $X_1$ could be His, Tyr, Phe
- $X_2$ could be Gly, D-Ala (ala), Aib (aminoisobutyric acyl), D-Ser(ser) Ac4c
- $X_3$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_4$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_5$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_6$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_7$ could be Tyr, Aib, Gln, MeLeu
- $X_8$ could be Asp, Glu
- $X_9$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_{10}$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_{11}$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_{12}$ could be Gln, Ala
- $X_{13}$ could be Gln, Lys, Aib, Gln, Arg
- $X_{14}$ could be Asp, Glu, Ala
- $X_{15}$ could be Val, Ile
- $X_{16}$ could be Gln, Ala, Glu, Asn
- $X_{17}$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_{18}$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_{19}$ could be Ala, Arg, Asn, Asp, Glu, Gln, Gly, His, Ile, Leu, Lys, Met, Phe, Pro, Ser, Thr, Trp, Tyr, Val, d-ala, Aib, d-ser, d-lys
- $X_{20}$ could be Lys or no amino acid, AEEA
- C-terminal carboxylic acid or amide

FIG.32

Weight Loss of Albenatide Equivalent to Semaglutide in Diet Induced Obese (DIO) Mouse Model
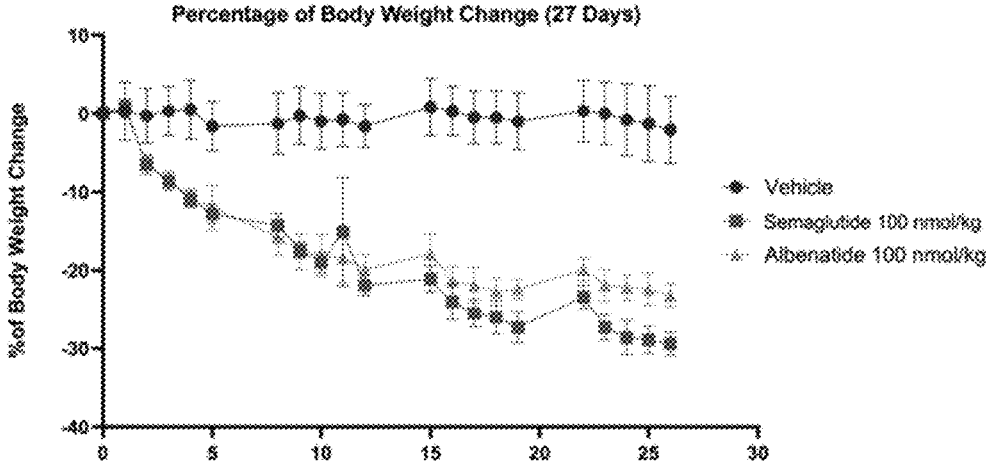
Weight Loss of Albenatide Equivalent to Semaglutide in Diet Induced Obese (DIO) Mouse Model
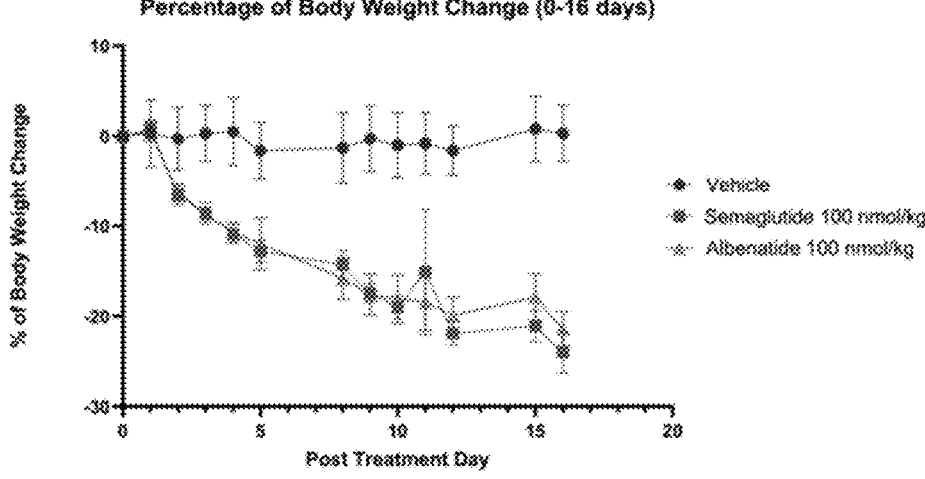
FIG.33

Equivalent Food Consumption Following Semaglutide Versus
Albenatide in Diet Induced Obese (DIO) Mouse Model
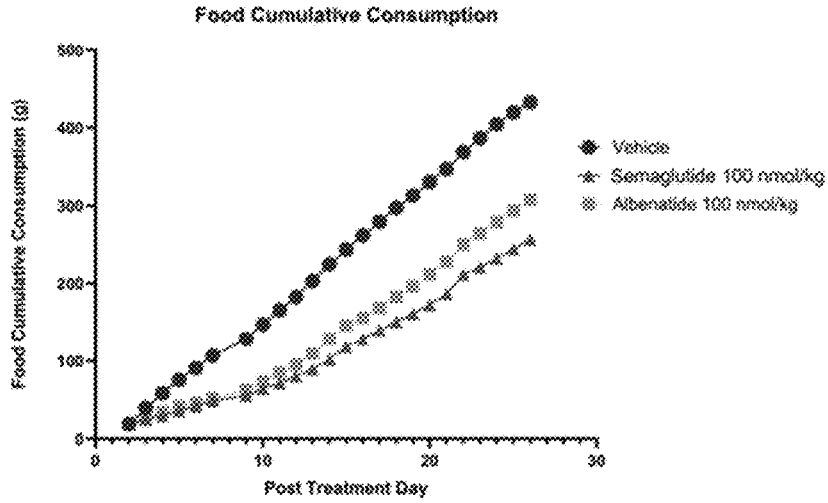
Equivalent Water Consumption Following Semaglutide Versus
Albenatide in Diet Induced Obese (DIO) Mouse Model
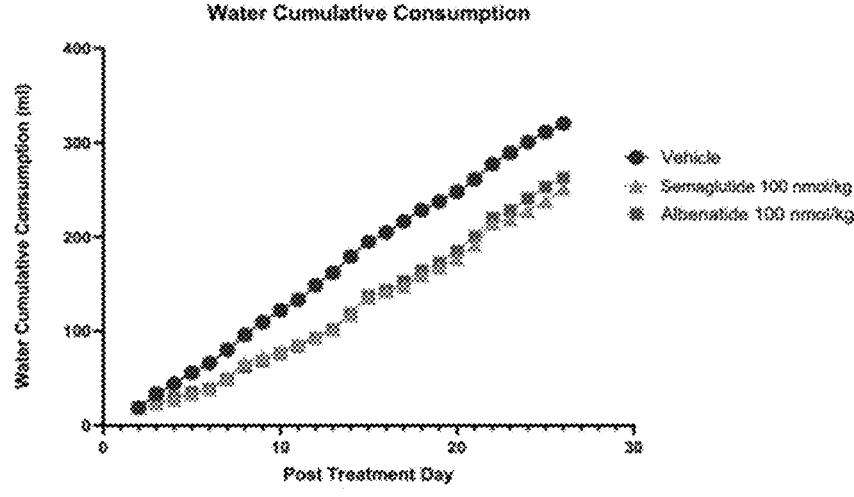
FIG.34

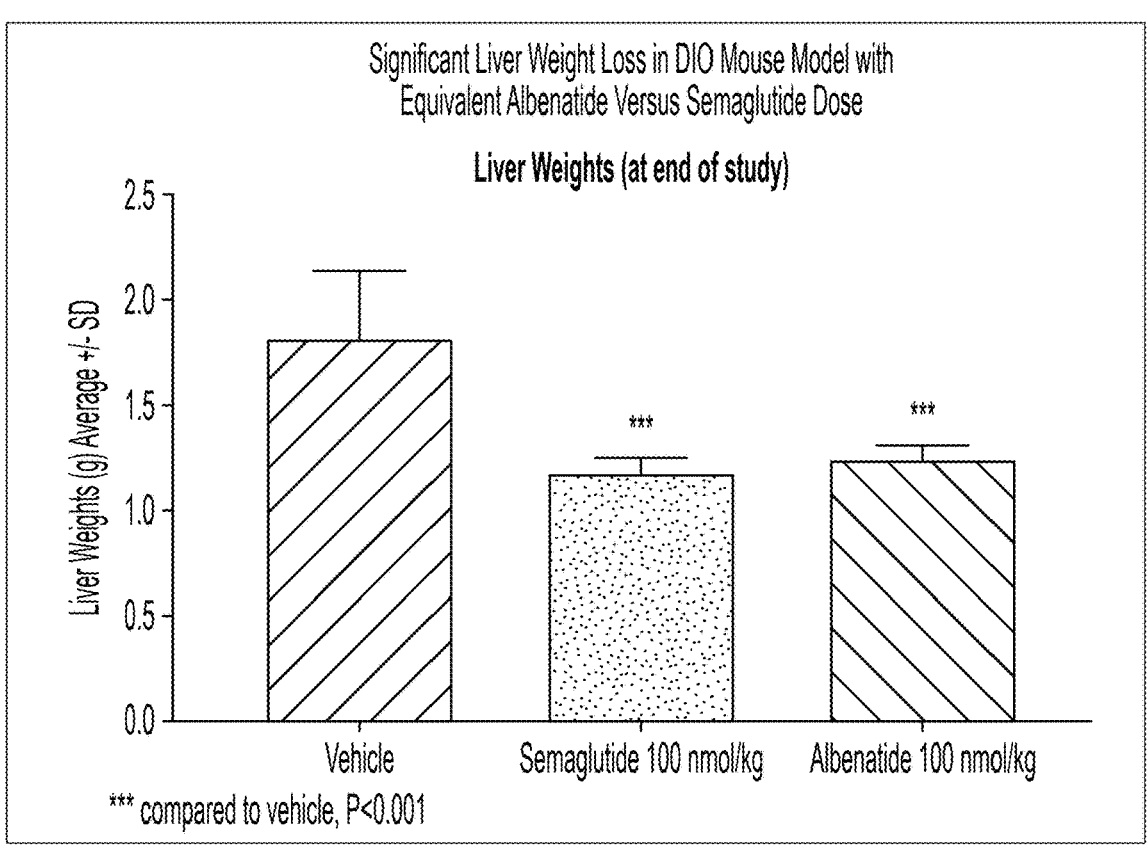
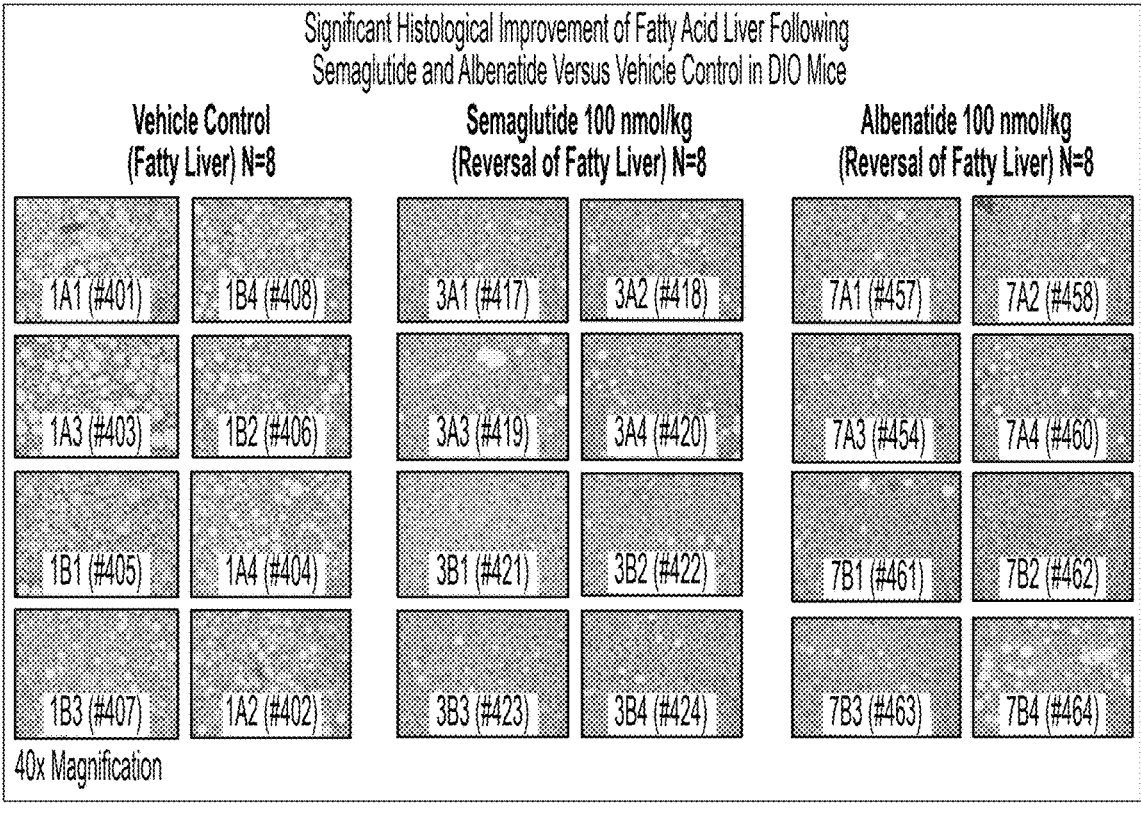
FIG.36

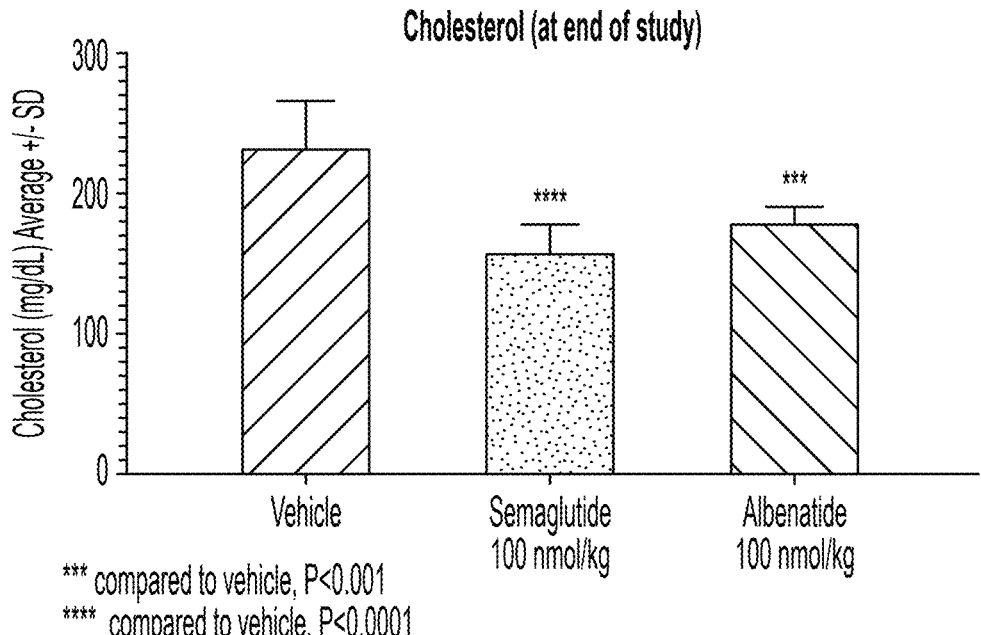

Significant Liver Function and Cholesterol Level Improvement in DIO Mouse Model with Equivalent Albenatide Versus Semaglutide Dose

Cholesterol (at end of study)

*** compared to vehicle, P<0.001
**** compared to vehicle, P<0.0001

FIG.37C

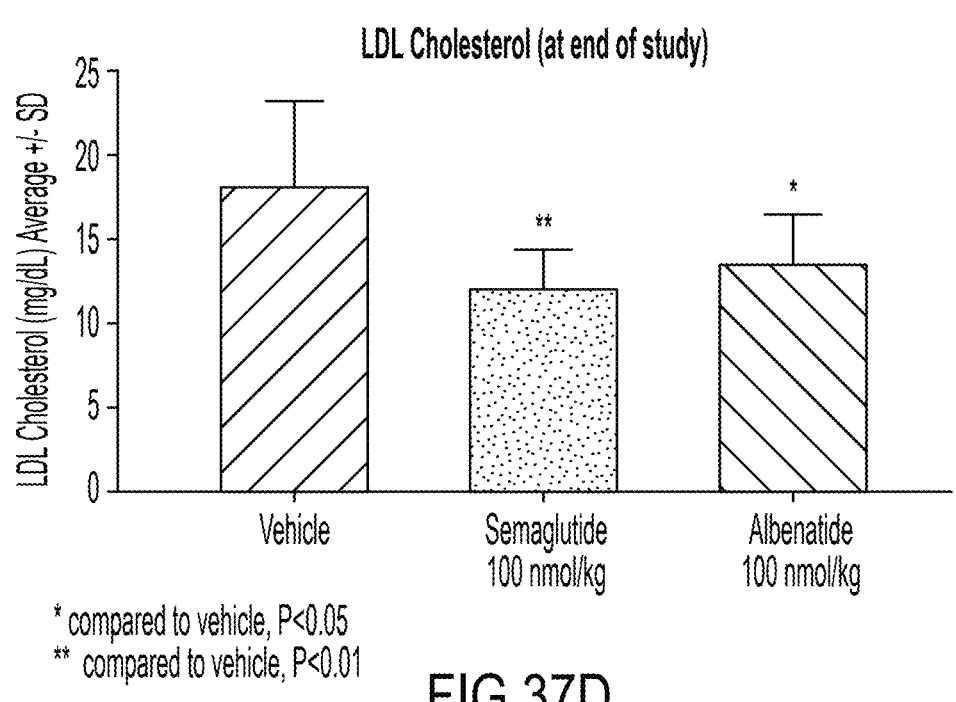

Significant Liver Function and Cholesterol Level Improvement in DIO Mouse Model with Equivalent Albenatide Versus Semaglutide Dose

LDL Cholesterol (at end of study)

* compared to vehicle, P<0.05
** compared to vehicle, P<0.01

FIG.37D

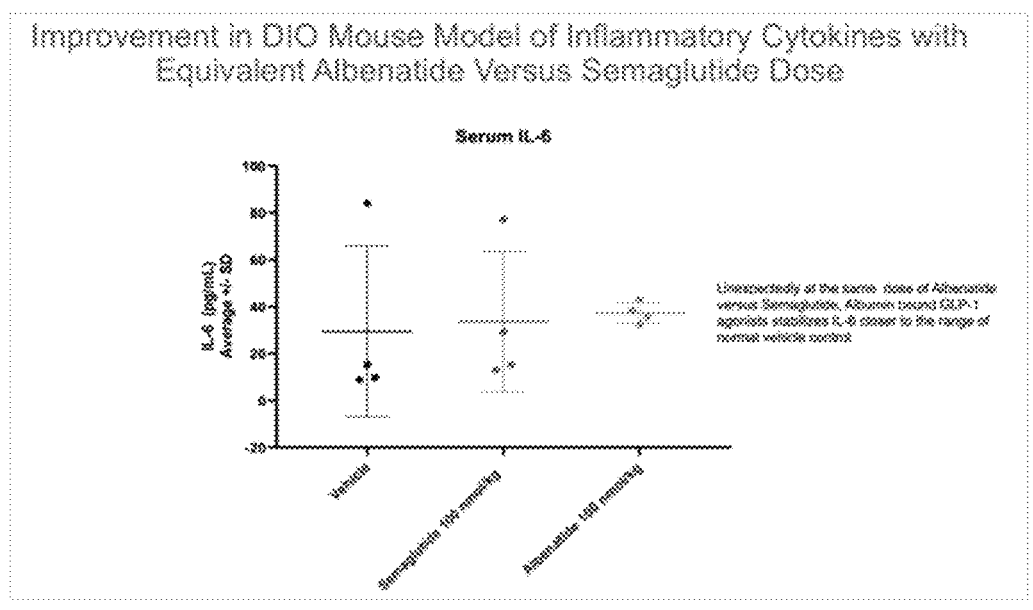
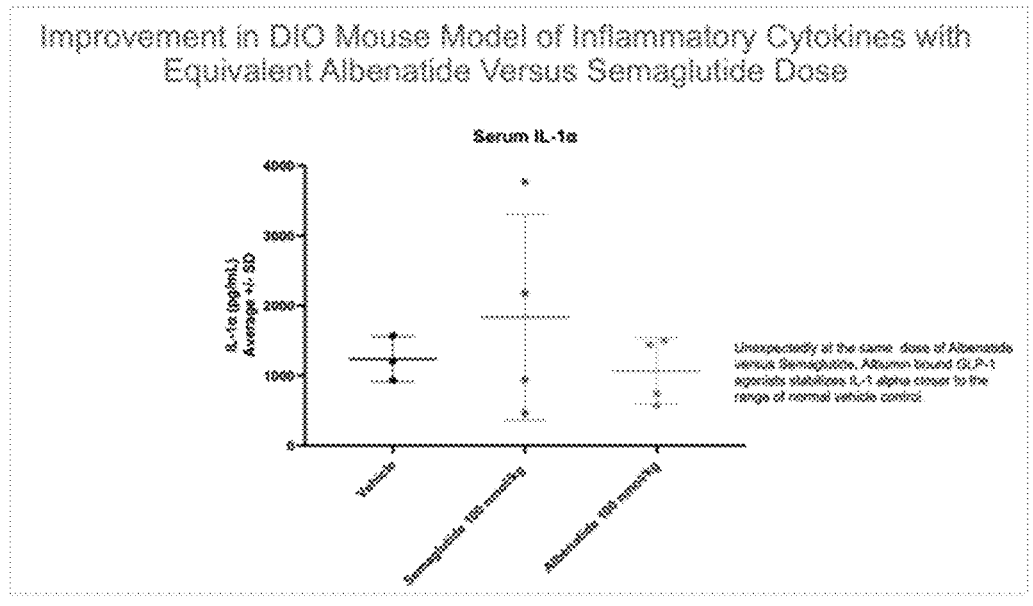
FIG.38

ALBUMIN BOUND MACROMOLECULE TRI-AGONIST ACTIVATING GLP-1/GIP/GLUCAGON RECEPTORS

This application claims priority to our US Provisional patent applications with the Ser. Nos. 63/523,324, filed Jun. 26, 2023, 63/619,584, filed Jan. 10, 2024, 63/624,692, filed Jan. 24, 2024, 63/625,169, filed Jan. 25, 2024, 63/551,315, filed Feb. 8, 2024, 63/551,334, filed Feb. 8, 2024, 63/551, 370, filed Feb. 8, 2024, 63/561,187, filed Mar. 4, 2024, 63/564,426, filed Mar. 12, 2024, 63/564,941, filed Mar. 13, 2024, 63/566,870, filed Mar. 18, 2024, 63/567,402, filed Mar. 19, 2024, 63/568,988, filed Mar. 22, 2024, 63/631,777, filed Apr. 9, 2024, 63/634,379, filed Apr. 15, 2024, 63/641, 782, filed May 2, 2024, and 63/650,095, filed May 21, 2024, each of which are incorporated by reference herein.

SEQUENCE LISTING

The content of the XML file of the sequence listing named 1026900063US-C, which is 1,005,155 bytes in size was created on Aug. 9, 2024, and electronically submitted via Patent Center along with the present application and is incorporated by reference in its entirety.

FIELD OF THE INVENTION

The field of the invention is pharmaceutical composition and methods, particularly as they relate to agonists, di-agonists, and tri-agonists of glucagon-like peptide 1 (GLP-1) receptors, glucose-dependent insulinotropic polypeptide (GIP) receptors, and/or glucagon (GcG) receptors.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Obesity, a global health crisis, is escalating at an alarming rate. As of 2020, 41.9% of adults in the U.S. were classified as obese. Globally, over 1 billion people, including 650 million adults, are affected by obesity. This condition is associated with a multitude of health complications, including hyperglycemia, type 2 diabetes, hypertension, dyslipidemia, obstructive sleep apnea, atherosclerosis, osteoarthritis, urinary incontinence, non-alcoholic steatohepatitis, cardiovascular diseases, certain cancers, and premature mortality. Furthermore, obesity negatively impacts both physical and mental health, leading to a diminished quality of life and reduced cardiorespiratory fitness, which in turn heightens the risk of cardiovascular diseases and overall mortality.

Similarly, diabetes mellitus has become an increasingly common illness with 537 million adults are affected worldwide in 2021 with a prediction of 783 million by 2045. Of these patients, approximately 90% have type 2 (or non-insulin dependent) diabetes. Often related to obesity, this disease is characterized by increased blood glucose levels, decreased insulin action, and impaired glucose tolerance. Treatment usually includes a diet, weight loss, and exercise regimen as well as the administration of anti-diabetic agents including metformin to decrease hepatic glucose output, sulfonylurea and metformin to increase insulin secretion, and/or thiazolidinediones to enhance insulin sensitivity.

While these drug treatment options are often effective, the disease may progress in spite of treatment, and patients may eventually require daily administration of insulin. Hence, new therapeutic strategies in the form of insulinotropic peptides have been developed for the treatment of Type 2 diabetes, including analogs of peptides that control blood glucose levels, such as glucagon-like peptide 1 (GLP-1), gastric inhibitory polypeptide (GIP), Glucagon, and Amylin.

GLP-1 is a naturally occurring hormone that is released by L cells in the lower intestine in response to nutrient ingestion. In addition to having potent insulinotropic effects, GLP-1 has been shown to suppress glucagon, stimulate pancreatic β-cell proliferation, inhibit gastric emptying, and decrease gastrointestinal (GI) motility, all actions that contribute to the glucose-dependent postprandial maintenance of normal blood glucose levels and regulation of appetite. Because of these pleiotropic effects, GLP-1 analogs make attractive candidates for the treatment of Type 2 diabetes.

One major drawback to the use of native GLP-1 is the extremely short half-life of several minutes, due to cleavage by the ubiquitous proteolytic enzyme dipeptidyl peptidase IV at an N-terminal alanine residue. In contrast to the short-lived GLP-1 peptide, exendin-4 (a 39 amino acid peptide agonist of the glucagon-like peptide 1 (GLP-1) receptor) is resistant to dipeptidyl peptidase IV degradation and has a circulating half-life of approximately 33 minutes in humans. Exendin-4 induces similar physiological effects as GLP-1, through the GLP-1 receptor, and is more potent than native GLP-1. Synthetic exendin-4 (Byetta) has been used as an adjunctive therapy with oral antidiabetic agents in the treatment of non-insulin dependent diabetes mellitus (T2DM). In an approach to further extend half-life of exendin-4, the agonist was encapsulated in poly-(D-L-Lactide-Co-Glycolide) microspheres (Bydureon).

The need for even longer active formulations led to the development of recombinant proteins such as the fusion protein described in CA 2434237 (not marketed) and the fusion protein albiglutide (TANZEUM™, GlaxoSmithkline, discontinued), as described in U.S. Pat. No. 7,141,547. Albiglutide is an albumin fusion protein of GLP-1 in which a tandem repeat of Gly8 GLP-1 is directly fused to the N-terminus of human serum albumin. Here, the tandem repeat was intended to improve affinity for the GLP-1 receptor by creating a longer distance between albumin and the distal GLP-1 peptide. While the half-life was extended to 6-8 days, making it suitable for once weekly dosing, the potency of albiglutide was significantly reduced (GLP-1 receptor affinity of albiglutide is 20 nM compared with 0.02 nM for exenatide), most likely due to a combination of the Gly8 modification and the direct covalent fusion with the albumin. When administered as a monotherapy, the decrease in HbA1c from baseline at the 30 mg weekly dose was −0.7% at week 52. At the 50 mg weekly dose, the change from baseline of HbA1c was −0.9%. Despite these high doses of GLP-1 at 30 and 50 mg, the change in HbA1c from baseline never achieved a decrease ≥1%. Based on these findings, it was taught by Knudsen et al (Knudsen L B, Lau J. The Discovery and Development of Liraglutide and Semaglutide. Front Endocrinol (Lausanne). 2019 Apr. 12;

10:155. doi: 10.3389/fendo.2019.00155. PMID: 31031702; PMCID: PMC6474072.) that a GLP-1 agonist, when fused to albumin, will not produce an effective composition, under the premise that GLP-1 agonists could bind to albumin or to the GLP-1 receptor, but not to both. Specifically, the industry taught against irreversible binding to albumin and instead implemented the idea "was to build on reversible binding to albumin as a solution for the systemic protraction of GLP-1 analogs. The main challenge identified in earlier studies was that strong binding to albumin had a negative impact on the potency of compounds for the GLP-1R, due to competition between binding to albumin and binding to the receptor). The theory was that only the free fraction in the plasma that was not bound to albumin would be available to activate the GLP-1R. Therefore, the stronger the affinity to albumin the smaller the free and active circulating fraction of the GLP-1 peptide. This phenomenon had previously been observed with liraglutide analogs, where there was a clear trend for longer fatty acids, with improved affinity for albumin, to be associated with diminished potency for the GLP-1R".

On the basis of this assumption, a modified approach by the pharmaceutical industry was adopted that made use of reversible non-covalent binding of GLP-1 analogs to albumin. In this approach, GLP-1 agonists were acylated to so facilitate non-covalent binding of the acylated GLP-1 agonists to the seven fatty acid binding sites in albumin, resulting in extended half-lives of these compositions. Examples for such approaches include VICTOZA™ (liraglutide, Novo Nordisk, albumin with modified GLP-1 agonist), OZEMPIC™/WEGOVY™ (semaglutide, Novo Nordisk, albumin with modified GLP-1 agonist), MOUNJARO™/ZEPBOUND™ (tirzepatide, Eli Lilly, albumin with modified GLP-1/GIP dual agonist), Pemvidutide (AltImmune, albumin with modified GLP-1/Glucagon dual agonist), efinopegdutide (Merck, albumin with modified GLP-1/Glucagon dual agonist), and survodutide (Zealand, Boehringer, albumin with modified GLP-1/Glucagon dual agonist). While at least some of these formulations provided an increased stability and serum half-life, dissociation of the modified agonist from the albumin carrier it nevertheless required for receptor activation, leading once more to renal clearance of the agonist as well as high doses of GLP-1 since in this reversable approach 99% was bound to albumin and only 1% active material available to ligate with the GLP-1 receptor. Moreover, numerous adverse effects such as nausea, vomiting, and diarrhea are common with formulations having reversible and non-covalent binding of GLP-1 analogs at these high doses. To increase tolerability of such compositions, it is routinely recommended to titrate a subject up to a tolerated therapeutic dosage, which can take several weeks.

In still further known compositions, exendin-4 is covalently bound via a linker to $Cys_{34}$ of albumin as is described in WO 2007/053946, WO 2009/075859, and WO 2011/109787, and CA 2501421 and CA 2550050 teach further insulinotropic agents with a linker that can be coupled to albumin. While conceptually attractive, similar difficulties as observed with the acylated GLP-1 agonists described above remain, as the covalent bond at the $Cys_{34}$ of albumin is in such compounds generally subject to a retro-Michael addition reaction and so liberates the formerly bound exendin-4, leading once more to fast renal clearance and potential adverse effects due to the unbound GLP-1 agonist.

Thus, even though various compositions and methods of GPCR agonists, and especially GLP-1, GIP, and glucagon receptor agonists, are known in the art, all or almost all of them suffer from several drawbacks. In particular, small agonist peptides such as GLP-1 are quickly degraded by endopeptidases, while small agonist peptide analogs such as exendin-4 are more stable, but still undergo fast renal clearance. On the other hand, GLP-1 albumin direct fusion proteins have significantly longer serum half-life times, however, are sterically hindered and therefore require very high dosages as shown in Albiglutide. Still further, fatty acid-modified GLP-1 and GLP-1 analogs that are non-covalently bound to hydrophobic pockets in albumin need to dissociate from albumin to activate their target receptor. Unfortunately, dissociated free fatty acid-modified GLP-1 and analogs thereof produce adverse effects once separated from albumin and will also not penetrate the blood brain barrier (BBB). Similarly, where linker-bound exendin-4 is coupled to $Cys_{34}$ in albumin via Michael addition, free exendin-4 is once more encountered due to a retro-Michael addition reaction, leading once more to fast Exendin-4 clearance and adverse effects due to unbound agonists.

Therefore, there is still a need to provide improved compositions in which a GPCR agonist has high stability in plasma/serum, has agonist activity at low concentrations while remining stably bound to a carrier, and in which the GPCR agonist can readily move from the blood compartment into a target tissue or even pass the blood brain barrier into neural tissues and which can be delivered both subcutaneously, sub dermally, intranasally, and orally.

SUMMARY OF THE INVENTION

The inventive subject matter is directed to various compositions and methods of GPCR agonists, and particularly insulinotropic agonists, with high stability in plasma/serum, with agonist activity while remaining stably bound to a carrier, and in which the GPCR agonist can readily move from the blood compartment into a target tissue or even pass the blood brain barrier into neural tissues. Advantageously, compositions presented herein are retro-Michael resistant and as such reduce or even entirely avoid adverse effects otherwise encountered with unbound or free agonists.

In one aspect of the inventive subject matter, the inventors contemplate a reaction intermediate that includes (a) isolated and conformationally modified albumin in a solvent, wherein at least one hydrophobic pocket of the albumin is not occupied by a non-covalently bound lipid, and (b) a Michael acceptor reagent.

Most typically, the isolated and conformationally modified albumin is recombinant human albumin, and in certain embodiments the isolated and conformationally modified albumin is a defatted albumin. It is further preferred (but not necessary) that the solvent is an aqueous solvent having a pH of the solvent is pH<7.0. Additionally, it is contemplated that Michael acceptor comprises a planar acceptor group (e.g., a maleimide group or a bromo maleimide group), and in most embodiments, the Michael acceptor reagent further includes a linker that is covalently coupled to a Class B G protein-coupled receptor (GPCR) agonist peptide.

Viewed form a different perspective, the inventors contemplate a chemically modified albumin, wherein the albumin is modified at $Cys_{34}$ with a coupling group such that a sulfur atom of the $Cys_{34}$ is covalently bound to a chiral carbon atom of the coupling group, and wherein the chiral atom has a favored stereochemical configuration. For example, the favored stereochemical configuration may be favored at a ratio of at least 70:30, or at a ratio of at least 90:10. As noted above, the albumin is typically human albumin, which may or may not be recombinant. It is further preferred that the albumin is a conformationally modified albumin, and/or that the albumin is in an aqueous solvent having a pH<7.0. Additionally, it is contemplated that the albumin is in an aqueous solvent that further comprises albumin having an unreacted $Cys_{34}$ group (free albumin), wherein the ratio of the free albumin to the chemically modified albumin is at least 1:1.2. In further contemplated embodiments, the coupling group is covalently coupled to a linker, and the linker may be covalently coupled to a Class B GPCR agonist peptide.

Therefore, it should be appreciated that the inventors also contemplate a chemically modified albumin, wherein the albumin is modified at $Cys_{34}$ with a Michael addition conjugate, and wherein the Michael addition conjugate is resistant to a retro-Michael addition reaction. Most preferably, the Michael addition conjugate comprises a hydrophilic linker of various lengths, which may be further covalently bound to a Class B GPCR agonist peptide. In still further contemplated embodiments, at least one hydrophobic pocket of the albumin is not occupied by a non-covalently bound lipid. Therefore, the albumin may be an at least partially (or even completely) defatted albumin. Moreover, it is also contemplated that a chiral carbon atom of the Michael addition conjugate forms a covalent bond with sulfur of the Cys34, wherein the chiral carbon atom has a favored stereochemical configuration (e.g., favored stereochemical configuration is favored at a ratio of at least 70:30).

Consequently, the inventors also contemplate a method of modifying albumin at $Cys_{34}$ that includes a step of providing or preparing a conformationally modified albumin in a solvent, wherein at least one hydrophobic pocket of the conformationally modified albumin is not occupied by a non-covalently bound lipid, and wherein a pH of the solvent is pH<7.0. In a further step, sulfur atom of the $Cys_{34}$ is then reacted with a coupling group to thereby produce the modified albumin.

In some embodiments, the conformationally modified albumin will be modified by at least partial defatting, and/or the pH of the solvent will be between 4.0 and 6.0. Typically, but not necessarily, the step of reacting is performed at an equimolar ratio between the conformationally modified albumin and the coupling group. As will be appreciated, the modified albumin is retro-Michael resistant with respect to the covalently bound coupling group. With further respect to the step of reacting it is contemplated that the step is at least stereo preferred (e.g., one chiral configuration at least occurs at 60%) or even stereoselective. Most typically, the coupling group will comprise a planar Michael acceptor group (e.g., a maleimide group or a bromo maleimide group), and the coupling group is further covalently coupled to a Class B GPCR agonist peptide.

Viewed from a different perspective, the inventors therefore also contemplate a method of reducing a retro-Michael addition reaction in a $Cys_{34}$ modified albumin in which the $Cys_{34}$ is reacted with a Michael addition reagent. Such method will typically include the steps of preparing a conformationally modified albumin in a solvent such that at least one hydrophobic pocket of the conformationally modified albumin is not occupied by a non-covalently bound lipid, wherein the pH of the solvent is pH<7.0; and a step of reacting the sulfur atom of $Cys_{34}$ with a coupling group of the Michael addition reagent to thereby produce the modified albumin. Most typically, but not necessarily, the conformationally modified albumin is modified by at least partial defatting. It is further preferred that the pH of the solvent is between 4.0 and 6.0.

Additionally, it is contemplated that the step of reacting is performed at an equimolar ratio between the conformationally modified albumin and the coupling group. In contemplated methods, retro-Michael addition reaction is typically reduced by at least 50%. In still further embodiments, it is contemplated that the Michael addition reagent comprises a linker of various lengths that is covalently coupled to a Class B GPCR agonist peptide, and/or that the Michael addition reagent has a structure according to any one of SEQ ID NO:1-471.

In another aspect of the inventive subject matter, the inventors also contemplate a method of producing a Class B G protein-coupled receptor (GPCR) agonist fusion protein that includes the steps of (a) providing or producing a conformationally modified albumin, and (b) covalently coupling a GPCR agonist peptide to $Cys_{34}$ of the conformationally modified albumin via a Michael addition reaction, wherein the step of coupling is performed at a pH of pH<7.0.

In at least some embodiments, the conformationally modified albumin is modified by at least partial defatting, and/or the step of coupling is performed with a molar excess of albumin relative to the GPCR agonist peptide. Preferably, but not necessarily, the pH is between 4.0 and 6.0. most typically, the GPCR agonist peptide comprises a linker with a planar Michael acceptor group (e.g., a maleimide group or a bromo maleimide group). In such case, it will be appreciated that the Michael addition reaction produces a stereopreferred or even stereoselective chiral carbon atom in the Michael acceptor group. Moreover, it is contemplated that the GPCR agonist peptide has a structure according to any one of SEQ ID NO:1-471.

Consequently, the inventors also contemplate a method of producing a retro-Michael addition resistant Class B GPCR fusion protein that includes the steps of (a) providing or producing a conformationally modified albumin, and (b) covalently coupling a GPCR agonist peptide to $Cys_{34}$ of the conformationally modified albumin via a Michael addition reaction, wherein the step of coupling is performed at a pH of pH<7.0.

Preferably, but not necessarily, the GPCR agonist peptide has a structure according to any one of SEQ ID NO:1-471, and/or the conformationally modified albumin is modified by at least partial defatting. Where desired, it is also contemplated that the step of coupling is performed with a molar excess of albumin to GPCR agonist peptide, and/or that the pH is between 4.0 and 6.0. As noted before, the GPCR agonist peptide may comprise a linker with a planar Michael acceptor group such as a maleimide group or a bromo maleimide group. Therefore, the Michael addition reaction will produce a stereopreferred or even stereoselective chiral carbon atom in the Michael acceptor group.

In yet another aspect of the inventive subject matter, the inventors also contemplate resin-immobilized cysteine-reactive Class B GPCR agonist peptide that includes a GPCR agonist peptide comprising a Lys amino acid to which (a) a linker is covalently bound via an amide bond formed by an epsilon amino group of the Lys amino acid, and (b) a synthetic resin with a spacer is covalently bound via an amide bond formed by a distal amino group in the spacer.

Among other options, especially contemplated linkers of various lengths and amino acid compositions include MPA, (bromo)MPA, AEEA, AEEA-MPA, AEEA-(bromo)MPA, (AEEA)₂-MPA, (AEEA)₂-(bromo)MPA, AEEEA-OA-MPA, AEEEA-OA-(bromo)MPA, AEEA-OA-AEEA-MPA, AEEA-OA-AEEA-(bromo)MPA, (AEEEA)₂-OA-MPA, and (AEEEA)₂-OA-(bromo)MPA. Moreover, it is generally contemplated that the synthetic resin comprises a polystyrene resin with a tricyclic spacer having the distal amino group (e.g., a Ramage resin), that the substitution level of the resin is approximately 0.4-0.6 mmol/gram, and/or that the synthetic resin is cross-linked with divinylbenzene at about 1%. For example, contemplated GPCR agonist peptides may have a structure according to any one of SEQ ID NO:1-471.

Therefore, and viewed from a different perspective, the inventors also contemplate a peptide solid state synthesis intermediate that includes a Ramage resin to which a first amino acid of a peptide is covalently coupled at a C-terminus of the peptide via an amide bond, wherein the first amino acid is further covalently coupled to a linker via an amide bond in a side chain of the first amino acid, and wherein the linker comprises a coupling group. Most typically, the first amino acid is lysine, and/or the linker is MPA, (bromo)MPA, AEEA, AEEA-MPA, AEEA-(bromo)MPA, $(AEEA)_2$-MPA, $(AEEA)_2$-(bromo)MPA, AEEEA-OA-MPA, AEEEA-OA-(bromo)MPA, AEEA-OA-AEEA-MPA, AEEA-OA-AEEA-(bromo)MPA, $(AEEEA)_2$-OA-MPA, and $(AEEEA)_2$-OA-(bromo)MPA. It is still further generally preferred that the coupling group comprises a planar Michael acceptor group (e.g., a maleimide group or a bromo maleimide group).

Consequently, the inventors also contemplate a method of synthesizing a peptide containing a linker with a coupling group, wherein the method includes the steps of (a) providing a synthetic resin with a spacer that comprises a distal amino group, (b) using the distal amino group to covalently couple a first amino acid to the resin, wherein the first amino acid has a protected reactive group in a side chain, (c) using solid state synthesis to sequentially couple a plurality of Fmoc-protected amino acids to the first amino acid, thereby obtaining a protected peptide, (d) selectively deprotecting the protected reactive group in the side chain, and reacting the reactive group with a linker, wherein the linker comprises a second protected reactive group, (e) selectively deprotecting the second protected reactive group in the linker, and reacting the second reactive group with a coupling group, and (f) deprotecting the protected peptide and cleaving the deprotected peptide from the resin, thereby forming the peptide containing the linker with the coupling group.

Most typically, the synthetic resin in such method is a Ramage resin, the first amino acid is lysine, and/or the linker is MPA, (bromo)MPA, AEEA, AEEA-MPA, AEEA-(bromo) MPA, $(AEEA)_2$-MPA, $(AEEA)_2$-(bromo)MPA, AEEEA-OA-MPA, AEEEA-OA-(bromo)MPA, AEEA-OA-AEEA-MPA, AEEA-OA-AEEA-(bromo)MPA, $(AEEEA)_2$-OA-MPA, and $(AEEEA)_2$-OA-(bromo)MPA. Likewise, it is typically preferred that the reactive group in the linker comprises a planar Michael acceptor group such as a maleimide group or a bromo maleimide group, and/or that the protected peptide comprises a Class B GPCR agonist peptide.

Therefore, the inventors also contemplate a Class B GPCR agonist peptide with a reactive linker, wherein the GPCR agonist peptide includes a Lys amino acid to which the linker is covalently bound via an amide bond formed by an epsilon amino group of the Lys amino acid, wherein the linker further comprises a thiol reactive group, and wherein the GPCR agonist peptide has a structure according to any one of SEQ ID NO:1-471.

As noted above, it is contemplated that the thiol reactive group comprises a planar Michael acceptor group such as a maleimide group or a bromo maleimide group, and/or that the linker is selected from the group consisting of MPA, (bromo)MPA, AEEA, AEEA-MPA, AEEA-(bromo)MPA, $(AEEA)_2$-MPA, $(AEEA)_2$-(bromo)MPA, AEEEA-OA-MPA, AEEEA-OA-(bromo)MPA, AEEA-OA-AEEA-MPA,

8

AEEA-OA-AEEA-(bromo)MPA, $(AEEEA)_2$-OA-MPA, and $(AEEEA)_2$-OA-(bromo)MPA.

In a still further aspect of the inventive subject matter, the inventor also contemplates Class B GPCR agonist peptide with a reactive linker that includes (a) a GPCR agonist peptide comprising a Lys amino acid, and (b) a linker covalently bound to the GPCR agonist peptide via an amide bond formed by an epsilon amino group of the Lys amino acid and a carboxyl group of the linker, and wherein the linker further comprises a maleimide group, wherein the GPCR agonist peptide has a structure according to any one of SEQ ID NO:1-471. The linker in such agonist peptides is preferably MPA, (bromo)MPA, AEEA, AEEA-MPA, AEEA-(bromo)MPA, $(AEEA)_2$-MPA, $(AEEA)_2$-(bromo) MPA, AEEEA-OA-MPA, AEEEA-OA-(bromo)MPA, AEEA-OA-AEEA-MPA, AEEA-OA-AEEA-(bromo)MPA, $(AEEEA)_2$-OA-MPA, or $(AEEEA)_2$-OA-(bromo)MPA.

In view of the above, the inventors therefore also contemplate a Class B GPCR agonist fusion protein that includes (a) a conformationally modified albumin comprising a $Cys_{34}$ amino acid, (b) a GPCR agonist peptide comprising a Lys amino acid, and (c) a linker covalently coupling the conformationally modified albumin to the GPCR agonist peptide, wherein the linker is covalently bound to the GPCR agonist peptide via an amide bond formed by an epsilon amino group of the Lys amino acid, and wherein the linker is covalently bound to the albumin via a covalent bond between a chiral carbon atom of a coupling group in the linker and a sulfur atom in the $Cys_{34}$ amino acid. Preferably, but not necessarily, the conformationally modified albumin is an at least partially defatted albumin, and/or the chiral carbon atom has a stereopreferred configuration. Most typically, the linker is retro-Michael resistant.

In particularly preferred embodiments, the fusion protein is retro-Michael resistant albenatide (AB-013-AEEA-succinimide (SEQ ID NO:2)-albumin), retro-Michael resistant albenatidex (AB-014-AEEA-succinimide (SEQ ID NO:185)-albumin), retro-Michael resistant albugiptide (AB-029-AEEA-succinimide (SEQ ID NO:7)-albumin), or retro-Michael resistant albutide (AB-044-AEEA-succinimide (SEQ ID NO:223)-albumin).

In yet another aspect of the inventive subject matter, the inventor also contemplates a pharmaceutical composition that includes a Class B GPCR agonist fusion protein in combination with an aqueous carrier, wherein the GPCR fusion protein comprises (a) a conformationally modified albumin comprising a $Cys_{34}$ amino acid, (b) a GPCR agonist peptide comprising a Lys amino acid, and (c) and a linker covalently coupling the conformationally modified albumin to the GPCR agonist peptide, wherein the linker is covalently bound to the GPCR agonist peptide via an amide bond formed by an epsilon amino group of the Lys amino acid, and wherein the linker is covalently bound to the albumin via a covalent bond between a chiral carbon atom of a coupling group in the linker and a sulfur atom in the $Cys_{34}$ amino acid. Most typically, the aqueous carrier has a pH of pH<7.0 (e.g., between 4.0 and 6.0).

In such composition it is generally preferred that the GPCR agonist peptide and linker has a structure according to any one of SEQ ID NO:1-471. Viewed from a different perspective, it is contemplated that the linker is MPA, (bromo)MPA, AEEA, AEEA-MPA, AEEA-(bromo)MPA, $(AEEA)_2$-MPA, $(AEEA)_2$-(bromo)MPA, AEEEA-OA-MPA, AEEEA-OA-(bromo)MPA, AEEA-OA-AEEA-MPA, AEEA-OA-AEEA-(bromo)MPA, $(AEEEA)_2$-OA-MPA, and $(AEEEA)_2$-OA-(bromo)MPA. Where desired, it is further contemplated that the composition further comprises albumin with an unreacted $Cys_{34}$ amino acid. Additionally, it is contemplated that the composition may be formulated for injection or intranasal administration. Moreover, in at least some embodiments the composition comprises the GPCR agonist peptide at a concentration of equal or less than 1.5 mg/mL, and/or the composition further comprises metformin and/or a thiazolidinedione.

In particularly preferred compositions, the GPCR agonist fusion protein is retro-Michael resistant albenatide (AB-013-AEEA-succinimide (SEQ ID NO:2)-albumin), retro-Michael resistant albenatidex (AB-014-AEEA-succinimide (SEQ ID NO:185)-albumin), retro-Michael resistant albugiptide (AB-029-AEEA-succinimide (SEQ ID NO:7)-albumin), or retro-Michael resistant albutide (AB-044-AEEA-succinimide (SEQ ID NO:223)-albumin).

Viewed from a different perspective, the inventors contemplate a pharmaceutical composition that comprises a Class B GPCR agonist fusion protein in combination with an aqueous carrier, wherein the GPCR fusion protein is a Michael addition product of a conformationally modified albumin and linker that is further covalently bound to a GPCR agonist peptide, and wherein the fusion protein is retro-Michael addition resistant. Most typically, the composition is formulated for injection or intranasal administration, the composition comprises the GPCR agonist peptide at a concentration of equal or less than 1.5 mg/mL, and/or the formulation has a pH of between 4.0 and 6.0.

Where desired, it is contemplated that the composition further comprises albumin with an unreacted $Cys_{34}$ amino acid. In addition, it is preferred that the Michael addition product is a stereopreferred or stereoselective Michael addition product and/or that the GPCR agonist peptide and linker has a structure according to any one of SEQ ID NO:1-471.

Therefore, the inventors also contemplate a pharmaceutical composition that includes a Class B GPCR agonist fusion protein in combination with an aqueous carrier, wherein the GPCR fusion protein is a Michael addition product of an albumin and linker that is further covalently bound to a GPCR agonist peptide, wherein the composition further comprises albumin with an unreacted $Cys_{34}$ amino acid, and wherein the aqueous carrier has a pH of pH<7.0. For example, the ratio of the albumin with the unreacted $Cys_{34}$ amino acid and the albumin to which the linker and GPCR agonist peptide is coupled is at least 0.3:1.0. Moreover, the albumin with the unreacted $Cys_{34}$ amino acid and the albumin to which the linker and GPCR agonist peptide is coupled are recombinant human albumin. In at least some embodiments, the albumin with the unreacted $Cys_{34}$ amino acid is a conformationally modified albumin, and/or the GPCR agonist peptide and linker has a structure according to any one of SEQ ID NO:1-471.

Viewed from a different perspective, the inventors also contemplate a pharmaceutical composition that comprises a pharmaceutically acceptable liquid carrier in combination with a Class B G protein-coupled receptor (GPCR) agonist fusion protein in which a GPCR agonist peptide is covalently coupled to albumin via a linker. A pharmaceutically accepted liquid carrier is contemplated which is safe and can accommodate sufficient concentration of the agonist and enables the delivery of the GPCR agonist fusion protein in the form of a subcutaneous, intradermal, intranasal, intrathecal and oral delivery to allow sufficient systemic, mucosal or neural absorption. In such composition, the pharmaceutically acceptable liquid carrier is substantially free of unbound GPCR agonist peptide. Among other suitable GPCR agonist fusion proteins, especially preferred GPCR agonist fusion proteins include retro-Michael resistant albenatide (AB-013-AEEA-succinimide (SEQ ID NO:2)-albumin), retro-Michael resistant albenatidex (AB-014-AEEA-succinimide (SEQ ID NO:185)-albumin), retro-Michael resistant albugiptide (AB-029-AEEA-succinimide (SEQ ID NO:7)-albumin), or retro-Michael resistant albutide (AB-044-AEEA-succinimide (SEQ ID NO:223)-albumin). Most typically, the quantity of unbound GPCR agonist peptide is equal or less than 1%, or equal or less than 0.1% of a quantity of the GPCR agonist peptide that is covalently coupled to albumin via the linker.

In yet additional aspects of the inventive subject matter, the inventors contemplate a method of making a pharmaceutical composition that includes the steps of (a) providing a pharmaceutically acceptable carrier having a pH that is pH<7.0, and (b) including into the pharmaceutically acceptable carrier a retro-Michael resistant G protein-coupled receptor (GPCR) agonist fusion protein to which a GPCR agonist peptide is covalently bound, wherein the GPCR agonist peptide is present in the composition at a concentration of equal or less than 1.5 mg/mL. Among other suitable routes of administration, it is generally preferred that the composition is formulated for injection or intranasal administration. A pharmaceutically accepted liquid carrier is contemplated which is safe and can accommodate sufficient concentration of the agonist and enables the delivery of the GPCR agonist fusion protein in the form of a subcutaneous, intradermal, intranasal, intrathecal and oral delivery to allow sufficient systemic, mucosal or neural absorption.

In especially preferred methods, the GPCR agonist fusion protein is retro-Michael resistant albenatide (AB-013-AEEA-succinimide (SEQ ID NO:2)-albumin), retro-Michael resistant albenatidex (AB-014-AEEA-succinimide (SEQ ID NO:185)-albumin), retro-Michael resistant albugiptide (AB-029-AEEA-succinimide (SEQ ID NO:7)-albumin), or retro-Michael resistant albutide (AB-044-AEEA-succinimide (SEQ ID NO:223)-albumin).

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 4 is an exemplary collection of GLP-1 agonist peptides suitable for use herein.

FIG. 6 is an exemplary collection of GLP-1/GcG dual agonist peptides suitable for use herein.

FIG. 7 is an exemplary collection of GLP-1/GIP/GcG tri-agonist peptides suitable for use herein.

FIG. 9 is an exemplary collection of still further GLP-1/GIP/GcG tri-agonist peptides suitable for use herein.

FIG. 10 is an exemplary collection of yet further GLP-1/GIP/GcG tri-agonist peptides suitable for use herein.

Figure 11:
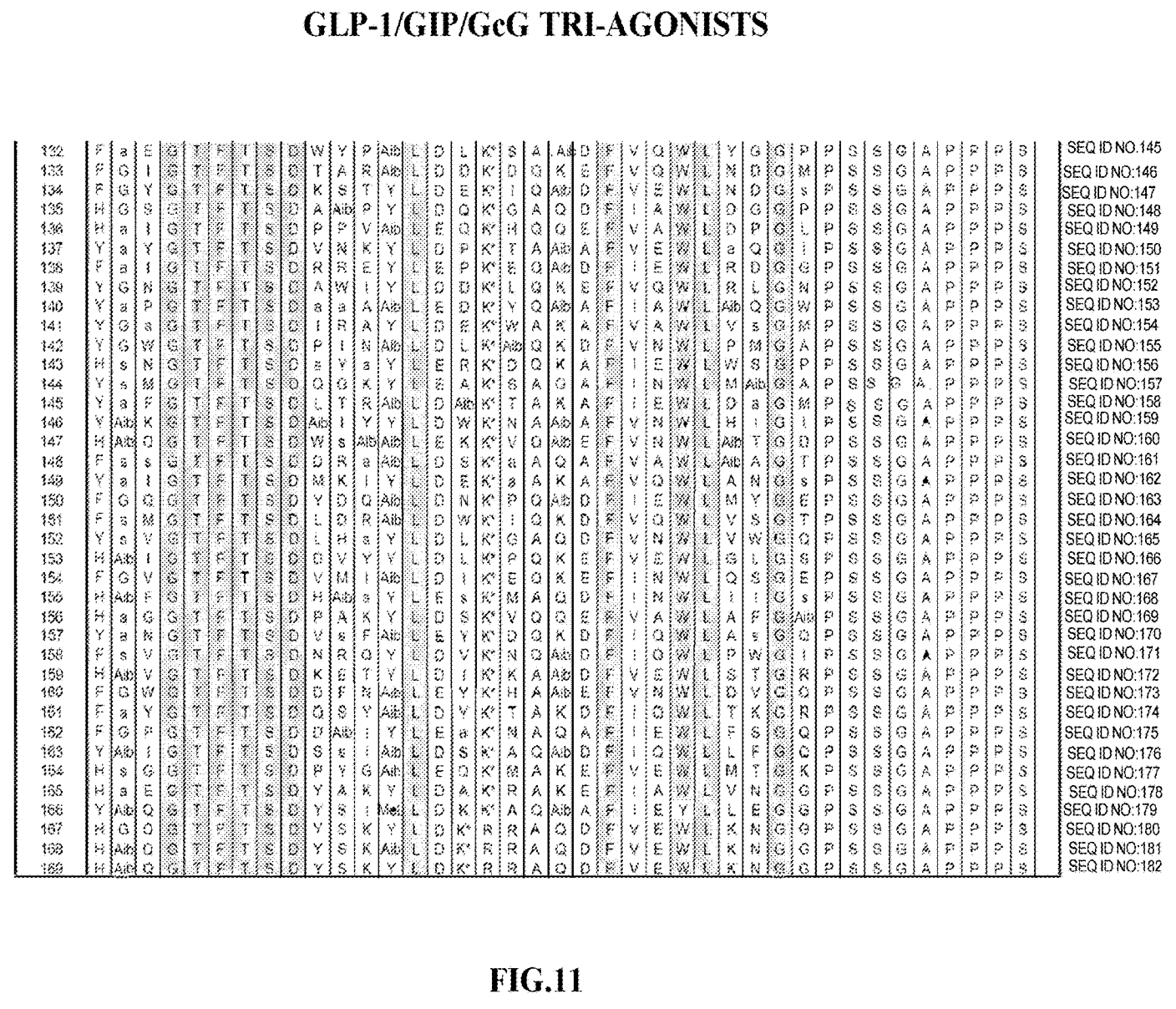

FIG. 11 is an exemplary collection of additional GLP-1/GIP/GcG tri-agonist peptides suitable for use herein.

FIG. 12A is an exemplary collection of also contemplated agonist peptide. with exemplary linker structures.

FIG. 13 is one exemplary generic sequence for tri-agonist peptides suitable for use herein.

FIG. 14 is another exemplary generic sequence for tri-agonist peptides suitable for use herein.

FIG. 15 depicts exemplary results for binding energy of the tested dual-agonist peptides with the GIP receptor and GLP-1 receptor.

FIG. 16 depicts calculated self-energies for the dual agonists using tirzepatide as control.

FIG. 17 depicts exemplary results for tirzepatide and GLP-1 and GIP receptors. The top chart depicts calculated binding energy of tirzepatide and GLP-1 receptors. The second chart depicts interaction pair count between tirzepatide and GLP-1 receptors. The third chard depicts calculated binding energy of tirzepatide and GIP receptors. Lastly, the fourth chart depicts interaction pair count between tirzepatide and GIP receptors.

FIG. 19 depicts exemplary results for AB-804-1 and GLP-1 receptors. The top chart depicts calculated binding energy of AB-804-1 and GLP-1 receptors. The second chart depicts interaction pair count between AB-804-1 and GLP-1 receptors. The last graph depicts a comparison between binding energies of AB-804-01 and GLP-1 receptors, tirzepatide and GLP-1 receptors, ex4 and GLP-1 receptors, and GLP-1 and GLP-1 receptors.

FIG. 20 depicts exemplary results for binding interactions and interaction pair counts for AB-804-02 and GIP receptors. The top chart depicts calculated binding energy of AB-804-2 and GIP receptors. The second chart depicts interaction pair count between AB-804-2 and GIP receptors. The last graph depicts a comparison between binding energies of AB-804-02 and GIP receptors, tirzepatide and GIP receptors, GIP30 and GIP receptors, and GIP and GIP receptors.

FIG. 21 depicts exemplary results for binding interactions and interaction pair counts for AB-804-2 and GLP-1 receptors. The top chart depicts calculated binding energy of AB-804-2 and GLP-1 receptors. The second chart depicts interaction pair count between AB-804-2 and GLP-1 receptors. The last graph depicts a comparison between binding energies of AB-804-02 and GLP-1 receptors, tirzepatide and GLP-1 receptors, ex4 and GLP-1 receptors, and GLP-1 and GLP-1 receptors.

FIG. 22 depicts exemplary results for binding interaction and interaction pair counts for AB-804-3 and GIP receptors. The top chart depicts calculated binding energy of AB-804-3 and GIP receptors. The second chart depicts interaction pair count between AB-804-3 and GIP receptors. The last graph depicts a comparison between binding energies of AB-804-03 and GIP receptors, tirzepatide and GIP receptors, GIP30 and GIP receptors, and GIP and GIP receptors.

FIG. 24 depicts comparative results for pair interaction energy for native GLP-1, GIP, and GcG complexes.

FIG. 25 depicts a selection of exemplary linkers suitable for use herein.

FIG. 29 is a graph depicting exemplary pharmacokinetic data for conformationally unmodified AB-013.

FIG. 30 is a graph depicting exemplary results from serum of the experiment in FIG. 29 when observed on a PAGE gel.

FIG. 31A-D depicts exemplary structures of peptide agonist intermediates bound to a Ramage or Rink resin. FIG. 31A shows a representative example using SEQ ID NO: 233 and 234. FIG. 31B shows a different example using SEQ ID NO: 235 and 190. FIG. 31C shows a further example using SEQ ID NO: 236 and 237. FIG. 31D shows yet another example using SEQ ID NO: 68.

FIG. 32 depicts generically agonist peptide intermediates.

FIG. 33 depicts the efficacy Albenatide in inducing weight loss in diet induced obese (DIO) mouse models demonstrating equivalence to semaglutide.

FIG. 34 depicts the food and water consumption following Albenatide compared to semaglutide.

FIG. 36 depicts the efficacy of Albenatide in reducing fatty livers (NASH) with histological evidence of control and semaglutide as comparators demonstrating that covalently bound GLP-1 agonists react with GLP-1 receptor and has a biological efficacy effect, contrary to the teaching of current formulations.

FIG. 37A-D depicts liver function and cholesterol improvements in the DIO mouse model following Albenatide demonstrating that covalently bound GLP-1 agonists react with GLP-1 receptor and has a biological efficacy effect, contrary to the teaching of current formulations.

FIG. 38 depicts anti-inflammatory improvement with cytokines following Albenatide

DETAILED DESCRIPTION

Figure 1:
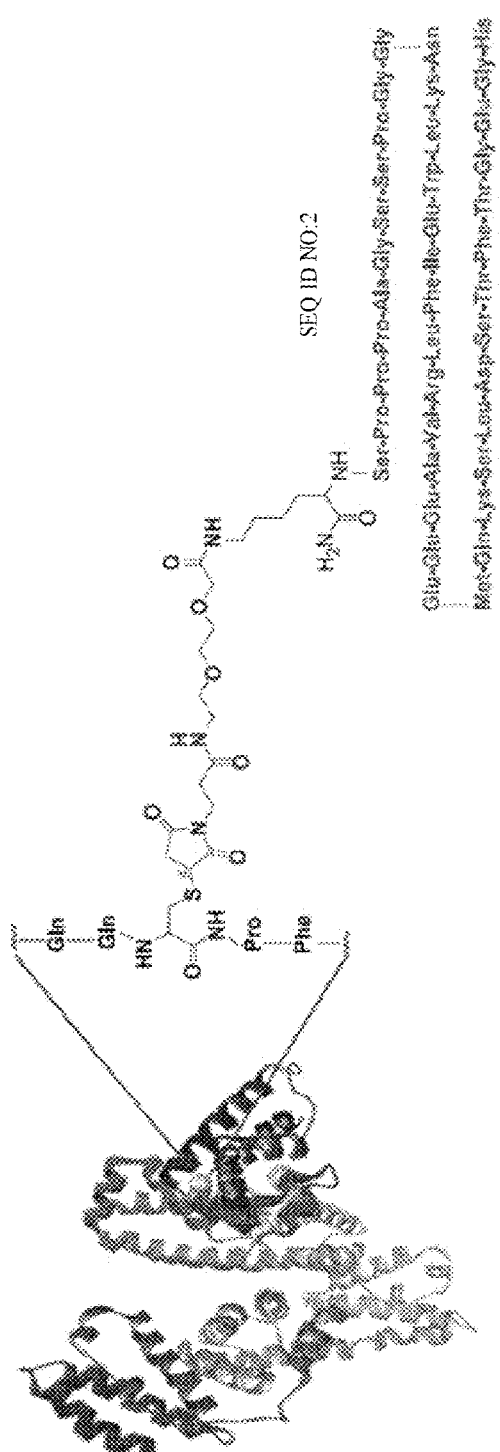
FIG. 1 shows a schematic illustration of the structure for retro-Michael resistant albenatide in which the peptide sequence surrounding $Cys_{34}$ is emphasized.

The inventors have now discovered that various GPCR agonist peptide fusion proteins can be prepared that exhibit high stability in plasma/serum, that have agonist activity at low concentrations while remining stably bound to a carrier, and that can readily move from the blood compartment into a target tissue and even pass the blood brain barrier. Such fusion proteins are prepared by use of a linker that irreversibly and covalently connects the albumin to a Class B GPCR agonist peptide (such as an incretin or insulinotropic agent or analog thereof). In this context, it should be appreciated that the term 'fusion protein' in conjunction with the compounds presented herein includes proteins in which a first peptide portion (e.g., agonist peptide) is covalently bound to a second peptide portion (e.g., albumin) via a linker moiety, where the linker may be a third peptide portion or a non-peptide portion (e.g., AEEA-MPA). Thus, the term 'fusion protein' in conjunction with the compounds presented herein may also be referred to as 'bioconjugate' or 'conjugate'.

For example, in some preferred embodiments, one end of the linker will be covalently bound to a reactive group at the C-terminus of the agonist peptide (e.g., via an amide bond) while the other end of the linker is covalently bound to the albumin at $Cys_{34}$ via a retro-Michael resistant thioether bond in which the carbon atom of the coupling group in the linker has a stereospecific configuration that renders the bond retro-Michael resistant within the context of the hydrophobic pocket in which the $Cys_{34}$ is located. In other preferred embodiments, one end of the linker will be covalently bound to a reactive group in a side chain of an amino acid at an intermediate position in the agonist peptide (e.g., via an amide bond) and the other end of the linker will be covalently bound to the albumin at $Cys_{34}$ via a retro-Michael resistant thioether bond in which the carbon atom of the coupling group in the linker has a stereospecific configuration that renders the bond retro-Michael resistant within the context of the hydrophobic pocket in which the $Cys_{34}$ is located. Moreover, suitable linkers will provide a rotational degree of freedom and a steric distance between the agonist peptide and the albumin so as to enable binding of the agonist peptide to the target receptor and activation of the target receptor while remining covalently bound to the albumin.

Advantageously, contemplated retro-Michael resistant albumin-bound insulinotropic agonists will transcytose rapidly to the tissue microenvironment of the pancreas and the brain, leaving the plasma compartment through the gp60/ caveolin-1/caveoli pathway with long-acting agonist via FcRn rescue. As such, contemplated compounds and compositions can take advantage of cell mediated transport, thereby allowing for ultra-low dose and ultra-low plasma concentration to so enable a therapeutic effect with a high therapeutic index and a substantially lower GI adverse event profile.

As will be appreciated, especially contemplated peptide agonists suitable for use in conjunction with the teachings presented herein will particularly include GPCR agonists (and especially Class B) and all derivatives, analogs, and fragments thereof. Therefore, and among other contemplated peptide agonists, GLP-1, GIP, Glucagon (GcG), Amylin, NPY2, Neuropeptide Y, and PYY, and derivatives, analogs, and fragments are especially preferred. It should furthermore be appreciated that the peptide agonists contemplated herein may have binding and activation specificity towards a single receptor (mono-agonist), two receptors (dual-agonist), or three receptors (tri-agonist). In this context, it should be particularly appreciated that contrary to conventional wisdom, compounds can be produced in which the ligand is covalently and irreversibly bound to the albumin, and in which the same ligand can bind to and activate two, or even three distinct G-protein coupled receptors (GLP-1, GIP, and/or GcG receptors). Consequently, it should be recognized that the biological activity of fusion proteins containing such peptide agonists may be tailored towards specific uses (e.g., insulinotropic, appetite suppressant, etc.).

Viewed from a different perspective, and as shown in more detail below, GPCR (and especially Class B GPCR) agonist fusion proteins with high stability, high receptor binding, and no peptide loss can be prepared that activate GLP-1, GIP, GcG, NPY2, Y2, or PYY as mono-agonists, or that activate GLP-1/GIP, GLP-1/GcG, GLP-1/NPY2, GLP-1/Y2, or GLP-1/PYY as di-agonists, or that activate GLP-1/GIP/GcG as tri-agonists. Moreover, as such agonist peptides are irreversibly covalently bound to conformationally modified albumin, gp60-mediated transcytosis and FcRn albumin recycling will allow these fusion proteins to cross the blood brain barrier and to achieve high half-life times while being quickly moved from the blood compartment to a target tissue compartment (e.g., neural tissue, hepatic tissue, adipose tissue, and/or pancreatic tissue).

In at least some embodiments, it is preferred that the peptide agonist will be exendin-4 or an exendin-4 derivative that includes a modified amino acid to avoid peptide cleavage by dipeptidyl peptidase-4, and that includes a C-terminal tryptophan cage ('fish-hook') structure to further enhance stability. Moreover, and depending on the particular amino acid substitutions (relative to exendin-4), contemplated peptide agonists will exhibit equal or higher affinity than native GLP-1 to the GLP-1 receptor, resulting in higher potency. Additionally, one or more amino acid substitutions (relative to exendin-4) will also enable multi-agonist activity (e.g., tri-agonist activity towards GLP-1/GIP/Glucagon receptors).

In one exemplary fusion protein, retro-Michael resistant albenatide (acting as a GLP-1 agonist) comprises exendin-4 (SEQ ID NO:3) to which on the C-terminus a modified lysine is covalently coupled, wherein the modified lysine contains a linker with a coupling group. In this example, the modified lysine forms a peptide bond with the C-terminal serine of exendin-4, and the modified lysine further includes an AEEA-MPA group that is covalently bound to the epsilon amino group of the lysine via an amide bond. Upon reaction of the MPA coupling group with the thiol group of $Cys_{34}$ in the albumin in a stereopreferred or stereoselective manner as described in more detail below, the retro-Michael resistant albenatide (AB-013-AEEA-succinimide-albumin). Of course, it should be appreciated that various alternative linker moieties may be used, and suitable alternative linkers with coupling groups include MPA, (bromo)MPA, AEEA, AEEA-MPA, AEEA-(bromo)MPA, $(AEEA)_2$-MPA, $(AEEA)_2$-(bromo)MPA, AEEEA-OA-MPA, AEEEA-OA-(bromo)MPA, AEEA-OA-AEEA-MPA, AEEA-OA-AEEA-(bromo)MPA, $(AEEEA)_2$-OA-MPA, and $(AEEEA)_2$-OA-(bromo)MPA (with MPA denoting maleimidopropionic acid, and with OA denoting 8-aminooctanoate).

Where desired, the modified lysine may also be coupled to the C-terminal serine via a single AEEA group. In such case, the modified lysine may once more include coupling groups such as MPA, (bromo)MPA, AEEA, AEEA-MPA, AEEA-(bromo)MPA, $(AEEA)_2$-MPA, $(AEEA)_2$-(bromo) MPA, AEEEA-OA-MPA, AEEEA-OA-(bromo)MPA, AEEA-OA-AEEA-MPA, AEEA-OA-AEEA-(bromo)MPA, $(AEEEA)_2$-OA-MPA, or $(AEEEA)_2$-OA-(bromo)MPA.

Figure 2:
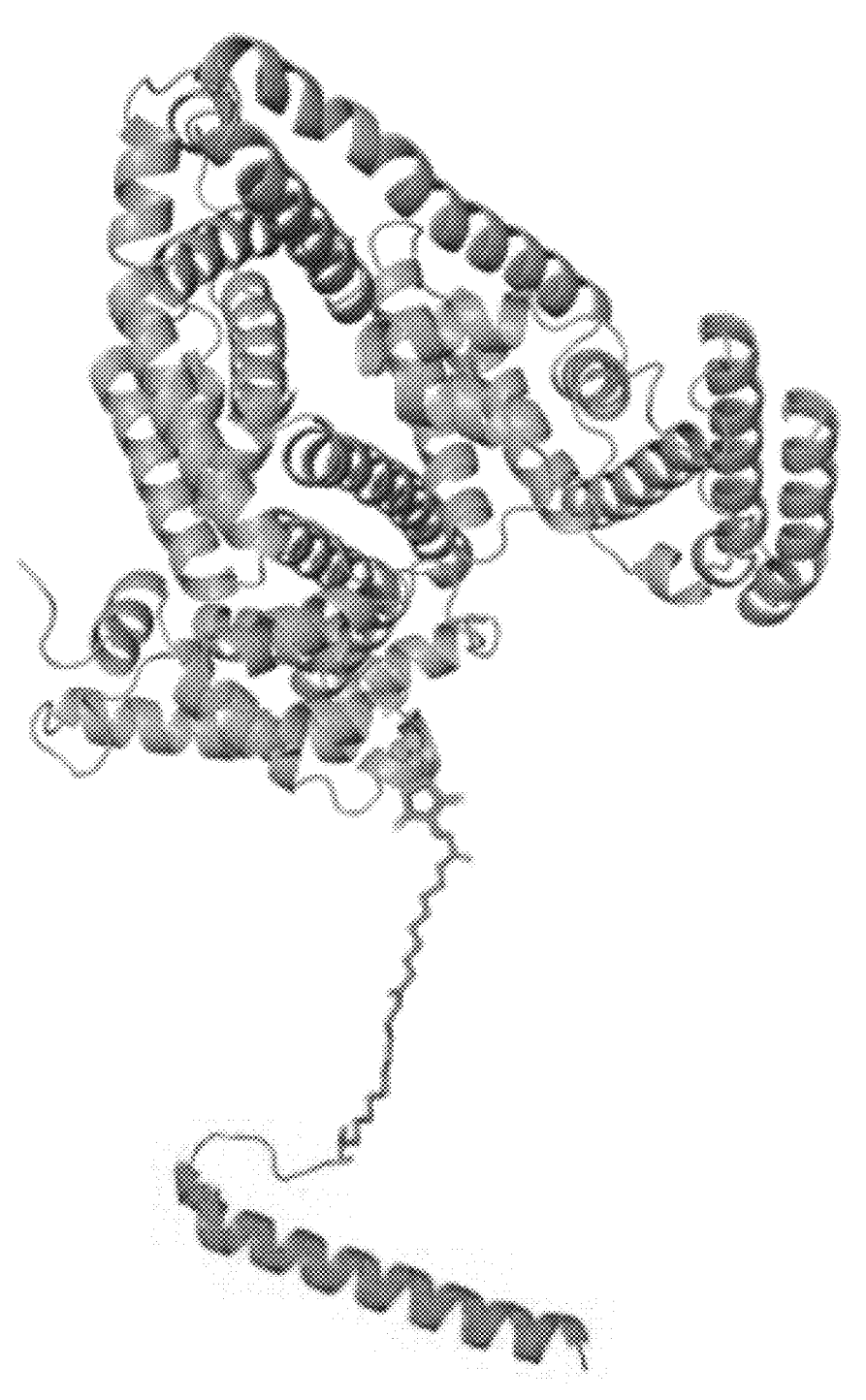
FIG. 2 shows a schematic illustration of the structure for retro-Michael resistant albenatide.
Figure 3:
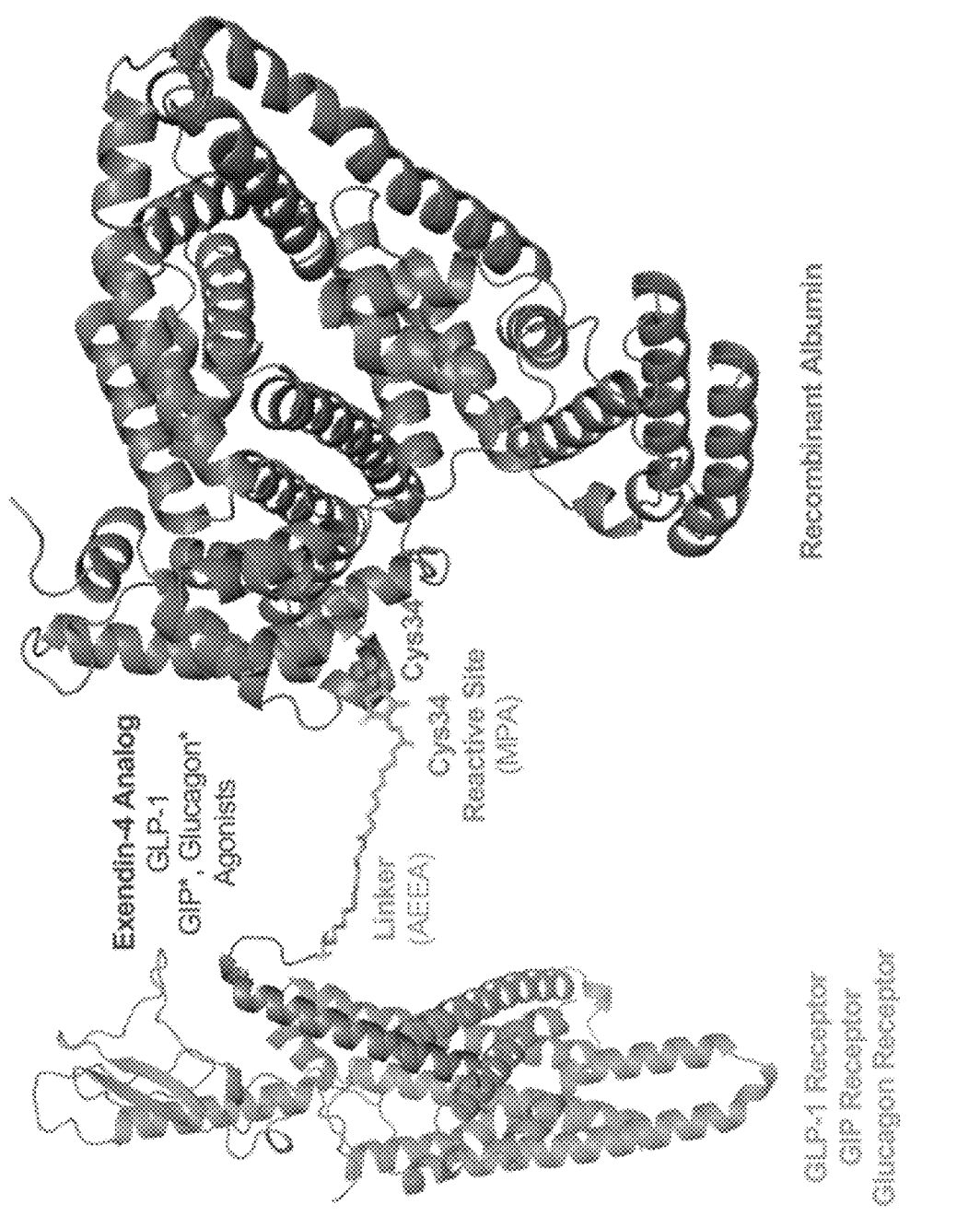
FIG. 3 shows a schematic overall structure of the retro-Michael resistant albenatide in which the agonist peptide portion has bound to a GLP-1 receptor.
Figure 5:
FIG. 5 is an exemplary collection of GLP-1/GIP dual agonist peptides suitable for use herein.
Figure 8:
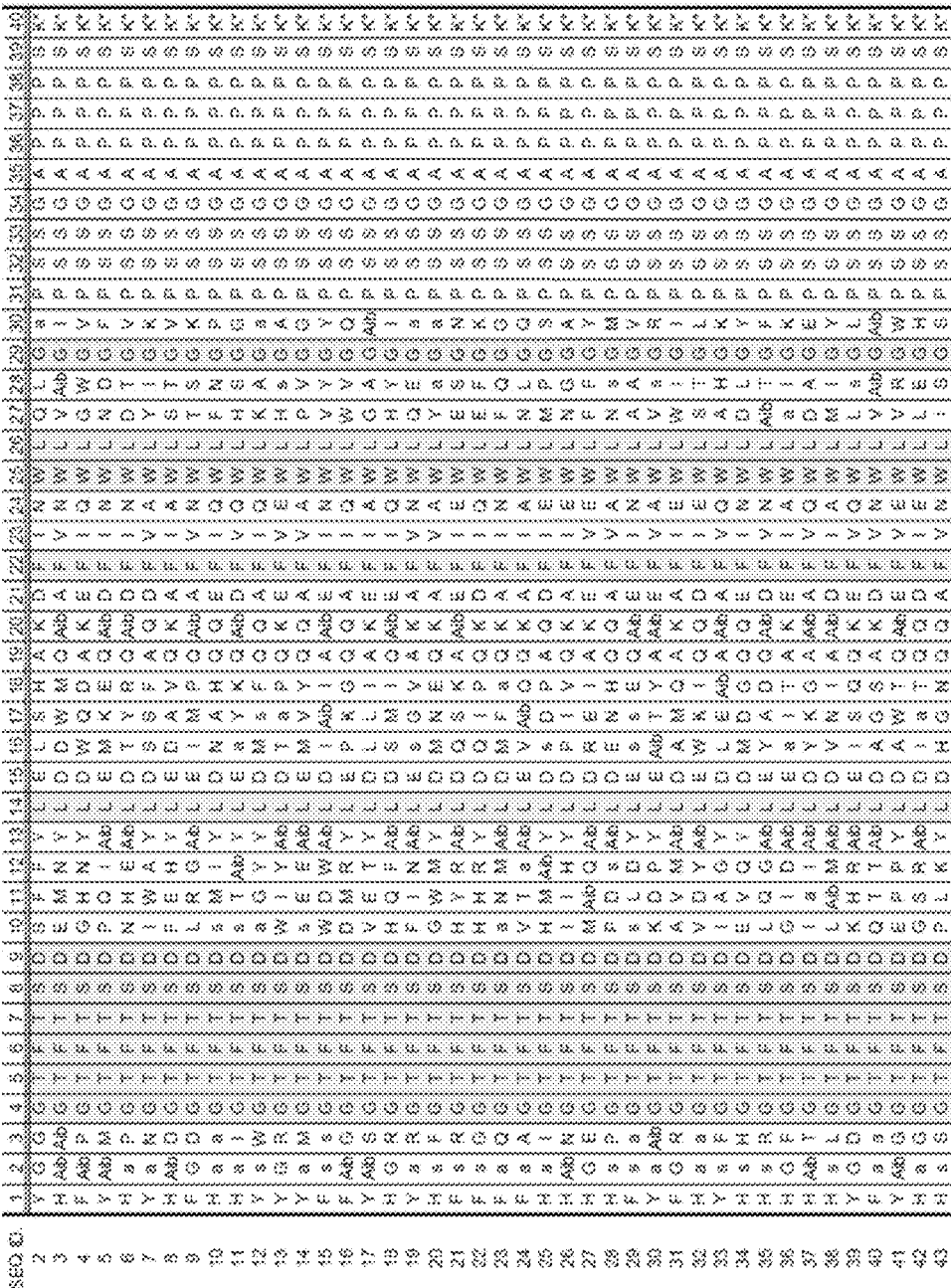
FIG. 8 is an exemplary collection of further GLP-1/GIP/GcG tri-agonist peptides suitable for use herein.

The retro-Michael resistant albenatide (AB-013-AEEA-succinimide (SEQ ID NO:2)-albumin) is exemplarily depicted in FIG. 1 in which the peptide sequence surrounding Cys$_{34}$ is emphasized and in which the #sign denotes the non-racemic chiral atom, and FIG. 2 exemplarily depicts the overall structure of the retro-Michael resistant albenatide of FIG. 1 above. FIG. 3 shows the overall structure of the retro-Michael resistant albenatide in which the agonist peptide has bound to a GLP-1 receptor (note that the GIP receptor and GcG receptor are structurally highly similar to the GLP-1 receptor, and as such FIG. 3 is also representative of these agonist receptor complexes). As will be readily recognized from FIG. 3, the linker affords sufficient flexibility and steric distance between the covalently bound agonist peptide and the target receptor such as to allow effective binding and activation of the receptor while the agonist remains covalently bound to the albumin.

In another exemplary fusion protein, and following the same approach, a retro-Michael resistant albenatidex (AB-014-AEEA-succinimide (SEQ ID NO:185)-albumin) (acting as a GLP-1 agonist) comprises a chimeric GLP-1/exendin-4 portion to which on the C-terminus a modified lysine is covalently coupled, wherein the modified lysine contains a linker with a coupling group. In this example, the modified lysine forms a peptide bond with the C-terminal serine of chimeric peptide, and the modified lysine further includes an AEEA-MPA group that is covalently bound to the epsilon amino group of the lysine via an amide bond as is shown in SEQ ID NO.185. Upon reaction of the MPA coupling group with the thiol group of Cys$_{34}$ in the albumin in a stereopreferred or stereoselective manner as described in more detail below, the retro-Michael resistant albenatidex is formed (AB-014-AEEA-succinimide-albumin). As noted above, it should be appreciated that various alternative linker moieties may be used, and suitable alternative linkers with coupling groups include MPA, (bromo)MPA, AEEA, AEEA-MPA, AEEA-(bromo)MPA, (AEEA)$_2$-MPA, (AEEA)$_2$-(bromo)MPA, AEEEA-OA-MPA, AEEEA-OA-(bromo)MPA, AEEA-OA-AEEA-MPA, AEEA-OA-AEEA-(bromo)MPA, (AEEEA)$_2$-OA-MPA, and (AEEEA)$_2$-OA-(bromo)MPA (with MPA denoting maleimidopropionic acid, and with OA denoting 8-aminooctanoate). Where desired, the modified lysine may also be coupled to the C-terminal serine via a single AEEA group. In such case, the modified lysine may once more include coupling groups such as MPA, (bromo)MPA, AEEA, AEEA-MPA, AEEA-(bromo) MPA, (AEEA)$_2$-MPA, (AEEA)$_2$-(bromo)MPA, AEEEA-OA-MPA, AEEEA-OA-(bromo)MPA, AEEA-OA-AEEA-MPA, AEEA-OA-AEEA-(bromo)MPA, (AEEEA)$_2$-OA-MPA, or (AEEEA)$_2$-OA-(bromo)MPA.

In still another exemplary fusion protein, and once more following the same approach, a retro-Michael resistant albugiptide (AB-029-AEEA-succinimide (SEQ ID NO:7)-albumin) (acting as a GIP/GLP-1 dual agonist) comprises a modified exendin-4 portion to which on the C-terminus a modified lysine is covalently coupled, wherein the modified lysine contains a linker with a coupling group. In this example, the modified lysine forms a peptide bond with the C-terminal serine of the modified exendin-4, and the modified lysine further includes an AEEA-MPA group that is covalently bound to the epsilon amino group of the lysine via an amide bond as is shown in SEQ ID NO:7. Once more, upon reaction of the MPA coupling group with the thiol group of Cys$_{34}$ in the albumin in a stereopreferred or stereoselective manner as described in more detail below, the retro-Michael resistant albugiptide is formed (AB-029-AEEA-succinimide-albumin). As already noted above, it should be appreciated that various alternative linker moieties may be used, and suitable alternative linkers with coupling groups include MPA, (bromo)MPA, AEEA, AEEA-MPA, AEEA-(bromo)MPA, (AEEA)$_2$-MPA, (AEEA)$_2$-(bromo) MPA, AEEEA-OA-MPA, AEEEA-OA-(bromo)MPA, AEEA-OA-AEEA-MPA, AEEA-OA-AEEA-(bromo)MPA, (AEEEA)$_2$-OA-MPA, and (AEEEA)$_2$-OA-(bromo)MPA (with MPA denoting maleimidopropionic acid, and with OA denoting 8-aminooctanoate). Where desired, the modified lysine may also be coupled to the C-terminal serine via a single AEEA group. In such case, the modified lysine may once more include coupling groups such as MPA, (bromo) MPA, AEEA, AEEA-MPA, AEEA-(bromo)MPA, (AEEA)$_2$-MPA, (AEEA)$_2$-(bromo)MPA, AEEEA-OA-MPA, AEEEA-OA-(bromo)MPA, AEEA-OA-AEEA-MPA, AEEA-OA-AEEA-(bromo)MPA, (AEEEA)$_2$-OA-MPA, or (AEEEA)$_2$-OA-(bromo)MPA.

In a still further exemplary fusion protein, and yet again following the same approach, a retro-Michael resistant albutide (AB-044-AEEA-succinimide (SEQ ID NO:223)-albumin) (acting as a GIP/GLP-1/GcG tri-agonist) comprises a modified exendin-4 portion to which on the C-terminus a modified lysine is covalently coupled, wherein the modified lysine contains a linker with a coupling group. In this example, the modified lysine forms a peptide bond with the C-terminal serine of the modified exendin-4, and the modified lysine further includes an AEEA-MPA group that is covalently bound to the epsilon amino group of the lysine via an amide bond as is shown in SEQ ID NO:223. Once more, upon reaction of the MPA coupling group with the thiol group of Cys$_{34}$ in the albumin in a stereopreferred or stereoselective manner as described in more detail below, the retro-Michael resistant albutide (AB-044-AEEA-succinimide (SEQ ID NO:223)-albumin) is formed. Additionally, a closely related retro-Michael resistant fusion protein is particularly contemplated, AB-045-AEEA-succinimide (SEQ ID NO:69)-albumin. Once more, it should be appreciated that various alternative linker moieties may be used, and suitable alternative linkers with coupling groups include MPA, (bromo)MPA, AEEA, AEEA-MPA, AEEA-(bromo) MPA, (AEEA)$_2$-MPA, (AEEA)$_2$-(bromo)MPA, AEEEA-OA-MPA, AEEEA-OA-(bromo)MPA, AEEA-OA-AEEA-MPA, AEEA-OA-AEEA-(bromo)MPA, (AEEEA)$_2$-OA-MPA, and (AEEEA)$_2$-OA-(bromo)MPA (with MPA denoting maleimidopropionic acid, and with OA denoting 8-aminooctanoate). Where desired, the modified lysine may also be coupled to the C-terminal serine via a single AEEA group. In such case, the modified lysine may once more include coupling groups such as MPA, (bromo)MPA, AEEA, AEEA-MPA, AEEA-(bromo)MPA, (AEEA)$_2$-MPA, (AEEA)$_2$-(bromo)MPA, AEEEA-OA-MPA, AEEEA-OA-(bromo)MPA, AEEA-OA-AEEA-MPA, AEEA-OA-AEEA-(bromo)MPA, (AEEEA)$_2$-OA-MPA, and (AEEEA)$_2$-OA-(bromo)MPA.

Based on the above examples, it should therefore be appreciated that numerous retro-Michael resistant fusion proteins with albumin can be prepared that avoid the shortcomings of fusion proteins in which the agonist peptide can deconjugate. Indeed, while numerous Class B GPCR agonist peptides are particularly contemplated herein, a large variety of alternative drug conjugates are also deemed suitable and include various peptide hormones, cytokines, chemokines, and other biologically active peptides and even larger proteins. In each of these fusion proteins, it is contemplated that the same or similar linkers can be used as discussed in more detail below, and that the fusion protein, once prepared, will have retro-Michael resistant properties.

Figure 12B:
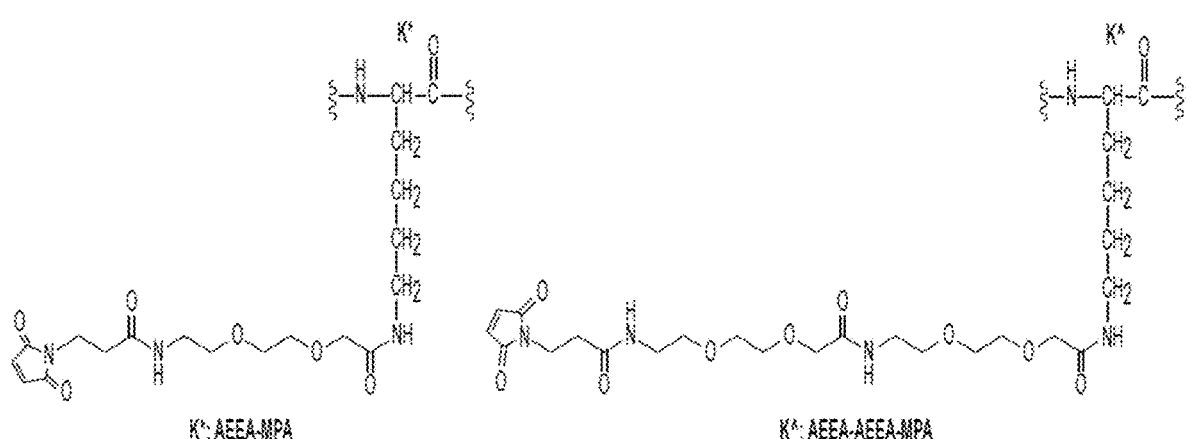
FIG. 12B depicts exemplary linkers.

Exemplary agonist peptides, each of which may be further bound to a linker with a coupling group, particularly include GLP-1 agonists, dual agonists, and tri-agonists as shown in FIGS. 4-11, and as listed below. Here, and unless indicated otherwise, K* denotes a modified lysine with an AEEA-MPA, AEEA-AEEA-MPA, AEEA-OA-MPA, or AEEA-OA-AEEA-MPA linker, where the lysine may or may not be preceded by an AEEA group. However, it should be appreciated that various alternative linkers with a coupling group may be used, including MPA, (bromo)MPA, AEEA, AEEA-(bromo)MPA, (AEEA)$_2$-(bromo)MPA, AEEEA-OA-(bromo)MPA, AEEA-OA-AEEA-(bromo)MPA, (AEEEA)$_2$-OA-MPA, and (AEEEA)$_2$-OA-(bromo)MPA. FIG. 12 depicts still further exemplary agonists and linker groups. FIG. 13 and FIG. 14 depict a generic sequence for tri-agonists where $X_{20}$ or $X_{21}$, when lysine, can be a modified lysine with an MPA, (bromo)MPA, AEEA, AEEA-MPA, AEEA-(bromo)MPA, (AEEA)$_2$-MPA, (AEEA)$_2$-(bromo)MPA, AEEEA-OA-MPA, AEEEA-OA-(bromo)MPA, AEEA-OA-AEEA-MPA, AEEA-OA-AEEA-(bromo)MPA, (AEEEA)$_2$-OA-MPA, and (AEEEA)$_2$-OA-(bromo)MPA linker, where the so modified lysine may or may not be preceded by an AEEA group.

While contemplated agonist peptides can be tested for their binding and activation parameters using in vitro cell-based experiments, SPR experiments, cell-based experiments, or in vivo tests well known in the art, it should be appreciated that stability and binding of the agonist peptides to the respective receptors may also be investigated in silico measuring complex binding energy and peptide self-energies. For example, the inventors have discovered a preferred sequence (AB-804-3, SEQ ID NO:467, optionally without linker/coupling group) with high binding energy in terms of both complex binding energy and peptide self-energies, which when covalently bound in a retro-Michael-resistant manner, can take advantage of the hydrophobic tryptophan cage with a hydrophilic linker for covalently linking to the free-thiol of $Cys_{34}$ of recombinant albumin, which may pr may not be conformationally modified. Studies have shown that the peptide domains of AB-804-3 including S1, S2, S3, S4, tryptophan cage, N and C terminus all interact with the extracellular domain and transmembrane domains of their respective receptors (GLP-1 and GIP), and exemplary data show AB-804-3 having highest binding energy.

Figure 18:
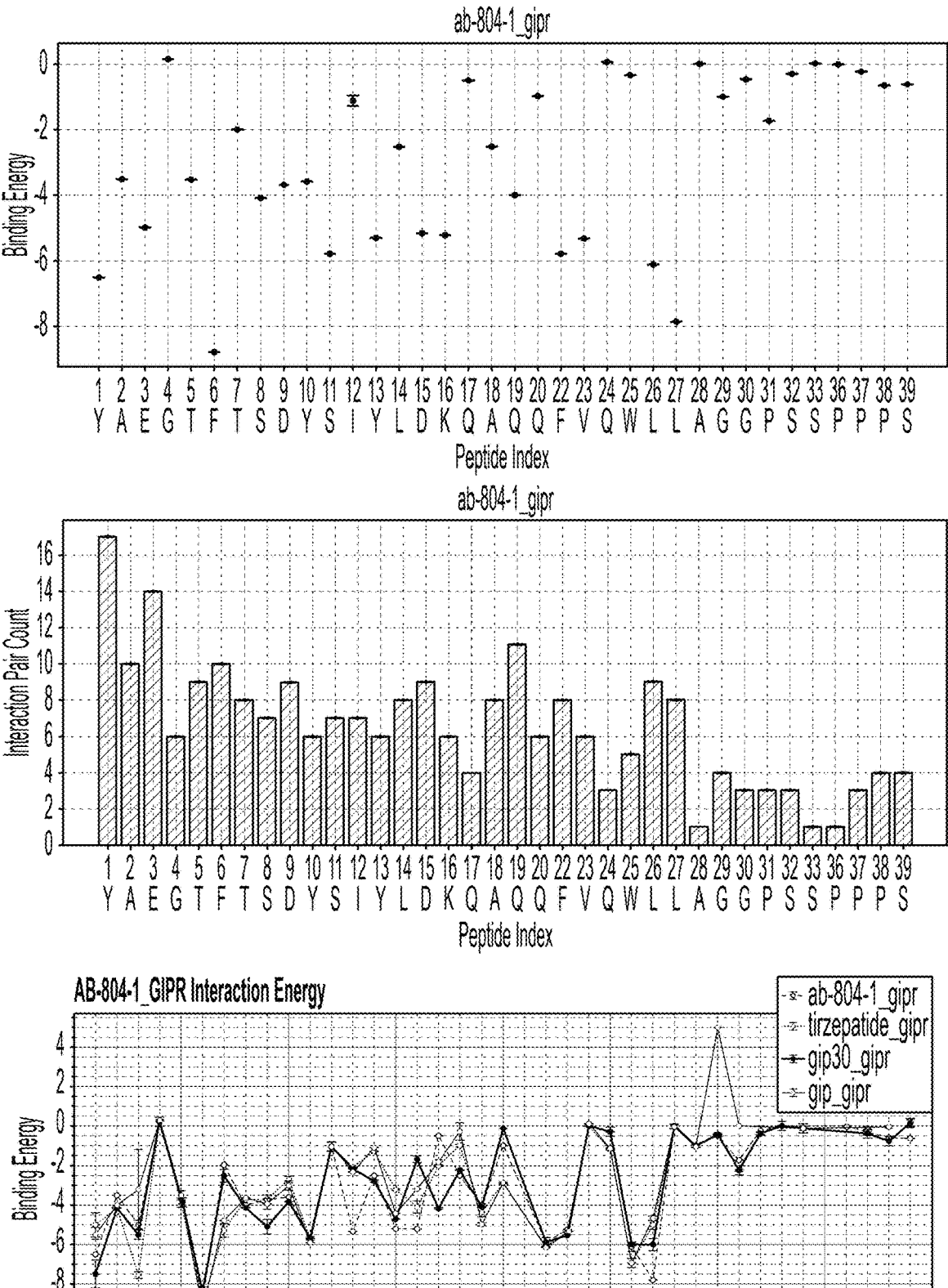
FIG. 18 depicts exemplary results for AB-804-1 and GIP receptors. The top chart depicts calculated binding energy of AB-804-1 and GIP receptors. The second chart depicts interaction pair count between AB-804-1 and GIP receptors. The last graph depicts a comparison between binding energies of AB-804-01 and GIP receptors, tirzepatide and GIP receptors, GIP30 and GIP receptors, and GIP and GIP receptors.
Figure 23:
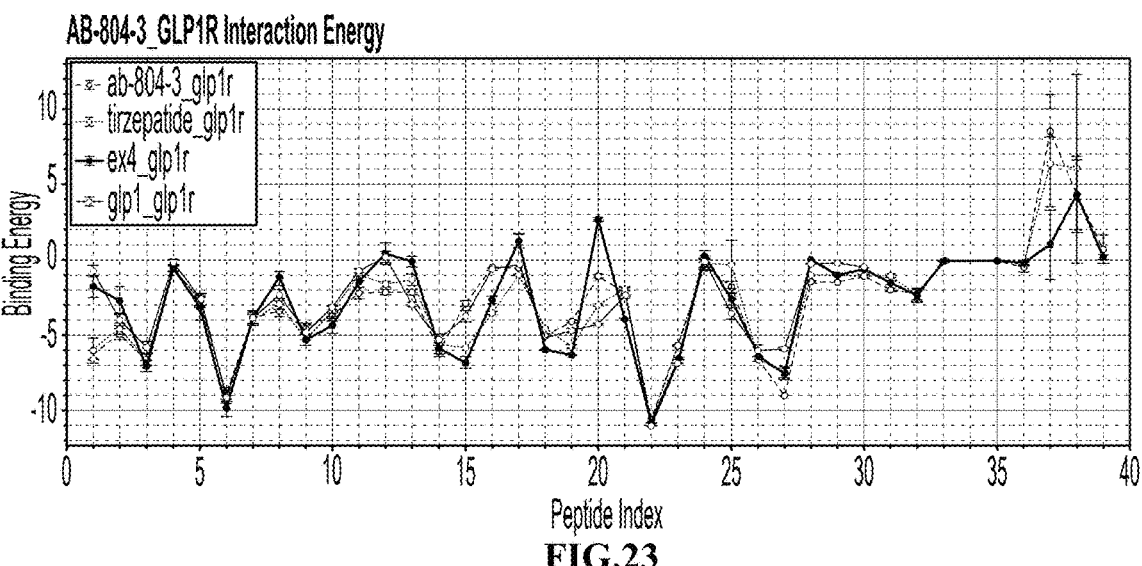
FIG. 23 depicts exemplary results for binding interactions and interaction pair counts for AB-804-3 and GLP-1 receptors. The top chart depicts calculated binding energy of AB-804-3 and GLP-1 receptors. The second chart depicts interaction pair count between AB-804-3 and GLP-1 receptors. The last graph depicts a comparison between binding energies of AB-804-03 and GLP-1 receptors, tirzepatide and GLP-1 receptors, ex4 and GLP-1 receptors, and GLP-1 and GLP-1 receptors.

In particular, FIG. 15 depicts binding energy of the tested dual-agonist peptides with the GIP receptor and GLP-1 receptor, and FIG. 16 depicts calculated self-energies for the dual agonists using tirzepatide as control. Binding interactions and interaction pair counts are shown for tirzepatide and GLP-1 and GIP receptors in FIG. 17, for AB-804-1 and GIP receptors in FIG. 18 and for AB-804-1 and GLP-1 receptors FIG. 19. FIG. 20 depicts binding interactions and interaction pair counts for AB-804-2 and GIP receptors, and FIG. 21 depicts binding interactions and interaction pair counts for AB-804-2 and GLP-1 receptors. Similarly, FIG. 22 depicts binding interactions and interaction pair counts for AB-804-3 and GIP receptors, and FIG. 23 depicts binding interactions and interaction pair counts for AB-804-3 and GLP-1 receptors. FIG. 24 provides a comparative table for pair interaction energy for native GLP-1, GIP, and GcG complexes.

With respect to contemplated linkers that can be used to couple the peptide agonists to the $Cys_{34}$ thiol group of albumin, it is generally contemplated that preferred linkers will provide sufficient flexibility and steric distance such that the bound agonist peptide will be able to bind (typically in a two-step process) to the GPCR such that the GPCR will be activated. Therefore, in at least some embodiments, the reactive group (e.g., maleimide group) that couples the linker to the $Cys_{34}$ thiol group of albumin and the group (e.g., amino group) that couples the linker to the agonist peptide will have a linear distance equivalent to at least 6 carbon-carbon bonds, or at least 8 carbon-carbon bonds, or at least 10 carbon-carbon bonds, or at least 12 carbon-carbon bonds, or at least 14 carbon-carbon bonds, or at least 18 carbon-carbon bonds, or at least 24 carbon-carbon bonds. As will also be readily appreciated, the linker may further include one or more non-carbon atoms to so form an amide bond, an ether bond, etc. Thus, in at least some embodiments preferred linkers will be hydrophilic linkers. FIG. 25 depicts a selection of exemplary linkers suitable for use herein in which AEEA denotes (amido(ethoxy)ethoxy acetic acyl), MPA denotes maleimidopropionic acid, OA denotes 8-aminooctanoate, and Lys denotes lysine.

In still further embodiments it is contemplated that the reactive group that couples the linker to the $Cys_{34}$ thiol group of albumin is a thiol reactive group such as a maleimide group, a bromo-maleimide group, a succinimide group, etc. However, it is particularly preferred that the reactive group that couples the linker to the $Cys_{34}$ thiol group will be a group that reacts with a cysteine in a Michael addition reaction. The Michael reaction or Michael 1,4 addition is a reaction between a Michael donor, such as an enolate, thiolate or other nucleophile and a Michael acceptor, usually an $\alpha$, $\beta$-unsaturated carbonyl, such as an MPA to produce a Michael adduct by creating a carbon-carbon or carbon-sulfur bond at the acceptor's $\beta$-carbon. In this context, it should be particularly appreciated that upon Michael reaction of a thiol group with a planar maleimide group, absent any stereochemically biasing factors, the reaction product includes a newly generated chiral carbon atom (to which the sulfur atom is covalently bound), which will result in a racemic product. Viewed from a different perspective, a Michael addition reaction product, absent any stereochemically biasing factors, will be an equal mixture of R- and S-configured chiral carbon atoms.

Moreover, it should be appreciated that (as with any other chemical reaction) a Michael addition reaction is a reversible reaction unless other factors will hinder such reaction. Indeed, such retro-Michael addition reaction is well known in the context of antibody-drug conjugates where a drug can readily de-conjugate in a retro-Michael addition reaction where the drug was attached to an exposed thiol group.

Figure 26:
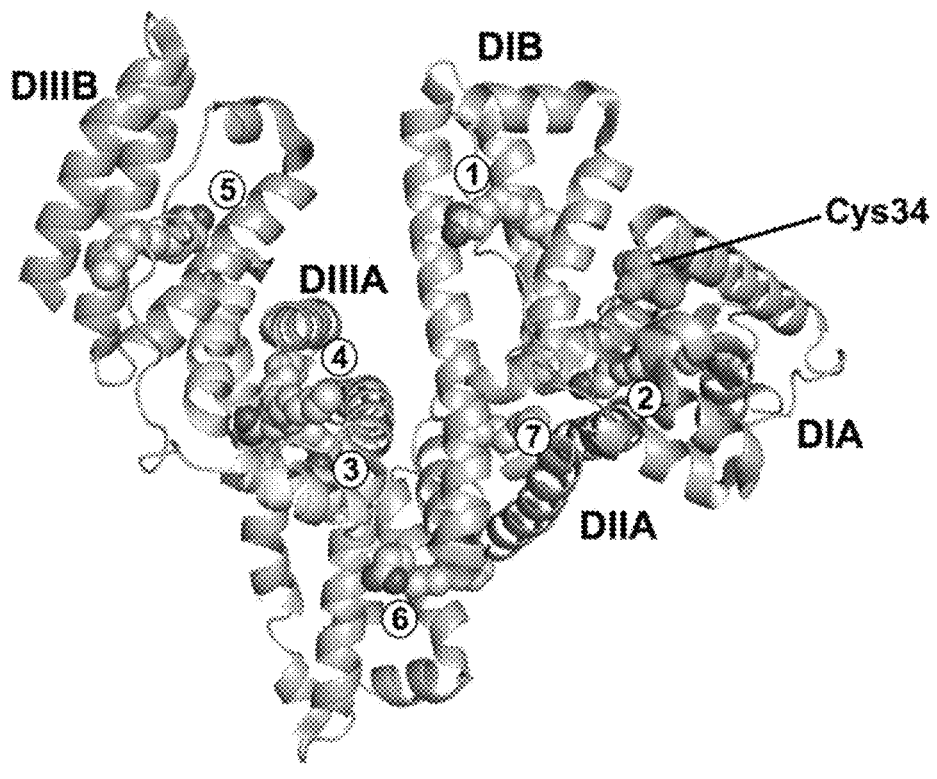
FIG. 26 shows a schematic overall structure of human albumin.

In view of the above, the inventors have unexpectedly discovered that a peptide agonist with a linker having a maleimide or bromo maleimide coupling group can be coupled to $Cys_{34}$ of albumin in a stereoselective and retro-Michael resistant manner such that the peptide agonist remains covalently bound to the albumin without decoupling. More specifically, the inventors recognized that as the $Cys_{34}$ is located in a hydrophobic crevice that is 9.5-10 A deep in which the walls of the crevice are populated by multiple amino acid side chains, the spatial organization surrounding the $Cys_{34}$ thiol group can have a substantial impact on the stereo-specificity of the newly created chiral center. Surprisingly, the inventors noticed that the spatial organization of the hydrophobic crevice can be modulated by changing the levels of sodium octanoate (or other fatty acids or hydrophobic ligands) present in the hydrophobic fatty acid binding pockets of albumin during the bioconjugation process. In particular, the inventors observed that where a Michael addition was performed when all or most hydrophobic fatty acid binding pockets were occupied by octanoate or other hydrophobic molecule, the reaction product was substantially a racemic mixture (i.e., a 50/50 mix of R- and S-configured chiral carbon in the conjugate), whereas stereospecificity of the reaction increased with decreasing octanoate levels in the binding pockets. Moreover, this unexpected finding was further accentuated where the pH during the conjugation reaction was below pH 7.0. FIG. 26 depicts human albumin with domains D1A through D3B, $Cys_{34}$ as indicated, and fatty acid binding pockets highlighted by numbers 1-7.

Without wishing to be bound by any theory or hypothesis, the inventors contemplate that fatty acid (or other hydrophobic ligand) binding to albumin changes the 3D conformation in such a manner that the thiol group at $Cys_{34}$ will be preferentially or be even exclusively available for a Michael addition reaction in only one plane of the maleimide ring and as such preferentially or even exclusively produce only one stereoisomer, resulting in a stereoselective chiral product. Moreover, and particularly at a lower pH (i.e., pH<7.0) the resulting micro-environment inside the "$Cys_{34}$ hydrophobic crevice" becomes prohibitive to the mechanistic steps required to support a retro-Michael reaction. Hence, unanticipatedly, the stereospecificity of the bioconjugation adduct and its corresponding microenvironment in conformationally modified albumin guard against retro-Michael bond $Cys_{34}$ sulfur-carbon (MPA) cleavage.

Figure 27:
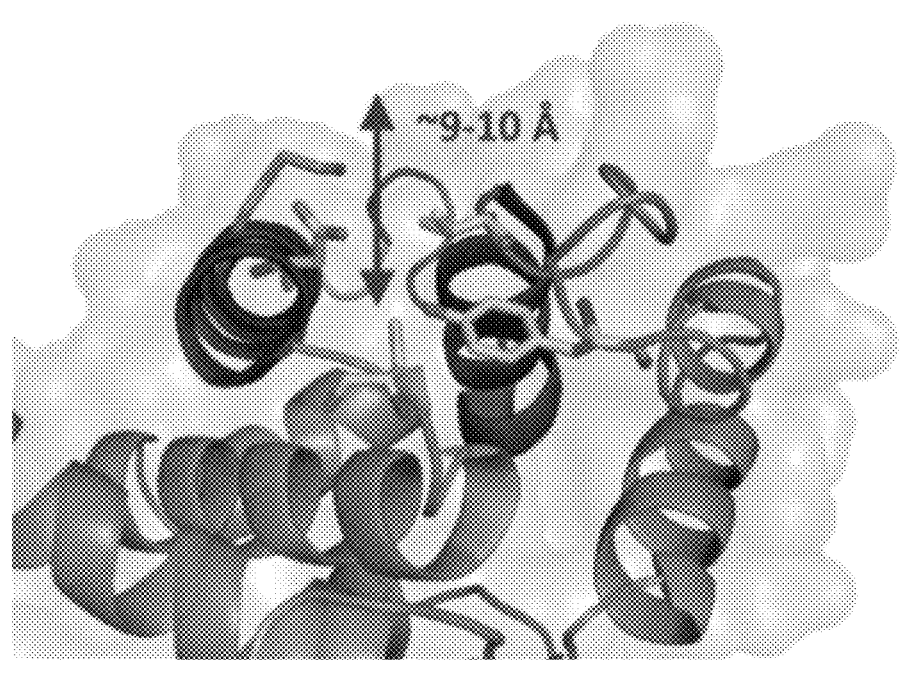
FIG. 27 illustrates a schematic side view of the $Cys_{34}$ hydrophobic pocket in conformationally modified human albumin.
Figure 28A:
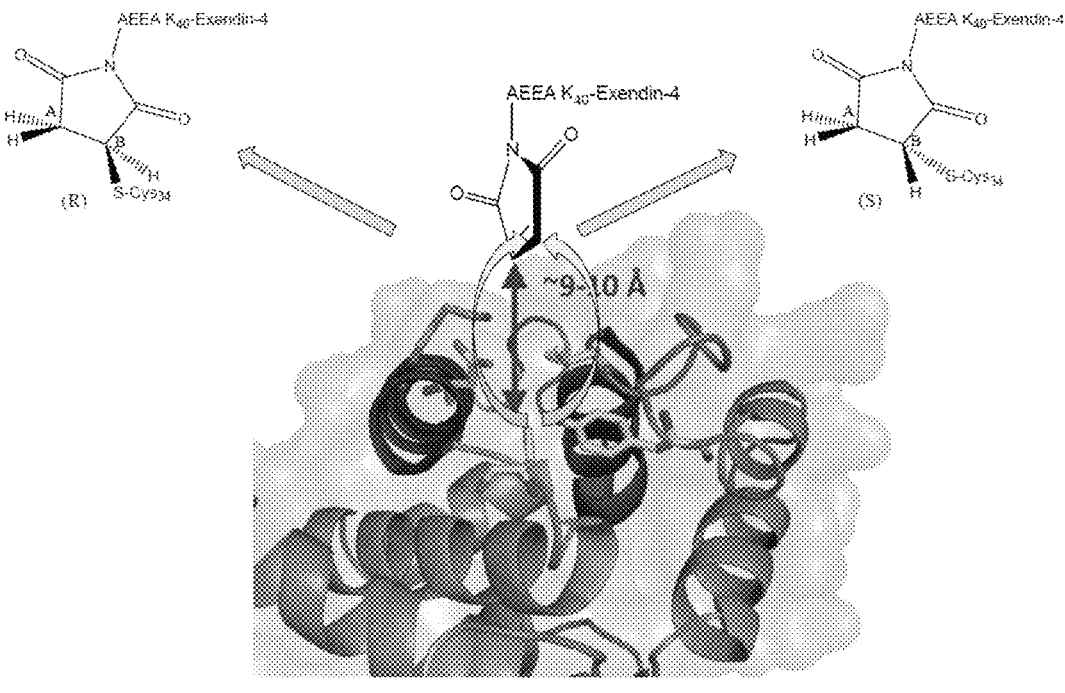
FIG. 28A shows a schematic view of the MPA coupling group entering the hydrophobic pocket of conformationally unmodified human albumin of FIG. 27, with the arrows indicating the indiscriminate direction of attack of the sulfur atom relative to the planar maleimide group of the MPA.
Figure 28B:
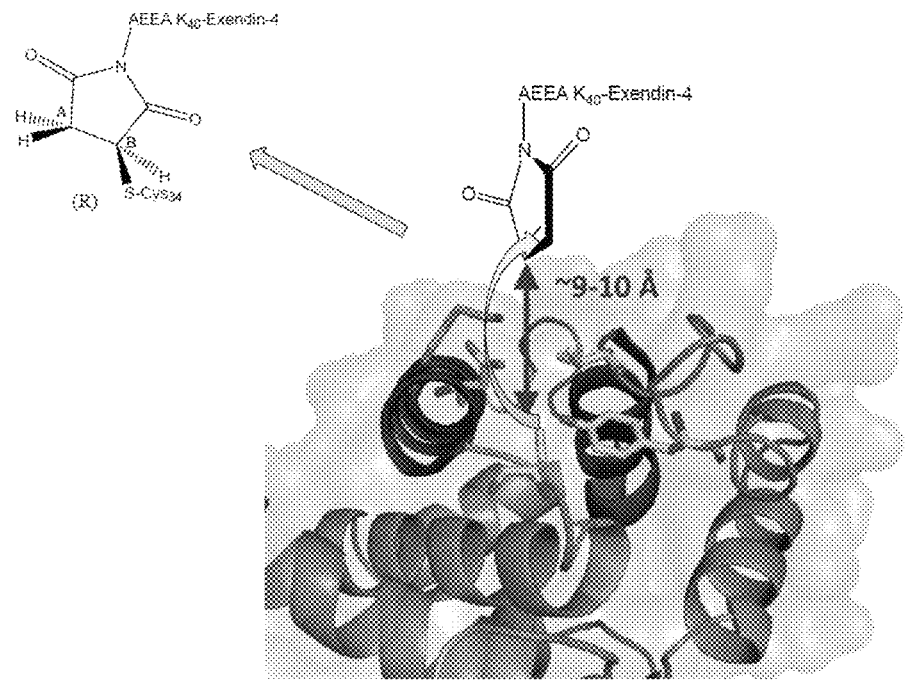
FIG. 28B shows a schematic view of the MPA coupling group entering the hydrophobic pocket of conformationally modified human albumin of FIG. 27 with the arrow indicating the stereopreferred or stereoselective direction of attack of the sulfur atom relative to the planar maleimide group of the MPA.
Figure 28C:
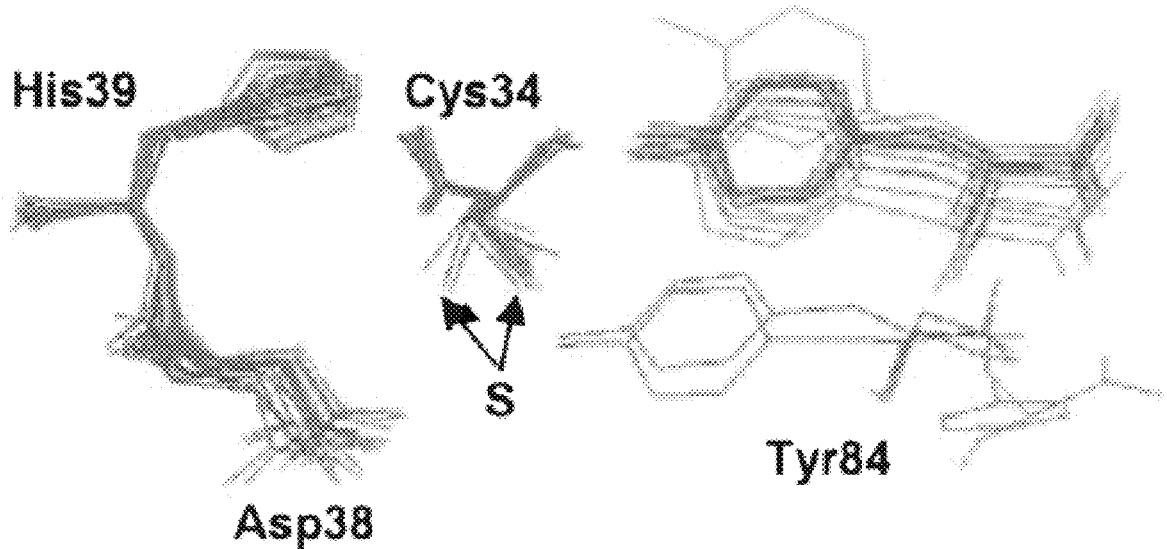
FIG. 28C shows a schematic superposition of conformationally unmodified human albumin (dark gray) and modified human albumin (light gray) with the arrows indicating the position of the sulfur atom in $Cys_{34}$.

FIG. 27 depicts a side view of the $Cys_{34}$ hydrophobic crevice with the thiol pointing upwards near the bottom of the crevice and the $Asp_{38}$ side chain pointing towards the center. In this unmodified albumin conformation, the hydrophobic pockets of albumin are occupied by octanoate, and the thiol group can participate in a reaction on both sides of a planar maleimide group. FIG. 28A depicts a schematic detail view of FIG. 27 where the $Asp_{38}$ carboxylate portion and thiol group of $Cys_{34}$ form hydrogen bonds with a water molecule. As is schematically shown by the two arrows in FIG. 28A, the Michael donor (sulfur atom of $Cys_{34}$) has indiscriminate access to the Michael acceptor group (planar maleimide ring) with regard to the plane of the acceptor. Consequently, as the reaction product creates a chiral carbon center, and as there is no discrimination with regard to the plane of nucleophilic attack, the reaction product is a racemic product (i.e., substantially equal proportion of R- and S-configuration). Upon removal of one or more hydrophobic ligands from the binding pockets in albumin, and particularly at a pH<7.0 (yielding a at $Asp_{38}$ protonated carboxylate group) the inventors discovered that the albumin is conformationally modified and that the $Cys_{34}$ hydrophobic crevice is changed in such a manner that not only stereochemically disfavors a retro-Michael deconjugation but also results in a stereopreferred or even stereoselective reaction product as is exemplarily depicted by the single arrow in FIG. 28B. the change in conformation of albumin is exemplarily depicted in FIG. 28C that illustrates a structural overlay of conformationally unmodified (dark gray) and conformationally modified albumin (light gray) prepared by aligning the backbone atom of residues $Cys_{34}$ and $His_{39}$ in each of the structures using Swiss pdb viewer (v3.7)(*FEBS Journal* 272 (2005) 353-362).

Unexpectedly, despite the relatively small changes in conformation in the hydrophobic pocket, the previously 'open' environment surrounding $Cys_{34}$ in the unmodified albumin changed to a stereochemically constrained environment. In addition, and as can also be seen from FIG. 28C, the sulfur atom of $Cys_{34}$ is now oriented away from $Tyr_{84}$. Such changes resulted in the generation of a chiral environment that now favored or even restricted the nucleophilic attack of the sulfur atom to a single plane of the planar Michael acceptor resulting in a stereoisomer that was retro-Michael resistant due to steric constraints in the hydrophobic pocket.

In contrast, retro-Michael reactions in other compositions (e.g., various antibody-drug conjugates) were heretofore only avoided by hydrolysis of the succinimide group formed after Michael addition. Such hydrolysis, however, occurs at a pH>9 and temperatures ranging from 37-50° C. over a period of 24-60 hours. Clearly, under such conditions both the protein and the pharmacophore, especially if peptide-based, will undergo deamidation on amino acid amide side chains, which would lead to loss of function in the GPCR agonist compounds presented herein.

As such, it should be recognized that the inventors were now able to produce an albumin carrier that covalently bound and retained a GPCR agonist such that upon administration of the compound substantially no GPCR agonist was released, leading to highly effective compounds without attendant release of agonist, thereby eliminating adverse effects associated with free or deconjugated agonists otherwise encountered. Moreover, due to the nature of the linker attachment to the albumin and the agonist as discussed in more detail below, it should also be appreciated that the agonist is sterically free to engage with the GPCR such that the agonist can bind with high affinity and such that the agonist can activate the GPCR in a two-step manner.

With respect to the removal of octanoate or other hydrophobic compounds including fatty acids from albumin it is contemplated that all methods that are able to reduce the octanoate or other hydrophobic compounds without denaturing the albumin are deemed suitable for use herein, and especially preferred methods include charcoal filtration, dialysis, ion exchange chromatography, etc. (see e.g., *Biochim Biophys Acta* 1970 Nov. 17; 221(2):376-8*; Nature Communications Materials;* (2020) 1:45). As will be readily appreciated, the albumin is preferably human serum albumin, which may be isolated and purified from human serum, or may be recombinantly produced using a bacterial, or more typically, yeast expression system. Thus, albumin contemplated herein may or may not be N or O glycosylated. In this context it should be appreciated that commercially available highly purified natural or recombinant albumin is typically stabilized with exogenously added octanoate or other short or medium-chain fatty acid.

Moreover, it should be appreciated that the albumin can be entirely or only partially defatted such that at least one, or at least two, or at least three, or at least four, or at least five, or at least five, or at least six, or all hydrophobic fatty acid binding pockets of the albumin are free from a hydrophobic ligand to so form the conformationally modified albumin. The suitable degree of defatting will be at least in part determined by the desired degree of a stereoselective reaction product. Thus, and most typically, the albumin will be fully (all hydrophobic fatty acid binding pockets of the albumin are free from a hydrophobic ligand) or almost fully (at least four hydrophobic fatty acid binding pockets of the albumin are free from a hydrophobic ligand) defatted. Once defatted, the so prepared conformationally modified albumin is then reacted with the linker containing the coupling group (typically comprising a maleimide or bromo-maleimide group) following standard Michael addition reaction conditions, preferably at an equimolar ratio, and preferably at a pH that is pH<7.0 (e.g., pH between 6.0 and 6.9, or pH between 5.5 and 6.0, or pH between 5.0 and 5.5, or pH between 4.5 and 5.0, or pH between 4.0 and 4.5). However, excess albumin during the coupling reaction is also deemed suitable, such as a molar excess of 1.1-fold, or 1.2-fold, or 1.3-fold, or 1.4-fold, or 1.5-fold, and even more. Exemplary reaction conditions for coupling the linker to the $Cys_{34}$ of the conformationally modified albumin are described, for example at *Endocrinology* (2005)146 3052-3058, *Bioorg. Med. Chem. Lett.* (2003) 13 3571-3575, and *Bioconjug. Chem.* (2005) 16 1000-1008, each of which are incorporated by reference herein.

As such, it should be noted that the inventors discovered that conformationally modified albumin can be readily prepared in solution and used in a variety of biochemical reactions that can take advantage of the conformational modification, and in particular of the modification in the steric environment of the hydrophobic crevice in which $Cys_{34}$ is located. Most advantageously, such modified environment can lead to stereopreferred or even stereoselective reactions, and with that enantiomeric preferred or even chirally pure reaction products. For example, where the conformationally modified albumin has at least one (or at least two, or at least three or at least four, or at least five, or at least six) hydrophobic pocket not occupied by a hydrophobic ligand such as octanoate, a stereopreferred or even stereoselective Michael addition can be performed using a (typically planar) Michael acceptor reagent. Among other Michael acceptor reagents, maleimide or bromo maleimide-containing reagents are particularly contemplated where the Michael donor is the thiol group of $Cys_{34}$. Consequently, and as already discussed above, a retro-Michael resistant product (e.g., containing a linker and Class B GPCR agonist peptide as discussed herein) can be readily obtained from a reaction intermediate, particularly where the pH is pH<7.0.

Therefore, and viewed from a different perspective, it should be appreciated that albumin can be modified at $Cys_{34}$ by reacting the sulfur atom of the $Cys_{34}$ with a coupling group, wherein the albumin is a conformationally modified albumin in which at least one hydrophobic pocket of the conformationally modified albumin is not occupied by a non-covalently bound lipid. As noted earlier, such reaction is preferably performed at a pH of pH<7.0, and more typically between 4.0 and 6.0. Advantageously, such reactions will lead to retro-Michael resistant reaction products where the coupling group is a planar Michael acceptor such as a maleimide or bromo maleimide group. As such, these reactions may be used to reduce or even entirely avoid retro-Michael reactions in albumin with Michael conjugates, particularly where such conjugates have therapeutic use such as with the agonist peptides with linkers and reactive group as listed in SEQ ID NO:1-471.

In yet another unexpected finding, the inventors discovered that even when octanoate levels are at higher levels during conjugation, a retro-Michael resistant fusion protein can nevertheless be generated via a stereoselective translocation to an unreacted albumin having an unreacted $Cys_{34}$ group (which may or may not be conformationally modified) in a pharmaceutical formulation post standard purification. Alternatively, the conjugation ratio of peptide intermediate with a linker and MPA as a reactive coupling moiety to the albumin can be adjusted such as to provide an excess amount of unreacted albumin having an unreacted $Cys_{34}$ group (which may or may not be conformationally modified) when the purification step is an ultrafiltration or diafiltration step, leading to a formulation that also contains an excess amount of unreacted albumin. This unexpected finding was based on the following observations:

Utilizing an albumin-exendin-4 MPA conjugated construct very similar to AB-013 in which albumin was not conformationally modified and in which the construct was in an aqueous solvent at pH 7.4, it was observed that such a construct underwent significant and massive retro-Michael deconjugation as determined by a sandwich ELISA within the first 10 minutes after being injected intravenously in mice. Based on this observation it was concluded that the conjugated peptide was cleaved from the albumin in a retro-Michael reaction and that the only remedy to prevent such reaction was hydrolysis of the succinimide ring in the coupling group by increasing the pH (i.e., pH>9) at elevated temperatures for a lengthy period of time to so stabilize the thiol bond.

To assess the pharmacokinetic profile of both the conformationally unmodified AB-013 conjugate and any free unconjugated peptide with the linker and MPA group that would be released in plasma, the inventors performed a study over 96 hours after subcutaneous or intravenous injection. To that end, an experiment was conducted in rats where the conformationally unmodified AB-013 conjugate was injected intravenously at a dose of 100 nmol/kg and subcutaneously at a dose of 500 nmol/kg. The conformationally unmodified AB-013 conjugate and the anticipated retro-Michael free peptide were quantitated separately via respective ELISA tests but within the same following time points: 2 min, 30 min, 1, 2, 4, 8, 24, 48, 72 and 96 hours for both routes of administration.

From this study, the inventors observed at the first intravenous (I.V.) time point a concentration for conformationally unmodified AB-013 and free unconjugated AB-013 intermediate to be 2528.8 nmol/L and 24.9 nmol/L respectively (leading to a ratio (0.98%). In addition, from the pharmacokinetic profile, the total area under the curve (AUC) I.V. for the conformationally unmodified AB-013 was 37418 (nmol/L*h) whereas the AUC for the free unconjugated material was 53.69 (nmol/L*h) leading to a ratio of 0.14%. Surprisingly, the conformationally unmodified AB-013 and unconjugated "free" peptide were respectively responsible for 99.86% and 0.14% of the presence of the drug in the plasma intravenously. Similarly, for subcutaneously (S.C.) administration, the pharmacokinetic profile leads to a total area under the curve (AUC) for the conformationally unmodified AB-013 of 18944 (nmol/L*h) whereas the AUC for the free unconjugated peptide was 143 (nmol/L*h) leading to a ratio of 0.7%.

Surprisingly, and contrary to the above observation of retro-Michael decoupling in the range of 20-40% during the first 10 mins post intravenous injection, no such retro-Michael reaction leading to a disconnection between the thiol of $Cys_{34}$ of albumin and the reactive moiety MPA was observed from this particular experiment. Nor did the inventor observe any pharmacokinetic parallel between the conformationally unmodified AB-013 and the free unconjugated or freshly formed retro-Michael product. Such parallel would have suggested that a retro-Michael reaction played a major role in the degradation of the conformationally unmodified AB-013. FIG. 29 depicts exemplary results for the above experiment.

In yet a further experimental set-up, utilizing a conformationally unmodified albumin-exendin-4 MPA driven covalent construct very similar to conformationally modified AB-013 it was reported that when such conformationally unmodified construct was placed in a solution with a pH>9 and warmed at 370 for 20 hours that a retro-Michael deconjugation occurred and that the deconjugation can be monitored by mass spectrum analysis. Interestingly, the retro-Michael process occurred in only 50% of the MPA driven covalent construct used in that study, leading to the assumption that some hydrolysis of the succinimide ring had occurred.

To further investigate the apparent inconsistencies supplementary electrophoresis experiments were conducted on the plasma samples collected from the rats that were injected s.c. and i.v. as noted above, and exemplary results are depicted in FIG. 30. As can be readily seen in the gel image, when conformationally unmodified AB-013 is tested in an electrophoresis experiment only one band is observed in the area where an albumin-exendin-4 MPA covalent construct would be observed. Completely unexpectedly, all time points taken during the experiment, including the earliest ones, had two bands in the area related to an albumin-exendin-4 MPA covalent construct. The first band observed on electrophoresis was related to conformationally unmodi-fied AB-013 and the second ban immediately above was related to an exendin-4 MPA covalent construct, but cova-lently attached to rat albumin whereas the conformationally unmodified AB-013 is a covalent attachment to human albumin.

Hence, the inventors surprisingly discovered a direct translocation, in vivo, of a retro-Michael decoupled exen-din-4 MPA construct from human albumin to the $Cys_{34}$ of rat albumin. Interestingly, the intensity of the two bands observed on the electrophoresis gel are of similar intensity (about 50-50), while there were no detectable levels of free (decoupled) exendin-4 MPA construct. This initial observa-tion was further supported when a dynorphin-A-MPA pep-tide was injected intravenously to rats. Importantly, this dynorphin-A-MPA peptide was not conjugated to human albumin or any other type of albumin. Hence it was injected with the intent of in vivo bioconjugation to rat albumin. Bioconjugation in vivo did indeed occur with rat albumin as monitored via electrophoresis gel (data not shown). Inter-estingly, for every time point tested only one band was observed on the electrophoresis gel when dynorphin-A-MPA peptide was injected intravenously. In a similar fash-ion, the dynorphin-A-MPA peptide was also conjugated to human conformationally unmodified albumin in vitro to form a covalent bond between it and the $Cys_{34}$ of human albumin. The dynorphin a human albumin covalent con-struct was injected intravenously to rats. Once more, the inventors then observed a direct translocation, in vivo, from an MPA peptide covalently bound to the $Cys_{34}$ of human albumin to rat albumin.

These results further confirm the inventors' discovery that a Michael addition occurring in a sterically constrained hydrophobic pocket of the albumin leads to the generation of a chiral center, and that conformational modification of the albumin will result in a conformationally modified hydro-phobic pocket that favors or even entirely produces a retro-Michael resistant stereoisomer. In addition, retro-Mi-chael reactions can be further disfavored by lower pH, and especially pH of less than 7.0 and lower. Viewed from a different perspective, for a retro-Michael reaction to occur, appropriate conformational architecture within the hydro-phobic pocket is required, along with appropriate stereo-chemical orientation. Indeed, even when experiments are designed to force a retro-Michael reaction under harsh conditions (pH>9, high temperature (e.g., 50° C.), and long time (about 20 hrs)), retro-Michael reaction is observed at a yield of only about 50% of theoretically possible retro-Michael reaction, strongly implicating the importance of the chirality created during the conjugation process and restric-tive nature of the sterically constrained hydrophobic pocket.

In view of the above, it should therefore be recognized that albumin can be chemically modified with a coupling group at $Cys_{34}$ such that a sulfur atom of the $Cys_{34}$ is covalently bound to a chiral carbon atom of the coupling group, and such that the chiral atom has a favored stereo-chemical configuration (instead of a racemic carbon atom where the thiol group is not sterically constrained as discussed above). Indeed, it is contemplated (and has been observed) that the favored stereochemical configuration can be favored at a ratio of at least 60:40, or at least 70:30, or at least 80:20, or at least 85:15, or at least 90:10, or at least 95:5, particularly with increasing degree of defatting (i.e., at least one, or at least two, or at least three or at least four, or at least five, or at least six, or all hydrophobic binding pockets are not occupied by a non-covalently bound lipid).

Therefore, it is noted that the inventors discovered that a chemically modified albumin can be produced, where the albumin is modified at $Cys_{34}$ with a Michael addition con-jugate, and where the Michael addition conjugate is resistant to a retro-Michael addition reaction. Indeed, it should be appreciated that it is now possible to prepare compositions in which a coupling group (carrying a (hydrophilic) linker and optionally a peptide coupled to the linker) can be covalently attached to $Cys_{34}$ of albumin in a stereopreferred (i.e., at least 55%, at least 60%, at least 75%, at least 80%, at least 85%, at least 90%, at least 95% of all chiral carbon atoms in C—S bonds in coupling groups have a configura-tion that is retro-Michael resistant) or even stereoselective (between 98 and 100% of all chiral carbon atoms in C—S bonds in coupling groups have a configuration that is retro-Michael resistant) manner, thereby rendering the molecular entity attached to the coupling group retro-Mi-chael resistant. While this chemically modified albumin is utilized for the delivery of insulin-tropic agents, it is con-templated that this form of albumin together with the linker described herein could also serve as delivery systems for other drug conjugates including cytotoxic agents, chemo-therapeutic agents in the treatment as a form of targeted therapy or antibody drug conjugates (ADCs) in the field of cancer.

Viewed from a different perspective, in an isotonic buff-ered (pH 7.0) solution containing contemplated retro-Mi-chael resistant conjugates of albumin and agonist peptide, no more than 40%, or no more than 30%, or no more than 20%, or no more than 15%, or no more than 10%, or no more than 8%, or no more than 6%, or no more than 4%, or no more than 2%, of all bound agonist peptide will dissociate from the albumin in a retro-Michael reaction over a period of 24 hours at room temperature. Therefore, it should be appreci-ated that the majority of the linkers with covalently bound GPCR agonist peptides will be bound to the $Cys_{34}$ amino acid of albumin in a retro-Michael resistant manner. Thus, pharmaceutical compositions in which a GPCR agonist peptide is covalently bound to a $Cys_{34}$ amino acid of albumin in a stereopreferred or stereoselective configuration will be substantially free of unbound GLP-1 agonist peptide (e.g., no more than 10%, or no more than 7%, or no more than 5%, or no more than 3%, or no more than 2% of total agonist peptide in the composition are unbound).

As already noted above, such compositions can be pre-pared via reacting the coupling group and linker (with or without attached peptide or other molecular entity) to the $Cys_{34}$ of a conformationally modified albumin, by perform-ing the Michael addition in the presence of free albumin in molar excess relative to the coupling group, and/or by adding free albumin to a Michael addition product that was produced by reacting $Cys_{34}$ of an albumin with a coupling group and linker (with or without attached peptide or other molecular entity such as a linker-bound GPCR agonist peptide). As will be readily appreciated, the ratio of free albumin to albumin with a ligand bound to $Cys_{34}$ can vary, and suitable ratios will typically be 1:5, or 1:4, or 1:3, or 1:2, or 1:1.5, or 1:1.2, or 1:1, or 1.2:1, or 1.5:1, or 2:1, or 3:1, or 4:1, or 5:1. In each of the cases where additional albumin is used, such albumin can be conformationally modified and/or conformationally unmodified albumin. Moreover, it should be recognized that once the coupling reaction of the linker (typically also containing the agonist peptide) with the albumin is concluded, the GPCR agonist fusion protein can then be purified using standard methods well known in the art. Moreover, and where desired, octanoate or hydrophobic agents may be added to the fusion protein to re-occupy the hydrophobic binding sites, thereby improving stability of the fusion protein.

Returning back to contemplated linkers, it should be noted that the linker that is coupled to the conformationally modified albumin will already be covalently bound to the GPCR agonist peptide, typically via an epsilon amino group of a lysine, preferably located at the C-terminus of the agonist peptide.

While at least conceptually simple, synthesis of the GPCR agonists that also contain a reactive linker is far from trivial, particularly where an automated Merrifield-type synthesis is desired. Synthesis is even further complicated where the agonist is exendin-4 or an exendin-4 derivative that contains a tryptophan cage at the C-terminus, which presents substantial steric hindrance for any chemistry proximal to the C-terminus. In addition, and particularly where the agonist peptide is coupled to a linker via a second reactive group, differential protection and deprotection is required, which may yet again be difficult to achieve in the proximity to the synthetic resin. Viewed from a different perspective, while linear GLP-1 analogs have been prepared on a solid phase as described in U.S. Pat. No. 6,514,500, protocols to perform orthogonal site-specific chemistries on the very first amino acid that is anchored on a solid support have not been established, nor are there known synthetic protocols for performing orthogonal site-specific chemistries on the very first amino acid anchored on a solid support when the structure of the peptide is highly organized at the C terminus end.

In view of the above difficulties, the inventors unexpectedly discovered that successful protocols to perform orthogonal site-specific chemistries on the first AA anchored on a solid support required a preferred distance between the solid support (here: polystyrene beads) and the anchoring site of the first amino acid. In one particularly preferred embodiment, a tricyclic amide resin (Ramage resin) provided the necessary and preferred distance to successfully perform orthogonal protection/deprotection. Advantageously, the inventors also recognized that such tricyclic amide resin was also suited for large scale and cGMP scale manufacturing.

In the following example, the small-scale peptide synthesis of AB-013 intermediate was performed on the modified tricyclic amide resin (Ramage resin) using an automated solid-phase procedure on a Symphony® peptide synthesizer with manual intervention to perform orthogonal chemistries of incorporating a linker like AEEA (Amido(Ethoxy) Ethoxy] Acetic acyl) and a reactive moiety such as male-imidopropionic acyl. As should be readily appreciated, the same synthetic strategy can also be implemented for the other GPCR agonist peptides presented herein.

As will be readily appreciated, the suitable choice of the resin substitution level will be a function of the desired synthetic efficiency, the length of the peptide intermediate, and the complexity of the structural conformation in combination with the location along the peptide chain of such complexity. That said, preferred agonist peptides will have a length between 30-45 amino acids with significant structural conformation complexity (here: Trp cage) at the C-terminal end of the peptide. Furthermore, in most (but not all of the contemplated) embodiments, orthogonal chemistries are conducted on the first amino acid that is anchored on the resin. Hence an appropriate distance between the polystyrene and the anchoring site of the first amino acid is preferred as noted above. Advantageously, the modified Ramage resin structure and substitution level addresses synthetic efficiency, length of the peptide intermediate, complexity/location of the structural conformation and orthogonal chemistries on the first amino acid anchored the resin. Preferably, but not necessarily, the substitution level is approximately 0.4-0.6 mmol/gram Ramage resin.

With regard to scale-up, it is noted that the peptide intermediate batch size will be dependent on the scale of the synthesis and the substitution of the Ramage resin. This in turn provides the necessary information regarding the amount of Ramage resin for a particular batch. For example, a 100-mmole synthesis scale using a modified Ramage resin with a substitution level of 0.5 mmol/g, will require an amount of starting Ramage resin of –200 g and would have a theoretical yield of –8.5% for a 40-mer peptide. Thus, a batch size of 100 mmol would be an appropriate large scale (e.g., cGMP) batch size for process validation, while for a research scale a batch size of 100 umol/g of modified Ramage resin would be appropriate.

The amino acid N-terminus is protected by groups that are termed "temporary" protecting groups, because they are relatively easily removed to allow peptide bond formation. Two common N-terminal protecting groups are tert-butoxy-carbonyl (Boc) and 9-fluorenylmethoxycarbonyl (Fmoc), and each group has distinct characteristics that determine their use. Boc requires a moderately strong acid such as trifluoracetic acid (TFA) to be removed from the newly added amino acid, while Fmoc is a base-labile protecting group that is removed with a mild base such as piperidine. Because of the mild deprotection conditions, Fmoc chemistry is more commonly used in commercial settings because of the higher quality and greater yield, while Boc is preferred for complex peptide synthesis or when non-natural peptides or analogs that are base sensitive are required. Hence, the protecting groups contemplated herein fall in two categories: base-labile and acid-labile. The base-labile protecting group is typically used to block the α-amino group during the coupling reaction and is then removed in the deblocking step to allow the introduction of the next amino acid in the sequence. For example, 9-Fluorenylmethoxy carbonyl (Fmoc) can be used as the base-labile, α-amino protecting group. In another example, the acid-labile protecting groups (e.g., triphenylmethyl (Trt)/t-butyl (tBu)/t-butyl ester (OtBu)/t-butyloxycarbonyl (Boc)/2,2,5,7,8, pentamethylchroman-6-sulfonyl (Pmc)/methyltrityl (Mt)) can be used to protect the side-chain reactive functional groups of the amino acids during synthesis, and must be resistant to the deblocking mixture (e.g., 20% piperidine in dimethylformamide (DMF), v/v). Upon completion of the peptide synthesis, these protecting groups are removed by a strong acid (e.g., 85% aqueous trifluoroacetic acid (TFA) with scavengers).

One particularly preferred method of preparing the peptide agonists presented herein involves solid phase peptide synthesis in which the amino acid N-terminus is protected by an acid or base sensitive group while being readily removable without destruction of the growing peptide chain or racemization of any of the chiral centers contained therein. Examples of N-protecting groups and carboxy-protecting groups are disclosed in Greene, "Protective Groups in Organic Synthesis," (John Wiley & Sons, New York pp. 152-186 (1981)), which is hereby incorporated by reference. Examples of N-protecting groups comprise, without limitation, lower alkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl,4-chlorobenzoyl, 4-bromobenzoyl, 4-nitrobenzoyl and the like; sulfonyl groups such as benzenesulfonyl, p-toluene-sulfonyl, o-nitrophenylsulfonyl, 2,2,5, 7,8-pentamethylchroman-6-sulfonyl (pme), and the like; carbamate forming groups such as t-amyloxycarbonyl, benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbony 1,2,4-dimethoxybenzyloxycarbonyl, 4-ethoxybenzyloxycarbonyl, 2-nitro-4, 5-dimethoxybenzyloxycarbony 1,3,4,5-trimethoxybenzyloxycarbony 1,1-(p-biphenylyl)-1-methylethoxycarbonyl, a,a-dimethyl-3,5-dimethoxybenzyloxycarbonyl, benzhydryloxycarbonyl, t-butyloxycarbonyl(boc), diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, isobomyloxycarbonyl, cyclopentyloxycarbonyl, adamantyloxycarbonyl, cyclohexyloxycarbonyl, phenylthiocarbonyl and the like; arylalkyl groups such as benzyl, biphenylisopropyloxycarbonyl, triphenylmethyl, benzyloxymethyl, 9-fluorenylmethyloxycarbonyl (Fmoc) and the like and silyl groups such as trimethylsilyl and the like. Preferred α-N-protecting group are o-nitrophenylsulfenyl; 9-fluorenylmethyloxycarbonyl; t-butyloxycarbonyl (boc), isobomyloxycarbonyl; 3,5-dimethoxybenzyloxycarbonyl; t-amyloxycarbonyl; 2-cyano-t-butyloxycarbonyl, and the like, 9-fluorenyl-methyloxycarbonyl (Fmoc) being more preferred, while preferred side chain N-protecting groups comprise 2,2,5,7,8-pentamethylchroman-6-sulfonyl (pmc), nitro, p-toluenesulfonyl, 4-methoxybenzene-sulfonyl, Cbz, Boe, and adamantyloxycarbonyl for side chain amino groups like lysine and arginine; benzyl, o-bromobenzyloxycarbonyl, 2,6-dichlorobenzyl, isopropyl, t-butyl (t-Bu), cyclohexyl, cyclopenyl and acetyl (Ac) for tyrosine; t-butyl, benzyl and tetrahydropyranyl for serine; trityl, benzyl, Cbz, p-toluenesulfonyl and 2,4-dinitrophenyl for histidine; formyl or Boc for tryptophan; benzyl and t-butyl for aspartic acid and glutamic acid; and triphenylmethyl (trityl) for cysteine.

A carboxy-protecting group conventionally refers to a carboxylic acid protecting ester or amide group. Such carboxy protecting groups are well known to those skilled in the art, having been extensively used in the protection of carboxyl groups in the penicillin and cephalosporin fields as described, for example, in U.S. Pat. Nos. 3,840,556 and 3,719,667, both of which are hereby incorporated herein by reference. Representative carboxy protecting groups include, without limitation, C1-C8 lower alkyl; arylalkyl such as phenethyl or benzyl and substituted derivatives thereof such as alkoxybenzyl or nitrobenzyl groups; arylalkenyl such as phenylethenyl; aryl and substituted derivatives thereof such as 5-indanyl; dialkylaminoalkyl such as dimethylaminoethyl; alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl,propionyloxymethyl; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl; aroyloxyalkyl such as benzoyloxymethyl, benzoyloxyethyl; arylalkylcarbonyloxyalkyl such as benzylcarbonyloxymethyl, 2-benzylcarbonyloxyethyl; alkoxycarbonylalkyl or cycloalkyloxycarbonylalkyl such as methoxycarbonylmethyl, cyclohexyloxycarbony 1methyl, 1-methoxycarbonyl-1-ethyl; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl; aryloxycarbonyloxyalkyl such as 2-(phenoxycarbonyloxy) ethyl, 2-(5-indanyloxycarbonyloxy)-ethyl; alkoxyalkylcarbonyloxyalkyl such as 2-(1-methoxy-2-methylpropan-2-oyloxy)-ethyl; arylalkyloxycarbonyloxyalkyl such as 2-(benzyloxycarbonyloxy)ethyl; arylalkenyloxycarbonyloxyalkyl such as 2-(3-phenylpropen-2-yloxycarbonyloxy)ethyl; alkoxycarbonylaminoalkyl such as t-butyloxycarbonylaminomethyl; alkylaminocarbonylaminoalkyl such as methylaminocarbonylaminomethyl; alkanoylaminoalkyl such as acetylaminomethyl; heterocycliccarbonyloxyalkyl such as 4-methylpiperazinylcarbonyloxymethyl; dialkylaminocarbonylalkyl such as dimethylaminocarbonylmethyl, diethylaminocarbonylmethyl; (5-(loweralkyl)-2-oxo-1,3-dioxolen4-yl)alkyl such as (5-t-butyl-2-oxo-1,3-dioxolen-4-yl)methyl; and (5-phenyl-2-oxo-1,3-dioxolen-4-yl)alkyl such as (5-phenyl-2-oxo-1,3-dioxolen-4-yl)methyl. Representative amide carboxy protecting groups comprise, without limitation, aminocarbonyl and lower alkylaminocarbonyl groups. Of the above carboxy-protecting groups, loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester are preferred. Preferred amide carboxy protecting groups are lower alkylaminocarbonyl groups.

The-C-terminal amino acid is coupled to the resin by means of N,N'-dicyclohexylcarbodiimide (DCC), N,N'-diisopropylcarbodiimide (DIC) or O-benzotriazol-1-yl-N,N, N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl), or Oxyma Ethylcyanohydroxyiminoacetate, or HATU (1-[bis (dimethylamino)methylene]-1H-1,2,3-triazolo[4,5-b]pyridinium 3-oxide hexaflurophosphate, or TBTU 2-(1H-benzotriazolel-yl)-1,1,3,3-tetramethylaminium tetrafluoroborate, or TNTU 2-(5-Norbornene-2,3-dicarboximido)-1,1,3,3-tetramethyluronium tetrafluoroborates, or PyOxim 1-Cyano-2-ethoxy-2-oxoethylideneaminooxy-tris-pyrrolidino-phosphonium hexafluorophosphate, or PyClock 6-chloro-benzotriazolelyloxy-tris-pyrrolidinophosphonium hexafluorophosphate diethylamine (DEA).

Coupling is performed from about 1 to about 24 hours at a temperature of between 10° C. and 50° C. in a solvent such as dichloromethane, DMF and NMP and/or a solvent mixture compatible with coupling of amino acids and/or acylation.

During the activation/coupling steps, the deprotected α-amino group is acylated by the next activated amino acid in the sequence. As will be readily appreciated, the reagents used to accomplish acylation are selected to create optimal reaction conditions and easy elimination of the excess reagents at the end of the coupling reaction. The activation for each acid coupling is performed with TBTU/HBTU and DIPEA. DIPEA is used as an additive to drive the reaction to completion. TBTU/HBTU and DIEA are dissolved in DMF:NMP (1:1) and added to the appropriate Fmoc protected amino acid to generate the acylation process on the free Na-amino functionality that is attached to fully protected peptide being elongated while remaining attached to the modified Ramage resin.

During the deprotection step, the base-labile protecting group (Fmoc) is cleaved from the α-amino function of the N-terminal amino acid on the growing peptide chain by treating the resin twice with a 20% solution of piperidine in DMF (v/v). Typically, the resin is stirred for a period of 20 minutes after which the 20% piperidine/DMF solution is filtered, and the treatment is repeated for a second period of 20 minutes with a new 20% piperidine/DMF solution. This treatment is typically sufficient to allow complete cleavage of the Fmoc protecting group without affecting the stability of the acid-labile protecting groups present on the growing peptide chain.

In one example, synthesis of an AB-013 intermediate was performed using the tricyclic amide resin composed of a Ramage "connector" that is structurally defined as (9H-fluoren-9-yl)methyl-N-(6-{[(1-{[(4-methylphenyl) (phenyl) methyl]carbamoyl}pentyl)-carb-amoyl]meth-oxy}tricyclo [9.4.0.03,8]pentadecal(11), 3(8),4,6,12,14-hexaen-2-yl) carb-amate bounded to the polystyrene supports cross-linked with 1% divinylbenzene (DVB). The Ramage "connector" was then modified to 2-[2-({2-aminotricyclo [9.4.0.03,8]pentadeca-1(11),3(8),4,6,12,14-hexaen-6-yl}oxy)acetamido]-N[(4methylphenyl) (phenyl)methyl] hexanamide (the modified Ramage resin), thus enabling the anchoring of the first amino acid on the solid support via standard coupling conditions.

The peptide synthesis methodology utilized a conventional Fmoc-protected amino acids approach with appropriately orthogonally protected amino acids. Coupling was achieved by using O-benzotriazol-1-yl-N,N,N',N'-tetramethyl-uronium hexafluorophosphate (HBTU) and diisopropylethylamine (DIEA) as the activator mixture in N,N-dimethylformamide (DMF) solution. The Fmoc protective group was removed using 20% piperidine/DMF (v/v). A Boc-protected amino acid was used at the N-terminus of the peptide on solid support in order to generate a free Na-terminus after the AB-013 was cleaved from the resin. All amino acids used during the synthesis were L-amino acids, and sigma-coated glass reaction vessels were used during synthesis. As noted above, the synthesis process for the production of various peptide analogs and derivatives will vary widely, depending upon the nature of the various elements, i.e., the peptide analogs sequence, the linking group and the reactive entity, comprised in the peptide analogs or derivatives. In most circumstances, the chemically reactive coupling group (such as MPA or bromo-MPA) is coupled at the last stage of the synthesis. As will be appreciated, the chemically reactive coupling group should be placed at a site to allow the peptide to bond to the conformationally modified albumin while retaining its biological activity.

Peptide elongation on solid support: Solid phase peptide synthesis was carried out using the modified Ramage resin (substitution level 0.45 mmol/g) on a 100 μmole scale. The following protected amino acids were sequentially added to the resin: Fmoc-Lys40(Aloc)-OH; Fmoc-Ser(tBu)-OH; Fmoc-Pro-OH; Fmoc-Pro-OH; Fmoc-Pro-OH; Fmoc-Ala-OH.(H2O); Fmoc-Gly-OH; Fmoc-Ser(tBu)-OH; Fmoc-Ser (tBu)-OH; Fmoc-Pro-OH; Fmoc-Gly-OH; Fmoc-Gly-OH;

Fmoc-Asn(Trt)-OH; Fmoc-Lys(Boc)-OH; Fmoc-Leu-OH; Fmoc-Trp(Boc)-OH; Fmoc-Glu(OtBu)-OH (H2O); Fmoc-Ile-OH; Fmoc-Phe-OH; Fmoc-Leu-OH; Fmoc-Arg(Pmc)-OH; Fmoc-Val-OH; Fmoc-Ala-OH.(H2O); Fmoc-Glu (OtBu)-OH (H2O); Fmoc-Glu(OtBu)-OH (H2O); Fmoc-Glu(OtBu)-OH (H2O); Fmoc-Met-OH; Fmoc-Gln(Trt)-OH; Fmoc-Lys(Boc)-OH; Fmoc-Ser(tBu)-OH; Fmoc-Leu-OH; Fmoc-Asp(OtBu)-OH; Fmoc-Ser(tBu)-OH; Fmoc-Thr (tBu)-OH; Fmoc-Phe-OH; Fmoc-Thr(tBu)-OH; Fmoc-Gly-OH; Fmoc-Glu(OtBu)-OH (H2O); Fmoc-Gly-OH; Boc-His1(Boc)-OH.

A molar excess of Fmoc-amino acid/HBTU/DIEA was used for each coupling of amino acids (3-5 eq.), which were dissolved in N,N-dimethylformamide (DMF) and, according to the sequence, activated using O-benzotriazol-1-yl-N,N, N',N'-tetramethyl-uronium hexafluoro-phosphate (HBTU) and diisopropylethylamine(DIEA). Removal of the Fmoc protecting group was achieved using a solution of 20% piperidine/DMF for 20 minutes. After each coupling and/or Fmoc removal, the modified Ramage resin underwent washing cycles of 3×DMF followed by 3× isopropanol. This was repeated 3 more times, and the final wash was 1×DMF to swell the resin and prepare it for the next chemical step. It should be noted that the first amino acid anchored on the solid support can also be be Fmoc-Lys(Mtt)-OH or Fmoc-Lys(ivDDE)-OH as an alternative to Fmoc-Lys(Alloc)-OH or any Na-Fmoc-amino acid with a suitably protected orthogonal functionality that could lead to perform orthogonal chemistries of incorporating linker(s) such as AEEA and a reactive moiety to maleimidopropionic acyl (MPA).

Removal of the orthogonal protecting group on the first amino acid anchored on the solid support followed coupling of the linker AEEA and reactive moiety MPA: Orthogonal chemistries were performed selectively on the first amino acid anchored to the modified Ramage resin. Hence the orthogonal protecting group Alloc on the Lys40 was removed with 0.2 eq. tetrakis(triphenylphosphine)palladium (0) (Pd(PPh3)4) and 2 eq. tributyltin-hydride (Bu3SnH) in dry DCM for 1 h. The resin underwent washing cycles of 3×DMF followed by 3× isopropanol. This was repeated 3 more times, and the final wash was 1×DMF to swell the resin and prepare it for the next chemical step. The free amino functionality on the side chain of the Lys40 directly anchored on the modified Ramage resin was then acylated with Fmoc-AEEA-COOH under standard HBTU/DIEA coupling condition, which was followed by a standard washing cycle. Then, the Fmoc protecting the AEEA hydrophilic linker was removed using 20% piperidine/DMF for 20 minutes followed by a standard washing cycle. The free terminal amino moiety of the AEEA was subsequently acylated under standard HBTU/DIEA coupling conditions to yield the AB-013 intermediate.

Cleavage of the AB-013 intermediate from the resin and removal of all orthogonal protecting groups: The AB-013 intermediate was cleaved from the resin using 85% trifluoroacetic acid (TFA)/5% triisopropylsilane (TIS)/5% thioanisole and 5% phenol, followed by precipitation using ice cold (0-4° C.) ethyl ether (Et20). The crude peptide was collected on a polypropylene sintered funnel, dried, redissolved in a 40% mixture of acetonitrile (CH3CN) in water (0.1% TFA) and lyophilized to generate the corresponding crude material utilized in the purification process.

Purification: The AB-013 intermediate was purified by preparative reversed phase HPLC preparative binary HPLC system. The purification was performed using a Phenomenex Luna 10 phenyl-hexyl, 50 mm×250 mm column (10) equilibrated with a water/TFA mixture (0.1% TFA in H20

(solvent A) and acetonitrile/TFA (0.1% TFA in CH3CN (solvent B). Elution was achieved at 50 mL/min by running a 28-38% B gradient over 180 min. Fractions containing peptide were detected by UV absorbance at 214 and 254 nm. The fractions were collected in 25 mL aliquots. Molecular weights of peptides are determined using Quadrupole Electro Spray mass spectroscopy. Those containing the desired product were identified by liquid-chromatography mass spectrometry (LC-MS). The selected fractions were subsequently analyzed by analytical HPLC (20-60% B over 20 min; Phenomenex Luna 5 phenylhexyl, 10 mm×250 mm column, 0.5 mL/min) to identify fractions with >90% purity for pooling. The pooled fractions were homogenized, freeze-dried using liquid nitrogen and subsequently lyophilized for 2-3 days to yield a white amorphous powder.

Figure 31B:
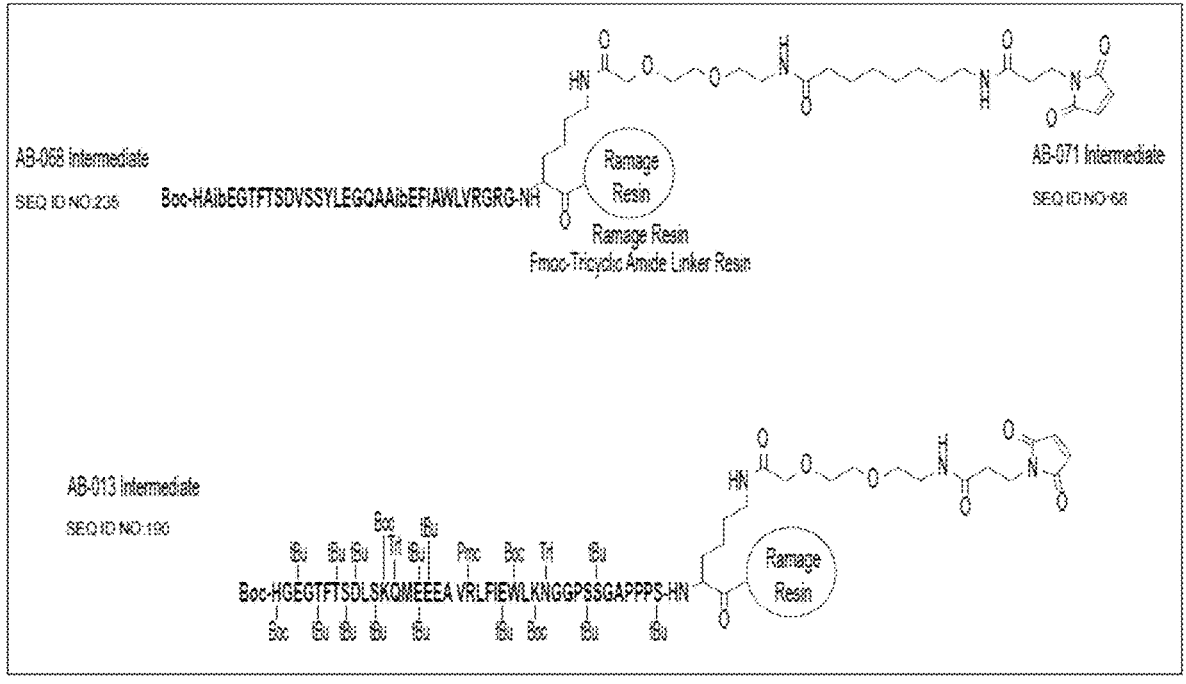
Figure 31C:
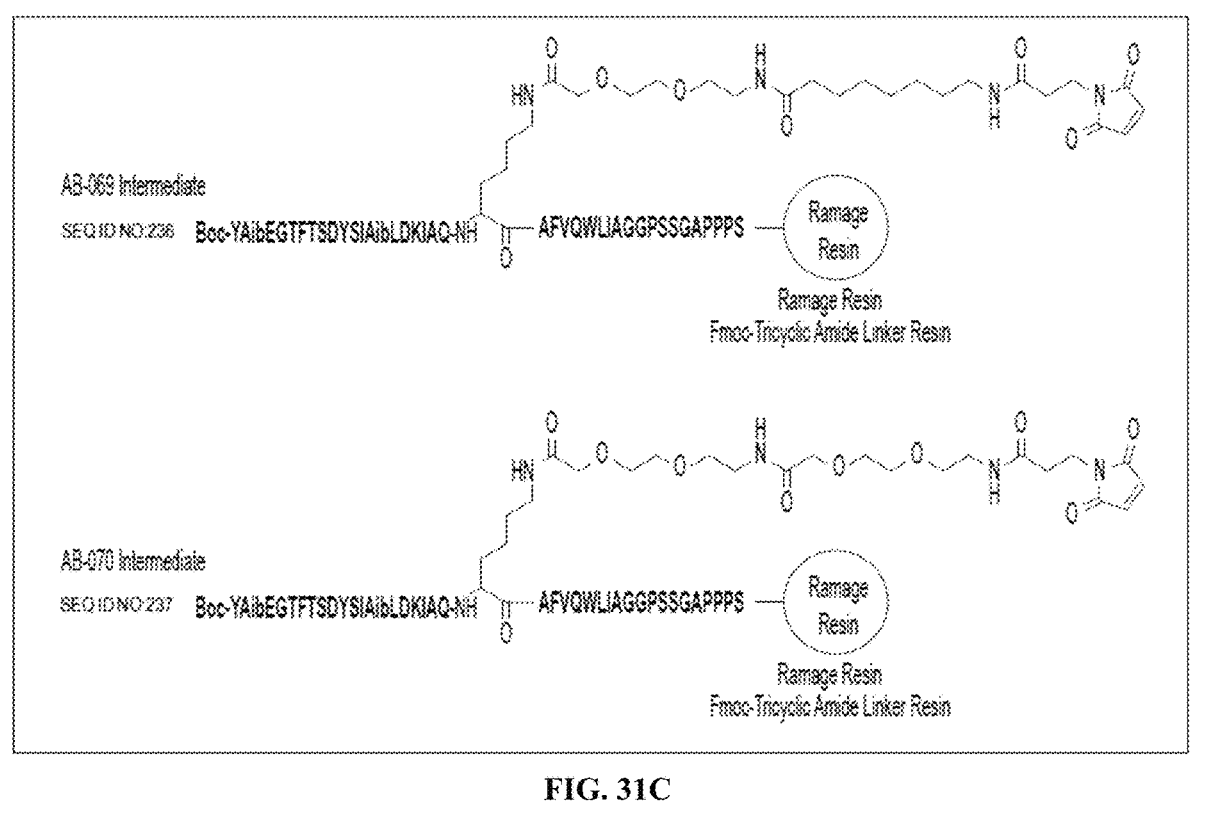

Of course, it should be appreciated that while the above examples and considerations are predominantly directed to linear peptide synthesis in which the reactive coupling group is covalently bound to the epsilon amino group of the C-terminal lysine amino acid, it should also be recognized that the reactive coupling group may also be covalently bound to the epsilon amino group of a lysine amino acid in a position other than a terminal position (e.g., at a position between the second and tenth amino acid, or at a position between the eleventh and twentieth amino acid, or at a position between the twenty first and thirtieth amino acid, or at a position between the thirty first and thirty ninth amino acid. FIG. 31 depicts exemplary structures of peptide agonist intermediates bound to a Ramage or Rink resin, and with protected intermediate for AB-013. Most typically, where the linker and reactive coupling group is at the C-terminal end of the agonist peptide, a Ramage resin is typically preferred. On the other hand, where the linker and reactive coupling group is coupled t the agonist in an intermediate position (and typically beyond the tryptophan cage where present) a Rink (amide) resin can be employed. As will be readily recognized, all resin-bound intermediates may be fully protected, or at least partially deprotected. Therefore, exemplary contemplated agonist peptide intermediates may have a sequence of SEQ ID NO:322, which is generically and schematically illustrated in FIG. 32. When bound to a resin, the intermediates may therefore also have a sequence of SEQ ID NO:322 and SEQ ID NO:323 shown below, with variable amino acids as shown in FIG. 32 and listed in the sequence listing.

$$\text{SEQ ID NO: } 322$$
$$X_1X_2X_3GTFTSDX_4X_5X_6X_7LX_8X_9X_{10}X_{11}X_{12}X_{13}X_{14}FX_{15}$$
$$X_{16}WLX_{17}X_{18}GX_{19}PSSGAPPPSX_{20}\text{-Ramage Resin}$$

$$\text{SEQ ID NO: } 323$$
$$X_1X_2X_3GTFTSDX_4X_5X_6X_7LX_8X_9X_{10}X_{11}X_{12}X_{13}X_{14}FX_{15}$$
$$X_{16}WLX_{17}X_{18}GX_{19}PSSGAPPPS\text{-Rink Resin}$$

Furthermore, it should be recognized that the agonist peptides may be synthesized in a single linear Merrifield synthesis process, or in a synthetic process in which two or more sub-sequences are condensed to a final sequence product. For example, a first peptide subsequence SEQ ID NO:324 may be coupled to a Ramage or Rink resin, while protected second and third subsequences SEQ ID NO:325 and SEQ ID NO:326 are prepared on respective chlorotrityl resins as shown below with variable amino acids as shown in FIG. 32.

$$\text{SEQ ID NO: } 324$$
$$NH_2X_{19}PSSGAPPPSX_{20}\text{-Ramage Resin}$$

$$\text{SEQ ID NO: } 325$$
$$Fmoc\text{-}X_{11}X_{12}X_{13}X_{14}FX_{15}X_{16}WLX_{17}$$
$$X_{18}G\text{-Chlorotrityl Resin}$$

$$\text{SEQ ID NO: } 326$$
$$Boc\text{-}X_1X_2X_3GTFTSDX_4X_5X_6X_7LX_8X_9$$
$$X_{10}\text{-Chlorotrityl Resin}$$

After decoupling from the resin of the second and third subsequences (resulting in N-terminal protected SEQ ID NO:325 and SEQ ID NO:326 having an unprotected C-terminus, respectively, $$\text{SEQ ID NO: } 325$$
$$Fmoc\text{-}X_{11}X_{12}X_{13}X_{14}FX_{15}X_{16}WLX_{17}X_{18}G\text{-COOH}$$

$$\text{SEQ ID NO: } 326$$
$$Boc\text{-}X_1X_2X_3GTFTSDX_4X_5X_6X_7LX_8X_9X_{10}\text{-COOH}$$

the second subsequence SEQ ID NO:325 is condensed with the first subsequence SEQ ID NO:324 to yield resin-bound SEQ ID NO:328 shown below. Of course, it should be appreciated that other first peptide subsequences are also deemed suitable, and an exemplary subsequence is SEQ ID NO:327, bound to a Rink resin.

$$\text{SEQ ID NO: } 328$$
$$Fmoc\text{-}X_{11}X_{12}X_{13}X_{14}FX_{15}X_{16}WLX_{17}X_{18}G\text{-}$$
$$X_{19}PSSGAPPPSX_{20}\text{-Ramage Resin}$$

While the reaction product remains on the resin, the N-terminal protecting group is removed, resulting in deprotected SEQ ID NO:328 with a free $NH_2$ group at the N-terminus, $$\text{SEQ ID NO: } 328$$
$$NH_2\text{-}X_{11}X_{12}X_{13}X_{14}FX_{15}X_{16}WLX_{17}X_{18}G\text{-}X_{19}$$
$$PSSGAPPPSX_{20}\text{-Ramage Resin}$$

to which the third deprotected subsequence SEQ ID NO:326 with deprotected C-terminus is coupled, resulting in the final resin-bound SEQ ID NO:329 with variable amino acids as shown in FIG. 32.

$$\text{SEQ ID NO: } 329$$
$$Boc\text{-}X_1X_2X_3GTFTSDX_4X_5X_6X_7LX_8X_9X_{10}\text{-}X_{11}$$
$$X_{12}X_{13}X_{14}FX_{15}X_{16}WLX_{17}X_{18}G\text{-}X_{19}PSSGAPP$$
$$PSX_{20}\text{-Ramage Resin}$$

In view of the above, it should therefore be appreciated that peptide solid state synthesis intermediates can be readily prepared that include a Ramage resin to which a first amino acid of a peptide is covalently coupled at a C-terminus of the peptide via an amide bond, wherein the first amino acid is further covalently coupled to a linker via an amide bond in a side chain of the first amino acid, and wherein the linker comprises a reactive coupling group.

As already noted above, agonists with a linker and reactive coupling group may also prepared where the linker and reactive coupling group is in an intermediate position in the agonist peptide. For example, synthesis of an intermediate with a reactive coupling group will typically follow known methodologies (see e.g., Stewart et al. in "Solid Phase Peptide Synthesis", W. H. Freeman Co. (San Francisco), 1963 and Meienhofer, Hormonal Proteins and Peptides, 1973, 2 46. For classical solution synthesis, see for example Schroder et al. in "The Peptides", volume 1, Academic Press (New York)). Such methodologies typically comprise the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complementary (amino or carboxyl) group suitably protected and under conditions suitable for forming the amide linkage. The protecting group is then removed from this newly added amino acid residue and the next amino acid (suitably protected) is added, and so forth. After all the desired amino acids have been linked in the proper sequence, any remaining protecting groups (and any solid support) are removed sequentially or concurrently to afford the final polypeptide. By simple modification of this general procedure, it is possible to add more than one amino 5 acid at a time to a growing chain, for example, by coupling (under conditions which do not racemize chiral centers) a protected tripeptide with a properly protected dipeptide to form, after deprotection, a pentapeptide.

Using the solid support 4-(2',4'-Dimethoxyphenyl-Fmoc-aminomethyl) phenoxy-acetamido MBHA resin (Rink amide MBHA resin), the Fmoc group is cleaved with a secondary amine, preferably piperidine in DMF (20% in DMF v:v), prior to coupling with the α-C-terminal amino acid. A method for coupling to the deprotected 4-(2',4'-Dimethoxyphenyl-Fmoc-aminomethyl) phenoxyacetamido MBHA resin is O-benzotriazol-1-ylN,N,N',N'-tetramethyl-uroniurnhexafluoro-phosphate (HBTU), diisopropylethyl-amine (DIEA), and optionally 1-hydroxybenzotriazole (HOBT), in DMF. The coupling of successive protected amino acids can be carried out in an automatic and/or semi-synthetic and/or manual peptide synthesizer in a conventional manner as is well known in the art. The removal of the Fmoc protecting group from the αN-terminal side of the growing peptide is accomplished conventionally, for example, by treatment with a secondary amine, preferably piperidine in DMF (20% v:v). Each protected amino acid is then introduced in 1-to-5-fold molar excess, and the coupling is preferably carried out in DMF and/or NMP. At the end of the peptide elongation on solid support and addition of the orthogonal functionalities such as linker(s) and a reactive moiety to the fully protected peptide it is removed from the resin and deprotected, either in successive operations or in a single operation. Removal of the polypeptide and deprotection can be accomplished conventionally in a single operation by treating the resin-bound polypeptide with a cleavage reagent comprising thioanisole, triisopropylsilane, phenol, and trifluoroacetic acid. In cases wherein the α-C-terminal of the polypeptide is an alkylamide, the resin is cleaved by aminolysis with an alkylamine. Alternatively, the peptide may be removed by transesterification, e.g., with methanol, followed by aminolysis or by direct transamidation. The protected peptide may be purified at this point or taken to the next step directly. The removal of the side chain protecting groups is accomplished using the cleavage mixture described above.

The fully deprotected peptide can be purified by a sequence of chromatographic steps employing any or all of the following types: ion exchange on a weakly basic resin (acetate form); hydrophobic adsorption chromatography on underivatized polystyrene-divinylbenzene (such as Amber-lite XAD™); silica gel adsorption chromatography; ion exchange chromatography on carboxymethylcellulose; partition chromatography, e.g., on Sephadex G-25™, LH-20™ or countercurrent distribution; high performance liquid chromatography (HPLC), especially reverse-phase HPLC on octyl- or octadecylsilylsilica bonded phase column packing. Anyone of ordinary skill in the art will be able to determine easily what would be the preferred chromatographic steps or sequences required to obtain acceptable purification of the peptide analogs.

For example, small scale peptide synthesis of the AB-092 intermediate can be performed as follows.

Peptide elongation on solid support: Solid phase peptide synthesis was carried out using the modified Rink MBHA resin (substitution level 0.5 mmol/g) on a 100 μmole scale. The following protected amino acids were sequentially added to resin: Fmoc-Ser39(tBu)-OH; Fmoc-Pro-OH; Fmoc-Pro-OH; Fmoc-Pro-OH; Fmoc-Ala-OH.(H2O); Fmoc-Gly-OH; Fmoc-Ser(tBu)-OH; Fmoc-Ser(tBu)-OH; Fmoc-Pro-OH; Fmoc-Gly-OH; Fmoc-Gly-OH; Fmoc-Glu (OtBu)-OH ($H_2O$); Fmoc-Leu-OH; Fmoc-Leu-OH; Fmoc-Tyr(OtBu)-OH; Fmoc-Glu(OtBu)-OH ($H_2O$); Fmoc-Ile-OH; Fmoc-Phe-OH; Fmoc-Ala-OH.(H2O); Fmoc-Aib-OH; Fmoc-Gln(Trt)-OH; Fmoc-Ala-OH ($H_2O$); Fmoc-Lys(Al-loc)-OH; Fmoc-Lys(Boc)-OH; Fmoc-Asp(OtBu)-OH; Fmoc-Leu-OH; Fmoc-αMetyl-Leu-OH; Fmoc-Ile-OH; Fmoc-Ser(tBu)-OH; Fmoc-Tyr(OtBu)-OH; Fmoc-Asp (OtBu)-OH; Fmoc-Ser(tBu)-OH; Fmoc-Thr(tBu)-OH; Fmoc-Phe-OH; Fmoc-Thr(tBu)-OH; Fmoc-Gly-OH; Fmoc-Gln(Trt)-OH (H2O); Fmoc-Aib-OH; Boc-Tyr1(OtBu)-OH. A molar excess of Fmoc-amino acid/HBTU/DIEA was used for each coupling of amino acids (3-5 eq.). They were dissolved in N,N-dimethylformamide (DMF) and, according to the sequence, activated using O-benzotriazol-1-yl-N,N, N',N'-tetramethyl-uronium hexafluorophosphate (HBTU) and diisopropylethylamine(DIEA). Removal of the Fmoc protecting group was achieved using a solution of 20% piperidine/DMF for 20 minutes. After each coupling and/or Fmoc removal the modified Ramage resin underwent washing cycles of 3×DMF followed by 3× Isopropanol. This was repeated 3 more times, and the final wash was 1×DMF to swell the resin and prepare it for the next chemical step. Alternatively, the first amino acid anchored on the solid support can be Fmoc-Lys(Mtt)-OH or Fmoc-Lys(ivDDE)-OH as an alternative to Fmoc-Lys(Alloc)-OH or any Na-Fmoc-amino acid with a suitably protected orthogonal functionality that could lead to perform orthogonal chemistries of incorporating linker(s) such as but not limited to AEEA and a reactive moiety such as but not limited to maleimi-dopropionic acyl (MPA).

Removal of the orthogonal protecting group on the first amino acid anchored on the solid support followed coupling of the linker AEEA twice and reactive moiety MPA. Orthogonal chemistries were performed selectively on the first amino acid anchored to the Rink amide MBHA resin. Hence the orthogonal protecting group Alloc on the Lys17 was removed with 0.2 eq. tetrakis(triphenylphosphine)pal-ladium (0) (Pd(PPh3)4) and 2 eq. tributyltin-hydride (Bu₃SnH) in dry DCM for 1 h. The resin underwent washing cycles of 3×DMF followed by 3× Isopropanol. This was repeated 3 more time, and the final wash was 1×DMF to swell the resin and prepare it for the next chemical step. The free amino functionality on the side chain of the $Lys_{17}$ directly anchored on the Rink amide MBHA resin was acylated with Fmoc-AEEA-COOH (twice) under standard HBTU/DIEA coupling condition. It was then followed by a standard washing cycle. Then, the Fmoc protecting the AEEA hydrophilic linker was removed using 20% piperidine/DMF for 20 minutes followed by a standard washing cycle. The free terminal amino moiety of the second AEEA was then acylated with under standard HBTU/DIEA coupling condition.

Cleavage of the AB-092 intermediate from the resin and removal of all orthogonal protecting groups: The AB-092 intermediate was cleaved from the resin using 85% trifluoroacetic acid (TFA)/5% triisopropylsilane (TIS)/5% thioanisole and 5% phenol, followed by precipitation using ice cold (0-4° C.) Ether (Et20). The crude peptide was collected on a polypropylene sintered funnel, dried, redissolved in a 40% mixture of acetonitrile (CH3CN) in water (0.1% TFA) and lyophilized to generate the corresponding crude material utilized in the purification process.

Purification protocol for small scale synthesis: The AB-092 intermediate was purified by preparative reversed phase HPLC preparative binary HPLC system. The purification was performed using a Phenomenex Luna 10 phenylhexyl, 50 mm×250 mm column (10) equilibrated with a water/TFA mixture (0.1% TFA in $H_2O$ (solvent A) and acetonitrile/TFA (0.1% TFA in $CH_3CN$ (solvent B). Elution was achieved at 50 mL/min by running a 28-38% B gradient over 180 min. Fractions containing peptide were detected by UV absorbance at 214 and 254 nm. The fractions were collected in 25 mL aliquots. Molecular weights of peptides are determined using Quadrupole Electro Spray mass spectroscopy. Those containing the desired product were identified by liquid-chromatography mass spectrometry (LC-MS). The selected fractions were subsequently analyzed by analytical HPLC (20-60% B over 20 min; Phenomenex Luna 5 phenylhexyl, 10 mm×250 mm column, 0.5 mL/min) to identify fractions with >90% purity for pooling. The pooled fractions were homogenized, freeze-dried using liquid nitrogen and subsequently lyophilized for at least 2-3 days to yield a white amorphous powder.

In view of the above, it should therefore be appreciated that contemplated resin-immobilized cysteine-reactive Class B GPCR agonist peptides will include a GPCR agonist peptide comprising a Lys amino acid to which (a) a linker is covalently bound via an amide bond formed by an epsilon amino group of the Lys amino acid, and (b) a synthetic resin with a spacer is covalently bound via an amide bond formed by a distal amino group in the spacer. With respect to suitable GPCR agonist peptides, linker, and resins, the same considerations as provided above apply.

With respect to suitable resin beads it is generally known that reaction kinetics are generally faster using smaller beads due to the higher surface area to volume ratio. In practice, however, too small a bead can lead to extended filtration times. Therefore, suitable resin beads will have a size in the range of 75 to 150 microns in diameter offer a good balance of reaction kinetics versus reliability or 35-75 microns respectively. Typically, the resins will have a substitution level varying from 0.1 to 2.0 mmol/g, and more preferably between 0.4 and 0.6 mmol/g.

It should further be appreciated that peptides have either a carboxylic acid group (—COOH) or an amide group (—CONH$_2$) at their C-terminus. Therefore, common resins for preparing peptide amides include MBHA, BHA, Rink amide, Knorr, DCHD, PAL, Seiber, and Ramage (tricyclic amide) resins. Alternatively, and especially where smaller peptides with less steric demand are prepared, suitable resins include Merrifield, hydroxymethyl polystyrene, Wang, and 2-chlorotrityl resins. Among other factors, suitable resins can be selected based on the following considerations: aminomethyl (AM) resins have long been used in solid phase peptide synthesis as a core resin to which various linkers could be attached through a stable amide bond. 4-Methylbenzhydryl amine (MBHA) resins, however, were originally developed for the formation of peptide amides using the Boc-N protection/TFA deprotection strategy. These resins form very stable amide or amine linkages to either carboxylic or electrophilic alkyl substrates. Generally, strong acid conditions are required to cleave substrates from these resins. Solid phase supports for the formation of amide products including Rink and Ramage resins were originally developed for peptide amide synthesis using the Fmoc strategy. These resins are favored due to their higher acid lability; cleavage can be performed under conditions as mild as 1% TFA. The Sieber resin is useful for preparing amides and amines and fully protected peptide amide fragments. Products can be cleaved under mild conditions using 1% TFA in DCM. This resin is less sterically hindered than Rink resin and thus allows for higher loading in sterically demanding applications than Rink resins. MBHA (methylbenzhydryl amine) is an amide-forming resin structurally similar to Rink however conditions for cleaving peptide products from MBHA are much harsher than from Rink as MBHA requires treatment with hydrofluoric acid or trifluoromethanesulfonic acid (TFMSA). Trityl and 2-Chlorotrityl resins have been widely used in peptide chemistry. These resins are very acid labile and can be cleaved with acetic acid and protected peptides can be cleaved with 1:4 v/v hexafluoroisopropyl alcohol/dichloromethane with all sidechain protecting groups intact, even trityl groups on sulfhydryl function of homocysteine. The Trityl and 2-Chlorotrityl resins are particularly useful when less acid labile protecting groups are required on the substrate following cleavage resulting in fully protected short peptides and/or peptide fragments/components capable of undergoing a hybrid manufacturing process leading to the desired larger peptide structure.

In view of the above, preferred resins for the solid phase synthesis of peptide intermediates will therefore include MBHA, BHA, Rink amide, Knorr, DCHD, PAL, Seiber, and Ramage (tricyclic amide) resins, and especially a Ramage (tricyclic amide) resin. Moreover, preferred resins will be about 1% cross-linked, with a size of between 200-400 Mesh.

As will be further appreciated, the peptide intermediates presented herein can be produced using one of three synthesis methods: solid phase peptide synthesis (SPPS), liquid phase peptide synthesis (LPPS) or a hybrid approach. LPPS could produce large quantities of high-quality short peptides and/or peptide fragments/components of a larger peptide structure. Alternatively, SPPS could provide peptides of longer lengths but, depending on the structure, could have diminished yields typically due to challenges in removing closely related impurities from the desired product. A hybrid approach could bring the SPPS and LPPS methodologies together to produce peptides. For example, to construct a 40-amino acid peptide intermediate, small peptides of 10 to 15 amino acid segments would be produced using SPPS and then the segment condensations would occur in LPPS to construct the full peptide intermediate sequence as exemplarily shown above.

Thus, and in view of the above, it should be appreciated that Class B GPCR agonist fusion proteins can be readily prepared by providing or producing a conformationally modified albumin as described above and by covalently coupling a GPCR agonist peptide to $Cys_{34}$ of the conformationally modified albumin via a Michael addition reaction, typically at a pH of pH<7.0. With respect to the GPCR agonist peptide, the linker, the reactive coupling group, and the albumin, the same considerations as provided above apply.

For example, especially suitable agonist peptides are provided in Table 1 below in which the amino acids and modifying characters are as provided in the sequence listing of this application. Moreover, it should be appreciated that (1) sequences in the table without linker modifications may also include a linker modification as described herein, particularly where the linker modification is covalently attached to an epsilon amino group of a lysine, and suitable linker modifications include MPA, (bromo)MPA, AEEA, AEEA-MPA, AEEA-(bromo)MPA, $(AEEA)_2$-MPA, $(AEEA)_2$-(bromo)MPA, AEEEA-OA-MPA, AEEEA-OA-(bromo)MPA, AEEA-OA-AEEA-MPA, AEEA-OA-AEEA-(bromo)

MPA, $(AEEEA)_2$-OA-MPA, and $(AEEEA)_2$-OA-(bromo)MPA; (2) any specific linker modification shown in the table below (e.g., AEEA-MPA) as indicated by a particular modifying character may be replaced with any other linker modification contemplated herein (e.g., AEEA-AEEA-MPA); (3) the C-terminal amino acid may be covalently attached to a solid phase (e.g., modified Ramage resin), preferably via a spacer group; (4) any sequence in the table below may be covalently coupled via a linker as described herein to albumin at $Cys_{34}$, preferably in a retro-Michael resistant manner (e.g., in a stereopreferred or stereoselective manner); and (5) any sequence in the table below having a linker modification is also contemplated as an agonist peptide sequence without the linker modification. Unless noted otherwise, * indicates a suitable linker modification of AEEA-MPA, # indicates a suitable linker modification of AEEA-OA-AEEA-MPA. " indicates a suitable linker modification of AEEEA-OA-MPA. and ^indicates a suitable linker modification of $(AEEA)_2$-MPA.

| SEQ ID NO: | SEQUENCE |
|---|---|
| 1 | HaEGTFTSDVSSYLEGQAAKEFIAWLVKGRK* |
| 2 | HGEGTFTSDLSKQMEEEAVRLFIEWLKNGGPSSGAPPPSK* (Albenatide-AB013 when bound to $Cys_{34}$ in retro-Michael resistant/stereopreferred or stereoselective manner via maleimide reactive group) |
| 3 | HGEGTFTSDLSKQMEEEAVRLFIEWLKNGGPSSGAPPPS |
| 4 | HAEGTFTSDVSSYLEGQAAKEFIAWLVKGR |
| 5 | YAEGTFISDYSIAMDKIHQQDFVNWLLAQKGKKNDWKHNITQ |
| 6 | HSQGTFTSDYSKYLDSRRAQDFVQWLMNT |
| 7 | HaEGTFTSDVSSYLEGQAAKEFIAWLVNGGPSSGAPPPSK* (Albugiptide-AB-029 when bound to $Cys_{34}$ in retro-Michael resistant/stereopreferred or stereoselective manner via maleimide reactive group) |
| 8 | HaEGTFTSDYAKYLDARRAKEFIAWLVKGRPSSGAPPPSK* |
| 9 | HGEGTFTSDLSKQMEEEAVRLFIEWLKNGGPK*SGAPPPS |
| 10 | HaEGTFTSDVSK*YLEGQAAKEFIAWLVKGRPSSGAPPPS |
| 11 | HaEGTFTSDVSSYLEK*QAAKEFIAWLVKGRPSSGAPPPS |
| 12 | HGEGTFTSDLSKQMEEEAVRLFIEWLKNGGPK*SGAPPPS |
| 13 | HaEGTFTSDINKVLDTIAAKEFIAWLVKGRPSSGAPPPSK* |
| 14 | YAibEGTFTSDYSIYLDKQAAAibEFVQWLLAGGPSSGAPPPSK* (* denotes a suitable linker modification of C16 Acyl) |
| 15 | YGGGTFTSDSFFYLELSHAKDFINWLQLGaPSSGAPPPSK* |
| 16 | HAibAibGTFTSDEMNYLDDWMQAibAFVNWLVAibGIPSSGAPPPSK* |
| 17 | FAibPGTFTSDGHNYLDWQDAKEFIQWLGWGVPSSGAPPPSK* |
| 18 | YAibMGTFTSDPQIAibLEMKEQAibDFINWLNDGFPSSGAPPPSK* |
| 19 | HaPGTFTSDNHEAibLDTYRQAibDFINWLDTGVPSSGAPPPSK* |
| 20 | YaNGTFTSDIWAYLDSSFAQDFVAWLYIGKPSSGAPPPSK* |
| 21 | HAibDGTFTSDFEHYLEDAVQKAFIAWLSTGVPSSGAPPPSK* |

-continued

| SEQ ID NO: | SEQUENCE |
|---|---|
| 22 | FGDGTFTSDLRGAibLEIMPQAibAFVNWLTSGKPSSGAPPPSK* |
| 23 | HaaGTFTSDsMIYLDNAHQQEFIQWLFNGPPSSGAPPPSK* |
| 24 | HaIGTFTSDsTAibYLEaYKQAibDFVQWLHSGGPSSGAPPPSK* |
| 25 | YsWGTFTSDaGYYLDMsFQQAFIQWLKAGaPSSGAPPPSK* |
| 26 | YGRGTFTSDWIYAibLDTaPQKEFVEWLHsGAPSSGAPPPSK* |
| 27 | YaMGTFTSDSEEAibLEMVYQQAFVAWLPVGGPSSGAPPPSK* |
| 28 | FssGTFTSDWDWAibLDIAibIAAibEFINWLVYGYPSSGAPPPSK* |
| 29 | FAibGGTFTSDDMRYLEPKGQQAFIQWLWVGQPSSGAPPPSK* |
| 30 | YAibSGTFTSDVETYLDLLIAKEFIAWLGAGAibPSSGAPPPSK* |
| 31 | HGRGTFTSDHQFAibLDSMIQAibEFIQWLHYGIPSSGAPPPSK* |
| 32 | YaRGTFTSDFINAibLEsGVAKAFVNWLQEGaPSSGAPPPSK* |
| 33 | HsFGTFTSDGWMYLDMNEQKAFVAWLYaGaPSSGAPPPSK* |
| 34 | FsRGTFTSDHYRAibLDQSKAAibEFIEWLESGNPSSGAPPPSK* |
| 35 | FsGGTFTSDHHRYLDQIPQKDFIQWLEFGKPSSGAPPPSK* |
| 36 | FaQGTFTSDaNMAibLDMFaQKAFINWLFQGGPSSGAPPPSK* |
| 37 | FaAGTFTSDVTaAibLEVAibQQKAFIAWLNLGQPSSGAPPPSK* |
| 38 | HaIGTFTSDHMAibYLDsDPAQDFIEWLMPGSPSSGAPPPSK* |
| 39 | HAibNGTFTSDIIHYLDPIVQKAFIEWLNGGAPSSGAPPPSK* |
| 40 | HGEGTFTSDMAibQAibLDREIAKEFVEWLFFGYPSSGAPPPSK* |
| 41 | HsPGTFTSDPDsAibLDENHQQAFVAWLNsGMPSSGAPPPSK* |
| 42 | FsaGTFTSDsLDYLEssEQAibEFINWLAAGVPSSGAPPPSK* |
| 43 | YaAibGTFTSDKDPYLEAibTYAAibEFVAWLVsGRPSSGAPPPSK* |
| 44 | FGRGTFTSDAVMAibLDAMQAKAFIEWLWIGIPSSGAPPPSK* |
| 45 | HaaGTFTSDVDYAibLEWKIQQDFIEWLSTGLPSSGAPPPSK* |
| 46 | YsFGTFTSDIAGYLDLEAibAAibAFVQWLAHGKPSSGAPPPSK* |
| 47 | HsHGTFTSDEVQYLDMDGQQEFINWLDLGYPSSGAPPPSK* |
| 48 | HsRGTFTSDLQGAibLEYADQAibDFVNWLAibTGFPSSGAPPPSK* |
| 49 | HGFGTFTSDGIDAibLEaITAKEFIAWLaIGKPSSGAPPPSK* |
| 50 | HAibTGTFTSDIalAibLDYKGAAibAFVQWLDAGEPSSGAPPPSK* |
| 51 | HsLGTFTSDLAibMAibLDVNIAAibDFIAWLMIGYPSSGAPPPSK* |
| 52 | YGDGTFTSDKHRAibLEISQQKEFVQWLLsGLPSSGAPPPSK* |
| 53 | FaaGTFTSDQTTAibLDAGSAKDFVNWLVAibGAibPSSGAPPPSK* |
| 54 | YAibGGTFTSDEPPYLDAWTQAibEFVEWLVRGWPSSGAPPPSK* |
| 55 | HaGGTFTSDGSRAibLDIaTQQDFIEWLLEGHPSSGAPPPSK* |
| 56 | HsSGTFTSDPLKYLDHGNQQAFVNWLISGSPSSGAPPPSK* |
| 57 | HAibTGTFTSDISFYLEEYVAQEFVAWLQAGsPSSGAPPPSK* |
| 58 | HsaGTFTSDaYEAibLEPAibDQKAFIAWLWHGLPSSGAPPPSK* |
| 59 | YsRGTFTSDATLAibLEGSKQKAFINWLLEGIPSSGAPPPSK* |

-continued

| SEQ ID NO: | SEQUENCE |
| --- | --- |
| 60 | FGWGTFTSDLEKAibLELARAQAFVEWLKVGSPSSGAPPPSK* |
| 61 | FAibMGTFTSDPYPYLEWEaAQAFINWLsGGSPSSGAPPPSK* |
| 62 | HaAibGTFTSDMPTAibLDHIQQQDFVAWLVQGIPSSGAPPPSK* |
| 63 | FasGTFTSDHSDAibLELKAQQEFVNWLRNGRPSSGAPPPSK* |
| 64 | HGQGTFTSDYSKYLDARRAQDFVEWLKNGGPSSGAPPPSK* |
| 65 | HAibQGTFTSDYSKAibLDKRRAKDFVEWLKNGGPSSGAPPPSK* |
| 66 | HAibQGTFTSDYSKYLDKRRAKDFVEWLKNGGPSSGAPPPSK* |
| 67 | YAibQGTFTSDYSImeILDKIAQAibAFIEYLLEGGPSSGAPPPSK* |
| 68 | YAibEGTFTSDYSIAibLDKIAQKAFVQWLIAGGPSSGAPPPSK* |
| 69 | HaEGTFTSDYAKYLDARRAKEFIAWLVNGGPSSGAPPPSK* |
| 70 | YAibEGTFTSDYSIYLDKQAAAibEFVQWLLAGGPSSGAPPPSK* |
| 71 | HAibHGTFTSDLSKLLEEQRQAibEFIEWLKAaGPPPSAibKPPPK* |
| 72 | HaMGTFTSDRHWYLDMSHQK*AFVQWLAYGNPSSGAPPPS |
| 73 | YasGTFTSDWGRYLELLIQK*EFVNWLIIGAPSSGAPPPS |
| 74 | HGKGTFTSDsAIAibLEVsaAK*AFIEWLaHGDPSSGAPPPS |
| 75 | HasGTFTSDILEAibLDQAAAK*EFVEWLaHGFPSSGAPPPS |
| 76 | HaYGTFTSDYMAibAibLDFLQQK*DFVAWLFMGVPSSGAPPPS |
| 77 | HAibsGTFTSDAibAYYLDNTTAK*DFIQWLDAGPPSSGAPPPS |
| 78 | FAibKGTFTSDDaVYLEAibHRAK*EFVEWLFGGsPSSGAPPPS |
| 79 | YAibHGTFTSDLTVAibLDEIKAK*EFVEWLAibVGPPSSGAPPPS |
| 80 | FsWGTFTSDFPaAibLEAibMKAK*DFVEWLLDGNPSSGAPPPS |
| 81 | HAibKGTFTSDDADAibLEWYRQK*AFVQWLPsGIPSSGAPPPS |
| 82 | YAibWGTFTSDSNSAibLEAKMQK*EFVNWLsQGFPSSGAPPPS |
| 83 | FaTGTFTSDDADYLELFsQK*AFIAWLDNGVPSSGAPPPS |
| 84 | YSYGTFTSDWDAAibLESAibMQK*EFVQWLFYGQPSSGAPPPS |
| 85 | YaNGTFTSDTNsAibLDSTQAK*EFVAWLVQGDPSSGAPPPS |
| 86 | FAibIGTFTSDKQAYLEHPRQK*AFVAWLDVGYPSSGAPPPS |
| 87 | HAibRGTFTSDKFIAibLEYHNAK*EFVAWLYKGsPSSGAPPPS |
| 88 | FGHGTFTSDSIWYLENYSQK*EFIEWLEKGPSSGAPPPS |
| 89 | HsaGTFTSDIRAibYLEIMLQK*EFVEWLaEGVPSSGAPPPS |
| 90 | HAibFGTFTSDMLNYLEENSQK*EFVNWLQLGMPSSGAPPPS |
| 91 | FGHGTFTSDIWIYLEVQTAK*DFINWLSWGEPSSGAPPPS |
| 92 | HsGGTFTSDSGPYLDKTDQK*AFINWLPIGNPSSGAPPPS |
| 93 | YSIGTFTSDHsPAibLDHLFAK*DFVEWLENGDPSSGAPPPS |
| 94 | FGYGTFTSDKEGAibLEQsAibAK*EFIQWLPHGPPSSGAPPPS |
| 95 | FsWGTFTSDFAibsAibLDTTRAK*DFVEWLIRGNPSSGAPPPS |
| 96 | HAibPGTFTSDHEKYLEMVSAK*DFIAWLRAibGDPSSGAPPPS |
| 97 | YaAGTFTSDTIaAibLDNaAAK*DFIAWLIQGYPSSGAPPPS |

-continued

| SEQ ID NO: | SEQUENCE |
|---|---|
| 98 | YAibLGTFTSDTIHAibLEFEAQK*DFINWLKAGEPSSGAPPPS |
| 99 | YAibQGTFTSDAMIYLDTPDAK*EFIAWLAibIGGPSSGAPPPS |
| 100 | YGAGTFTSDHAibGAibLDIAibQQK*EFVQWLETGTPSSGAPPPS |
| 101 | YaVGTFTSDLSEYLEMNIAK*DFVQWLLVGGPSSGAPPPS |
| 102 | YGPGTFTSDRYSYLEQHMAK*EFIQWLGPGHPSSGAPPPS |
| 103 | YAibRGTFTSDMRVYLEETLOK*AFVQWLIaGDPSSGAPPPS |
| 104 | YsAibGTFTSDFMEAibLDKKIQK*DFIQWLWYGSPSSGAPPPS |
| 105 | FAibsGTFTSDELRYLEEMHQK*AFIQWLAibTGFPSSGAPPPS |
| 106 | YGPGTFTSDWAKYLEGRDAK*AFINWLsQGSPSSGAPPPS |
| 107 | HGVGTFTSDHHFAibLEIIMAK*AFIEWLWHGaPSSGAPPPS |
| 108 | HGIGTFTSDVPAYLDPAaAK*DFIQWLVSGGPSSGAPPPS |
| 109 | HsNGTFTSDRRKAibLEPPIAK*EFVQWLIAibGIPSSGAPPPS |
| 110 | FAibTGTFTSDTMaYLDYTHAK*DFIAWLIDGKPSSGAPPPS |
| 111 | YaTGTFTSDsVQYLEHPMQK*AFVAWLHTGRPSSGAPPPS |
| 112 | YAibTGTFTSDEEWYLDNWMQK*AFVQWLSNGAibPSSGAPPPS |
| 113 | YSIGTFTSDGNKAibLEAibGRAK*AFIAWLQYGRPSSGAPPPS |
| 114 | YsPGTFTSDMYVYLEPGDAK*EFVQWLKNGGPSSGAPPPS |
| 115 | FsIGTFTSDLMaAibLERAAQK*EFVNWLIIGSPSSGAPPPS |
| 116 | YAibNGTFTSDIEQYLEPMVQK*EFVQWLSPGNPSSGAPPPS |
| 117 | YGWGTFTSDSFsAibLDWMMAK*AFIQWLIVGIPSSGAPPPS |
| 118 | HsPGTFTSDAibTHYLDNDQQK*DFVNWLPEGWPSSGAPPPS |
| 119 | YGaGTFTSDNHTAibLESFAAK*EFIQWLNSGQPSSGAPPPS |
| 120 | YaMGTFTSDRLRAibLDQFSAK*AFVNWLSWGEPSSGAPPPS |
| 121 | FAibaGTFTSDSLAibAibLDHHNQK*AFVEWLaPGLPSSGAPPPS |
| 122 | HGQGTFTSDYSKYLDK*RRAQDFVEWLKNGGPSSGAPPPS |
| 123 | HAibQGTFTSDYSKAibLDKRRAK*DFVEWLKNGGPSSGAPPPS |
| 124 | HAibQGTFTSDYSKYLDK*RRAQDFVEWLKNGGPSSGAPPPS |
| 125 | YAibEGTFTSDYSIAibLDKIAQK*AFVQWLIAGGPSSGAPPPS |
| 126 | YAibQGTFTSDYSImeILDKIAQK*AFIEYLLEGGPSSGAPPPS |
| 127 | HaEGTFTSDYAKYLDARRAK*EFIAWLVNGGPSSGAPPPS |
| 128 | YaWGTFTSDsKDYLEFK*WAAibEFIQWLDPGDPSSGAPPPS |
| 129 | FAibYGTFTSDINVAibLDIK*WAAibAFINWLPGGIPSSGAPPPS |
| 130 | FaaGTFTSDRQEAibLDVK*LAAibEFVQWLVSGDPSSGAPPPS |
| 131 | FaRGTFTSDSMQAibLETK*RQQEFVNWLsMGVPSSGAPPPS |
| 132 | YaHGTFTSDTNRAibLESK*AAAibEFIAWLEVGAPSSGAPPPS |
| 133 | FAibGGTFTSDFRsAibLDsK*IAAibEFINWLFKGFPSSGAPPPS |
| 134 | YAibNGTFTSDMMPYLEPK*HQKDFVEWLTSGDPSSGAPPPS |
| 135 | HaPGTFTSDIIHYLETK*IAAibEFIQWLKRGSPSSGAPPPS |

-continued

| SEQ ID NO: | SEQUENCE |
| --- | --- |
| 136 | FsVGTFTSDAibSAAibLDLK*IAAibEFINWLFaGFPSSGAPPPS |
| 137 | YAibaGTFTSDGNMYLDKK*HAKDFIEWLsSGPPSSGAPPPS |
| 138 | YaIGTFTSDPsHAibLEVK*NQKEFVQWLNRGIPSSGAPPPS |
| 139 | FsTGTFTSDFVEAibLEIK*EQKAFIEWLAQGGPSSGAPPPS |
| 140 | FGTGTFTSDFDGYLEDK*aAKAFIQWLsGGMPSSGAPPPS |
| 141 | HsWGTFTSDWYIAibLEEK*NAAibDFIAWLYAGYPSSGAPPPS |
| 142 | FGPGTFTSDKKFAibLELK*GAKAFIAWLAibAibGFPSSGAPPPS |
| 143 | HsNGTFTSDaNsYLEPK*AAAibDFVNWLDAibGWPSSGAPPPS |
| 144 | FsTGTFTSDPWVYLDSK*QQQAFVEWLHFGNPSSGAPPPS |
| 145 | FaEGTFTSDWYPAibLDLK*SAAibDFVQWLYGGPSSGAPPPS |
| 146 | FGIGTFTSDTARAibLDDK*DQKEFVQWLNDGMPSSGAPPPS |
| 147 | FGYGTFTSDKSTYLDEK*IQAibDFVEWLNDGsPSSGAPPPS |
| 148 | HGSGTFTSDAAibPYLDQK*GAQDFIAWLDGGPSSGAPPPS |
| 149 | HaIGTFTSDPPVAibLEQK*HQQEFVAWLDPGLPSSGAPPPS |
| 150 | YaYGTFTSDVNKYLDPK*TAAibAFVEWLaQGIPSSGAPPPS |
| 151 | FaIGTFTSDRREYLEPK*EQAibDFIEWLRDGGPSSGAPPPS |
| 152 | YGNGTFTSDAWIYLDDK*LQKEFVQWLRLGNPSSGAPPPS |
| 153 | YaPGTFTSDaaAAibLEDK*YQAibAFIAWLAibQGWPSSGAPPPS |
| 154 | YGaGTFTSDIRAYLDEK*WAKAFVAWLVsGMPSSGAPPPS |
| 155 | YGWGTFTSDPINAibLDLK*AibQKDFVNWLPMGAPSSGAPPPS |
| 156 | HsNGTFTSDsYaYLERK*DQKAFIEWLWSGPPSSGAPPPS |
| 157 | YsMGTFTSDQGKYLEAK*SAQAFINWLMAibGAPSSGAPPPS |
| 158 | YaFGTFTSDLTRAibLDAibK*TAKAFIEWLDaGMPSSGAPPPS |
| 159 | YAibKGTFTSDAibIYYLDWK*NAAibAFVNWLHIGIPSSGAPPPS |
| 160 | HAibQGTFTSDWsAibAibLEKK*VQAibEFVNWLAibTGDP SSGAPPPS |
| 161 | FssGTFTSDDRaAibLDSK*aAQAFVAWLAibAGTPSSGAPPPS |
| 162 | YaIGTFTSDMKIYLDEK*aAKAFVQWLANGSPSSGAPPPS |
| 163 | FGQGTFTSDYDQAibLDNK*PQAibDFIEWLMYGEPSSGAPPPS |
| 164 | FsMGTFTSDLDRAibLDWK*IQKDFVQWLVSGTPSSGAPPPS |
| 165 | YsVGTFTSDLHSYLDLK*GAQDFVNWLVWGQPSSGAPPPS |
| 166 | HAibIGTFTSDDVYYLDLK*PQKEFVEWLGLGSPSSGAPPPS |
| 167 | FGVGTFTSDVMIAibLDIK*EQKEFINWLQSGEPSSGAPPPS |
| 168 | HAibFGTFTSDHAibsYLEsK*MAQDFINWLIIGsPSSGAPPPS |
| 169 | HaGGTFTSDPAKYLDSK*VQQEFVAWLAFGAibPSSGAPPPS |
| 170 | YaNGTFTSDVsFAibLEYK*DQKDFIQWLASGQPSSGAPPPS |
| 171 | FsVGTFTSDNRQYLDVK*NQAibDFIQWLPWGIPSSGAPPPS |
| 172 | HAibVGTFTSDKETYLDIK*KAAibDFVEWLSTGRPSSGAPPPS |
| 173 | FGWGTFTSDDFNAibLEYK*HAAibEFVNWLDVGQPSSGAPPPS |

-continued

| SEQ ID NO: | SEQUENCE |
| --- | --- |
| 174 | FaYGTFTSDQSYAibLDYK*TAKDFIQWLTKGRPSSGAPPPS |
| 175 | FGPGTFTSDDAibIYLEaK*NAQAFIEWLFSGQPSSGAPPPS |
| 176 | YAibIGTFTSDSsIAibLDSK*AQAibDFIQWLLFGQPSSGAPPPS |
| 177 | HsGGTFTSDPYGAibLEQK*MAKEFVEWLMTGKPSSGAPPPS |
| 178 | HaEGTFTSDYAKYLDAK*RAKEFIAWLVNGGPSSGAPPPS |
| 179 | YAibQGTFTSDYSImeILDKK*AQAibAFIEYLLEGGPSSGAPPPS |
| 180 | HGQGTFTSDYSKYLDK*RRAQDFVEWLKNGGPSSGAPPPS |
| 181 | HAibQGTFTSDYSKAibLDK*RRAQDFVEWLKNGGPSSGAPPPS |
| 182 | HAibQGTFTSDYSKYLDK*RRAQDFVEWLKNGGPSSGAPPPS |
| 183 | X1X2X3GTFTSDX4X5X6X7LX8X9X10X11X12X13X14 FX15X16WLX17X18GX19PSSGAPPPSX20 |
| 184 | X1X2X3GTFTSDX4X5X6X7LX8X9X10X11X12X13X14 FX15X16WLX17X18GX19PSSGAPPPSX20X21 |
| 185 | HAibEGTFTSDVSSYLEGQAAKEFIAWLVKGRK* (Albenatidex-AB-014 when bound to Cys34 in retro-Michael resistant/ stereopreferred or stereoselective manner via maleimide reactive group) |
| 186 | HAibEGTFTSDVSSYLEGQAAKEFIAWLVKGRK^ |
| 187 | HAibEGTFTSDVSSYLEGQAAKEFIAWLVKGRK" |
| 188 | HAibEGTFTSDVSSYLEGQAAKEFIAWLVKGRK |
| 189 | HAibEGTFTSDVSSYLEGQAAKEFIAWLVKGR9K* |
| 190 | HGEGTFTSDLSKQMEEEAVRLFIEWLKNGGPSSGAPPPSK^ |
| 191 | HGEGTFTSDLSKQMEEEAVRLFIEWLKNGGPSSGAPPPSK" |
| 192 | HGEGTFTSDLSKQMEEEAVRLFIEWLKNGGPSSGAPPPSK |
| 193 | HGEGTFTSDLSKQMEEEAVRLFIEWLKNGGPSSGAPPPS9K* |
| 194 | HsQGTFTSDYSKYLDSRRAQDFVQWLMNTGPSSGAPPPSK* |
| 195 | HsQGTFTSDYSKYLDSRRAQDFVQWLMNTGPSSGAPPPSK^ |
| 196 | HsQGTFTSDYSKYLDSRRAQDFVQWLMNTGPSSGAPPPSK" |
| 197 | HsQGTFTSDYSKYLDSRRAQDFVQWLMNTGPSSGAPPPSK |
| 198 | HsQGTFTSDYSKYLDSRRAQDFVQWLMNTGPSSGAPPPS9K* |
| 199 | YaEGTFISDYSIAMDKIHQQDFVNWLLAQGPSSGAPPPSK* |
| 200 | YaEGTFISDYSIAMDKIHQQDFVNWLLAQGPSSGAPPPSK^ |
| 201 | YaEGTFISDYSIAMDKIHQQDFVNWLLAQGPSSGAPPPSK" |
| 202 | YaEGTFISDYSIAMDKIHQQDFVNWLLAQGPSSGAPPPSK |
| 203 | YaEGTFISDYSIAMDKIHQQDFVNWLLAQGPSSGAPPPS9K* |
| 204 | HAEGTFTSDVSSYLEGQAAK*EFIAWLVRGR |
| 205 | HAibEGTFTSDVSSYLEGQAAK*EFIAWLVRGRG |
| 206 | HVEGTFTSDVSSYLEEQAAREFIK*WLVRGRG |
| 207 | HaEGTFTSDVSSYLEGQAAKEFIAWLVNGGPSSGAPPPSK^ |

| SEQ ID NO: | SEQUENCE |
|---|---|
| 208 | HaEGTFTSDVSSYLEGQAAKEFIAWLVNGGPSSGAPPPSK" |
| 209 | HaEGTFTSDVSSYLEGQAAKEFIAWLVNGGPSSGAPPPSK |
| 210 | HaEGTFTSDVSSYLEGQAAKEFIAWLVNGGPSSGAPPPS9K* |
| 211 | HaEGTFTSDVASYLEGQAAKEFIAWLVNGGPSSGAPPPSK* |
| 212 | YAibEGTFTSDYSIYLDKQAAAibEFVNWLLAGGPSSGAPPPSK* |
| 213 | HAibQGTFTSDYSKYLDEKKAK*EFVEWLLEGGPSSG |
| 214 | HAibQGTFTSDYSKYLDEK*AAKEFIQWLLQT |
| 215 | HAibQGTFTSDYSKYLDEKRAKEFVQWLMNTC* |
| 216 | HsQGTFTSDK*SKYLDARAAQDFVQWLLDT |
| 217 | HAc4cQGTFTSDYSKYLDERAAKDFIK*WLESA |
| 218 | HsQGTFTSDLSKQK*ESKAAQDFIEWLKAGGPSSGAPPPS |
| 219 | HSQGTFTSDK*SEYLDSERARDFVAWLEAGG |
| 220 | HAibQGTFTSDK*SKYLDERAAQDFVQWLLDGGPSSGAPPPS |
| 221 | HSQGTFTSDK*SKYLDERRAQDFVQWLLDGGPSSGAPPPS |
| 222 | HAibHGTGTSDLSKLK*EEQRQAibEFIEWLKAaGPPSAibKPPPK |
| 223 | HaQGTFTSDYAKYLDARRAKEFIAWLVNGGPSSGAPPPSK* (Albutide AB-044 when bound to Cys$_{34}$ in retro-Michael resistant/stereopreferred or stereoselective manner via maleimide reactive group) |
| 224 | HaQGTFTSDYAKYLDARRAKEFIAWLVNGGPSSGAPPPSK^ |
| 225 | HaQGTFTSDYAKYLDARRAKEFIAWLVNGGPSSGAPPPSK" |
| 226 | HaQGTFTSDYAKYLDARRAKEFIAWLVNGGPSSGAPPPSK |
| 227 | HaEGTFTSDYAKYLDARRAKEFIAWLVNGGPSSGAPPPSK^ |
| 228 | HaEGTFTSDYAKYLDARRAKEFIAWLVNGGPSSGAPPPSK" |
| 229 | HaEGTFTSDYAKYLDARRAKEFIAWLVNGGPSSGAPPPSK |
| 230 | HaEGTFTSDYAKYLDARRAKEFIAWLVNGGPSSGAPPPS9K* |
| 231 | YAEGTFISDYSIAMDKIHQQDFVNWLLAQKGKKNDWKHNITQ |
| 232 | HaEGTFTSDVASYLEGQAAKEFIAWLVNGGPSSGAPPPS9K* |
| 233 | HAibEGTFTSDVSSYLEGQAAK^EFIAWLVRGRG |
| 234 | HAibEGTFTSDVSSYLEGQAAKEFIAWLVRGRGK* |
| 235 | HAibEGTFTSDVSSYLEGQAAAibEFIAWLVRGRGK" |
| 236 | YAibEGTFTSDYSIAibLDKIAQK"AFVQWLIAGGPSSGAPPPS |
| 237 | YAibEGTFTSDYSIAibLDKIAQK^AFVQWLIAGGPSSGAPPPS |
| 238 | YAibEGTFTSDYSIYLDKQAAAibEFVQWLLAGGPSSGAPPPSK^ |
| 239 | YAibEGTFTSDYSIYLDKQAAAibEFVQWLLAGGPSSGAPPPSK# |
| 240 | HAibQGTFTSDYSKYLDEKKAK^EFVEWLLEGGPSSG |
| 241 | HAibQGTFTSDYSKYLDEKKAK"EFVEWLLEGGPSSG |
| 242 | HAibQGTFTSDYSKYLDEKKAK#EFVEWLLEGGPSSG |
| 243 | HAibQGTFTSDYSKYLDEKKAKEFVEWLLEGGPSSGK* |

-continued

| SEQ ID NO: | SEQUENCE |
|---|---|
| 244 | HAibQGTFTSDYSKYLDEK^AAKEFIQWLLQT |
| 245 | HAibQGTFTSDYSKYLDEK"AAKEFIQWLLQT |
| 246 | HsQGTFTSDLSKOK^ESKAAQDFIEWLKAGGPSSGAPPPS |
| 247 | HsQGTFTSDLSKQK#ESKAAQDFIEWLKAGGPSSGAPPPS |
| 248 | HsQGTFTSDLSKQLESKAAQDFIEWLKAGGPSSGAPPPSK* |
| 249 | HsQGTFTSDLSKQLESKAAQDFIEWLKAGGPSSGAPPPSK" |
| 250 | HSQGTFTSDLSEYLDSERARDFVAWLEAGGK** <br> (* denotes a suitable linker modification of AEEA-(Bromo)MPA) |
| 251 | YAibQGTFTSDYSIMeLLDKK^AQAibAFIEYLLEGGPSSGAPPPS |
| 252 | YAibQGTFTSDYSIMeLLDKK"AQAibAFIEYLLEGGPSSGAPPPS |
| 253 | YAibQGTFTSDYSIMeLLDKK#AQAibAFIEYLLEGGPSSGAPPPS |
| 254 | YAibQGTFTSDYSIMeLLDKIAQAibAFIEYLLEGGPSSGAPPPSK^ |
| 255 | YAibQGTFTSDYSIMeLLDKIAQAibAFIEYLLEGGPSSGAPPPSK" |
| 256 | YAibQGTFTSDYSIMeLLDKIAQAibAFIEYLLEGGPSSGAPPPSK# |
| 257 | HSQGTFTSDK^SKYLDERRAQDFVQWLLDGGPSSGAPPPS |
| 258 | HSQGTFTSDK"SKYLDERRAQDFVQWLLDGGPSSGAPPPS |
| 259 | HSQGTFTSDYSKYLDERRAQDFVQWLLDGGPSSGAPPPSK* |
| 260 | HSQGTFTSDYSKYLDERRAQDFVQWLLDGGPSSGAPPPSK** <br> (* denotes a suitable linker modification of AEEA-(Bromo)MPA) |
| 261 | HAibHGTGTSDLSKLK^EEQRQAibEFIEWLKAaGPPSAibKPPPK |
| 262 | HAibHGTGTSDLSKLLEEQRQAibEFIEWLKAaGPPSAibKPPPK* |
| 263 | HAibHGTGTSDLSKLLEEQRQAibEFIEWLKAaGPPSAibKPPP9K* |
| 264 | YaEGTFTSDYAKYLDARRAAibEFIAWLVNGGPSSGAPPPSK* |
| 265 | YAibEGTFTSDYAKYLDARRAAibEFIAWLVNGGPSSGAPPPSK* |
| 266 | YAibEGTFTSDYSIAibLDKRRAAibEFIAWLVNGGPSSGAPPPSK* |
| 267 | HaEGTFTSDYSIAibLDKRRAAibEFIAWLVNGGPSSGAPPPSK* |
| 268 | YaEGTFTSDYSIAibLDKRRAAibEFIAWLVNGGPSSGAPPPSK* |
| 269 | YAibEGTFTSDYSIAibLDKIAQAibAFIAWLVNGGPSSGAPPPSK* |
| 270 | HaEGTFTSDYSIAibLDKIAQAibAFIAWLVNGGPSSGAPPPSK* |
| 271 | YaEGTFTSDYSIAibLDKIAQAibAFIAWLVNGGPSSGAPPPSK* |
| 272 | HaEGTFTSDYSIAibLDKIAQAibAFVQWLIAGGPSSGAPPPSK* |
| 273 | YaEGTFTSDYSIAibLDKIAQAibAFVQWLIAGGPSSGAPPPSK* |
| 274 | YAibEGTFTSDYSIAibLDKIAQAibAFVQWLIAGGPSSGAPPPS9K* |
| 275 | HaEGTFTSDYAKYLDARRAAibEFVQWLIAGGPSSGAPPPSK* |
| 276 | YaEGTFTSDYAKYLDARRAAibEFVQWLIAGGPSSGAPPPSK* |
| 277 | YAibEGTFTSDYAKYLDARRAAibEFVQWLIAGGPSSGAPPPSK* |
| 278 | HaEGTFTSDYAKYLDKIAQAibAFVQWLIAGGPSSGAPPPSK* |
| 279 | YaEGTFTSDYAKYLDKIAQAibAFVQWLIAGGPSSGAPPPSK* |
| 280 | YAibEGTFTSDYAKYLDKIAQAibAFVQWLIAGGPSSGAPPPSK* |

-continued

| SEQ ID NO: | SEQUENCE |
|---|---|
| 281 | YAibQGTFTSDYAKYLDARRAKEFIAWLVNGGPSSGAPPPSK* |
| 282 | YaQGTFTSDYAKYLDARRAKEFIAWLVNGGPSSGAPPPSK* |
| 283 | YAibQGTFTSDYSIMeLLDKRRAKEFIAWLVNGGPSSGAPPPSK* |
| 284 | YaQGTFTSDYSIMeLLDKRRAKEFIAWLVNGGPSSGAPPPSK* |
| 285 | HaQGTFTSDYSIMeLLDKRRAKEFIAWLVNGGPSSGAPPPSK* |
| 286 | YAibQGTFTSDYSIMeLLDKIAQAibAFIAWLVNGGPSSGAPPPSK* |
| 287 | YaQGTFTSDYSIMeLLDKIAQAibAFIAWLVNGGPSSGAPPPSK* |
| 288 | HaQGTFTSDYSIMeLLDKIAQAibAFIAWLVNGGPSSGAPPPSK* |
| 289 | YaQGTFTSDYSIMeLLDKIAQAibAFIEYLLEGGPSSGAPPPSK* |
| 290 | HaQGTFTSDYSIMeLLDKIAQAibAFIEYLLEGGPSSGAPPPSK* |
| 291 | YAibQGTFTSDYSIMeLLDKIAQAibAFIEYLLEGGPSSGAPPPS9K* |
| 292 | HaQGTFTSDYAKYLDARRAKEFIEYLLEGGPSSGAPPPSK* |
| 293 | HAibQGTFTSDYAKYLDARRAKEFIEYLLEGGPSSGAPPPSK* |
| 294 | YAibQGTFTSDYAKYLDARRAKEFIEYLLEGGPSSGAPPPSK* |
| 295 | YaQGTFTSDYAKYLDARRAKEFIEYLLEGGPSSGAPPPSK* |
| 296 | HaQGTFTSDYAKYLDKIAQAibAFIEYLLEGGPSSGAPPPSK* |
| 297 | HAibQGTFTSDYAKYLDKIAQAibAFIEYLLEGGPSSGAPPPSK* |
| 298 | YAibQGTFTSDYAKYLDKIAQAibAFIEYLLEGGPSSGAPPPSK* |
| 299 | YaQGTFTSDYAKYLDKIAQAibAFIEYLLEGGPSSGAPPPSK* |
| 300 | HAibQGTFTSDYSIMeLLDKIAQAibAFIEYLLEGGPSSGAPPPSK* |
| 301 | HaQGTFTSDYAKYLDARRAKEFIAWLVNGGPSSGAPPPSK# |
| 302 | HaEGTFTSDYAKYLDAK*RAKEFIAWLVNGGPSSGAPPPS |
| 303 | HaEGTFTSDYAKYLDAKARAKEFIAWLVNGGPSSGAPPPS |
| 304 | HaEGTFTSDYAKYLDAK&RAKEFIAWLVNGGPSSGAPPPS |
| 305 | HaEGTFTSDYAKYLDAK'RAKEFIAWLVNGGPSSGAPPPS |
| 306 | HaEGTFTSDYAKYLDARRAK^EFIAWLVNGGPSSGAPPPS |
| 307 | HaEGTFTSDYAKYLDARRAK&EFIAWLVNGGPSSGAPPPS |
| 308 | HaEGTFTSDYAKYLDARRAK'EFIAWLVNGGPSSGAPPPS |
| 309 | HaQGTFTSDYAKYLDARRAKEFIAWLVNGGPSSGAPPPSK2 |
| 310 | HaQGTFTSDYAKYLDARRAKEFIAWLVNGGPSSGAPPPSK3 |
| 311 | HaQGTFTSDYAKYLDARRAKEFIAWLVNGGPSSGAPPPSK1 |
| 312 | HaQGTFTSDYAKYLDARRAKEFIAWLVNGGPSSGAPPPSC2 |
| 313 | HaQGTFTSDYAKYLDAK2RAKEFIAWLVNGGPSSGAPPPS |
| 314 | HaQGTFTSDYAKYLDAK5RAKEFIAWLVNGGPSSGAPPPS |
| 315 | HaQGTFTSDYAKYLDAKIRAKEFIAWLVNGGPSSGAPPPS |
| 316 | HaQGTFTSDYAKYLDAK4RAKEFIAWLVNGGPSSGAPPPS |

-continued

| SEQ ID NO: | SEQUENCE |
|---|---|
| 317 | YAibQGTFTSDYSILLDKK*AQAibAFIEYLLEGGPSSGAPPPS (* denotes a suitable linker modification of (AEEA)$_2$-y-Glu-C20 diacid, or (AEEA)-y-Glu-C20 diacid, or -y-Glu-C16, or (AEEA)$_2$-y-Glu-C18 diacid) |
| 318 | HADGSFSDEMNTILDNLAARDFINWLIQTKITD |
| 319 | HSDAVFTDNYTRLRKQMAVKKYLNSILN |
| 320 | KCNTATCATQRLANFLVHSSNNFGAILSSTNVGSNTY |
| 321 | YADAIFTNSYRKVLGQLSARKLLQDIMSR |
| 322 | X1X2X3GTFTSDX4X5X6X7LX8X9X10X11X12 X13X14FX15X16WLX17X18GX19PSSG APPPSX20 |
| 323 | X1X2X3GTFTSDX4X5X6X7LX8X9X10X11X12 X13X14FX15X16WLX17X18GX19PSSG APPPS |
| 324 | X19PSSGAPPPSX20 |
| 325 | X11X12X13X14FX15X16WLX17X18G |
| 326 | X1X2X3GTFTSDX4X5X6X7LX8X9X10 |
| 327 | X19PSSGAPPPSK |
| 328 | X11X12X13X14FX15X16WLX17X18G-X19PSSGAPPPSX20 |
| 329 | X1X2X3GTFTSDX4X5X6X7LX8X9X10-X11X12X13X14FX15X16WLX17X18G-X19PSSGAPPPSX20 |
| 330 | HaEGTFTSDVSSYLEGQAAKEFIAWLVKGRPSSGAPPPSK* |
| 331 | HAEGTFTSDVSSYLEGQAAKEFIAWLVKGRPSSGAPPPSK* |
| 332 | HaEGTFTSDVSSYLEGQAAKEFIAWLVNGGK* |
| 333 | HaEGTFTSDINKVLDTIAAKEFIAWLVKGRK* |
| 334 | HaEGTFTSDAEKAKEAEKAKEFIAWLVKGRK* |
| 335 | HaEGTFTSDAibEKAibKEAibEKAKEFIAWLVKGRK* |
| 336 | HaEGTFTSDAibESAibKEAibEKAibKEFIAWLVKGRP SSGAPPPSK* |
| 337 | HaEGTFTSDVAibSYAibEGQAibAKEFIAWLVKGRPSSGAPPPSK* |
| 338 | HaEGTFTSDVSSYLEGK*AAKEFIAWLVKGRPSSGAPPPS |
| 339 | HaEGTFTSDVSSYLEGQAAKEFIAWLVKGRLLLLLLLLLK* |
| 340 | HaEGTFTSDVSSYLEGQAAKEFIAWLVKGRPEAPTDPEAPTD |
| 341 | HGEGTFTSDLSKQMEEEAVRLFIEWLKNGGGGGGGGGGGK* |
| 342 | HaEGTFTSDVSSYLEGQAAKEFIAWLVKGRK% (% denotes a suitable linker modification of (AEEA)$_4$-MPA |
| 343 | HaEGTFTSDVSSYLEGK*AAKEFIAWLVKGR |
| 344 | HaEGTFTSDVSSYLEGQAAKEFIAWLVKGRK@ (@ denotes a suitable linker modification of MPA) |
| 345 | HSQGTFTSDYSKYLDSRRAQDFVQWLMNTKRNKNNIA |
| 346 | HaEGTFTSDVSSYLEGQAAKEFIAWLVKGPEAPTDPEAPTD |
| 347 | HaEGTFTSDVSSYLEGQAAKEFIAWLVKGRK** |

-continued

| SEQ ID NO: | SEQUENCE |
| --- | --- |
| 348 | HaEGTFTSDINKVLDIIAAKEFIAWLVKGRPSSGAPPPSK* |
| 349 | HaEGTFTSDINKVLDIIAAKEFIAWLVKGRK* |
| 350 | HGEGTFTSDLSKQMEEEAVRLFIEWLKNGGPSSGAPPPSK** |
| 351 | HAibEGTFTSDYSKYLDKIRAQEFVAWLMNGGPSSGAPPPSK* |
| 352 | HAibQGTFTSDYSKYLDKIAAQDFVAWLLNGGPSSGAPPPSK* |
| 353 | HAibQGTFTSDYAKYLDKIAAQDFVAWLLDGGPSSGAPPPSK* |
| 354 | HAibQGTFTSDYSKYLDKIAAQDFVAWLLDGGPSSGAPPPSK* |
| 355 | HAibQGTFTSDYSKYLDKIAAQDFVAYLLDGGPSSGAPPPSK* |
| 356 | HAibQGTFTSDLSKYLDEIAVQDFIEWLLDGGPSSGAPPPSK* |
| 357 | HSQGTFTSDYSKYLDSRRAQDFVQWLMNTKRNRNNIA |
| 358 | IKPEAPGEDASPEELNRYYASLRHYLNLVTRQRY |
| 359 | HAibEGTFTSDVSSYLEGQALRHYINWLTRQRY |
| 360 | HGEGTFTSDLSKQMEEEAVRLFIEWLKNGGPSSRHYLNLVTRQRY |
| 361 | HdsQGTFTSDLSKYLEEEAVREFIAWLKNGGPSSGAPPPSRHYLN LVTRQRY |
| 362 | HdsQGTYTNDVSKYXDSRRAQDFIEWLKNGGPSSGAPPPS |
| 363 | HdsQGTYTNDVSKYKDSRRAQDFIEWLKNGGPSSGAPPPSC |
| 364 | HdsQGTFTSDLSKQKDSRRAQDFIEWLKNGGPSSGAPPPSC |
| 365 | HdsQGTYTNDVSKYXDSRRAQDFIEWLKNGGPSSGAPPPSC |
| 366 | PKPEAPGKDASPEEWNRYYADLRHYLNWLTRQRY |
| 367 | IKPEAPGEDASPEELNRYYASLRHYLNWVTRQXY |
| 368 | YAibEGTFTSDYSIYLDKQAAAibAFVQWLIAGGPSSGAPPPSK* (* denotes a suitable linker modification of AEEA-MPA or (AEEA)$^2$-MPA |
| 369 | YAibEGTFTSDYSIYLDKQAAAibAFVQWLLAGGPSSGAPPPSK* (* denotes a suitable linker modification of AEEA-MPA or (AEEA)$^2$-MPA |
| 370 | YAibEGTFTSDYSIYLDKQAAAibEFVQWLIAGGPSSGAPPPSK* (* denotes a suitable linker modification of AEEA-MPA or (AEEA)$^2$-MPA |
| 371 | HaEGTFTSDYSIYLDKQAAAibEFVQWLLAGGPSSGAPPPSK* (* denotes a suitable linker modification of AEEA-MPA or (AEEA)$^2$-MPA |
| 372 | YaEGTFTSDYSIYLDKQAAAibEFVQWLLAGGPSSGAPPPSK* (* denotes a suitable linker modification of AEEA-MPA or (AEEA)$^2$-MPA |
| 373 | HAibEGTFTSDYSIYLDKQAAAibEFVQWLLAGGPSSGAPPPSK* (* denotes a suitable linker modification of AEEA-MPA or (AEEA)$^2$-MPA |
| 374 | HaEGTFTSDYSIYLDKQAAAibAFVQWLIAGGPSSGAPPPSK* (* denotes a suitable linker modification of AEEA-MPA or (AEEA)$^2$-MPA |
| 375 | HaEGTFTSDYSIYLDKQAAAibAFVQWLLAGGPSSGAPPPSK* (* denotes a suitable linker modification of AEEA-MPA or (AEEA)$^2$-MPA |
| 376 | HaEGTFTSDYSIYLDKQAAAibEFVQWLIAGGPSSGAPPPSK* (* denotes a suitable linker modification of AEEA-MPA or (AEEA)$^2$-MPA |

-continued

| SEQ ID NO: | SEQUENCE |
|---|---|
| 377 | YaEGTFTSDYSIYLDKQAAAibAFVQWLIAGGPSSGAPPPSK*<br>(* denotes a suitable linker modification of AEEA-MPA<br>or (AEEA)$^2$-MPA |
| 378 | YaEGTFTSDYSIYLDKQAAAibAFVQWLLAGGPSSGAPPPSK*<br>(* denotes a suitable linker modification of AEEA-MPA<br>or (AEEA)$^2$-MPA |
| 379 | YaEGTFTSDYSIYLDKQAAAibEFVQWLIAGGPSSGAPPPSK*<br>(* denotes a suitable linker modification of AEEA-MPA<br>or (AEEA)$^2$-MPA |
| 380 | YAibEGTFTSDYAKYLDARRAKEFVQWLLAGGPSSGAPPPSK*<br>(* denotes a suitable linker modification of AEEA-MPA<br>or (AEEA)$^2$-MPA |
| 381 | YAibEGTFTSDYSKYLDARRAKEFVQWLLAGGPSSGAPPPSK*<br>(* denotes a suitable linker modification of AEEA-MPA<br>or (AEEA)$^2$-MPA |
| 382 | YAibEGTFTSDYSKYLDKRRAKEFVQWLLAGGPSSGAPPPSK*<br>(* denotes a suitable linker modification of AEEA-MPA<br>or (AEEA)$^2$-MPA |
| 383 | HaEGTFTSDYAKYLDARRAKEFVQWLLAGGPSSGAPPPSK*<br>(* denotes a suitable linker modification of AEEA-MPA<br>or (AEEA)$^2$-MPA |
| 384 | HaEGTFTSDYSKYLDARRAKEFVQWLLAGGPSSGAPPPSK*<br>(* denotes a suitable linker modification of AEEA-MPA<br>or (AEEA)$^2$-MPA |
| 385 | HaEGTFTSDYSKYLDKRRAKEFVQWLLAGGPSSGAPPPSK*<br>(* denotes a suitable linker modification of AEEA-MPA<br>or (AEEA)$^2$-MPA |
| 386 | YaEGTFTSDYAKYLDARRAKEFVQWLLAGGPSSGAPPPSK*<br>(* denotes a suitable linker modification of AEEA-MPA<br>or (AEEA)$^2$-MPA |
| 387 | YaEGTFTSDYSKYLDARRAKEFVQWLLAGGPSSGAPPPSK*<br>(* denotes a suitable linker modification of AEEA-MPA<br>or (AEEA)$^2$-MPA |
| 388 | YaEGTFTSDYSKYLDKRRAKEFVQWLLAGGPSSGAPPPSK*<br>(* denotes a suitable linker modification of AEEA-MPA<br>or (AEEA)$^2$-MPA |
| 389 | HAibEGTFTSDYAKYLDARRAKEFVQWLLAGGPSSGAPPPSK*<br>(* denotes a suitable linker modification of AEEA-MPA<br>or (AEEA)$^2$-MPA |
| 390 | HAibEGTFTSDYSKYLDARRAKEFVQWLLAGGPSSGAPPPSK*<br>(* denotes a suitable linker modification of AEEA-MPA<br>or (AEEA)$^2$-MPA |
| 391 | HAibEGTFTSDYSKYLDKRRAKEFVQWLLAGGPSSGAPPPSK*<br>(* denotes a suitable linker modification of AEEA-MPA<br>or (AEEA)$^2$-MPA |
| 392 | YAibEGTFTSDYAKYLDARRAKAFVQWLIAGGPSSGAPPPSK*<br>(* denotes a suitable linker modification of AEEA-MPA<br>or (AEEA)$^2$-MPA |
| 393 | YAibEGTFTSDYSKYLDARRAKAFVQWLIAGGPSSGAPPPSK*<br>(* denotes a suitable linker modification of AEEA-MPA<br>or (AEEA)$^2$-MPA |
| 394 | YAibEGTFTSDYSKYLDKRRAKAFVQWLIAGGPSSGAPPPSK*<br>(* denotes a suitable linker modification of AEEA-MPA<br>or (AEEA)$^2$-MPA |
| 395 | HaEGTFTSDYAKYLDARRAKAFVQWLIAGGPSSGAPPPSK*<br>(* denotes a suitable linker modification of AEEA-MPA<br>or (AEEA)$^2$-MPA |

-continued

| SEQ ID NO: | SEQUENCE |
|---|---|
| 396 | HaEGTFTSDYSKYLDARRAKAFVQWLIAGGPSSGAPPPSK*<br>(* denotes a suitable linker modification of AEEA-MPA<br>or (AEEA)$^2$-MPA |
| 397 | HaEGTFTSDYSKYLDKRRAKAFVQWLIAGGPSSGAPPPSK*<br>(* denotes a suitable linker modification of AEEA-MPA<br>or (AEEA)$^2$-MPA |
| 398 | YaEGTFTSDYAKYLDARRAKAFVQWLIAGGPSSGAPPPSK*<br>(* denotes a suitable linker modification of AEEA-MPA<br>or (AEEA)$^2$-MPA |
| 399 | YaEGTFTSDYSKYLDARRAKAFVQWLIAGGPSSGAPPPSK*<br>(* denotes a suitable linker modification of AEEA-MPA<br>or (AEEA)$^2$-MPA |
| 400 | YaEGTFTSDYSKYLDKRRAKAFVQWLIAGGPSSGAPPPSK*<br>(* denotes a suitable linker modification of AEEA-MPA<br>or (AEEA)$^2$-MPA |
| 401 | HAibEGTFTSDYAKYLDARRAKAFVQWLIAGGPSSGAPPPSK*<br>(* denotes a suitable linker modification of AEEA-MPA<br>or (AEEA)$^2$-MPA |
| 402 | HAibEGTFTSDYSKYLDARRAKAFVQWLIAGGPSSGAPPPSK*<br>(* denotes a suitable linker modification of AEEA-MPA<br>or (AEEA)$^2$-MPA |
| 403 | HAibEGTFTSDYSKYLDKRRAKAFVQWLIAGGPSSGAPPPSK*<br>(* denotes a suitable linker modification of AEEA-MPA<br>or (AEEA)$^2$-MPA |
| 404 | HaQGTFTSDLSKQLESKAAQDFIEWLKAGGPSSGAPPPSK*<br>(* denotes a suitable linker modification of AEEA-MPA<br>or (AEEA)$^2$-MPA |
| 405 | HsQGTFTSDYAKYLDARRAKEFIEWLKAGGPSSGAPPPSK*<br>(* denotes a suitable linker modification of AEEA-MPA<br>or (AEEA)$^2$-MPA |
| 406 | HsQGTFTSDYSKYLDARRAKEFIEWLKAGGPSSGAPPPSK*<br>(* denotes a suitable linker modification of AEEA-MPA<br>or (AEEA)$^2$-MPA |
| 407 | HsQGTFTSDYAKYLDSRRAKEFIEWLKAGGPSSGAPPPSK*<br>(* denotes a suitable linker modification of AEEA-MPA<br>or (AEEA)$^2$-MPA |
| 408 | HsQGTFTSDYSKYLDSRRAKEFIEWLKAGGPSSGAPPPSK*<br>(* denotes a suitable linker modification of AEEA-MPA<br>or (AEEA)$^2$-MPA |
| 409 | HaQGTFTSDYSKYLDSRRAKEFIEWLKAGGPSSGAPPPSK*<br>(* denotes a suitable linker modification of AEEA-MPA<br>or (AEEA)$^2$-MPA |
| 410 | HaQGTFTSDYAKYLDARRAKEFIEWLKAGGPSSGAPPPSK*<br>(* denotes a suitable linker modification of AEEA-MPA<br>or (AEEA)$^2$-MPA |
| 411 | HaQGTFTSDLSKQLESKAAQDFIAWLVNGGPSSGAPPPSK*<br>(* denotes a suitable linker modification of AEEA-MPA<br>or (AEEA)$^2$-MPA |
| 412 | HaQGTFTSDYAKYLDARRAKDFIEWLKAGGPSSGAPPPSK*<br>(* denotes a suitable linker modification of AEEA-MPA<br>or (AEEA)$^2$-MPA |
| 413 | HaQGTFTSDYSKYLDARRAQEFIEWLKAGGPSSGAPPPSK*<br>(* denotes a suitable linker modification of AEEA-MPA<br>or (AEEA)$^2$-MPA |
| 414 | HaQGTFTSDYAKYLDSRAAKEFIEWLKAGGPSSGAPPPSK*<br>(* denotes a suitable linker modification of AEEA-MPA<br>or (AEEA)$^2$-MPA |

-continued

| SEQ ID NO: | SEQUENCE |
|------------|----------|
| 415 | HaQGTFTSDYSKYLDSKRAKEFIEWLKAGGPSSGAPPPSK*<br>(* denotes a suitable linker modification of AEEA-MPA<br>or (AEEA)$^2$-MPA |
| 416 | HaQGTFTSDYAKYLEARRAKEFIEWLKAGGPSSGAPPPSK*<br>(* denotes a suitable linker modification of AEEA-MPA<br>or (AEEA)$^2$-MPA |
| 417 | HaQGTFTSDYAKQLEARRAKEFIEWLKAGGPSSGAPPPSK*<br>(* denotes a suitable linker modification of AEEA-MPA<br>or (AEEA)$^2$-MPA |
| 418 | HAibQGTFTSDYSKYLDERAAQAFIEYLLEGGPSSGAPPPSK*<br>(* denotes a suitable linker modification of AEEA-MPA<br>or (AEEA)$^2$-MPA |
| 419 | HaQGTFTSDYSKYLDERAAQDFVQWLLDGGPSSGAPPPSK*<br>(* denotes a suitable linker modification of AEEA-MPA<br>or (AEEA)$^2$-MPA |
| 420 | HaQGTFTSDYSKYLDERAAQAFIEYLLEGGPSSGAPPPSK*<br>(* denotes a suitable linker modification of AEEA-MPA<br>or (AEEA)$^2$-MPA |
| 421 | HAibQGTFTSDYSKYLDARRAKEFVQWLLDGGPSSGAPPPSK*<br>(* denotes a suitable linker modification of AEEA-MPA<br>or (AEEA)$^2$-MPA |
| 422 | HAibQGTFTSDYSKYLDARRAKEFIEYLLEGGPSSGAPPPSK*<br>(* denotes a suitable linker modification of AEEA-MPA<br>or (AEEA)$^2$-MPA |
| 423 | HAibQGTFTSDYAKYLDARRAKEFVQWLLDGGPSSGAPPPSK*<br>(* denotes a suitable linker modification of AEEA-MPA<br>or (AEEA)$^2$-MPA |
| 424 | HaQGTFTSDYSKYLDARRAKEFVQWLLDGGPSSGAPPPSK*<br>(* denotes a suitable linker modification of AEEA-MPA<br>or (AEEA)$^2$-MPA |
| 425 | HaQGTFTSDYAKYLDARRAKEFVQWLLDGGPSSGAPPPSK*<br>(* denotes a suitable linker modification of AEEA-MPA<br>or (AEEA)$^2$-MPA |
| 426 | HaQGTFTSDYSKYLDARRAKEFIEYLLEGGPSSGAPPPSK*<br>(* denotes a suitable linker modification of AEEA-MPA<br>or (AEEA)$^2$-MPA |
| 427 | HAibQGTFTSDYSKYLDERAAQAFIEYLLDGGPSSGAPPPSK*<br>(* denotes a suitable linker modification of AEEA-MPA<br>or (AEEA)$^2$-MPA |
| 428 | HaQGTFTSDYSKYLDERAAQDFVQWLLEGGPSSGAPPPSK*<br>(* denotes a suitable linker modification of AEEA-MPA<br>or (AEEA)$^2$-MPA |
| 429 | HaQGTFTSDYSKYLDERAAQAFIEYLLDGGPSSGAPPPSK*<br>(* denotes a suitable linker modification of AEEA-MPA<br>or (AEEA)$^2$-MPA |
| 430 | HAibQGTFTSDYSKYLDARRAKEFVQWLLEGGPSSGAPPPSK*<br>(* denotes a suitable linker modification of AEEA-MPA<br>or (AEEA)$^2$-MPA |
| 431 | HAibQGTFTSDYSKYLDARRAKEFIEYLLDGGPSSGAPPPSK*<br>(* denotes a suitable linker modification of AEEA-MPA<br>or (AEEA)$^2$-MPA |
| 432 | HAibQGTFTSDYAKYLDARRAKEFVQWLLEGGPSSGAPPPSK*<br>(* denotes a suitable linker modification of AEEA-MPA<br>or (AEEA)$^2$-MPA |
| 433 | HAibQGTFTSDYAKYLDARRAKEFIEYLLDGGPSSGAPPPSK*<br>(* denotes a suitable linker modification of AEEA-MPA<br>or (AEEA)$^2$-MPA |

-continued

| SEQ ID NO: | SEQUENCE |
|---|---|
| 434 | HaQGTFTSDYSKYLDARRAKEFVQWLLEGGPSSGAPPPSK* (* denotes a suitable linker modification of AEEA-MPA or (AEEA)$^2$-MPA |
| 435 | HaQGTFTSDYAKYLDARRAKEFVQWLLEGGPSSGAPPPSK* (* denotes a suitable linker modification of AEEA-MPA or (AEEA)$^2$-MPA |
| 436 | HaQGTFTSDYSKYLDARRAKEFIEYLLDGGPSSGAPPPSK* (* denotes a suitable linker modification of AEEA-MPA or (AEEA)$^2$-MPA |
| 437 | HaQGTFTSDYAKYLDARRAKEFIEYLLDGGPSSGAPPPSK* (* denotes a suitable linker modification of AEEA-MPA or (AEEA)$^2$-MPA |
| 438 | HAibQGTFTSDYSKYLDERAAQAFIEWLLEGGPSSGAPPPSK* (* denotes a suitable linker modification of AEEA-MPA or (AEEA)$^2$-MPA |
| 439 | HaQGTFTSDYSKYLDERAAQDFVQYLLDGGPSSGAPPPSK* (* denotes a suitable linker modification of AEEA-MPA or (AEEA)$^2$-MPA |
| 440 | HaQGTFTSDYSKYLDERAAQAFIEWLLEGGPSSGAPPPSK* (* denotes a suitable linker modification of AEEA-MPA or (AEEA)$^2$-MPA |
| 441 | HAibQGTFTSDYSKYLDARRAKEFVQYLLDGGPSSGAPPPSK* (* denotes a suitable linker modification of AEEA-MPA or (AEEA)$^2$-MPA |
| 442 | HAibQGTFTSDYSKYLDARRAKEFIEWLLEGGPSSGAPPPSK* (* denotes a suitable linker modification of AEEA-MPA or (AEEA)$^2$-MPA |
| 443 | HAibQGTFTSDYAKYLDARRAKEFVQYLLDGGPSSGAPPPSK* (* denotes a suitable linker modification of AEEA-MPA or (AEEA)$^2$-MPA |
| 444 | HAibQGTFTSDYAKYLDARRAKEFIEWLLEGGPSSGAPPPSK* (* denotes a suitable linker modification of AEEA-MPA or (AEEA)$^2$-MPA |
| 445 | HaQGTFTSDYSKYLDARRAKEFVQYLLDGGPSSGAPPPSK* (* denotes a suitable linker modification of AEEA-MPA or (AEEA)$^2$-MPA |
| 446 | HaQGTFTSDYAKYLDARRAKEFVQYLLDGGPSSGAPPPSK* (* denotes a suitable linker modification of AEEA-MPA or (AEEA)$^2$-MPA |
| 447 | HaQGTFTSDYSKYLDARRAKEFIEWLLEGGPSSGAPPPSK* (* denotes a suitable linker modification of AEEA-MPA or (AEEA)$^2$-MPA |
| 448 | HaQGTFTSDYAKYLDARRAKEFIEWLLEGGPSSGAPPPSK* (* denotes a suitable linker modification of AEEA-MPA or (AEEA)$^2$-MPA |
| 449 | HAibQGTFTSDYSKYLDERAAQAFVQYLLEGGPSSGAPPPSK* (* denotes a suitable linker modification of AEEA-MPA or (AEEA)$^2$-MPA |
| 450 | HaQGTFTSDYSKYLDERAAQDFIEWLLDGGPSSGAPPPSK* (* denotes a suitable linker modification of AEEA-MPA or (AEEA)$^2$-MPA |
| 451 | HaQGTFTSDYSKYLDERAAQAFVQYLLEGGPSSGAPPPSK* (* denotes a suitable linker modification of AEEA-MPA or (AEEA)$^2$-MPA |
| 452 | HAibQGTFTSDYSKYLDARRAKEFIEWLLDGGPSSGAPPPSK* (* denotes a suitable linker modification of AEEA-MPA or (AEEA)$^2$-MPA |

-continued

| SEQ ID NO: | SEQUENCE |
|---|---|
| 453 | HAibQGTFTSDYSKYLDARRAKEFVQYLLEGGPSSGAPPPSK*<br>(* denotes a suitable linker modification of AEEA-MPA<br>or (AEEA)$^2$-MPA |
| 454 | HAibQGTFTSDYAKYLDARRAKEFIEWLLDGGPSSGAPPPSK*<br>(* denotes a suitable linker modification of AEEA-MPA<br>or (AEEA)$^2$-MPA |
| 455 | HAibQGTFTSDYAKYLDARRAKEFVQYLLEGGPSSGAPPPSK*<br>(* denotes a suitable linker modification of AEEA-MPA<br>or (AEEA)$^2$-MPA |
| 456 | HaQGTFTSDYSKYLDARRAKEFIEWLLDGGPSSGAPPPSK*<br>(* denotes a suitable linker modification of AEEA-MPA<br>or (AEEA)$^2$-MPA |
| 457 | HaQGTFTSDYAKYLDARRAKEFIEWLLDGGPSSGAPPPSK*<br>(* denotes a suitable linker modification of AEEA-MPA<br>or (AEEA)$^2$-MPA |
| 458 | HaQGTFTSDYSKYLDARRAKEFVQYLLEGGPSSGAPPPSK*<br>(* denotes a suitable linker modification of AEEA-MPA<br>or (AEEA)$^2$-MPA |
| 459 | HaQGTFTSDYAKYLDARRAKEFVQYLLEGGPSSGAPPPSK*<br>(* denotes a suitable linker modification of AEEA-MPA<br>or (AEEA)$^2$-MPA |
| 460 | HaEGTFTSDYAKYLDARRAKEFVQWLVNGGPSSGAPPPSK*<br>(* denotes a suitable linker modification of AEEA-MPA<br>or (AEEA)$^2$-MPA |
| 461 | HaEGTFTSDYAKYLDARRAKEFIAWLLDGGPSSGAPPPSK*<br>(* denotes a suitable linker modification of AEEA-MPA<br>or (AEEA)$^2$-MPA |
| 462 | HaEGTFTSDYAKYLDARRAKEFIEYLVNGGPSSGAPPPSK*<br>(* denotes a suitable linker modification of AEEA-MPA<br>or (AEEA)$^2$-MPA |
| 463 | HaEGTFTSDYAKYLDARRAKEFIAYLLEGGPSSGAPPPSK*<br>(* denotes a suitable linker modification of AEEA-MPA<br>or (AEEA)$^2$-MPA |
| 464 | HaEGTFTSDYAKYLDARRAKEFIEWLVNGGPSSGAPPPSK*<br>(* denotes a suitable linker modification of AEEA-MPA<br>or (AEEA)$^2$-MPA |
| 465 | HaEGTFTSDYAKYLDARRAKEFVQWLKAGGPSSGAPPPSK*<br>(* denotes a suitable linker modification of AEEA-MPA<br>or (AEEA)$^2$-MPA |
| 466 | YaEGTFTSDYAIYLDAQAQQDFVQWLLAGGPSSGAPPPSK^ |
| 467 | YaEGTFTSDYSIYLDKIAQQDFVQWLLAGGPSSGAPPPSK^ |
| 468 | HAibQGTFTSDYSKYLDERAAQDFVQWLLDGGPSSGAPPPSK* |
| 469 | HAibQGTFTSDYSKYLDKIAAQDFVAYLLDGGPSSGAPPPSK^ |
| 470 | YaEGTFTSDYSIYLDKIAQQDFVQWLLAGGPSSGAPPPSK* |
| 471 | YAibEGTFTSDYSIAibLDKIAQK^AFV<br>QWLIAGGPSSGAPPPS |

Figure 35:
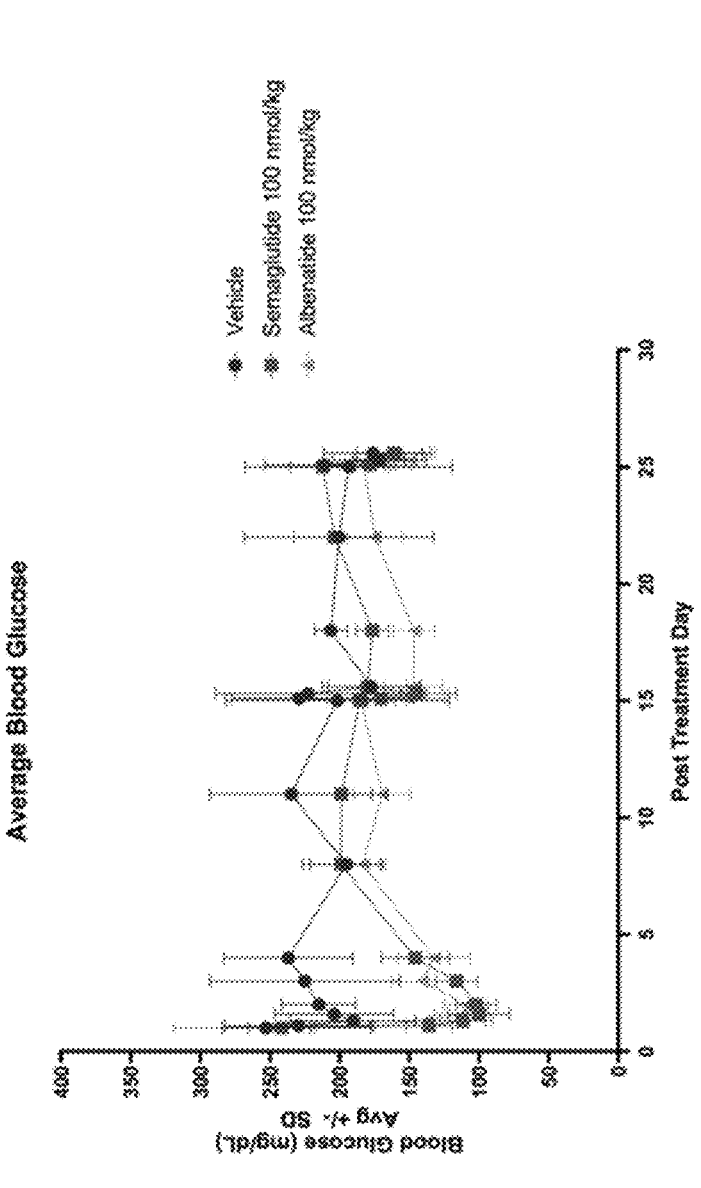
FIG. 35 depicts the efficacy of Albenatide in glucose control in DIO mice demonstrating that covalently bound GLP-1 agonists react with GLP-1 receptor and has a biological efficacy effect, contrary to the teaching of current formulations.

In further aspects of the inventive subject matter, it should be appreciated that the compositions and compounds presented herein will have significant biological activity in vivo when administered to a subject. For example, when retro-Michael resistant albenatide (AB-013-AEEA-succinimide (SEQ ID NO:2)-albumin) is administered to mice in a diet induced obese mouse model at a single dosage of 100 nmol/kg (s.c. injection), the retro-Michael resistant albenatide had significant physiological activity with regard to weight loss and was comparable to semaglutide over a period of 16 and 26 days as is shown in FIG. 33., which is also reflected in reduced cumulative food and water consumption show in FIG. 34. In addition, it was also observed in this model that the retro-Michael resistant albenatide had a profound and sustained effect on blood glucose levels as is exemplarily illustrated in FIG. 35.

Figure 37A:
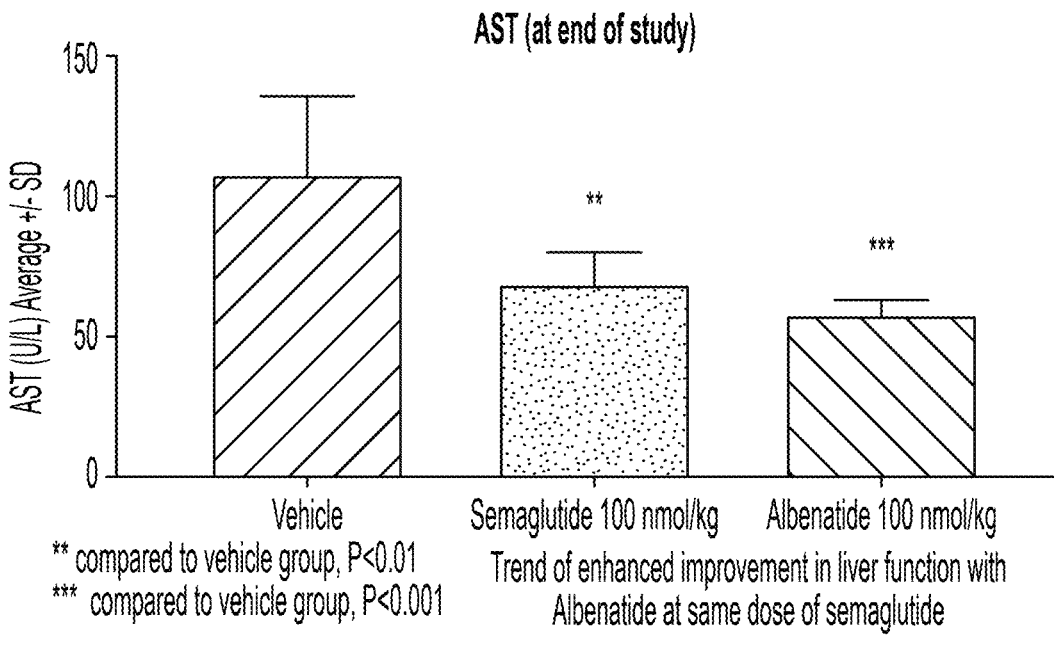
Figure 37B:
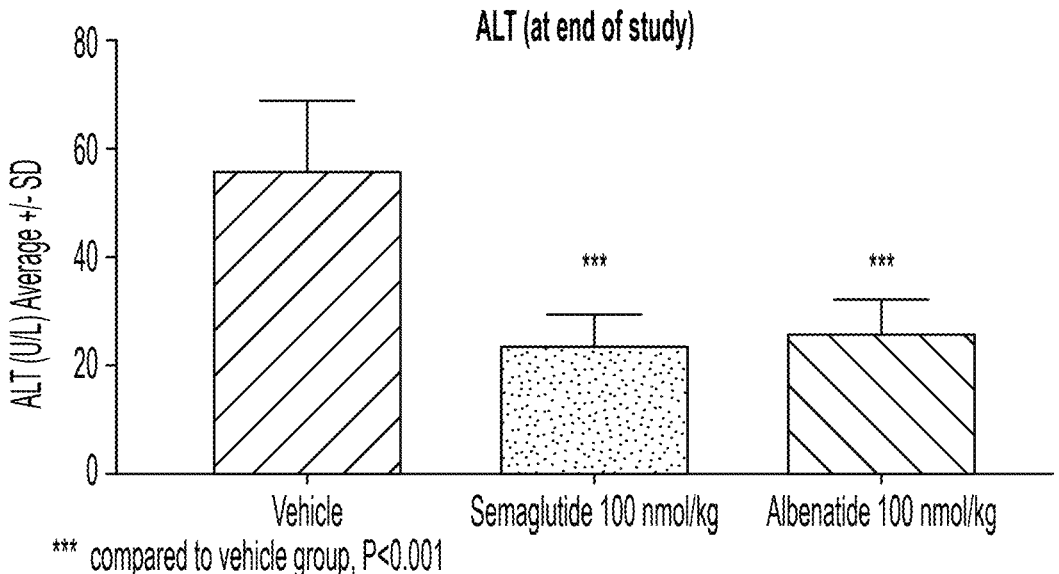

Moreover, and in addition to the metabolic modulation shown above, retro-Michael resistant albenatide also had a significant effect on hepatic lipid metabolism as can be readily taken from FIG. 36. Here, the single administration of retro-Michael resistant albenatide led to a substantial reduction in liver weight that was equivalent to the reduction obtained with semaglutide. This weight reduction was attributable to the quantity of lipid vesicles in the parenchyma as can be seen in the photomicrographs in FIG. 36. Notably, the retro-Michael resistant albenatide was thus effective in body weight control as well as with a reduction in blood glucose and was even capable of reversing fatty liver. In line with these observations were also the data shown in FIG. 37A and FIG. 37B that demonstrated a significant reduction in AST (37A) and ALT (37B) in serum. Likewise, administration of retro-Michael resistant albenatide further led to significantly reduced total serum cholesterol and LDL cholesterol as is shown in the data of FIG. 37C and FIG. 37D, respectively.

Additionally, the inventors also observed that retro-Michael resistant albenatide was able to reduce levels of pro-inflammatory cytokines IL-1$\alpha$ and IL-6 as depicted in FIG. 38. In this context, it should be particularly appreciated that the reduction and more compact data range is notable as the cytokines were measured at the end of the study, suggestion an even stronger effect closer to the time of administration.

Further aspects, examples, and methods of use for compounds presented herein are described in Applicant's International application with the title "Albumin Bound Macromolecule Tri-Agonist Activating GLP-1/GIP/Glucagon Receptors And Methods Therefor", filed on or about 06/25/2024, incorporated by reference herein.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID No:1-471 and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants. Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance. Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAP-DIST=4. Those skilled in the art will be aware that it may be necessary to vary these and other parameters for optimal sequence alignment.

Preferably, suitable calculations of the percentage identities between two amino acid/polynucleotide/polypeptide sequences may then be calculated from such an alignment as (N/T)*100, where N is the number of positions at which the sequences share an identical residue, and T is the total number of positions compared including gaps and either including or excluding overhangs. Preferably, overhangs are included in the calculation. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100. Alternative methods for identifying similar sequences will be known to those skilled in the art. For example, a substantially similar nucleotide sequence will be encoded by a sequence which hybridizes to DNA sequences or their complements under stringent conditions. By stringent conditions, we mean the nucleotide hybridizes to filter-bound DNA or RNA in 3× sodium chloride/sodium citrate (SSC) at approximately 45° C. followed by at least one wash in 0.2×SSC/0.1% SDS at approximately 20-65° C.

Alternatively, a substantially similar polypeptide may differ by at least 1, but less than 5, 10, 20, 50 or 100 amino acids from the sequences shown in, for example, in the amino acid sequence that are included within SEQ ID Nos: 1-471. Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example, small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

It should be noted that any language directed to a computer should be read to include any suitable combination of computing devices, including servers, interfaces, systems, databases, agents, peers, engines, modules, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

In some embodiments, the numbers expressing quantities of ingredients, properties such as concentration, reaction conditions, and so forth, used to describe and claim certain embodiments of the invention are to be understood as being modified in some instances by the term "about." As used herein, the terms "about" and "approximately", when referring to a specified, measurable value (such as a parameter, an amount, a temporal duration, and the like), is meant to encompass the specified value and variations of and from the specified value, such as variations of +/−10% or less, alternatively +1-5% or less, alternatively +/−1% or less, alternatively +/−0.1% or less of and from the specified value, insofar as such variations are appropriate to perform in the disclosed embodiments. Thus, the value to which the modifier "about" or "approximately" refers is itself also specifically disclosed. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A method of producing a retro-Michael resistant Class B G protein-coupled receptor agonist (GPCR) fusion protein, comprising:

providing or producing a conformationally modified albumin, wherein the conformationally modified albumin is an at least partially defatted albumin;

covalently coupling a GPCR agonist peptide to $Cys_{34}$ of the conformationally modified albumin via a Michael addition reaction, wherein the GPCR agonist peptide comprises a linker with a planar Michael acceptor group comprising a maleimide group or a bromo maleimide group;

wherein the Michael addition reaction produces a stereopreferred or stereoselective chiral carbon atom having an (R) configuration in the Michael acceptor group; and wherein the step of coupling is performed at a pH of pH<7.0.

2. The method of claim 1, wherein the pH is between 4.0 and 6.0.

3. The method of claim 1, wherein the Michael addition reaction produces a stereopreferred chiral carbon atom in the Michael acceptor group.

4. The method of claim 1, wherein the Michael addition reaction produces a stereoselective chiral carbon atom in the Michael acceptor group.

5. The method of claim 1, wherein the GPCR agonist peptide has a structure according to any one of SEQ ID NO:1-471, with the proviso that where the GPCR agonist peptide has a structure according to any one of SEQ ID NO:1-2, 7-34, 36-182, 184-187, 189-191, 193-196, 198-201, 203-208, 210-214, 216-225, 227-228, 230, 232-317, 322, 324, 328-334, 336-339, 341-344, 346-356, 368-471, the structure is the structure without linker modification.

6. A Class B G protein-coupled receptor (GPCR) agonist fusion protein, comprising:

a conformationally modified albumin comprising a $Cys_{34}$ amino acid, wherein the conformationally modified albumin is an at least partially defatted albumin;

a GPCR agonist peptide comprising a Lys amino acid; and a linker covalently coupling the conformationally modified albumin to the GPCR agonist peptide, wherein the linker comprises a planar Michael acceptor group comprising a maleimide group or a bromo maleimide group;

(a) wherein the linker is covalently bound to the GPCR agonist peptide via an amide bond formed by an epsilon amino group of the Lys amino acid;

(b) wherein the linker is covalently bound to the albumin via a covalent bond between a chiral carbon atom of a coupling group in the linker and a sulfur atom in the $Cys_{34}$ amino acid; and (d) wherein the chiral carbon atom has a stereopreferred or stereoselective (R) configuration and is retro-Michael resistant.

7. The agonist fusion protein of claim 6, wherein the chiral carbon atom has a stereoselective configuration.

8. The agonist fusion protein of claim 6, wherein the fusion protein is retro-Michael resistant albenatide (AB-013-AEEA-succinimide (SEQ ID NO:2)-albumin).

9. A pharmaceutical composition, comprising:

a pharmaceutically acceptable liquid carrier in combination with a retro-Michael resistant Class B G protein-coupled receptor (GPCR) agonist fusion protein in which a GPCR agonist peptide is covalently coupled to a conformationally modified albumin via a linker;

wherein the conformationally modified albumin is an at least partially defatted albumin, wherein the pharmaceutically acceptable liquid carrier is comprised of less than 1% of unbound GPCR agonist peptide; and wherein the linker comprises a chiral carbon having an (R) configuration.

10. The pharmaceutical composition of claim 9, wherein the GPCR agonist fusion protein is retro-Michael resistant albenatide (AB-013-AEEA-succinimide (SEQ ID NO:2)-albumin).

11. The pharmaceutical composition of claim 9, wherein the liquid carrier has a pH of between pH 4.0-6.0.

* * * * *

SEQUENCE LISTING

```
Sequence total quantity: 471
SEQ ID NO: 1          moltype = AA  length = 31
FEATURE               Location/Qualifiers
source                1..31
                      mol_type = protein
                      organism = synthetic construct
```

-continued

```
MOD_RES              31
                     note = AminoEthoxyEthoxyAcetic Acyl-MaleimidoPropionic Acyl
SITE                 2
                     note = D-alanine
SEQUENCE: 1
HAEGTFTSDV SSYLEGQAAK EFIAWLVKGR K                                    31

SEQ ID NO: 2         moltype = AA  length = 40
FEATURE              Location/Qualifiers
source               1..40
                     mol_type = protein
                     organism = synthetic construct
MOD_RES              40
                     note = AminoEthoxyEthoxyAcetic Acyl-MaleimidoPropionic Acyl
SEQUENCE: 2
HGEGTFTSDL SKQMEEEAVR LFIEWLKNGG PSSGAPPPSK                            40

SEQ ID NO: 3         moltype = AA  length = 39
FEATURE              Location/Qualifiers
source               1..39
                     mol_type = protein
                     organism = synthetic construct
SEQUENCE: 3
HGEGTFTSDL SKQMEEEAVR LFIEWLKNGG PSSGAPPPS                             39

SEQ ID NO: 4         moltype = AA  length = 30
FEATURE              Location/Qualifiers
source               1..30
                     mol_type = protein
                     organism = synthetic construct
SEQUENCE: 4
HAEGTFTSDV SSYLEGQAAK EFIAWLVKGR                                       30

SEQ ID NO: 5         moltype = AA  length = 42
FEATURE              Location/Qualifiers
source               1..42
                     mol_type = protein
                     organism = synthetic construct
SEQUENCE: 5
YAEGTFISDY SIAMDKIHQQ DFVNWLLAQK GKKNDWKHNI TQ                         42

SEQ ID NO: 6         moltype = AA  length = 29
FEATURE              Location/Qualifiers
source               1..29
                     mol_type = protein
                     organism = synthetic construct
SEQUENCE: 6
HSQGTFTSDY SKYLDSRRAQ DFVQWLMNT                                        29

SEQ ID NO: 7         moltype = AA  length = 40
FEATURE              Location/Qualifiers
source               1..40
                     mol_type = protein
                     organism = synthetic construct
SITE                 2
                     note = D-alanine
MOD_RES              40
                     note = AminoEthoxyEthoxyAcetic Acyl-MaleimidoPropionic Acyl
SEQUENCE: 7
HAEGTFTSDV SSYLEGQAAK EFIAWLVNGG PSSGAPPPSK                            40

SEQ ID NO: 8         moltype = AA  length = 40
FEATURE              Location/Qualifiers
source               1..40
                     mol_type = protein
                     organism = synthetic construct
SITE                 2
                     note = D-alanine
MOD_RES              40
                     note = AminoEthoxyEthoxyAcetic Acyl-MaleimidoPropionic Acyl
SEQUENCE: 8
HAEGTFTSDY AKYLDARRAK EFIAWLVKGR PSSGAPPPSK                            40

SEQ ID NO: 9         moltype = AA  length = 39
FEATURE              Location/Qualifiers
source               1..39
                     mol_type = protein
                     organism = synthetic construct
MOD_RES              32
```

```
                              note = AminoEthoxyEthoxyAcetic Acyl-MaleimidoPropionic Acyl
SEQUENCE: 9
HGEGTFTSDL SKQMEEEAVR LFIEWLKNGG PKSGAPPPS                                    39

SEQ ID NO: 10              moltype = AA  length = 39
FEATURE                    Location/Qualifiers
source                     1..39
                           mol_type = protein
                           organism = synthetic construct
SITE                       2
                           note = D-alanine
MOD_RES                    12
                           note = AminoEthoxyEthoxyAcetic Acyl-MaleimidoPropionic Acyl
SEQUENCE: 10
HAEGTFTSDV SKYLEGQAAK EFIAWLVKGR PSSGAPPPS                                    39

SEQ ID NO: 11              moltype = AA  length = 39
FEATURE                    Location/Qualifiers
source                     1..39
                           mol_type = protein
                           organism = synthetic construct
MOD_RES                    16
                           note = AminoEthoxyEthoxyAcetic Acyl-MaleimidoPropionic Acyl
SITE                       2
                           note = D-alanine
SEQUENCE: 11
HAEGTFTSDV SSYLEKQAAK EFIAWLVKGR PSSGAPPPS                                    39

SEQ ID NO: 12              moltype = AA  length = 39
FEATURE                    Location/Qualifiers
source                     1..39
                           mol_type = protein
                           organism = synthetic construct
MOD_RES                    32
                           note = AminoEthoxyEthoxyAcetic Acyl-MaleimidoPropionic Acyl
SEQUENCE: 12
HGEGTFTSDL SKQMEEEAVR LFIEWLKNGG PKSGAPPPS                                    39

SEQ ID NO: 13              moltype = AA  length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-MaleimidoPropionic Acyl
SEQUENCE: 13
HAEGTFTSDI NKVLDTIAAK EFIAWLVKGR PSSGAPPPSK                                   40

SEQ ID NO: 14              moltype = AA  length = 40
FEATURE                    Location/Qualifiers
source                     1..40
                           mol_type = protein
                           organism = synthetic construct
MOD_RES                    40
                           note = Palmitic acyl // Hexadecanoic acyl
MOD_RES                    2
                           note = Aib
MOD_RES                    20
                           note = Aib
SEQUENCE: 14
YXEGTFTSDY SIYLDKQAAX EFVQWLLAGG PSSGAPPPSK                                   40

SEQ ID NO: 15              moltype = AA  length = 40
FEATURE                    Location/Qualifiers
source                     1..40
                           mol_type = protein
                           organism = synthetic construct
MOD_RES                    40
                           note = AminoEthoxyEthoxyAcetic Acyl-MaleimidoPropionic Acyl
SITE                       30
                           note = D-alanine
SEQUENCE: 15
YGGGTFTSDS FFYLELSHAK DFINWLQLGA PSSGAPPPSK                                   40

SEQ ID NO: 16              moltype = AA  length = 40
FEATURE                    Location/Qualifiers
source                     1..40
```

```
                          mol_type = protein
                          organism = synthetic construct
MOD_RES                   2..3
                          note = Aib
MOD_RES                   20
                          note = Aib
MOD_RES                   28
                          note = Aib
MOD_RES                   40
                          note = AminoEthoxyEthoxyAcetic Acyl-MaleimidoPropionic Acyl
SEQUENCE: 16
HXXGTFTSDE MNYLDDWMQX AFVNWLVXGI PSSGAPPPSK                                  40

SEQ ID NO: 17             moltype = AA  length = 40
FEATURE                   Location/Qualifiers
source                    1..40
                          mol_type = protein
                          organism = synthetic construct
MOD_RES                   2
                          note = Aib
MOD_RES                   40
                          note = AminoEthoxyEthoxyAcetic Acyl-MaleimidoPropionic Acyl
SEQUENCE: 17
FXPGTFTSDG HNYLDWQDAK EFIQWLGWGV PSSGAPPPSK                                  40

SEQ ID NO: 18             moltype = AA  length = 40
FEATURE                   Location/Qualifiers
source                    1..40
                          mol_type = protein
                          organism = synthetic construct
MOD_RES                   2
                          note = Aib
MOD_RES                   13
                          note = Aib
MOD_RES                   20
                          note = Aib
MOD_RES                   40
                          note = AminoEthoxyEthoxyAcetic Acyl-MaleimidoPropionic Acyl
SEQUENCE: 18
YXMGTFTSDP QIXLEMKEQX DFINWLNDGF PSSGAPPPSK                                  40

SEQ ID NO: 19             moltype = AA  length = 40
FEATURE                   Location/Qualifiers
source                    1..40
                          mol_type = protein
                          organism = synthetic construct
SITE                      2
                          note = D-alanine
MOD_RES                   13
                          note = Aib
MOD_RES                   20
                          note = Aib
MOD_RES                   40
                          note = AminoEthoxyEthoxyAcetic Acyl-MaleimidoPropionic Acyl
SEQUENCE: 19
HAPGTFTSDN HEXLDTYRQX DFINWLDTGV PSSGAPPPSK                                  40

SEQ ID NO: 20             moltype = AA  length = 40
FEATURE                   Location/Qualifiers
source                    1..40
                          mol_type = protein
                          organism = synthetic construct
SITE                      2
                          note = D-alanine
MOD_RES                   40
                          note = AminoEthoxyEthoxyAcetic Acyl-MaleimidoPropionic Acyl
SEQUENCE: 20
YANGTFTSDI WAYLDSSFAQ DFVAWLYIGK PSSGAPPPSK                                  40

SEQ ID NO: 21             moltype = AA  length = 40
FEATURE                   Location/Qualifiers
source                    1..40
                          mol_type = protein
                          organism = synthetic construct
MOD_RES                   2
                          note = Aib
MOD_RES                   40
                          note = AminoEthoxyEthoxyAcetic Acyl-MaleimidoPropionic Acyl
SEQUENCE: 21
```

```
HXDGTFTSDF EHYLEDAVQK AFIAWLSTGV PSSGAPPPSK                           40

SEQ ID NO: 22            moltype = AA   length = 40
FEATURE                  Location/Qualifiers
source                   1..40
                         mol_type = protein
                         organism = synthetic construct
MOD_RES                  13
                         note = Aib
MOD_RES                  20
                         note = Aib
MOD_RES                  40
                         note = AminoEthoxyEthoxyAcetic Acyl-MaleimidoPropionic Acyl
SEQUENCE: 22
FGDGTFTSDL RGXLEIMPQX AFVNWLTSGK PSSGAPPPSK                           40

SEQ ID NO: 23            moltype = AA   length = 40
FEATURE                  Location/Qualifiers
source                   1..40
                         mol_type = protein
                         organism = synthetic construct
SITE                     2..3
                         note = D-alanine
SITE                     10
                         note = D-serine
MOD_RES                  40
                         note = AminoEthoxyEthoxyAcetic Acyl-MaleimidoPropionic Acyl
SEQUENCE: 23
HAAGTFTSDS MIYLDNAHQQ EFIQWLFNGP PSSGAPPPSK                           40

SEQ ID NO: 24            moltype = AA   length = 40
FEATURE                  Location/Qualifiers
source                   1..40
                         mol_type = protein
                         organism = synthetic construct
SITE                     2
                         note = D-alanine
SITE                     10
                         note = D-serine
MOD_RES                  12
                         note = Aib
SITE                     16
                         note = D-alanine
MOD_RES                  20
                         note = Aib
MOD_RES                  40
                         note = AminoEthoxyEthoxyAcetic Acyl-MaleimidoPropionic Acyl
SEQUENCE: 24
HAIGTFTSDS TXYLEAYKQX DFVQWLHSGG PSSGAPPPSK                           40

SEQ ID NO: 25            moltype = AA   length = 40
FEATURE                  Location/Qualifiers
source                   1..40
                         mol_type = protein
                         organism = synthetic construct
SITE                     2
                         note = D-serine
SITE                     10
                         note = D-alanine
SITE                     17
                         note = D-serine
MOD_RES                  40
                         note = AminoEthoxyEthoxyAcetic Acyl-MaleimidoPropionic Acyl
SITE                     30
                         note = D-alanine
SEQUENCE: 25
YSWGTFTSDA GYYLDMSFQQ AFIQWLKAGA PSSGAPPPSK                           40

SEQ ID NO: 26            moltype = AA   length = 40
FEATURE                  Location/Qualifiers
source                   1..40
                         mol_type = protein
                         organism = synthetic construct
MOD_RES                  13
                         note = Aib
SITE                     17
                         note = D-alanine
SITE                     28
                         note = D-serine
```

-continued

```
MOD_RES                   40
                          note = AminoEthoxyEthoxyAcetic Acyl-MaleimidoPropionic Acyl
SEQUENCE: 26
YGRGTFTSDW IYXLDTAPQK EFVEWLHSGA PSSGAPPPSK                              40

SEQ ID NO: 27             moltype = AA   length = 40
FEATURE                   Location/Qualifiers
source                    1..40
                          mol_type = protein
                          organism = synthetic construct
SITE                      2
                          note = D-alanine
SITE                      10
                          note = D-serine
MOD_RES                   13
                          note = Aib
MOD_RES                   40
                          note = AminoEthoxyEthoxyAcetic Acyl-MaleimidoPropionic Acyl
SEQUENCE: 27
YAMGTFTSDS EEXLEMVYQQ AFVAWLPVGG PSSGAPPPSK                              40

SEQ ID NO: 28             moltype = AA   length = 40
FEATURE                   Location/Qualifiers
source                    1..40
                          mol_type = protein
                          organism = synthetic construct
SITE                      2..3
                          note = D-serine
MOD_RES                   13
                          note = Aib
MOD_RES                   17
                          note = Aib
MOD_RES                   20
                          note = Aib
MOD_RES                   40
                          note = AminoEthoxyEthoxyAcetic Acyl-MaleimidoPropionic Acyl
SEQUENCE: 28
FSSGTFTSDW DWXLDIXIAX EFINWLVYGY PSSGAPPPSK                              40

SEQ ID NO: 29             moltype = AA   length = 40
FEATURE                   Location/Qualifiers
source                    1..40
                          mol_type = protein
                          organism = synthetic construct
MOD_RES                   2
                          note = Aib
MOD_RES                   40
                          note = AminoEthoxyEthoxyAcetic Acyl-MaleimidoPropionic Acyl
SEQUENCE: 29
FXGGTFTSDD MRYLEPKGQQ AFIQWLWVGQ PSSGAPPPSK                              40

SEQ ID NO: 30             moltype = AA   length = 40
FEATURE                   Location/Qualifiers
source                    1..40
                          mol_type = protein
                          organism = synthetic construct
MOD_RES                   2
                          note = Aib
MOD_RES                   30
                          note = Aib
MOD_RES                   40
                          note = AminoEthoxyEthoxyAcetic Acyl-MaleimidoPropionic Acyl
SEQUENCE: 30
YXSGTFTSDV ETYLDLLIAK EFIAWLGAGX PSSGAPPPSK                              40

SEQ ID NO: 31             moltype = AA   length = 40
FEATURE                   Location/Qualifiers
source                    1..40
                          mol_type = protein
                          organism = synthetic construct
MOD_RES                   13
                          note = Aib
MOD_RES                   20
                          note = Aib
MOD_RES                   40
                          note = AminoEthoxyEthoxyAcetic Acyl-MaleimidoPropionic Acyl
SEQUENCE: 31
HGRGTFTSDH QFXLDSMIQX EFIQWLHYGI PSSGAPPPSK                              40
```

```
SEQ ID NO: 32            moltype = AA   length = 40
FEATURE                  Location/Qualifiers
source                   1..40
                         mol_type = protein
                         organism = synthetic construct
SITE                     2
                         note = D-alanine
MOD_RES                  13
                         note = Aib
SITE                     16
                         note = D-serine
SITE                     30
                         note = D-alanine
MOD_RES                  40
                         note = AminoEthoxyEthoxyAcetic Acyl-MaleimidoPropionic Acyl
SEQUENCE: 32
YARGTFTSDF INXLESGVAK AFVNWLQEGA PSSGAPPPSK                                  40

SEQ ID NO: 33            moltype = AA   length = 40
FEATURE                  Location/Qualifiers
source                   1..40
                         mol_type = protein
                         organism = synthetic construct
SITE                     2
                         note = D-serine
SITE                     28
                         note = D-alanine
SITE                     30
                         note = D-alanine
MOD_RES                  40
                         note = AminoEthoxyEthoxyAcetic Acyl-MaleimidoPropionic Acyl
SEQUENCE: 33
HSFGTFTSDG WMYLDMNEQK AFVAWLYAGA PSSGAPPPSK                                  40

SEQ ID NO: 34            moltype = AA   length = 40
FEATURE                  Location/Qualifiers
source                   1..40
                         mol_type = protein
                         organism = synthetic construct
SITE                     2
                         note = D-serine
MOD_RES                  13
                         note = Aib
MOD_RES                  20
                         note = Aib
MOD_RES                  40
                         note = AminoEthoxyEthoxyAcetic Acyl-MaleimidoPropionic Acyl
SEQUENCE: 34
FSRGTFTSDH YRXLDQSKAX EFIEWLESGN PSSGAPPPSK                                  40

SEQ ID NO: 35            moltype = AA   length = 40
FEATURE                  Location/Qualifiers
source                   1..40
                         mol_type = protein
                         organism = synthetic construct
SITE                     2
                         note = D-serine
MOD_RES                  40
                         note = Aib
SEQUENCE: 35
FSGGTFTSDH HRYLDQIPQK DFIQWLEFGK PSSGAPPPSK                                  40

SEQ ID NO: 36            moltype = AA   length = 40
FEATURE                  Location/Qualifiers
source                   1..40
                         mol_type = protein
                         organism = synthetic construct
SITE                     2
                         note = D-alanine
SITE                     10
                         note = D-alanine
MOD_RES                  13
                         note = Aib
SITE                     18
                         note = D-alanine
MOD_RES                  40
                         note = AminoEthoxyEthoxyAcetic Acyl-MaleimidoPropionic Acyl
SEQUENCE: 36
FAQGTFTSDA NMXLDMFAQK AFINWLFQGG PSSGAPPPSK                                  40
```

-continued

```
SEQ ID NO: 37          moltype = AA   length = 40
FEATURE                Location/Qualifiers
source                 1..40
                       mol_type = protein
                       organism = synthetic construct
SITE                   2
                       note = D-alanine
SITE                   12
                       note = D-alanine
MOD_RES                13
                       note = Aib
MOD_RES                17
                       note = Aib
MOD_RES                40
                       note = AminoEthoxyEthoxyAcetic Acyl-MaleimidoPropionic Acyl
SEQUENCE: 37
FAAGTFTSDV TAXLEVXQQK AFIAWLNLGQ PSSGAPPPSK                    40

SEQ ID NO: 38          moltype = AA   length = 40
FEATURE                Location/Qualifiers
source                 1..40
                       mol_type = protein
                       organism = synthetic construct
SITE                   2
                       note = D-alanine
MOD_RES                12
                       note = Aib
SITE                   16
                       note = D-serine
MOD_RES                40
                       note = AminoEthoxyEthoxyAcetic Acyl-MaleimidoPropionic Acyl
SEQUENCE: 38
HAIGTFTSDH MXYLDSDPAQ DFIEWLMPGS PSSGAPPPSK                    40

SEQ ID NO: 39          moltype = AA   length = 40
FEATURE                Location/Qualifiers
source                 1..40
                       mol_type = protein
                       organism = synthetic construct
MOD_RES                2
                       note = Aib
MOD_RES                40
                       note = AminoEthoxyEthoxyAcetic Acyl-MaleimidoPropionic Acyl
SEQUENCE: 39
HXNGTFTSDI IHYLDPIVQK AFIEWLNGGA PSSGAPPPSK                    40

SEQ ID NO: 40          moltype = AA   length = 40
FEATURE                Location/Qualifiers
source                 1..40
                       mol_type = protein
                       organism = synthetic construct
MOD_RES                11
                       note = Aib
MOD_RES                13
                       note = Aib
MOD_RES                40
                       note = AminoEthoxyEthoxyAcetic Acyl-MaleimidoPropionic Acyl
SEQUENCE: 40
HGEGTFTSDM XQXLDREIAK EFVEWLFFGY PSSGAPPPSK                    40

SEQ ID NO: 41          moltype = AA   length = 40
FEATURE                Location/Qualifiers
source                 1..40
                       mol_type = protein
                       organism = synthetic construct
SITE                   2
                       note = D-serine
SITE                   12
                       note = D-serine
MOD_RES                13
                       note = Aib
SITE                   28
                       note = D-serine
MOD_RES                40
                       note = AminoEthoxyEthoxyAcetic Acyl-MaleimidoPropionic Acyl
SEQUENCE: 41
HSPGTFTSDP DSXLDENHQQ AFVAWLNSGM PSSGAPPPSK                    40
```

-continued

```
SEQ ID NO: 42           moltype = AA  length = 40
FEATURE                 Location/Qualifiers
source                  1..40
                        mol_type = protein
                        organism = synthetic construct
SITE                    2
                        note = D-serine
SITE                    3
                        note = D-alanine
SITE                    10
                        note = D-serine
SITE                    16..17
                        note = D-serine
MOD_RES                 20
                        note = Aib
MOD_RES                 40
                        note = AminoEthoxyEthoxyAcetic Acyl-MaleimidoPropionic Acyl
SEQUENCE: 42
FSAGTFTSDS LDYLESSEQX EFINWLAAGV PSSGAPPPSK                           40

SEQ ID NO: 43           moltype = AA  length = 40
FEATURE                 Location/Qualifiers
source                  1..40
                        mol_type = protein
                        organism = synthetic construct
SITE                    2
                        note = D-alanine
MOD_RES                 3
                        note = Aib
MOD_RES                 16
                        note = Aib
MOD_RES                 20
                        note = Aib
SITE                    28
                        note = D-serine
MOD_RES                 40
                        note = AminoEthoxyEthoxyAcetic Acyl-MaleimidoPropionic Acyl
SEQUENCE: 43
YAXGTFTSDK DPYLEXTYAX EFVAWLVSGR PSSGAPPPSK                           40

SEQ ID NO: 44           moltype = AA  length = 40
FEATURE                 Location/Qualifiers
source                  1..40
                        mol_type = protein
                        organism = synthetic construct
MOD_RES                 13
                        note = Aib
MOD_RES                 40
                        note = AminoEthoxyEthoxyAcetic Acyl-MaleimidoPropionic Acyl
SEQUENCE: 44
FGRGTFTSDA VMXLDAMQAK AFIEWLWIGI PSSGAPPPSK                           40

SEQ ID NO: 45           moltype = AA  length = 40
FEATURE                 Location/Qualifiers
source                  1..40
                        mol_type = protein
                        organism = synthetic construct
SITE                    2..3
                        note = D-alanine
MOD_RES                 13
                        note = Aib
MOD_RES                 40
                        note = AminoEthoxyEthoxyAcetic Acyl-MaleimidoPropionic Acyl
SEQUENCE: 45
HAAGTFTSDV DYXLEWKIQQ DFIEWLSTGL PSSGAPPPSK                           40

SEQ ID NO: 46           moltype = AA  length = 40
FEATURE                 Location/Qualifiers
source                  1..40
                        mol_type = protein
                        organism = synthetic construct
SITE                    2
                        note = D-serine
MOD_RES                 18
                        note = Aib
MOD_RES                 20
                        note = Aib
MOD_RES                 40
                        note = AminoEthoxyEthoxyAcetic Acyl-MaleimidoPropionic Acyl
```

```
SEQUENCE: 46
YSFGTFTSDI AGYLDLEXAX AFVQWLAHGK PSSGAPPPSK                                  40

SEQ ID NO: 47              moltype = AA  length = 40
FEATURE                    Location/Qualifiers
source                     1..40
                           mol_type = protein
                           organism = synthetic construct
SITE                       2
                           note = D-serine
MOD_RES                    40
                           note = AminoEthoxyEthoxyAcetic Acyl-MaleimidoPropionic Acyl
SEQUENCE: 47
HSHGTFTSDE VQYLDMDGQQ EFINWLDLGY PSSGAPPPSK                                  40

SEQ ID NO: 48              moltype = AA  length = 40
FEATURE                    Location/Qualifiers
source                     1..40
                           mol_type = protein
                           organism = synthetic construct
SITE                       2
                           note = D-serine
MOD_RES                    13
                           note = Aib
MOD_RES                    20
                           note = Aib
MOD_RES                    27
                           note = Aib
MOD_RES                    40
                           note = AminoEthoxyEthoxyAcetic Acyl-MaleimidoPropionic Acyl
SEQUENCE: 48
HSRGTFTSDL QGXLEYADQX DFVNWLXTGF PSSGAPPPSK                                  40

SEQ ID NO: 49              moltype = AA  length = 40
FEATURE                    Location/Qualifiers
source                     1..40
                           mol_type = protein
                           organism = synthetic construct
MOD_RES                    13
                           note = Aib
SITE                       16
                           note = D-alanine
MOD_RES                    27
                           note = D-alanine
MOD_RES                    40
                           note = AminoEthoxyEthoxyAcetic Acyl-MaleimidoPropionic Acyl
SEQUENCE: 49
HGFGTFTSDG IDXLEAITAK EFIAWLAIGK PSSGAPPPSK                                  40

SEQ ID NO: 50              moltype = AA  length = 40
FEATURE                    Location/Qualifiers
source                     1..40
                           mol_type = protein
                           organism = synthetic construct
MOD_RES                    2
                           note = Aib
SITE                       11
                           note = D-alanine
MOD_RES                    13
                           note = Aib
MOD_RES                    20
                           note = Aib
MOD_RES                    40
                           note = AminoEthoxyEthoxyAcetic Acyl-MaleimidoPropionic Acyl
SEQUENCE: 50
HXTGTFTSDI AIXLDYKGAX AFVQWLDAGE PSSGAPPPSK                                  40

SEQ ID NO: 51              moltype = AA  length = 40
FEATURE                    Location/Qualifiers
source                     1..40
                           mol_type = protein
                           organism = synthetic construct
SITE                       2
                           note = D-serine
MOD_RES                    11
                           note = Aib
MOD_RES                    13
                           note = Aib
MOD_RES                    20
```

-continued

```
                              note = Aib
MOD_RES                       40
                              note = AminoEthoxyEthoxyAcetic Acyl-MaleimidoPropionic Acyl
SEQUENCE: 51
HSLGTFTSDL XMXLDVNIAX DFIAWLMIGY PSSGAPPPSK                           40

SEQ ID NO: 52                 moltype = AA  length = 40
FEATURE                       Location/Qualifiers
source                        1..40
                              mol_type = protein
                              organism = synthetic construct
MOD_RES                       13
                              note = Aib
SITE                          28
                              note = D-serine
MOD_RES                       40
                              note = AminoEthoxyEthoxyAcetic Acyl-MaleimidoPropionic Acyl
SEQUENCE: 52
YGDGTFTSDK HRXLEISQQK EFVQWLLSGL PSSGAPPPSK                           40

SEQ ID NO: 53                 moltype = AA  length = 40
FEATURE                       Location/Qualifiers
source                        1..40
                              mol_type = protein
                              organism = synthetic construct
SITE                          2..3
                              note = D-alanine
MOD_RES                       13
                              note = Aib
MOD_RES                       28
                              note = Aib
MOD_RES                       30
                              note = Aib
MOD_RES                       40
                              note = AminoEthoxyEthoxyAcetic Acyl-MaleimidoPropionic Acyl
SEQUENCE: 53
FAAGTFTSDQ TTXLDAGSAK DFVNWLVXGX PSSGAPPPSK                           40

SEQ ID NO: 54                 moltype = AA  length = 40
FEATURE                       Location/Qualifiers
source                        1..40
                              mol_type = protein
                              organism = synthetic construct
MOD_RES                       2
                              note = Aib
MOD_RES                       20
                              note = Aib
MOD_RES                       40
                              note = AminoEthoxyEthoxyAcetic Acyl-MaleimidoPropionic Acyl
SEQUENCE: 54
YXGGTFTSDE PPYLDAWTQX EFVEWLVRGW PSSGAPPPSK                           40

SEQ ID NO: 55                 moltype = AA  length = 40
FEATURE                       Location/Qualifiers
source                        1..40
                              mol_type = protein
                              organism = synthetic construct
SITE                          2
                              note = D-alanine
MOD_RES                       13
                              note = Aib
SITE                          17
                              note = D-alanine
MOD_RES                       40
                              note = AminoEthoxyEthoxyAcetic Acyl-MaleimidoPropionic Acyl
SEQUENCE: 55
HAGGTFTSDG SRXLDIATQQ DFIEWLLEGH PSSGAPPPSK                           40

SEQ ID NO: 56                 moltype = AA  length = 40
FEATURE                       Location/Qualifiers
source                        1..40
                              mol_type = protein
                              organism = synthetic construct
SITE                          2
                              note = D-serine
MOD_RES                       40
                              note = AminoEthoxyEthoxyAcetic Acyl-MaleimidoPropionic Acyl
SEQUENCE: 56
HSSGTFTSDP LKYLDHGNQQ AFVNWLISGS PSSGAPPPSK                           40
```

-continued

```
SEQ ID NO: 57          moltype = AA  length = 40
FEATURE                Location/Qualifiers
source                 1..40
                       mol_type = protein
                       organism = synthetic construct
MOD_RES                2
                       note = Aib
SITE                   30
                       note = D-serine
MOD_RES                40
                       note = AminoEthoxyEthoxyAcetic Acyl-MaleimidoPropionic Acyl
SEQUENCE: 57
HXTGTFTSDI SFYLEEYVAQ EFVAWLQAGS PSSGAPPPSK                              40

SEQ ID NO: 58          moltype = AA  length = 40
FEATURE                Location/Qualifiers
source                 1..40
                       mol_type = protein
                       organism = synthetic construct
SITE                   2
                       note = D-serine
SITE                   3
                       note = D-alanine
SITE                   10
                       note = D-alanine
MOD_RES                13
                       note = Aib
MOD_RES                17
                       note = Aib
MOD_RES                40
                       note = AminoEthoxyEthoxyAcetic Acyl-MaleimidoPropionic Acyl
SEQUENCE: 58
HSAGTFTSDA YEXLEPXDQK AFIAWLWHGL PSSGAPPPSK                              40

SEQ ID NO: 59          moltype = AA  length = 40
FEATURE                Location/Qualifiers
source                 1..40
                       mol_type = protein
                       organism = synthetic construct
SITE                   2
                       note = D-serine
MOD_RES                13
                       note = Aib
SITE                   17
                       note = D-serine
MOD_RES                40
                       note = AminoEthoxyEthoxyAcetic Acyl-MaleimidoPropionic Acyl
SEQUENCE: 59
YSRGTFTSDA TLXLEGSKQK AFINWLLEGI PSSGAPPPSK                              40

SEQ ID NO: 60          moltype = AA  length = 40
FEATURE                Location/Qualifiers
source                 1..40
                       mol_type = protein
                       organism = synthetic construct
MOD_RES                13
                       note = Aib
MOD_RES                40
                       note = AminoEthoxyEthoxyAcetic Acyl-MaleimidoPropionic Acyl
SEQUENCE: 60
FGWGTFTSDL EKXLELARAQ AFVEWLKVGS PSSGAPPPSK                              40

SEQ ID NO: 61          moltype = AA  length = 40
FEATURE                Location/Qualifiers
source                 1..40
                       mol_type = protein
                       organism = synthetic construct
MOD_RES                2
                       note = Aib
SITE                   18
                       note = D-alanine
SITE                   27
                       note = D-serine
MOD_RES                40
                       note = AminoEthoxyEthoxyAcetic Acyl-MaleimidoPropionic Acyl
SEQUENCE: 61
FXMGTFTSDP YPYLEWEAAQ AFINWLSGGS PSSGAPPPSK                              40
```

```
SEQ ID NO: 62            moltype = AA   length = 40
FEATURE                  Location/Qualifiers
source                   1..40
                         mol_type = protein
                         organism = synthetic construct
SITE                     2
                         note = D-alanine
MOD_RES                  3
                         note = Aib
MOD_RES                  13
                         note = Aib
MOD_RES                  40
                         note = AminoEthoxyEthoxyAcetic Acyl-MaleimidoPropionic Acyl
SEQUENCE: 62
HAXGTFTSDM PTXLDHIQQQ DFVAWLVQGI PSSGAPPPSK                         40

SEQ ID NO: 63            moltype = AA   length = 40
FEATURE                  Location/Qualifiers
source                   1..40
                         mol_type = protein
                         organism = synthetic construct
SITE                     2
                         note = D-alanine
SITE                     3
                         note = D-serine
MOD_RES                  13
                         note = Aib
MOD_RES                  40
                         note = AminoEthoxyEthoxyAcetic Acyl-MaleimidoPropionic Acyl
SEQUENCE: 63
FASGTFTSDH SDXLELKAQQ EFVNWLRNGR PSSGAPPPSK                         40

SEQ ID NO: 64            moltype = AA   length = 40
FEATURE                  Location/Qualifiers
source                   1..40
                         mol_type = protein
                         organism = synthetic construct
MOD_RES                  40
                         note = AminoEthoxyEthoxyAcetic Acyl-MaleimidoPropionic Acyl
SEQUENCE: 64
HGQGTFTSDY SKYLDARRAQ DFVEWLKNGG PSSGAPPPSK                         40

SEQ ID NO: 65            moltype = AA   length = 40
FEATURE                  Location/Qualifiers
source                   1..40
                         mol_type = protein
                         organism = synthetic construct
MOD_RES                  2
                         note = Aib
MOD_RES                  13
                         note = Aib
MOD_RES                  40
                         note = AminoEthoxyEthoxyAcetic Acyl-MaleimidoPropionic Acyl
SEQUENCE: 65
HXQGTFTSDY SKXLDKRRAK DFVEWLKNGG PSSGAPPPSK                         40

SEQ ID NO: 66            moltype = AA   length = 40
FEATURE                  Location/Qualifiers
source                   1..40
                         mol_type = protein
                         organism = synthetic construct
MOD_RES                  2
                         note = Aib
MOD_RES                  40
                         note = AminoEthoxyEthoxyAcetic Acyl-MaleimidoPropionic Acyl
SEQUENCE: 66
HXQGTFTSDY SKYLDKRRAK DFVEWLKNGG PSSGAPPPSK                         40

SEQ ID NO: 67            moltype = AA   length = 40
FEATURE                  Location/Qualifiers
source                   1..40
                         mol_type = protein
                         organism = synthetic construct
MOD_RES                  2
                         note = Aib
MOD_RES                  13
                         note = Alpha-Methyl-Leucine
MOD_RES                  20
                         note = Aib
```

-continued

```
MOD_RES                  40
                         note = AminoEthoxyEthoxyAcetic Acyl-MaleimidoPropionic Acyl
SEQUENCE: 67
YXQGTFTSDY SIXLDKIAQX AFIEYLLEGG PSSGAPPPSK                      40

SEQ ID NO: 68            moltype = AA  length = 40
FEATURE                  Location/Qualifiers
source                   1..40
                         mol_type = protein
                         organism = synthetic construct
MOD_RES                  2
                         note = Aib
MOD_RES                  13
                         note = Aib
MOD_RES                  40
                         note = AminoEthoxyEthoxyAcetic Acyl-MaleimidoPropionic Acyl
SEQUENCE: 68
YXEGTFTSDY SIXLDKIAQK AFVQWLIAGG PSSGAPPPSK                      40

SEQ ID NO: 69            moltype = AA  length = 40
FEATURE                  Location/Qualifiers
source                   1..40
                         mol_type = protein
                         organism = synthetic construct
SITE                     2
                         note = D-alanine
MOD_RES                  40
                         note = AminoEthoxyEthoxyAcetic Acyl-MaleimidoPropionic Acyl
SEQUENCE: 69
HAEGTFTSDY AKYLDARRAK EFIAWLVNGG PSSGAPPPSK                      40

SEQ ID NO: 70            moltype = AA  length = 40
FEATURE                  Location/Qualifiers
source                   1..40
                         mol_type = protein
                         organism = synthetic construct
MOD_RES                  2
                         note = Aib
MOD_RES                  20
                         note = Aib
MOD_RES                  40
                         note = AminoEthoxyEthoxyAcetic Acyl-MaleimidoPropionic Acyl
SEQUENCE: 70
YXEGTFTSDY SIYLDKQAAX EFVQWLLAGG PSSGAPPPSK                      40

SEQ ID NO: 71            moltype = AA  length = 40
FEATURE                  Location/Qualifiers
source                   1..40
                         mol_type = protein
                         organism = synthetic construct
MOD_RES                  2
                         note = Aib
MOD_RES                  20
                         note = Aib
MOD_RES                  35
                         note = Aib
MOD_RES                  40
                         note = AminoEthoxyEthoxyAcetic Acyl-MaleimidoPropionic Acyl
SITE                     29
                         note = D-alanine
SEQUENCE: 71
HXHGTFTSDL SKLLEEQRQX EFIEWLKAAG PPPSXKPPPK                      40

SEQ ID NO: 72            moltype = AA  length = 39
FEATURE                  Location/Qualifiers
source                   1..39
                         mol_type = protein
                         organism = synthetic construct
SITE                     2
                         note = D-alanine
MOD_RES                  20
                         note = AminoEthoxyEthoxyAcetic Acyl-MaleimidoPropionic Acyl
SEQUENCE: 72
HAMGTFTSDR HWYLDMSHQK AFVQWLAYGN PSSGAPPPS                       39

SEQ ID NO: 73            moltype = AA  length = 39
FEATURE                  Location/Qualifiers
source                   1..39
                         mol_type = protein
```

```
                              organism = synthetic construct
SITE                          2
                              note = D-alanine
SITE                          3
                              note = D-serine
MOD_RES                       20
                              note = AminoEthoxyEthoxyAcetic Acyl-MaleimidoPropionic Acyl
SEQUENCE: 73
YASGTFTSDW GRYLELLIQK EFVNWLIIGA PSSGAPPPS                                          39

SEQ ID NO: 74                 moltype = AA  length = 39
FEATURE                       Location/Qualifiers
source                        1..39
                              mol_type = protein
                              organism = synthetic construct
SITE                          10
                              note = D-serine
MOD_RES                       13
                              note = Aib
SITE                          17
                              note = D-serine
SITE                          18
                              note = D-alanine
SITE                          27
                              note = D-alanine
MOD_RES                       20
                              note = AminoEthoxyEthoxyAcetic Acyl-AminoEthoxyEthoxyAcetic
                               Acyl-MaleimidoPropionic Acyl
SEQUENCE: 74
HGKGTFTSDS AIXLEVSAAK AFIEWLAHGD PSSGAPPPS                                          39

SEQ ID NO: 75                 moltype = AA  length = 39
FEATURE                       Location/Qualifiers
source                        1..39
                              mol_type = protein
                              organism = synthetic construct
SITE                          3
                              note = D-serine
SITE                          2
                              note = D-alanine
MOD_RES                       13
                              note = Aib
SITE                          27
                              note = D-alanine
MOD_RES                       20
                              note = AminoEthoxyEthoxyAcetic Acyl-MaleimidoPropionic Acyl
SEQUENCE: 75
HASGTFTSDI LEXLDQAAAK EFVEWLAHGF PSSGAPPPS                                          39

SEQ ID NO: 76                 moltype = AA  length = 39
FEATURE                       Location/Qualifiers
source                        1..39
                              mol_type = protein
                              organism = synthetic construct
SITE                          2
                              note = D-alanine
MOD_RES                       12..13
                              note = Aib
MOD_RES                       20
                              note = AminoEthoxyEthoxyAcetic Acyl-MaleimidoPropionic Acyl
SEQUENCE: 76
HAYGTFTSDY MXXLDFLQQK DFVAWLFMGV PSSGAPPPS                                          39

SEQ ID NO: 77                 moltype = AA  length = 39
FEATURE                       Location/Qualifiers
source                        1..39
                              mol_type = protein
                              organism = synthetic construct
MOD_RES                       2
                              note = Aib
SITE                          3
                              note = D-serine
MOD_RES                       10
                              note = Aib
MOD_RES                       20
                              note = AminoEthoxyEthoxyAcetic Acyl-MaleimidoPropionic Acyl
SEQUENCE: 77
HXSGTFTSDX AYYLDNTTAK DFIQWLDAGP PSSGAPPPS                                          39
```

-continued

```
SEQ ID NO: 78          moltype = AA   length = 39
FEATURE                Location/Qualifiers
source                 1..39
                       mol_type = protein
                       organism = synthetic construct
MOD_RES                2
                       note = Aib
SITE                   11
                       note = D-alanine
MOD_RES                16
                       note = Aib
SITE                   30
                       note = D-serine
MOD_RES                20
                       note = AminoEthoxyEthoxyAcetic Acyl-MaleimidoPropionic Acyl
SEQUENCE: 78
FXKGTFTSDD AVYLEXHRAK EFVEWLFGGS PSSGAPPPS                                  39

SEQ ID NO: 79          moltype = AA   length = 39
FEATURE                Location/Qualifiers
source                 1..39
                       mol_type = protein
                       organism = synthetic construct
MOD_RES                2
                       note = Aib
MOD_RES                13
                       note = Aib
MOD_RES                27
                       note = Aib
MOD_RES                20
                       note = AminoEthoxyEthoxyAcetic Acyl-MaleimidoPropionic Acyl
SEQUENCE: 79
YXHGTFTSDL TVXLDEIKAK EFVEWLXVGP PSSGAPPPS                                  39

SEQ ID NO: 80          moltype = AA   length = 39
FEATURE                Location/Qualifiers
source                 1..39
                       mol_type = protein
                       organism = synthetic construct
SITE                   2
                       note = D-serine
SITE                   12
                       note = D-alanine
MOD_RES                13
                       note = Aib
MOD_RES                16
                       note = Aib
MOD_RES                20
                       note = AminoEthoxyEthoxyAcetic Acyl-MaleimidoPropionic Acyl
SEQUENCE: 80
FSWGTFTSDF PAXLEXMKAK DFVEWLLDGN PSSGAPPPS                                  39

SEQ ID NO: 81          moltype = AA   length = 39
FEATURE                Location/Qualifiers
source                 1..39
                       mol_type = protein
                       organism = synthetic construct
MOD_RES                2
                       note = Aib
MOD_RES                13
                       note = Aib
SITE                   28
                       note = D-serine
MOD_RES                20
                       note = AminoEthoxyEthoxyAcetic Acyl-MaleimidoPropionic Acyl
SEQUENCE: 81
HXKGTFTSDD ADXLEWYRQK AFVQWLPSGI PSSGAPPPS                                  39

SEQ ID NO: 82          moltype = AA   length = 39
FEATURE                Location/Qualifiers
source                 1..39
                       mol_type = protein
                       organism = synthetic construct
MOD_RES                2
                       note = Aib
MOD_RES                13
                       note = Aib
SITE                   27
                       note = D-serine
```

```
MOD_RES                   20
                          note = AminoEthoxyEthoxyAcetic Acyl-MaleimidoPropionic Acyl
SEQUENCE: 82
YXWGTFTSDS NSXLEAKMQK EFVNWLSQGF PSSGAPPPS                            39

SEQ ID NO: 83             moltype = AA  length = 39
FEATURE                   Location/Qualifiers
source                    1..39
                          mol_type = protein
                          organism = synthetic construct
SITE                      2
                          note = D-alanine
SITE                      18
                          note = D-serine
MOD_RES                   20
                          note = AminoEthoxyEthoxyAcetic Acyl-MaleimidoPropionic Acyl
SEQUENCE: 83
FATGTFTSDD ADYLELFSQK AFIAWLDNGV PSSGAPPPS                            39

SEQ ID NO: 84             moltype = AA  length = 39
FEATURE                   Location/Qualifiers
source                    1..39
                          mol_type = protein
                          organism = synthetic construct
SITE                      2
                          note = D-serine
MOD_RES                   13
                          note = Aib
MOD_RES                   17
                          note = Aib
MOD_RES                   20
                          note = AminoEthoxyEthoxyAcetic Acyl-MaleimidoPropionic Acyl
SEQUENCE: 84
YSYGTFTSDW DAXLESXMQK EFVQWLFYGQ PSSGAPPPS                            39

SEQ ID NO: 85             moltype = AA  length = 39
FEATURE                   Location/Qualifiers
source                    1..39
                          mol_type = protein
                          organism = synthetic construct
SITE                      2
                          note = D-alanine
SITE                      12
                          note = D-serine
MOD_RES                   13
                          note = Aib
MOD_RES                   20
                          note = AminoEthoxyEthoxyAcetic Acyl-MaleimidoPropionic Acyl
SEQUENCE: 85
YANGTFTSDT NSXLDSTQAK EFVAWLVQGD PSSGAPPPS                            39

SEQ ID NO: 86             moltype = AA  length = 39
FEATURE                   Location/Qualifiers
source                    1..39
                          mol_type = protein
                          organism = synthetic construct
MOD_RES                   2
                          note = Aib
MOD_RES                   20
                          note = AminoEthoxyEthoxyAcetic Acyl-MaleimidoPropionic Acyl
SEQUENCE: 86
FXIGTFTSDK QAYLEHPRQK AFVAWLDVGY PSSGAPPPS                            39

SEQ ID NO: 87             moltype = AA  length = 39
FEATURE                   Location/Qualifiers
source                    1..39
                          mol_type = protein
                          organism = synthetic construct
MOD_RES                   2
                          note = Aib
MOD_RES                   13
                          note = Aib
SITE                      30
                          note = D-serine
MOD_RES                   20
                          note = AminoEthoxyEthoxyAcetic Acyl-MaleimidoPropionic Acyl
SEQUENCE: 87
HXRGTFTSDK FIXLEYHNAK EFVAWLYKGS PSSGAPPPS                            39
```

```
SEQ ID NO: 88              moltype = AA  length = 39
FEATURE                    Location/Qualifiers
source                     1..39
                           mol_type = protein
                           organism = synthetic construct
SITE                       10
                           note = D-serine
MOD_RES                    20
                           note = AminoEthoxyEthoxyAcetic Acyl-MaleimidoPropionic Acyl
SEQUENCE: 88
FGHGTFTSDS IWYLENYSQK EFIEWLEKGP PSSGAPPPS                         39

SEQ ID NO: 89              moltype = AA  length = 39
FEATURE                    Location/Qualifiers
source                     1..39
                           mol_type = protein
                           organism = synthetic construct
SITE                       2
                           note = D-serine
SITE                       3
                           note = D-alanine
MOD_RES                    12
                           note = Aib
SITE                       27
                           note = D-alanine
MOD_RES                    20
                           note = AminoEthoxyEthoxyAcetic Acyl-MaleimidoPropionic Acyl
SEQUENCE: 89
HSAGTFTSDI RXYLEIMLQK EFVEWLAEGV PSSGAPPPS                         39

SEQ ID NO: 90              moltype = AA  length = 39
FEATURE                    Location/Qualifiers
source                     1..39
                           mol_type = protein
                           organism = synthetic construct
MOD_RES                    2
                           note = Aib
SITE                       18
                           note = D-serine
MOD_RES                    20
                           note = AminoEthoxyEthoxyAcetic Acyl-MaleimidoPropionic Acyl
SEQUENCE: 90
HXFGTFTSDM LNYLEENSQK EFVNWLQLGM PSSGAPPPS                         39

SEQ ID NO: 91              moltype = AA  length = 39
FEATURE                    Location/Qualifiers
source                     1..39
                           mol_type = protein
                           organism = synthetic construct
MOD_RES                    20
                           note = AminoEthoxyEthoxyAcetic Acyl-MaleimidoPropionic Acyl
SEQUENCE: 91
FGHGTFTSDI WIYLEVQTAK DFINWLSWGE PSSGAPPPS                         39

SEQ ID NO: 92              moltype = AA  length = 39
FEATURE                    Location/Qualifiers
source                     1..39
                           mol_type = protein
                           organism = synthetic construct
SITE                       2
                           note = D-serine
MOD_RES                    20
                           note = AminoEthoxyEthoxyAcetic Acyl-MaleimidoPropionic Acyl
SEQUENCE: 92
HSGGTFTSDS GPYLDKTDQK AFINWLPIGN PSSGAPPPS                         39

SEQ ID NO: 93              moltype = AA  length = 39
FEATURE                    Location/Qualifiers
source                     1..39
                           mol_type = protein
                           organism = synthetic construct
SITE                       2
                           note = D-serine
SITE                       11
                           note = D-serine
MOD_RES                    13
                           note = Aib
MOD_RES                    20
                           note = AminoEthoxyEthoxyAcetic Acyl-MaleimidoPropionic Acyl
```

-continued

```
SEQUENCE: 93
YSIGTFTSDH SPXLDHLFAK DFVEWLENGD PSSGAPPPS                            39

SEQ ID NO: 94            moltype = AA  length = 39
FEATURE                  Location/Qualifiers
source                   1..39
                         mol_type = protein
                         organism = synthetic construct
MOD_RES                  13
                         note = Aib
MOD_RES                  18
                         note = Aib
SITE                     17
                         note = D-serine
MOD_RES                  20
                         note = AminoEthoxyEthoxyAcetic Acyl-MaleimidoPropionic Acyl
SEQUENCE: 94
FGYGTFTSDK EGXLEQSXAK EFIQWLPHGP PSSGAPPPS                            39

SEQ ID NO: 95            moltype = AA  length = 39
FEATURE                  Location/Qualifiers
source                   1..39
                         mol_type = protein
                         organism = synthetic construct
SITE                     2
                         note = D-serine
MOD_RES                  11
                         note = Aib
MOD_RES                  13
                         note = Aib
MOD_RES                  20
                         note = AminoEthoxyEthoxyAcetic Acyl-MaleimidoPropionic Acyl
SEQUENCE: 95
FSWGTFTSDF XSXLDTTRAK DFVEWLIRGN PSSGAPPPS                            39

SEQ ID NO: 96            moltype = AA  length = 39
FEATURE                  Location/Qualifiers
source                   1..39
                         mol_type = protein
                         organism = synthetic construct
MOD_RES                  2
                         note = Aib
SITE                     18
                         note = D-serine
MOD_RES                  28
                         note = Aib
MOD_RES                  20
                         note = AminoEthoxyEthoxyAcetic Acyl-MaleimidoPropionic Acyl
SEQUENCE: 96
HXPGTFTSDH EKYLEMVSAK DFIAWLRXGD PSSGAPPPS                            39

SEQ ID NO: 97            moltype = AA  length = 39
FEATURE                  Location/Qualifiers
source                   1..39
                         mol_type = protein
                         organism = synthetic construct
SITE                     2
                         note = D-alanine
SITE                     12
                         note = D-alanine
MOD_RES                  13
                         note = Aib
SITE                     17
                         note = D-alanine
MOD_RES                  20
                         note = AminoEthoxyEthoxyAcetic Acyl-MaleimidoPropionic Acyl
SEQUENCE: 97
YAAGTFTSDT IAXLDNAAAK DFIAWLIQGY PSSGAPPPS                            39

SEQ ID NO: 98            moltype = AA  length = 39
FEATURE                  Location/Qualifiers
source                   1..39
                         mol_type = protein
                         organism = synthetic construct
MOD_RES                  2
                         note = Aib
MOD_RES                  13
                         note = Aib
MOD_RES                  20
```

-continued

```
                            note = AminoEthoxyEthoxyAcetic Acyl-MaleimidoPropionic Acyl
SEQUENCE: 98
YXLGTFTSDT IHXLEFEAQK DFINWLKAGE PSSGAPPPS                    39

SEQ ID NO: 99           moltype = AA  length = 39
FEATURE                 Location/Qualifiers
source                  1..39
                        mol_type = protein
                        organism = synthetic construct
MOD_RES                 2
                        note = Aib
MOD_RES                 27
                        note = Aib
MOD_RES                 20
                        note = AminoEthoxyEthoxyAcetic Acyl-MaleimidoPropionic Acyl
SEQUENCE: 99
YXQGTFTSDA MIYLDTPDAK EFIAWLXIGG PSSGAPPPS                    39

SEQ ID NO: 100          moltype = AA  length = 39
FEATURE                 Location/Qualifiers
source                  1..39
                        mol_type = protein
                        organism = synthetic construct
MOD_RES                 11
                        note = Aib
MOD_RES                 13
                        note = Aib
MOD_RES                 17
                        note = Aib
MOD_RES                 20
                        note = AminoEthoxyEthoxyAcetic Acyl-MaleimidoPropionic Acyl
SEQUENCE: 100
YGAGTFTSDH XGXLDIXQQK EFVQWLETGT PSSGAPPPS                    39

SEQ ID NO: 101          moltype = AA  length = 39
FEATURE                 Location/Qualifiers
source                  1..39
                        mol_type = protein
                        organism = synthetic construct
SITE                    2
                        note = D-alanine
MOD_RES                 20
                        note = AminoEthoxyEthoxyAcetic Acyl-MaleimidoPropionic Acyl
SEQUENCE: 101
YAVGTFTSDL SEYLEMNIAK DFVQWLLVGG PSSGAPPPS                    39

SEQ ID NO: 102          moltype = AA  length = 39
FEATURE                 Location/Qualifiers
source                  1..39
                        mol_type = protein
                        organism = synthetic construct
SITE                    12
                        note = D-serine
MOD_RES                 20
                        note = AminoEthoxyEthoxyAcetic Acyl-MaleimidoPropionic Acyl
SEQUENCE: 102
YGPGTFTSDR YSYLEQHMAK EFIQWLGPGH PSSGAPPPS                    39

SEQ ID NO: 103          moltype = AA  length = 39
FEATURE                 Location/Qualifiers
source                  1..39
                        mol_type = protein
                        organism = synthetic construct
MOD_RES                 2
                        note = Aib
SITE                    28
                        note = D-alanine
MOD_RES                 20
                        note = AminoEthoxyEthoxyAcetic Acyl-MaleimidoPropionic Acyl
SEQUENCE: 103
YXRGTFTSDM RVYLEETLQK AFVQWLIAGD PSSGAPPPS                    39

SEQ ID NO: 104          moltype = AA  length = 39
FEATURE                 Location/Qualifiers
source                  1..39
                        mol_type = protein
                        organism = synthetic construct
SITE                    2
                        note = D-serine
```

```
MOD_RES              3
                     note = Aib
MOD_RES              13
                     note = Aib
MOD_RES              20
                     note = AminoEthoxyEthoxyAcetic Acyl-MaleimidoPropionic Acyl
SEQUENCE: 104
YSXGTFTSDF MEXLDKKIQK DFIQWLWYGS PSSGAPPPS                                39

SEQ ID NO: 105       moltype = AA  length = 39
FEATURE              Location/Qualifiers
source               1..39
                     mol_type = protein
                     organism = synthetic construct
MOD_RES              2
                     note = Aib
SITE                 3
                     note = D-serine
MOD_RES              27
                     note = Aib
MOD_RES              20
                     note = AminoEthoxyEthoxyAcetic Acyl-MaleimidoPropionic Acyl
SEQUENCE: 105
FXSGTFTSDE LRYLEEMHQK AFIQWLXTGF PSSGAPPPS                                39

SEQ ID NO: 106       moltype = AA  length = 39
FEATURE              Location/Qualifiers
source               1..39
                     mol_type = protein
                     organism = synthetic construct
SITE                 27
                     note = D-serine
MOD_RES              20
                     note = AminoEthoxyEthoxyAcetic Acyl-MaleimidoPropionic Acyl
SEQUENCE: 106
YGPGTFTSDW AKYLEGRDAK AFINWLSQGS PSSGAPPPS                                39

SEQ ID NO: 107       moltype = AA  length = 39
FEATURE              Location/Qualifiers
source               1..39
                     mol_type = protein
                     organism = synthetic construct
MOD_RES              13
                     note = Aib
SITE                 30
                     note = D-alanine
MOD_RES              20
                     note = AminoEthoxyEthoxyAcetic Acyl-MaleimidoPropionic Acyl
SEQUENCE: 107
HGVGTFTSDH HFXLEIIMAK AFIEWLWHGA PSSGAPPPS                                39

SEQ ID NO: 108       moltype = AA  length = 39
FEATURE              Location/Qualifiers
source               1..39
                     mol_type = protein
                     organism = synthetic construct
SITE                 18
                     note = D-alanine
MOD_RES              20
                     note = AminoEthoxyEthoxyAcetic Acyl-MaleimidoPropionic Acyl
SEQUENCE: 108
HGIGTFTSDV PAYLDPAAAK DFIQWLVSGG PSSGAPPPS                                39

SEQ ID NO: 109       moltype = AA  length = 39
FEATURE              Location/Qualifiers
source               1..39
                     mol_type = protein
                     organism = synthetic construct
SITE                 2
                     note = D-serine
MOD_RES              13
                     note = Aib
MOD_RES              28
                     note = Aib
MOD_RES              20
                     note = AminoEthoxyEthoxyAcetic Acyl-MaleimidoPropionic Acyl
SEQUENCE: 109
HSNGTFTSDR RKXLEPPIAK EFVQWLIXGI PSSGAPPPS                                39
```

-continued

```
SEQ ID NO: 110            moltype = AA   length = 39
FEATURE                   Location/Qualifiers
source                    1..39
                          mol_type = protein
                          organism = synthetic construct
MOD_RES                   2
                          note = Aib
SITE                      12
                          note = D-alanine
MOD_RES                   20
                          note = AminoEthoxyEthoxyAcetic Acyl-MaleimidoPropionic Acyl
SEQUENCE: 110
FXTGTFTSDT MAYLDYTHAK DFIAWLIDGK PSSGAPPPS                      39

SEQ ID NO: 111            moltype = AA   length = 39
FEATURE                   Location/Qualifiers
source                    1..39
                          mol_type = protein
                          organism = synthetic construct
SITE                      2
                          note = D-alanine
SITE                      10
                          note = D-serine
MOD_RES                   20
                          note = AminoEthoxyEthoxyAcetic Acyl-MaleimidoPropionic Acyl
SEQUENCE: 111
YATGTFTSDS VQYLEHPMQK AFVAWLHTGR PSSGAPPPS                      39

SEQ ID NO: 112            moltype = AA   length = 39
FEATURE                   Location/Qualifiers
source                    1..39
                          mol_type = protein
                          organism = synthetic construct
MOD_RES                   2
                          note = Aib
MOD_RES                   30
                          note = Aib
MOD_RES                   20
                          note = AminoEthoxyEthoxyAcetic Acyl-MaleimidoPropionic Acyl
SEQUENCE: 112
YXTGTFTSDE EWYLDNWMQK AFVQWLSNGX PSSGAPPPS                      39

SEQ ID NO: 113            moltype = AA   length = 39
FEATURE                   Location/Qualifiers
source                    1..39
                          mol_type = protein
                          organism = synthetic construct
SITE                      2
                          note = D-serine
MOD_RES                   13
                          note = Aib
MOD_RES                   16
                          note = Aib
MOD_RES                   20
                          note = AminoEthoxyEthoxyAcetic Acyl-MaleimidoPropionic Acyl
SEQUENCE: 113
YSIGTFTSDG NKXLEXGRAK AFIAWLQYGR PSSGAPPPS                      39

SEQ ID NO: 114            moltype = AA   length = 39
FEATURE                   Location/Qualifiers
source                    1..39
                          mol_type = protein
                          organism = synthetic construct
SITE                      2
                          note = D-serine
MOD_RES                   20
                          note = AminoEthoxyEthoxyAcetic Acyl-MaleimidoPropionic Acyl
SEQUENCE: 114
YSPGTFTSDM YVYLEPGDAK EFVQWLKNGG PSSGAPPPS                      39

SEQ ID NO: 115            moltype = AA   length = 39
FEATURE                   Location/Qualifiers
source                    1..39
                          mol_type = protein
                          organism = synthetic construct
SITE                      2
                          note = D-alanine
MOD_RES                   13
                          note = Aib
```

-continued

```
SITE                    30
                        note = D-serine
MOD_RES                 20
                        note = AminoEthoxyEthoxyAcetic Acyl-MaleimidoPropionic Acyl
SEQUENCE: 115
FSIGTFTSDL MAXLERAAQK EFVNWLIIGS PSSGAPPPS                          39

SEQ ID NO: 116          moltype = AA  length = 39
FEATURE                 Location/Qualifiers
source                  1..39
                        mol_type = protein
                        organism = synthetic construct
MOD_RES                 2
                        note = Aib
MOD_RES                 20
                        note = AminoEthoxyEthoxyAcetic Acyl-MaleimidoPropionic Acyl
SEQUENCE: 116
YXNGTFTSDI EQYLEPMVQK EFVQWLSPGN PSSGAPPPS                          39

SEQ ID NO: 117          moltype = AA  length = 39
FEATURE                 Location/Qualifiers
source                  1..39
                        mol_type = protein
                        organism = synthetic construct
SITE                    12
                        note = D-serine
MOD_RES                 13
                        note = Aib
MOD_RES                 20
                        note = AminoEthoxyEthoxyAcetic Acyl-MaleimidoPropionic Acyl
SEQUENCE: 117
YGWGTFTSDS FSXLDWMMAK AFIQWLIVGI PSSGAPPPS                          39

SEQ ID NO: 118          moltype = AA  length = 39
FEATURE                 Location/Qualifiers
source                  1..39
                        mol_type = protein
                        organism = synthetic construct
SITE                    2
                        note = D-serine
MOD_RES                 10
                        note = Aib
MOD_RES                 20
                        note = AminoEthoxyEthoxyAcetic Acyl-MaleimidoPropionic Acyl
SEQUENCE: 118
HSPGTFTSDX THYLDNDQQK DFVNWLPEGW PSSGAPPPS                          39

SEQ ID NO: 119          moltype = AA  length = 39
FEATURE                 Location/Qualifiers
source                  1..39
                        mol_type = protein
                        organism = synthetic construct
SITE                    3
                        note = D-alanine
MOD_RES                 13
                        note = Aib
SITE                    16
                        note = D-serine
MOD_RES                 20
                        note = AminoEthoxyEthoxyAcetic Acyl-MaleimidoPropionic Acyl
SEQUENCE: 119
YGAGTFTSDN HTXLESFAAK EFIQWLNSGQ PSSGAPPPS                          39

SEQ ID NO: 120          moltype = AA  length = 39
FEATURE                 Location/Qualifiers
source                  1..39
                        mol_type = protein
                        organism = synthetic construct
SITE                    2
                        note = D-alanine
MOD_RES                 13
                        note = Aib
MOD_RES                 20
                        note = AminoEthoxyEthoxyAcetic Acyl-MaleimidoPropionic Acyl
SEQUENCE: 120
YAMGTFTSDR LRXLDQFSAK AFVNWLSWGE PSSGAPPPS                          39

SEQ ID NO: 121          moltype = AA  length = 39
FEATURE                 Location/Qualifiers
```

```
source                  1..39
                        mol_type = protein
                        organism = synthetic construct
MOD_RES                 2
                        note = Aib
MOD_RES                 12..13
                        note = Aib
SITE                    3
                        note = D-alanine
SITE                    27
                        note = D-alanine
MOD_RES                 20
                        note = AminoEthoxyEthoxyAcetic Acyl-MaleimidoPropionic Acyl
SEQUENCE: 121
FXAGTFTSDS LXXLDHHNQK AFVEWLAPGL PSSGAPPPS                           39

SEQ ID NO: 122          moltype = AA   length = 39
FEATURE                 Location/Qualifiers
source                  1..39
                        mol_type = protein
                        organism = synthetic construct
MOD_RES                 16
                        note = AminoEthoxyEthoxyAcetic Acyl-MaleimidoPropionic Acyl
SEQUENCE: 122
HGQGTFTSDY SKYLDKRRAQ DFVEWLKNGG PSSGAPPPS                           39

SEQ ID NO: 123          moltype = AA   length = 39
FEATURE                 Location/Qualifiers
source                  1..39
                        mol_type = protein
                        organism = synthetic construct
MOD_RES                 2
                        note = Aib
MOD_RES                 13
                        note = Aib
MOD_RES                 20
                        note = AminoEthoxyEthoxyAcetic Acyl-MaleimidoPropionic Acyl
SEQUENCE: 123
HXQGTFTSDY SKXLDKRRAK DFVEWLKNGG PSSGAPPPS                           39

SEQ ID NO: 124          moltype = AA   length = 39
FEATURE                 Location/Qualifiers
source                  1..39
                        mol_type = protein
                        organism = synthetic construct
MOD_RES                 2
                        note = Aib
MOD_RES                 16
                        note = AminoEthoxyEthoxyAcetic Acyl-MaleimidoPropionic Acyl
SEQUENCE: 124
HXQGTFTSDY SKYLDKRRAQ DFVEWLKNGG PSSGAPPPS                           39

SEQ ID NO: 125          moltype = AA   length = 39
FEATURE                 Location/Qualifiers
source                  1..39
                        mol_type = protein
                        organism = synthetic construct
MOD_RES                 2
                        note = Aib
MOD_RES                 13
                        note = Aib
MOD_RES                 20
                        note = AminoEthoxyEthoxyAcetic Acyl-MaleimidoPropionic Acyl
SEQUENCE: 125
YXEGTFTSDY SIXLDKIAQK AFVQWLIAGG PSSGAPPPS                           39

SEQ ID NO: 126          moltype = AA   length = 39
FEATURE                 Location/Qualifiers
source                  1..39
                        mol_type = protein
                        organism = synthetic construct
MOD_RES                 2
                        note = Aib
MOD_RES                 13
                        note = Alpha-Methyl-Leucine
MOD_RES                 20
                        note = AminoEthoxyEthoxyAcetic Acyl-MaleimidoPropionic Acyl
SEQUENCE: 126
YXQGTFTSDY SIXLDKIAQK AFIEYLLEGG PSSGAPPPS                           39
```

-continued

```
SEQ ID NO: 127          moltype = AA  length = 39
FEATURE                 Location/Qualifiers
source                  1..39
                        mol_type = protein
                        organism = synthetic construct
SITE                    2
                        note = D-alanine
MOD_RES                 20
                        note = AminoEthoxyEthoxyAcetic Acyl-MaleimidoPropionic Acyl
SEQUENCE: 127
HAEGTFTSDY AKYLDARRAK EFIAWLVNGG PSSGAPPPS                               39

SEQ ID NO: 128          moltype = AA  length = 39
FEATURE                 Location/Qualifiers
source                  1..39
                        mol_type = protein
                        organism = synthetic construct
SITE                    2
                        note = D-alanine
SITE                    10
                        note = D-serine
MOD_RES                 20
                        note = Aib
MOD_RES                 17
                        note = AminoEthoxyEthoxyAcetic Acyl-MaleimidoPropionic Acyl
SEQUENCE: 128
YAWGTFTSDS KDYLEFKWAX EFIQWLDPGD PSSGAPPPS                               39

SEQ ID NO: 129          moltype = AA  length = 39
FEATURE                 Location/Qualifiers
source                  1..39
                        mol_type = protein
                        organism = synthetic construct
MOD_RES                 2
                        note = Aib
MOD_RES                 13
                        note = Aib
MOD_RES                 17
                        note = AminoEthoxyEthoxyAcetic Acyl-MaleimidoPropionic Acyl
MOD_RES                 20
                        note = Aib
SEQUENCE: 129
FXYGTFTSDI NVXLDIKWAX AFINWLPGGI PSSGAPPPS                               39

SEQ ID NO: 130          moltype = AA  length = 39
FEATURE                 Location/Qualifiers
source                  1..39
                        mol_type = protein
                        organism = synthetic construct
SITE                    2..3
                        note = D-alanine
MOD_RES                 13
                        note = Aib
MOD_RES                 20
                        note = Aib
MOD_RES                 17
                        note = AminoEthoxyEthoxyAcetic Acyl-MaleimidoPropionic Acyl
SEQUENCE: 130
FAAGTFTSDR QEXLDVKLAX EFVQWLVSGD PSSGAPPPS                               39

SEQ ID NO: 131          moltype = AA  length = 39
FEATURE                 Location/Qualifiers
source                  1..39
                        mol_type = protein
                        organism = synthetic construct
SITE                    2
                        note = D-alanine
MOD_RES                 13
                        note = Aib
SITE                    27
                        note = D-serine
MOD_RES                 17
                        note = AminoEthoxyEthoxyAcetic Acyl-MaleimidoPropionic Acyl
SEQUENCE: 131
FARGTFTSDS MQXLETKRQQ EFVNWLSMGV PSSGAPPPS                               39

SEQ ID NO: 132          moltype = AA  length = 39
FEATURE                 Location/Qualifiers
```

-continued

```
source                  1..39
                        mol_type = protein
                        organism = synthetic construct
SITE                    2
                        note = D-alanine
MOD_RES                 13
                        note = Aib
MOD_RES                 20
                        note = Aib
MOD_RES                 17
                        note = AminoEthoxyEthoxyAcetic Acyl-MaleimidoPropionic Acyl
SEQUENCE: 132
YAHGTFTSDT NRXLESKAAX EFIAWLEVGA PSSGAPPPS                                   39

SEQ ID NO: 133          moltype = AA  length = 39
FEATURE                 Location/Qualifiers
source                  1..39
                        mol_type = protein
                        organism = synthetic construct
MOD_RES                 2
                        note = Aib
SITE                    12
                        note = D-serine
MOD_RES                 13
                        note = Aib
MOD_RES                 20
                        note = Aib
SITE                    16
                        note = D-serine
MOD_RES                 17
                        note = AminoEthoxyEthoxyAcetic Acyl-MaleimidoPropionic Acyl
SEQUENCE: 133
FXGGTFTSDF RSXLDSKIAX EFINWLFKGF PSSGAPPPS                                   39

SEQ ID NO: 134          moltype = AA  length = 39
FEATURE                 Location/Qualifiers
source                  1..39
                        mol_type = protein
                        organism = synthetic construct
MOD_RES                 2
                        note = Aib
MOD_RES                 17
                        note = AminoEthoxyEthoxyAcetic Acyl-MaleimidoPropionic Acyl
SEQUENCE: 134
YXNGTFTSDM MPYLEPKHQK DFVEWLTSGD PSSGAPPPS                                   39

SEQ ID NO: 135          moltype = AA  length = 39
FEATURE                 Location/Qualifiers
source                  1..39
                        mol_type = protein
                        organism = synthetic construct
SITE                    2
                        note = D-alanine
MOD_RES                 20
                        note = Aib
MOD_RES                 17
                        note = AminoEthoxyEthoxyAcetic Acyl-MaleimidoPropionic Acyl
SEQUENCE: 135
HAPGTFTSDI IHYLETKIAX EFIQWLKRGS PSSGAPPPS                                   39

SEQ ID NO: 136          moltype = AA  length = 39
FEATURE                 Location/Qualifiers
source                  1..39
                        mol_type = protein
                        organism = synthetic construct
SITE                    2
                        note = D-serine
MOD_RES                 10
                        note = Aib
MOD_RES                 13
                        note = Aib
MOD_RES                 20
                        note = Aib
SITE                    28
                        note = D-alanine
MOD_RES                 17
                        note = AminoEthoxyEthoxyAcetic Acyl-MaleimidoPropionic Acyl
SEQUENCE: 136
FSVGTFTSDX SAXLDLKIAX EFINWLFAGF PSSGAPPPS                                   39
```

-continued

```
SEQ ID NO: 137          moltype = AA  length = 39
FEATURE                 Location/Qualifiers
source                  1..39
                        mol_type = protein
                        organism = synthetic construct
MOD_RES                 2
                        note = Aib
SITE                    3
                        note = D-alanine
SITE                    27
                        note = D-serine
MOD_RES                 17
                        note = AminoEthoxyEthoxyAcetic Acyl-MaleimidoPropionic Acyl
SEQUENCE: 137
YXAGTFTSDG NMYLDKKHAK DFIEWLSSGP PSSGAPPPS                                39

SEQ ID NO: 138          moltype = AA  length = 39
FEATURE                 Location/Qualifiers
source                  1..39
                        mol_type = protein
                        organism = synthetic construct
SITE                    2
                        note = D-alanine
SITE                    11
                        note = D-serine
MOD_RES                 13
                        note = Aib
MOD_RES                 17
                        note = AminoEthoxyEthoxyAcetic Acyl-MaleimidoPropionic Acyl
SEQUENCE: 138
YAIGTFTSDP SHXLEVKNQK EFVQWLNRGI PSSGAPPPS                                39

SEQ ID NO: 139          moltype = AA  length = 39
FEATURE                 Location/Qualifiers
source                  1..39
                        mol_type = protein
                        organism = synthetic construct
SITE                    2
                        note = D-serine
MOD_RES                 13
                        note = Aib
MOD_RES                 17
                        note = AminoEthoxyEthoxyAcetic Acyl-MaleimidoPropionic Acyl
SEQUENCE: 139
FSTGTFTSDF VEXLEIKEQK AFIEWLAQGG PSSGAPPPS                                39

SEQ ID NO: 140          moltype = AA  length = 39
FEATURE                 Location/Qualifiers
source                  1..39
                        mol_type = protein
                        organism = synthetic construct
SITE                    18
                        note = D-alanine
SITE                    27
                        note = D-serine
MOD_RES                 17
                        note = AminoEthoxyEthoxyAcetic Acyl-MaleimidoPropionic Acyl
SEQUENCE: 140
FGTGTFTSDF DGYLEDKAAK AFIQWLSGGM PSSGAPPPS                                39

SEQ ID NO: 141          moltype = AA  length = 39
FEATURE                 Location/Qualifiers
source                  1..39
                        mol_type = protein
                        organism = synthetic construct
SITE                    2
                        note = D-serine
MOD_RES                 13
                        note = Aib
MOD_RES                 20
                        note = Aib
MOD_RES                 17
                        note = AminoEthoxyEthoxyAcetic Acyl-MaleimidoPropionic Acyl
SEQUENCE: 141
HSWGTFTSDW YIXLEEKNAX DFIAWLYAGY PSSGAPPPS                                39

SEQ ID NO: 142          moltype = AA  length = 39
FEATURE                 Location/Qualifiers
```

-continued

```
source                    1..39
                          mol_type = protein
                          organism = synthetic construct
MOD_RES                   13
                          note = Aib
MOD_RES                   27..28
                          note = Aib
MOD_RES                   17
                          note = AminoEthoxyEthoxyAcetic Acyl-MaleimidoPropionic Acyl
SEQUENCE: 142
FGPGTFTSDK KFXLELKGAK AFIAWLXXGF PSSGAPPPS                        39

SEQ ID NO: 143            moltype = AA  length = 39
FEATURE                   Location/Qualifiers
source                    1..39
                          mol_type = protein
                          organism = synthetic construct
SITE                      2
                          note = D-serine
SITE                      10
                          note = D-alanine
SITE                      12
                          note = D-serine
MOD_RES                   20
                          note = Aib
MOD_RES                   28
                          note = Aib
MOD_RES                   17
                          note = AminoEthoxyEthoxyAcetic Acyl-MaleimidoPropionic Acyl
SEQUENCE: 143
HSNGTFTSDA NSYLEPKAAX DFVNWLDXGW PSSGAPPPS                        39

SEQ ID NO: 144            moltype = AA  length = 39
FEATURE                   Location/Qualifiers
source                    1..39
                          mol_type = protein
                          organism = synthetic construct
SITE                      2
                          note = D-serine
MOD_RES                   17
                          note = AminoEthoxyEthoxyAcetic Acyl-MaleimidoPropionic Acyl
SEQUENCE: 144
FSTGTFTSDP WVYLDSKQQQ AFVEWLHFGN PSSGAPPPS                        39

SEQ ID NO: 145            moltype = AA  length = 39
FEATURE                   Location/Qualifiers
source                    1..39
                          mol_type = protein
                          organism = synthetic construct
SITE                      2
                          note = D-alanine
MOD_RES                   13
                          note = Aib
MOD_RES                   20
                          note = Aib
MOD_RES                   17
                          note = AminoEthoxyEthoxyAcetic Acyl-MaleimidoPropionic Acyl
SEQUENCE: 145
FAEGTFTSDW YPXLDLKSAX DFVQWLYGGP PSSGAPPPS                        39

SEQ ID NO: 146            moltype = AA  length = 39
FEATURE                   Location/Qualifiers
source                    1..39
                          mol_type = protein
                          organism = synthetic construct
MOD_RES                   13
                          note = Aib
MOD_RES                   17
                          note = AminoEthoxyEthoxyAcetic Acyl-MaleimidoPropionic Acyl
SEQUENCE: 146
FGIGTFTSDT ARXLDDKDQK EFVQWLNDGM PSSGAPPPS                        39

SEQ ID NO: 147            moltype = AA  length = 39
FEATURE                   Location/Qualifiers
source                    1..39
                          mol_type = protein
                          organism = synthetic construct
MOD_RES                   20
                          note = Aib
```

-continued

```
SITE                    30
                        note = D-serine
MOD_RES                 17
                        note = AminoEthoxyEthoxyAcetic Acyl-MaleimidoPropionic Acyl
SEQUENCE: 147
FGYGTFTSDK STYLDEKIQX DFVEWLNDGS PSSGAPPPS                            39

SEQ ID NO: 148          moltype = AA  length = 39
FEATURE                 Location/Qualifiers
source                  1..39
                        mol_type = protein
                        organism = synthetic construct
MOD_RES                 11
                        note = Aib
MOD_RES                 17
                        note = AminoEthoxyEthoxyAcetic Acyl-MaleimidoPropionic Acyl
SEQUENCE: 148
HGSGTFTSDA XPYLDQKGAQ DFIAWLDGGP PSSGAPPPS                            39

SEQ ID NO: 149          moltype = AA  length = 39
FEATURE                 Location/Qualifiers
source                  1..39
                        mol_type = protein
                        organism = synthetic construct
SITE                    2
                        note = D-alanine
MOD_RES                 13
                        note = Aib
MOD_RES                 17
                        note = AminoEthoxyEthoxyAcetic Acyl-MaleimidoPropionic Acyl
SEQUENCE: 149
HAIGTFTSDP PVXLEQKHQQ EFVAWLDPGL PSSGAPPPS                            39

SEQ ID NO: 150          moltype = AA  length = 39
FEATURE                 Location/Qualifiers
source                  1..39
                        mol_type = protein
                        organism = synthetic construct
SITE                    2
                        note = D-alanine
MOD_RES                 20
                        note = Aib
SITE                    27
                        note = D-alanine
MOD_RES                 17
                        note = AminoEthoxyEthoxyAcetic Acyl-MaleimidoPropionic Acyl
SEQUENCE: 150
YAYGTFTSDV NKYLDPKTAX AFVEWLAQGI PSSGAPPPS                            39

SEQ ID NO: 151          moltype = AA  length = 39
FEATURE                 Location/Qualifiers
source                  1..39
                        mol_type = protein
                        organism = synthetic construct
SITE                    2
                        note = D-alanine
MOD_RES                 20
                        note = Aib
MOD_RES                 17
                        note = AminoEthoxyEthoxyAcetic Acyl-MaleimidoPropionic Acyl
SEQUENCE: 151
FAIGTFTSDR REYLEPKEQX DFIEWLRDGG PSSGAPPPS                            39

SEQ ID NO: 152          moltype = AA  length = 39
FEATURE                 Location/Qualifiers
source                  1..39
                        mol_type = protein
                        organism = synthetic construct
MOD_RES                 17
                        note = AminoEthoxyEthoxyAcetic Acyl-MaleimidoPropionic Acyl
SEQUENCE: 152
YGNGTFTSDA WIYLDDKLQK EFVQWLRLGN PSSGAPPPS                            39

SEQ ID NO: 153          moltype = AA  length = 39
FEATURE                 Location/Qualifiers
source                  1..39
                        mol_type = protein
                        organism = synthetic construct
SITE                    2
```

```
                              note = D-alanine
SITE                          10..11
                              note = D-alanine
MOD_RES                       13
                              note = Aib
MOD_RES                       20
                              note = Aib
MOD_RES                       27
                              note = Aib
MOD_RES                       17
                              note = AminoEthoxyEthoxyAcetic Acyl-MaleimidoPropionic Acyl
SEQUENCE: 153
YAPGTFTSDA AAXLEDKYQX AFIAWLXQGW PSSGAPPPS                                           39

SEQ ID NO: 154                moltype = AA   length = 39
FEATURE                       Location/Qualifiers
source                        1..39
                              mol_type = protein
                              organism = synthetic construct
SITE                          3
                              note = D-alanine
SITE                          28
                              note = D-serine
MOD_RES                       17
                              note = AminoEthoxyEthoxyAcetic Acyl-MaleimidoPropionic Acyl
SEQUENCE: 154
YGAGTFTSDI RAYLDEKWAK AFVAWLVSGM PSSGAPPPS                                           39

SEQ ID NO: 155                moltype = AA   length = 39
FEATURE                       Location/Qualifiers
source                        1..39
                              mol_type = protein
                              organism = synthetic construct
MOD_RES                       13
                              note = Aib
MOD_RES                       18
                              note = Aib
MOD_RES                       17
                              note = AminoEthoxyEthoxyAcetic Acyl-MaleimidoPropionic Acyl
SEQUENCE: 155
YGWGTFTSDP INXLDLKXQK DFVNWLPMGA PSSGAPPPS                                           39

SEQ ID NO: 156                moltype = AA   length = 39
FEATURE                       Location/Qualifiers
source                        1..39
                              mol_type = protein
                              organism = synthetic construct
SITE                          2
                              note = D-serine
SITE                          10
                              note = D-serine
SITE                          12
                              note = D-alanine
MOD_RES                       17
                              note = AminoEthoxyEthoxyAcetic Acyl-MaleimidoPropionic Acyl
SEQUENCE: 156
HSNGTFTSDS YAYLERKDQK AFIEWLWSGP PSSGAPPPS                                           39

SEQ ID NO: 157                moltype = AA   length = 39
FEATURE                       Location/Qualifiers
source                        1..39
                              mol_type = protein
                              organism = synthetic construct
SITE                          2
                              note = D-serine
MOD_RES                       28
                              note = Aib
MOD_RES                       17
                              note = AminoEthoxyEthoxyAcetic Acyl-MaleimidoPropionic Acyl
SEQUENCE: 157
YSMGTFTSDQ GKYLEAKSAQ AFINWLMXGA PSSGAPPPS                                           39

SEQ ID NO: 158                moltype = AA   length = 39
FEATURE                       Location/Qualifiers
source                        1..39
                              mol_type = protein
                              organism = synthetic construct
SITE                          2
                              note = D-alanine
```

```
MOD_RES              13
                     note = Aib
MOD_RES              16
                     note = Aib
SITE                 28
                     note = D-alanine
MOD_RES              17
                     note = AminoEthoxyEthoxyAcetic Acyl-MaleimidoPropionic Acyl
SEQUENCE: 158
YAFGTFTSDL TRXLDXKTAK AFIEWLDAGM PSSGAPPPS                            39

SEQ ID NO: 159       moltype = AA  length = 39
FEATURE              Location/Qualifiers
source               1..39
                     mol_type = protein
                     organism = synthetic construct
MOD_RES              2
                     note = Aib
MOD_RES              10
                     note = Aib
MOD_RES              20
                     note = Aib
MOD_RES              17
                     note = AminoEthoxyEthoxyAcetic Acyl-MaleimidoPropionic Acyl
SEQUENCE: 159
YXKGTFTSDX IYYLDWKNAX AFVNWLHIGI PSSGAPPPS                            39

SEQ ID NO: 160       moltype = AA  length = 39
FEATURE              Location/Qualifiers
source               1..39
                     mol_type = protein
                     organism = synthetic construct
MOD_RES              2
                     note = Aib
SITE                 11
                     note = D-serine
MOD_RES              12..13
                     note = Aib
MOD_RES              20
                     note = Aib
MOD_RES              27
                     note = Aib
MOD_RES              17
                     note = AminoEthoxyEthoxyAcetic Acyl-MaleimidoPropionic Acyl
SEQUENCE: 160
HXQGTFTSDW SXXLEKKVQX EFVNWLXTGD PSSGAPPPS                            39

SEQ ID NO: 161       moltype = AA  length = 39
FEATURE              Location/Qualifiers
source               1..39
                     mol_type = protein
                     organism = synthetic construct
SITE                 2..3
                     note = D-serine
SITE                 12
                     note = D-alanine
MOD_RES              13
                     note = Aib
SITE                 18
                     note = D-alanine
MOD_RES              27
                     note = Aib
MOD_RES              17
                     note = AminoEthoxyEthoxyAcetic Acyl-MaleimidoPropionic Acyl
SEQUENCE: 161
FSSGTFTSDD RAXLDSKAAQ AFVAWLXAGT PSSGAPPPS                            39

SEQ ID NO: 162       moltype = AA  length = 39
FEATURE              Location/Qualifiers
source               1..39
                     mol_type = protein
                     organism = synthetic construct
SITE                 2
                     note = D-alanine
SITE                 18
                     note = D-alanine
SITE                 30
                     note = D-serine
MOD_RES              17
```

```
                          note = AminoEthoxyEthoxyAcetic Acyl-MaleimidoPropionic Acyl
SEQUENCE: 162
YAIGTFTSDM KIYLDEKAAK AFVQWLANGS PSSGAPPPS                              39

SEQ ID NO: 163           moltype = AA   length = 39
FEATURE                  Location/Qualifiers
source                   1..39
                         mol_type = protein
                         organism = synthetic construct
MOD_RES                  13
                         note = Aib
MOD_RES                  20
                         note = Aib
MOD_RES                  17
                         note = AminoEthoxyEthoxyAcetic Acyl-MaleimidoPropionic Acyl
SEQUENCE: 163
FGQGTFTSDY DQXLDNKPQX DFIEWLMYGE PSSGAPPPS                              39

SEQ ID NO: 164           moltype = AA   length = 39
FEATURE                  Location/Qualifiers
source                   1..39
                         mol_type = protein
                         organism = synthetic construct
SITE                     2
                         note = D-serine
MOD_RES                  13
                         note = Aib
MOD_RES                  17
                         note = AminoEthoxyEthoxyAcetic Acyl-MaleimidoPropionic Acyl
SEQUENCE: 164
FSMGTFTSDL DRXLDWKIQK DFVQWLVSGT PSSGAPPPS                              39

SEQ ID NO: 165           moltype = AA   length = 39
FEATURE                  Location/Qualifiers
source                   1..39
                         mol_type = protein
                         organism = synthetic construct
SITE                     8
                         note = D-serine
SITE                     12
                         note = D-serine
MOD_RES                  17
                         note = AminoEthoxyEthoxyAcetic Acyl-MaleimidoPropionic Acyl
SITE                     2
                         note = D-serine
SEQUENCE: 165
YSVGTFTSDL HSYLDLKGAQ DFVNWLVWGQ PSSGAPPPS                              39

SEQ ID NO: 166           moltype = AA   length = 39
FEATURE                  Location/Qualifiers
source                   1..39
                         mol_type = protein
                         organism = synthetic construct
MOD_RES                  2
                         note = Aib
MOD_RES                  17
                         note = AminoEthoxyEthoxyAcetic Acyl-MaleimidoPropionic Acyl
SEQUENCE: 166
HXIGTFTSDD VYYLDLKPQK EFVEWLGLGS PSSGAPPPS                              39

SEQ ID NO: 167           moltype = AA   length = 39
FEATURE                  Location/Qualifiers
source                   1..39
                         mol_type = protein
                         organism = synthetic construct
MOD_RES                  13
                         note = Aib
MOD_RES                  17
                         note = AminoEthoxyEthoxyAcetic Acyl-MaleimidoPropionic Acyl
SEQUENCE: 167
FGVGTFTSDV MIXLDIKEQK EFINWLQSGE PSSGAPPPS                              39

SEQ ID NO: 168           moltype = AA   length = 39
FEATURE                  Location/Qualifiers
source                   1..39
                         mol_type = protein
                         organism = synthetic construct
MOD_RES                  2
                         note = Aib
```

-continued

```
MOD_RES              11
                     note = Aib
SITE                 12
                     note = D-serine
SITE                 16
                     note = D-serine
SITE                 30
                     note = D-serine
MOD_RES              17
                     note = AminoEthoxyEthoxyAcetic Acyl-MaleimidoPropionic Acyl
SEQUENCE: 168
HXFGTFTSDH XSYLESKMAQ DFINWLIIGS PSSGAPPPS                          39

SEQ ID NO: 169       moltype = AA  length = 39
FEATURE              Location/Qualifiers
source               1..39
                     mol_type = protein
                     organism = synthetic construct
SITE                 2
                     note = D-alanine
MOD_RES              30
                     note = Aib
MOD_RES              17
                     note = AminoEthoxyEthoxyAcetic Acyl-MaleimidoPropionic Acyl
SEQUENCE: 169
HAGGTFTSDP AKYLDSKVQQ EFVAWLAFGX PSSGAPPPS                          39

SEQ ID NO: 170       moltype = AA  length = 39
FEATURE              Location/Qualifiers
source               1..39
                     mol_type = protein
                     organism = synthetic construct
SITE                 2
                     note = D-alanine
SITE                 11
                     note = D-serine
MOD_RES              13
                     note = Aib
SITE                 28
                     note = D-serine
MOD_RES              17
                     note = AminoEthoxyEthoxyAcetic Acyl-MaleimidoPropionic Acyl
SEQUENCE: 170
YANGTFTSDV SFXLEYKDQK DFIQWLASGQ PSSGAPPPS                          39

SEQ ID NO: 171       moltype = AA  length = 39
FEATURE              Location/Qualifiers
source               1..39
                     mol_type = protein
                     organism = synthetic construct
SITE                 2
                     note = D-serine
MOD_RES              20
                     note = Aib
MOD_RES              17
                     note = AminoEthoxyEthoxyAcetic Acyl-MaleimidoPropionic Acyl
SEQUENCE: 171
FSVGTFTSDN RQYLDVKNQX DFIQWLPWGI PSSGAPPPS                          39

SEQ ID NO: 172       moltype = AA  length = 39
FEATURE              Location/Qualifiers
source               1..39
                     mol_type = protein
                     organism = synthetic construct
MOD_RES              2
                     note = Aib
MOD_RES              20
                     note = Aib
MOD_RES              17
                     note = AminoEthoxyEthoxyAcetic Acyl-MaleimidoPropionic Acyl
SEQUENCE: 172
HXVGTFTSDK ETYLDIKKAX DFVEWLSTGR PSSGAPPPS                          39

SEQ ID NO: 173       moltype = AA  length = 39
FEATURE              Location/Qualifiers
source               1..39
                     mol_type = protein
                     organism = synthetic construct
MOD_RES              13
```

```
                              note = Aib
MOD_RES                       20
                              note = Aib
MOD_RES                       17
                              note = AminoEthoxyEthoxyAcetic Acyl-MaleimidoPropionic Acyl
SEQUENCE: 173
FGWGTFTSDD FNXLEYKHAX EFVNWLDVGQ PSSGAPPPS                                  39

SEQ ID NO: 174                moltype = AA   length = 39
FEATURE                       Location/Qualifiers
source                        1..39
                              mol_type = protein
                              organism = synthetic construct
SITE                          2
                              note = D-alanine
MOD_RES                       13
                              note = Aib
MOD_RES                       17
                              note = AminoEthoxyEthoxyAcetic Acyl-MaleimidoPropionic Acyl
SEQUENCE: 174
FAYGTFTSDQ SYXLDYKTAK DFIQWLTKGR PSSGAPPPS                                  39

SEQ ID NO: 175                moltype = AA   length = 39
FEATURE                       Location/Qualifiers
source                        1..39
                              mol_type = protein
                              organism = synthetic construct
MOD_RES                       11
                              note = Aib
SITE                          16
                              note = D-alanine
MOD_RES                       17
                              note = AminoEthoxyEthoxyAcetic Acyl-MaleimidoPropionic Acyl
SEQUENCE: 175
FGPGTFTSDD XIYLEAKNAQ AFIEWLFSGQ PSSGAPPPS                                  39

SEQ ID NO: 176                moltype = AA   length = 39
FEATURE                       Location/Qualifiers
source                        1..39
                              mol_type = protein
                              organism = synthetic construct
MOD_RES                       2
                              note = Aib
SITE                          11
                              note = D-serine
MOD_RES                       13
                              note = Aib
MOD_RES                       20
                              note = Aib
MOD_RES                       17
                              note = AminoEthoxyEthoxyAcetic Acyl-MaleimidoPropionic Acyl
SEQUENCE: 176
YXIGTFTSDS SIXLDSKAQX DFIQWLLFGQ PSSGAPPPS                                  39

SEQ ID NO: 177                moltype = AA   length = 39
FEATURE                       Location/Qualifiers
source                        1..39
                              mol_type = protein
                              organism = synthetic construct
SITE                          2
                              note = D-serine
MOD_RES                       13
                              note = Aib
MOD_RES                       17
                              note = AminoEthoxyEthoxyAcetic Acyl-MaleimidoPropionic Acyl
SEQUENCE: 177
HSGGTFTSDP YGXLEQKMAK EFVEWLMTGK PSSGAPPPS                                  39

SEQ ID NO: 178                moltype = AA   length = 39
FEATURE                       Location/Qualifiers
source                        1..39
                              mol_type = protein
                              organism = synthetic construct
SITE                          2
                              note = D-alanine
MOD_RES                       17
                              note = AminoEthoxyEthoxyAcetic Acyl-MaleimidoPropionic Acyl
SEQUENCE: 178
HAEGTFTSDY AKYLDAKRAK EFIAWLVNGG PSSGAPPPS                                  39
```

-continued

```
SEQ ID NO: 179          moltype = AA   length = 39
FEATURE                 Location/Qualifiers
source                  1..39
                        mol_type = protein
                        organism = synthetic construct
MOD_RES                 2
                        note = Aib
MOD_RES                 13
                        note = Alpha-Methyl-Leucine
MOD_RES                 20
                        note = Aib
MOD_RES                 17
                        note = AminoEthoxyEthoxyAcetic Acyl-MaleimidoPropionic Acyl
SEQUENCE: 179
YXQGTFTSDY SIXLDKKAQX AFIEYLLEGG PSSGAPPPS                                 39

SEQ ID NO: 180          moltype = AA   length = 39
FEATURE                 Location/Qualifiers
source                  1..39
                        mol_type = protein
                        organism = synthetic construct
MOD_RES                 16
                        note = AminoEthoxyEthoxyAcetic Acyl-MaleimidoPropionic Acyl
SEQUENCE: 180
HGQGTFTSDY SKYLDKRRAQ DFVEWLKNGG PSSGAPPPS                                 39

SEQ ID NO: 181          moltype = AA   length = 39
FEATURE                 Location/Qualifiers
source                  1..39
                        mol_type = protein
                        organism = synthetic construct
MOD_RES                 2
                        note = Aib
MOD_RES                 13
                        note = Aib
MOD_RES                 16
                        note = AminoEthoxyEthoxyAcetic Acyl-MaleimidoPropionic Acyl
SEQUENCE: 181
HXQGTFTSDY SKXLDKRRAQ DFVEWLKNGG PSSGAPPPS                                 39

SEQ ID NO: 182          moltype = AA   length = 39
FEATURE                 Location/Qualifiers
source                  1..39
                        mol_type = protein
                        organism = synthetic construct
MOD_RES                 2
                        note = Aib
MOD_RES                 16
                        note = AminoEthoxyEthoxyAcetic Acyl-MaleimidoPropionic Acyl
SEQUENCE: 182
HXQGTFTSDY SKYLDKRRAQ DFVEWLKNGG PSSGAPPPS                                 39

SEQ ID NO: 183          moltype = AA   length = 40
FEATURE                 Location/Qualifiers
source                  1..40
                        mol_type = protein
                        organism = synthetic construct
VARIANT                 1
                        note = X can be H, Y or F
VARIANT                 2
                        note = X can be G, D-Alanine, Aib or D-serine
SITE                    2
                        note = D-alanine or D-serine
VARIANT                 3
                        note = X can be
                         A,R,N,D,E,Q,G,H,I,L,K,M,F,P,S,T,W,Y,D-alanine,Aib,D-serine
                         or D-Lysine
SITE                    3
                        note = D-alanine,D-serine or D-Lysine
MOD_RES                 2
                        note = Aib
MOD_RES                 3
                        note = Aib
VARIANT                 10
                        note = X can be
                         A,R,N,D,E,Q,G,H,I,L,K,M,F,P,S,T,W,Y,D-alanine,Aib,D-serine
                         or D-Lysine
SITE                    10
```

-continued

```
                   note = D-alanine,D-serine or D-Lysine
MOD_RES            10
                   note = Aib
VARIANT            11
                   note = X can be
                   A,R,N,D,E,Q,G,H,I,L,K,M,F,P,S,T,W,Y,D-alanine,Aib,D-serine
                   or D-Lysine
SITE               11
                   note = D-alanine,D-serine or D-Lysine
MOD_RES            11
                   note = Aib
VARIANT            12
                   note = X can be
                   A,R,N,D,E,Q,G,H,I,L,K,M,F,P,S,T,W,Y,D-alanine,Aib,D-serine
                   or D-Lysine
SITE               12
                   note = D-alanine,D-serine or D-Lysine
MOD_RES            12
                   note = Aib
VARIANT            13
                   note = X can be Y or Aib
MOD_RES            13
                   note = Aib
VARIANT            15
                   note = X can be D or E
VARIANT            16
                   note = X can be
                   A,R,N,D,E,Q,G,H,I,L,K,M,F,P,S,T,W,Y,D-alanine,Aib,D-serine
                   or D-Lysine
SITE               16
                   note = D-alanine,D-serine or D-Lysine
MOD_RES            16
                   note = Aib
VARIANT            17
                   note = X can be
                   A,R,N,D,E,Q,G,H,I,L,K,M,F,P,S,T,W,Y,D-alanine,Aib,D-serine
                   or D-Lysine
SITE               17
                   note = D-alanine,D-serine or D-Lysine
MOD_RES            17
                   note = Aib
VARIANT            18
                   note = X can be
                   A,R,N,D,E,Q,G,H,I,L,K,M,F,P,S,T,W,Y,D-alanine,Aib,D-serine
                   or D-Lysine
SITE               18
                   note = D-alanine,D-serine or D-Lysine
MOD_RES            18
                   note = Aib
VARIANT            19
                   note = X can be Q or A
VARIANT            20
                   note = X can be Q, K or Aib
MOD_RES            20
                   note = Aib
VARIANT            21
                   note = X can be D, E or A
VARIANT            23
                   note = X can be V or I
VARIANT            24
                   note = X can be Q, A, E or N
VARIANT            28
                   note = X can be
                   A,R,N,D,E,Q,G,H,I,L,K,M,F,P,S,T,W,Y,D-alanine,Aib,D-serine
                   or D-Lysine
SITE               28
                   note = D-alanine,D-serine or D-Lysine
MOD_RES            28
                   note = Aib
VARIANT            27
                   note = X can be
                   A,R,N,D,E,Q,G,H,I,L,K,M,F,P,S,T,W,Y,D-alanine,Aib,D-serine
                   or D-Lysine
SITE               27
                   note = D-alanine,D-serine or D-Lysine
MOD_RES            30
                   note = Aib
VARIANT            30
                   note = X can be
```

-continued

```
                          A,R,N,D,E,Q,G,H,I,L,K,M,F,P,S,T,W,Y,D-alanine,Aib,D-serine
                          or D-Lysine
SITE                      30
                          note = D-alanine,D-serine or D-Lysine
MOD_RES                   27
                          note = Aib
VARIANT                   40
                          note = X can be K or absent
SEQUENCE: 183
XXXGTFTSDX XXXLXXXXXX XFXXWLXXGX PSSGAPPPSX                                  40

SEQ ID NO: 184            moltype = AA  length = 41
FEATURE                   Location/Qualifiers
source                    1..41
                          mol_type = protein
                          organism = synthetic construct
VARIANT                   1
                          note = X can be H, Y or F
VARIANT                   2
                          note = X can be G, D-Alanine, Aib or D-serine
SITE                      2
                          note = D-alanine or D-serine
VARIANT                   3
                          note = X can be
                          A,R,N,D,E,Q,G,H,I,L,K,M,F,P,S,T,W,Y,D-alanine,Aib,D-serine
                          or D-Lysine
SITE                      3
                          note = D-alanine,D-serine or D-Lysine
MOD_RES                   2
                          note = Aib
MOD_RES                   3
                          note = Aib
VARIANT                   10
                          note = X can be
                          A,R,N,D,E,Q,G,H,I,L,K,M,F,P,S,T,W,Y,D-alanine,Aib,D-serine
                          or D-Lysine
SITE                      10
                          note = D-alanine,D-serine or D-Lysine
MOD_RES                   10
                          note = Aib
VARIANT                   11
                          note = X can be
                          A,R,N,D,E,Q,G,H,I,L,K,M,F,P,S,T,W,Y,D-alanine,Aib,D-serine
                          or D-Lysine
SITE                      11
                          note = D-alanine,D-serine or D-Lysine
MOD_RES                   11
                          note = Aib
VARIANT                   12
                          note = X can be
                          A,R,N,D,E,Q,G,H,I,L,K,M,F,P,S,T,W,Y,D-alanine,Aib,D-serine
                          or D-Lysine
SITE                      12
                          note = D-alanine,D-serine or D-Lysine
MOD_RES                   12
                          note = Aib
VARIANT                   13
                          note = X can be Y, Q, N-Methyl-L-Leucine or Aib
MOD_RES                   13
                          note = Aib
VARIANT                   15
                          note = X can be D or E
VARIANT                   16
                          note = X can be
                          A,R,N,D,E,Q,G,H,I,L,K,M,F,P,S,T,W,Y,D-alanine,Aib,D-serine
                          or D-Lysine
SITE                      16
                          note = D-alanine,D-serine or D-Lysine
MOD_RES                   16
                          note = Aib
VARIANT                   17
                          note = X can be
                          A,R,N,D,E,Q,G,H,I,L,K,M,F,P,S,T,W,Y,D-alanine,Aib,D-serine
                          or D-Lysine
SITE                      17
                          note = D-alanine,D-serine or D-Lysine
MOD_RES                   17
                          note = Aib
VARIANT                   18
```

-continued

```
                             note = X can be
                             A,R,N,D,E,Q,G,H,I,L,K,M,F,P,S,T,W,Y,D-alanine,Aib,D-serine
                             or D-Lysine
SITE                         18
                             note = D-alanine,D-serine or D-Lysine
MOD_RES                      18
                             note = Aib
VARIANT                      19
                             note = X can be Q or A
VARIANT                      20
                             note = X can be Q, K, Q, R  or Aib
MOD_RES                      20
                             note = Aib
VARIANT                      21
                             note = X can be D, E or A
VARIANT                      23
                             note = X can be V or I
VARIANT                      24
                             note = X can be Q, A, E or N
VARIANT                      28
                             note = X can be
                             A,R,N,D,E,Q,G,H,I,L,K,M,F,P,S,T,W,Y,D-alanine,Aib,D-serine
                             or D-Lysine
SITE                         28
                             note = D-alanine,D-serine or D-Lysine
MOD_RES                      28
                             note = Aib
VARIANT                      27
                             note = X can be
                             A,R,N,D,E,Q,G,H,I,L,K,M,F,P,S,T,W,Y,D-alanine,Aib,D-serine
                             or D-Lysine
SITE                         27
                             note = D-alanine,D-serine or D-Lysine
MOD_RES                      30
                             note = Aib
VARIANT                      30
                             note = X can be
                             A,R,N,D,E,Q,G,H,I,L,K,M,F,P,S,T,W,Y,D-alanine,Aib,D-serine
                             or D-Lysine
SITE                         30
                             note = D-alanine,D-serine or D-Lysine
MOD_RES                      27
                             note = Aib
VARIANT                      40
                             note = X can be K or absent
MOD_RES                      2
                             note = Amino-cyclobutyl-1-carboxylic acid
MOD_RES                      13
                             note = N-Methyl-L-Leucine
MOD_RES                      41
                             note = AminoEthoxyEthoxyAcetic Acid //
                             8-amino-3,6-dioxa-octanoic acid
SEQUENCE: 184
XXXGTFTSDX XXXLXXXXXX XFXXWLXXGX PSSGAPPPSX K                            41

SEQ ID NO: 185               moltype = AA  length = 31
FEATURE                      Location/Qualifiers
source                       1..31
                             mol_type = protein
                             organism = synthetic construct
MOD_RES                      2
                             note = Aib
MOD_RES                      31
                             note = AminoEthoxyEthoxyAcetic Acyl-MaleimidoPropionic Acyl
SEQUENCE: 185
HXEGTFTSDV SSYLEGQAAK EFIAWLVKGR K                                       31

SEQ ID NO: 186               moltype = AA  length = 31
FEATURE                      Location/Qualifiers
source                       1..31
                             mol_type = protein
                             organism = synthetic construct
MOD_RES                      2
                             note = Aib
MOD_RES                      31
                             note = AminoEthoxyEthoxyAcetic Acyl-AminoEthoxyEthoxyAcetic
                             Acyl-MaleimidoPropionic Acyl
SEQUENCE: 186
HXEGTFTSDV SSYLEGQAAK EFIAWLVKGR K                                       31
```

-continued

```
SEQ ID NO: 187              moltype = AA   length = 31
FEATURE                     Location/Qualifiers
source                      1..31
                            mol_type = protein
                            organism = synthetic construct
MOD_RES                     2
                            note = Aib
MOD_RES                     31
                            note = AminoEthoxyEthoxyAcetic Acyl-8-AminoOctanoic
                             Acyl-MaleimidoPropionic Acyl
SEQUENCE: 187
HXEGTFTSDV SSYLEGQAAK EFIAWLVKGR K                              31

SEQ ID NO: 188              moltype = AA   length = 31
FEATURE                     Location/Qualifiers
source                      1..31
                            mol_type = protein
                            organism = synthetic construct
MOD_RES                     2
                            note = Aib
SEQUENCE: 188
HXEGTFTSDV SSYLEGQAAK EFIAWLVKGR K                              31

SEQ ID NO: 189              moltype = AA   length = 32
FEATURE                     Location/Qualifiers
source                      1..32
                            mol_type = protein
                            organism = synthetic construct
MOD_RES                     2
                            note = Aib
MOD_RES                     32
                            note = AminoEthoxyEthoxyAcetic Acyl-MaleimidoPropionic Acyl
MOD_RES                     31
                            note = AminoEthoxyEthoxyAcetic Acid //
                             8-amino-3,6-dioxa-octanoic acid
SEQUENCE: 189
HXEGTFTSDV SSYLEGQAAK EFIAWLVKGR XK                             32

SEQ ID NO: 190              moltype = AA   length = 40
FEATURE                     Location/Qualifiers
source                      1..40
                            mol_type = protein
                            organism = synthetic construct
MOD_RES                     40
                            note = AminoEthoxyEthoxyAcetic Acyl-AminoEthoxyEthoxyAcetic
                             Acyl-MaleimidoPropionic Acyl
SEQUENCE: 190
HGEGTFTSDL SKQMEEEAVR LFIEWLKNGG PSSGAPPPSK                     40

SEQ ID NO: 191              moltype = AA   length = 40
FEATURE                     Location/Qualifiers
source                      1..40
                            mol_type = protein
                            organism = synthetic construct
MOD_RES                     40
                            note = AminoEthoxyEthoxyAcetic Acyl-8-AminoOctanoic
                             Acyl-MaleimidoPropionic Acyl
SEQUENCE: 191
HGEGTFTSDL SKQMEEEAVR LFIEWLKNGG PSSGAPPPSK                     40

SEQ ID NO: 192              moltype = AA   length = 40
FEATURE                     Location/Qualifiers
source                      1..40
                            mol_type = protein
                            organism = synthetic construct
SEQUENCE: 192
HGEGTFTSDL SKQMEEEAVR LFIEWLKNGG PSSGAPPPSK                     40

SEQ ID NO: 193              moltype = AA   length = 41
FEATURE                     Location/Qualifiers
source                      1..41
                            mol_type = protein
                            organism = synthetic construct
MOD_RES                     40
                            note = AminoEthoxyEthoxyAcetic Acid //
                             8-amino-3,6-dioxa-octanoic acid
MOD_RES                     41
                            note = AminoEthoxyEthoxyAcetic Acyl-MaleimidoPropionic Acyl
```

```
SEQUENCE: 193
HGEGTFTSDL SKQMEEEAVR LFIEWLKNGG PSSGAPPPSX K                        41

SEQ ID NO: 194          moltype = AA  length = 40
FEATURE                 Location/Qualifiers
source                  1..40
                        mol_type = protein
                        organism = synthetic construct
SITE                    2
                        note = D-serine
MOD_RES                 40
                        note = AminoEthoxyEthoxyAcetic Acyl-MaleimidoPropionic Acyl
SEQUENCE: 194
HSQGTFTSDY SKYLDSRRAQ DFVQWLMNTG PSSGAPPPSK                          40

SEQ ID NO: 195          moltype = AA  length = 40
FEATURE                 Location/Qualifiers
source                  1..40
                        mol_type = protein
                        organism = synthetic construct
SITE                    2
                        note = D-serine
MOD_RES                 40
                        note = AminoEthoxyEthoxyAcetic Acyl-AminoEthoxyEthoxyAcetic
                        Acyl-MaleimidoPropionic Acyl
SEQUENCE: 195
HSQGTFTSDY SKYLDSRRAQ DFVQWLMNTG PSSGAPPPSK                          40

SEQ ID NO: 196          moltype = AA  length = 40
FEATURE                 Location/Qualifiers
source                  1..40
                        mol_type = protein
                        organism = synthetic construct
SITE                    2
                        note = D-serine
MOD_RES                 40
                        note = AminoEthoxyEthoxyAcetic Acyl-8-AminoOctanoic
                        Acyl-MaleimidoPropionic Acyl
SEQUENCE: 196
HSQGTFTSDY SKYLDSRRAQ DFVQWLMNTG PSSGAPPPSK                          40

SEQ ID NO: 197          moltype = AA  length = 40
FEATURE                 Location/Qualifiers
source                  1..40
                        mol_type = protein
                        organism = synthetic construct
SITE                    2
                        note = D-serine
SEQUENCE: 197
HSQGTFTSDY SKYLDSRRAQ DFVQWLMNTG PSSGAPPPSK                          40

SEQ ID NO: 198          moltype = AA  length = 41
FEATURE                 Location/Qualifiers
source                  1..41
                        mol_type = protein
                        organism = synthetic construct
SITE                    2
                        note = D-serine
MOD_RES                 40
                        note = AminoEthoxyEthoxyAcetic Acid //
                        8-amino-3,6-dioxa-octanoic acid
MOD_RES                 41
                        note = AminoEthoxyEthoxyAcetic Acyl-MaleimidoPropionic Acyl
SEQUENCE: 198
HSQGTFTSDY SKYLDSRRAQ DFVQWLMNTG PSSGAPPPSX K                        41

SEQ ID NO: 199          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 199
YAEGTFISDY SIAMDKIHQQ DFVNWLLAQG PSSGAPPPSK                          40

SEQ ID NO: 200          moltype = AA  length = 40
```

-continued

```
FEATURE              Location/Qualifiers
source               1..40
                     mol_type = protein
                     organism = synthetic construct
SITE                 2
                     note = D-alanine
MOD_RES              40
                     note = AminoEthoxyEthoxyAcetic Acyl-AminoEthoxyEthoxyAcetic
                     Acyl-MaleimidoPropionic Acyl
SEQUENCE: 200
YAEGTFISDY SIAMDKIHQQ DFVNWLLAQG PSSGAPPPSK                            40

SEQ ID NO: 201       moltype = AA   length = 40
FEATURE              Location/Qualifiers
source               1..40
                     mol_type = protein
                     organism = synthetic construct
SITE                 2
                     note = D-alanine
MOD_RES              40
                     note = AminoEthoxyEthoxyAcetic Acyl-8-AminoOctanoic
                     Acyl-MaleimidoPropionic Acyl
SEQUENCE: 201
YAEGTFISDY SIAMDKIHQQ DFVNWLLAQG PSSGAPPPSK                            40

SEQ ID NO: 202       moltype = AA   length = 40
FEATURE              Location/Qualifiers
source               1..40
                     mol_type = protein
                     organism = synthetic construct
SITE                 2
                     note = D-alanine
SEQUENCE: 202
YAEGTFISDY SIAMDKIHQQ DFVNWLLAQG PSSGAPPPSK                            40

SEQ ID NO: 203       moltype = AA   length = 41
FEATURE              Location/Qualifiers
source               1..41
                     mol_type = protein
                     organism = synthetic construct
SITE                 2
                     note = D-alanine
MOD_RES              40
                     note = AminoEthoxyEthoxyAcetic Acid //
                     8-amino-3,6-dioxa-octanoic acid
MOD_RES              41
                     note = AminoEthoxyEthoxyAcetic Acyl-MaleimidoPropionic Acyl
SEQUENCE: 203
YAEGTFISDY SIAMDKIHQQ DFVNWLLAQG PSSGAPPPSX K                          41

SEQ ID NO: 204       moltype = AA   length = 30
FEATURE              Location/Qualifiers
source               1..30
                     mol_type = protein
                     organism = synthetic construct
MOD_RES              20
                     note = AminoEthoxyEthoxyAcetic Acyl-MaleimidoPropionic Acyl
SEQUENCE: 204
HAEGTFTSDV SSYLEGQAAK EFIAWLVRGR                                       30

SEQ ID NO: 205       moltype = AA   length = 31
FEATURE              Location/Qualifiers
source               1..31
                     mol_type = protein
                     organism = synthetic construct
MOD_RES              20
                     note = AminoEthoxyEthoxyAcetic Acyl-MaleimidoPropionic Acyl
MOD_RES              2
                     note = Aib
SEQUENCE: 205
HXEGTFTSDV SSYLEGQAAK EFIAWLVRGR G                                     31

SEQ ID NO: 206       moltype = AA   length = 31
FEATURE              Location/Qualifiers
source               1..31
                     mol_type = protein
                     organism = synthetic construct
MOD_RES              24
                     note = AminoEthoxyEthoxyAcetic Acyl-MaleimidoPropionic Acyl
```

```
SEQUENCE: 206
HVEGTFTSDV SSYLEEQAAR EFIKWLVRGR G                                    31

SEQ ID NO: 207             moltype = AA   length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-AminoEthoxyEthoxyAcetic
                             Acyl-MaleimidoPropionic Acyl
SEQUENCE: 207
HAEGTFTSDV SSYLEGQAAK EFIAWLVNGG PSSGAPPPSK                           40

SEQ ID NO: 208             moltype = AA   length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-8-AminoOctanoic
                             Acyl-MaleimidoPropionic Acyl
SEQUENCE: 208
HAEGTFTSDV SSYLEGQAAK EFIAWLVNGG PSSGAPPPSK                           40

SEQ ID NO: 209             moltype = AA   length = 40
FEATURE                    Location/Qualifiers
source                     1..40
                           mol_type = protein
                           organism = synthetic construct
SITE                       2
                           note = D-alanine
SEQUENCE: 209
HAEGTFTSDV SSYLEGQAAK EFIAWLVNGG PSSGAPPPSK                           40

SEQ ID NO: 210             moltype = AA   length = 41
FEATURE                    Location/Qualifiers
source                     1..41
                           mol_type = protein
                           organism = synthetic construct
SITE                       2
                           note = D-alanine
MOD_RES                    40
                           note = AminoEthoxyEthoxyAcetic Acid //
                             8-amino-3,6-dioxa-octanoic acid
MOD_RES                    41
                           note = AminoEthoxyEthoxyAcetic Acyl-MaleimidoPropionic Acyl
SEQUENCE: 210
HAEGTFTSDV SSYLEGQAAK EFIAWLVNGG PSSGAPPPSX K                         41

SEQ ID NO: 211             moltype = AA   length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-MaleimidoPropionic Acyl
SEQUENCE: 211
HAEGTFTSDV ASYLEGQAAK EFIAWLVNGG PSSGAPPPSK                           40

SEQ ID NO: 212             moltype = AA   length = 40
FEATURE                    Location/Qualifiers
source                     1..40
                           mol_type = protein
                           organism = synthetic construct
MOD_RES                    2
                           note = Aib
MOD_RES                    20
                           note = Aib
MOD_RES                    40
                           note = AminoEthoxyEthoxyAcetic Acyl-MaleimidoPropionic Acyl
SEQUENCE: 212
YXEGTFTSDY SIYLDKQAAX EFVNWLLAGG PSSGAPPPSK                           40
```

```
SEQ ID NO: 213            moltype = AA   length = 34
FEATURE                   Location/Qualifiers
source                    1..34
                          mol_type = protein
                          organism = synthetic construct
MOD_RES                   2
                          note = Aib
MOD_RES                   20
                          note = AminoEthoxyEthoxyAcetic Acyl-MaleimidoPropionic Acyl
SEQUENCE: 213
HXQGTFTSDY SKYLDEKKAK EFVEWLLEGG PSSG                                34

SEQ ID NO: 214            moltype = AA   length = 29
FEATURE                   Location/Qualifiers
source                    1..29
                          mol_type = protein
                          organism = synthetic construct
MOD_RES                   2
                          note = Aib
MOD_RES                   17
                          note = AminoEthoxyEthoxyAcetic Acyl-MaleimidoPropionic Acyl
SEQUENCE: 214
HXQGTFTSDY SKYLDEKAAK EFIQWLLQT                                      29

SEQ ID NO: 215            moltype = AA   length = 30
FEATURE                   Location/Qualifiers
source                    1..30
                          mol_type = protein
                          organism = synthetic construct
MOD_RES                   2
                          note = Aib
SEQUENCE: 215
HXQGTFTSDY SKYLDEKRAK EFVQWLMNTC                                     30

SEQ ID NO: 216            moltype = AA   length = 29
FEATURE                   Location/Qualifiers
source                    1..29
                          mol_type = protein
                          organism = synthetic construct
SITE                      2
                          note = D-serine
MOD_RES                   10
                          note = AminoEthoxyEthoxyAcetic Acyl-MaleimidoPropionic Acyl
SEQUENCE: 216
HSQGTFTSDK SKYLDARAAQ DFVQWLLDT                                      29

SEQ ID NO: 217            moltype = AA   length = 29
FEATURE                   Location/Qualifiers
source                    1..29
                          mol_type = protein
                          organism = synthetic construct
MOD_RES                   24
                          note = AminoEthoxyEthoxyAcetic Acyl-MaleimidoPropionic Acyl
MOD_RES                   2
                          note = Amino-cyclobutyl-1-carboxylic acid
SEQUENCE: 217
HXQGTFTSDY SKYLDERAAK DFIKWLESA                                      29

SEQ ID NO: 218            moltype = AA   length = 39
FEATURE                   Location/Qualifiers
source                    1..39
                          mol_type = protein
                          organism = synthetic construct
SITE                      2
                          note = D-serine
MOD_RES                   14
                          note = AminoEthoxyEthoxyAcetic Acyl-MaleimidoPropionic Acyl
SEQUENCE: 218
HSQGTFTSDL SKQKESKAAQ DFIEWLKAGG PSSGAPPPS                           39

SEQ ID NO: 219            moltype = AA   length = 30
FEATURE                   Location/Qualifiers
source                    1..30
                          mol_type = protein
                          organism = synthetic construct
MOD_RES                   10
                          note = AminoEthoxyEthoxyAcetic Acyl-MaleimidoPropionic Acyl
SEQUENCE: 219
```

-continued

```
HSQGTFTSDK SEYLDSERAR DFVAWLEAGG                                     30

SEQ ID NO: 220          moltype = AA   length = 39
FEATURE                 Location/Qualifiers
source                  1..39
                        mol_type = protein
                        organism = synthetic construct
MOD_RES                 2
                        note = Aib
MOD_RES                 10
                        note = AminoEthoxyEthoxyAcetic Acyl-MaleimidoPropionic Acyl
SEQUENCE: 220
HXQGTFTSDK SKYLDERAAQ DFVQWLLDGG PSSGAPPPS                           39

SEQ ID NO: 221          moltype = AA   length = 39
FEATURE                 Location/Qualifiers
source                  1..39
                        mol_type = protein
                        organism = synthetic construct
MOD_RES                 10
                        note = AminoEthoxyEthoxyAcetic Acyl-MaleimidoPropionic Acyl
SEQUENCE: 221
HSQGTFTSDK SKYLDERRAQ DFVQWLLDGG PSSGAPPPS                           39

SEQ ID NO: 222          moltype = AA   length = 39
FEATURE                 Location/Qualifiers
source                  1..39
                        mol_type = protein
                        organism = synthetic construct
MOD_RES                 2
                        note = Aib
MOD_RES                 20
                        note = Aib
MOD_RES                 34
                        note = Aib
MOD_RES                 14
                        note = AminoEthoxyEthoxyAcetic Acyl-MaleimidoPropionic Acyl
SEQUENCE: 222
HXHGTGTSDL SKLKEEQRQX EFIEWLKAAG PPSXKPPPK                           39

SEQ ID NO: 223          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 223
HAQGTFTSDY AKYLDARRAK EFIAWLVNGG PSSGAPPPSK                          40

SEQ ID NO: 224          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-AminoEthoxyEthoxyAcetic
                        Acyl-MaleimidoPropionic Acyl
SEQUENCE: 224
HAQGTFTSDY AKYLDARRAK EFIAWLVNGG PSSGAPPPSK                          40

SEQ ID NO: 225          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-8-AminoOctanoic
                        Acyl-MaleimidoPropionic Acyl
SEQUENCE: 225
HAQGTFTSDY AKYLDARRAK EFIAWLVNGG PSSGAPPPSK                          40

SEQ ID NO: 226          moltype = AA   length = 40
```

-continued

```
FEATURE             Location/Qualifiers
source              1..40
                    mol_type = protein
                    organism = synthetic construct
SITE                2
                    note = D-alanine
SEQUENCE: 226
HAQGTFTSDY AKYLDARRAK EFIAWLVNGG PSSGAPPPSK                              40

SEQ ID NO: 227      moltype = AA   length = 40
FEATURE             Location/Qualifiers
source              1..40
                    mol_type = protein
                    organism = synthetic construct
SITE                2
                    note = D-alanine
MOD_RES             40
                    note = AminoEthoxyEthoxyAcetic Acyl-AminoEthoxyEthoxyAcetic
                     Acyl-MaleimidoPropionic Acyl
SEQUENCE: 227
HAEGTFTSDY AKYLDARRAK EFIAWLVNGG PSSGAPPPSK                              40

SEQ ID NO: 228      moltype = AA   length = 40
FEATURE             Location/Qualifiers
source              1..40
                    mol_type = protein
                    organism = synthetic construct
MOD_RES             40
                    note = AminoEthoxyEthoxyAcetic Acyl-8-AminoOctanoic
                     Acyl-MaleimidoPropionic Acyl
SITE                2
                    note = D-alanine
SEQUENCE: 228
HAEGTFTSDY AKYLDARRAK EFIAWLVNGG PSSGAPPPSK                              40

SEQ ID NO: 229      moltype = AA   length = 40
FEATURE             Location/Qualifiers
source              1..40
                    mol_type = protein
                    organism = synthetic construct
SITE                2
                    note = D-alanine
SEQUENCE: 229
HAEGTFTSDY AKYLDARRAK EFIAWLVNGG PSSGAPPPSK                              40

SEQ ID NO: 230      moltype = AA   length = 41
FEATURE             Location/Qualifiers
source              1..41
                    mol_type = protein
                    organism = synthetic construct
SITE                2
                    note = D-alanine
MOD_RES             40
                    note = AminoEthoxyEthoxyAcetic Acid //
                     8-amino-3,6-dioxa-octanoic acid
MOD_RES             41
                    note = AminoEthoxyEthoxyAcetic Acyl-MaleimidoPropionic Acyl
SEQUENCE: 230
HAEGTFTSDY AKYLDARRAK EFIAWLVNGG PSSGAPPPSX K                            41

SEQ ID NO: 231      moltype = AA   length = 42
FEATURE             Location/Qualifiers
source              1..42
                    mol_type = protein
                    organism = synthetic construct
SEQUENCE: 231
YAEGTFISDY SIAMDKIHQQ DFVNWLLAQK GKKNDWKHNI TQ                           42

SEQ ID NO: 232      moltype = AA   length = 41
FEATURE             Location/Qualifiers
source              1..41
                    mol_type = protein
                    organism = synthetic construct
SITE                2
                    note = D-alanine
MOD_RES             40
                    note = AminoEthoxyEthoxyAcetic Acid //
                     8-amino-3,6-dioxa-octanoic acid
MOD_RES             41
```

-continued

```
                          note = AminoEthoxyEthoxyAcetic Acyl-MaleimidoPropionic Acyl
SEQUENCE: 232
HAEGTFTSDV ASYLEGQAAK EFIAWLVNGG PSSGAPPPSX K                              41

SEQ ID NO: 233           moltype = AA  length = 31
FEATURE                  Location/Qualifiers
source                   1..31
                         mol_type = protein
                         organism = synthetic construct
MOD_RES                  2
                         note = Aib
MOD_RES                  20
                         note = AminoEthoxyEthoxyAcetic Acyl-AminoEthoxyEthoxyAcetic
                          Acyl-MaleimidoPropionic Acyl
SEQUENCE: 233
HXEGTFTSDV SSYLEGQAAK EFIAWLVRGR G                                         31

SEQ ID NO: 234           moltype = AA  length = 32
FEATURE                  Location/Qualifiers
source                   1..32
                         mol_type = protein
                         organism = synthetic construct
MOD_RES                  2
                         note = Aib
MOD_RES                  32
                         note = AminoEthoxyEthoxyAcetic Acyl-MaleimidoPropionic Acyl
SEQUENCE: 234
HXEGTFTSDV SSYLEGQAAK EFIAWLVRGR GK                                        32

SEQ ID NO: 235           moltype = AA  length = 32
FEATURE                  Location/Qualifiers
source                   1..32
                         mol_type = protein
                         organism = synthetic construct
MOD_RES                  2
                         note = Aib
MOD_RES                  32
                         note = AminoEthoxyEthoxyAcetic Acyl-8-AminoOctanoic
                          Acyl-MaleimidoPropionic Acyl
MOD_RES                  20
                         note = Aib
SEQUENCE: 235
HXEGTFTSDV SSYLEGQAAX EFIAWLVRGR GK                                        32

SEQ ID NO: 236           moltype = AA  length = 39
FEATURE                  Location/Qualifiers
source                   1..39
                         mol_type = protein
                         organism = synthetic construct
MOD_RES                  2
                         note = Aib
MOD_RES                  13
                         note = Aib
MOD_RES                  20
                         note = AminoEthoxyEthoxyAcetic Acyl-8-AminoOctanoic
                          Acyl-MaleimidoPropionic Acyl
SEQUENCE: 236
YXEGTFTSDY SIXLDKIAQK AFVQWLIAGG PSSGAPPPS                                 39

SEQ ID NO: 237           moltype = AA  length = 39
FEATURE                  Location/Qualifiers
source                   1..39
                         mol_type = protein
                         organism = synthetic construct
MOD_RES                  2
                         note = Aib
MOD_RES                  13
                         note = Aib
MOD_RES                  20
                         note = AminoEthoxyEthoxyAcetic Acyl-AminoEthoxyEthoxyAcetic
                          Acyl-MaleimidoPropionic Acyl
SEQUENCE: 237
YXEGTFTSDY SIXLDKIAQK AFVQWLIAGG PSSGAPPPS                                 39

SEQ ID NO: 238           moltype = AA  length = 40
FEATURE                  Location/Qualifiers
source                   1..40
                         mol_type = protein
                         organism = synthetic construct
```

```
MOD_RES                  2
                         note = Aib
MOD_RES                  20
                         note = Aib
MOD_RES                  40
                         note = AminoEthoxyEthoxyAcetic Acyl-AminoEthoxyEthoxyAcetic
                           Acyl-MaleimidoPropionic Acyl
SEQUENCE: 238
YXEGTFTSDY SIYLDKQAAX EFVQWLLAGG PSSGAPPPSK                                   40

SEQ ID NO: 239           moltype = AA  length = 40
FEATURE                  Location/Qualifiers
source                   1..40
                         mol_type = protein
                         organism = synthetic construct
MOD_RES                  2
                         note = Aib
MOD_RES                  20
                         note = Aib
MOD_RES                  40
                         note = AminoEthoxyEthoxyAcetic Acyl-8-AminoOctanoic
                           Acyl-AminoEthoxyEthoxyAcetic Acyl-MaleimidoPropionic Acyl
SEQUENCE: 239
YXEGTFTSDY SIYLDKQAAX EFVQWLLAGG PSSGAPPPSK                                   40

SEQ ID NO: 240           moltype = AA  length = 34
FEATURE                  Location/Qualifiers
source                   1..34
                         mol_type = protein
                         organism = synthetic construct
MOD_RES                  2
                         note = Aib
MOD_RES                  20
                         note = AminoEthoxyEthoxyAcetic Acyl-AminoEthoxyEthoxyAcetic
                           Acyl-MaleimidoPropionic Acyl
SEQUENCE: 240
HXQGTFTSDY SKYLDEKKAK EFVEWLLEGG PSSG                                         34

SEQ ID NO: 241           moltype = AA  length = 34
FEATURE                  Location/Qualifiers
source                   1..34
                         mol_type = protein
                         organism = synthetic construct
MOD_RES                  2
                         note = Aib
MOD_RES                  20
                         note = AminoEthoxyEthoxyAcetic Acyl-8-AminoOctanoic
                           Acyl-MaleimidoPropionic Acyl
SEQUENCE: 241
HXQGTFTSDY SKYLDEKKAK EFVEWLLEGG PSSG                                         34

SEQ ID NO: 242           moltype = AA  length = 34
FEATURE                  Location/Qualifiers
source                   1..34
                         mol_type = protein
                         organism = synthetic construct
MOD_RES                  2
                         note = Aib
MOD_RES                  20
                         note = AminoEthoxyEthoxyAcetic Acyl-8-AminoOctanoic
                           Acyl-AminoEthoxyEthoxyAcetic Acyl-MaleimidoPropionic Acyl
SEQUENCE: 242
HXQGTFTSDY SKYLDEKKAK EFVEWLLEGG PSSG                                         34

SEQ ID NO: 243           moltype = AA  length = 35
FEATURE                  Location/Qualifiers
source                   1..35
                         mol_type = protein
                         organism = synthetic construct
MOD_RES                  2
                         note = Aib
MOD_RES                  35
                         note = AminoEthoxyEthoxyAcetic Acyl-MaleimidoPropionic Acyl
SEQUENCE: 243
HXQGTFTSDY SKYLDEKKAK EFVEWLLEGG PSSGK                                        35

SEQ ID NO: 244           moltype = AA  length = 29
FEATURE                  Location/Qualifiers
source                   1..29
```

```
                                  mol_type = protein
                                  organism = synthetic construct
MOD_RES                           2
                                  note = Aib
MOD_RES                           17
                                  note = AminoEthoxyEthoxyAcetic Acyl-AminoEthoxyEthoxyAcetic
                                   Acyl-MaleimidoPropionic Acyl
SEQUENCE: 244
HXQGTFTSDY SKYLDEKAAK EFIQWLLQT                                            29

SEQ ID NO: 245          moltype = AA   length = 29
FEATURE                 Location/Qualifiers
source                  1..29
                                  mol_type = protein
                                  organism = synthetic construct
MOD_RES                           2
                                  note = Aib
MOD_RES                           17
                                  note = AminoEthoxyEthoxyAcetic Acyl-8-AminoOctanoic
                                   Acyl-MaleimidoPropionic Acyl
SEQUENCE: 245
HXQGTFTSDY SKYLDEKAAK EFIQWLLQT                                            29

SEQ ID NO: 246          moltype = AA   length = 39
FEATURE                 Location/Qualifiers
source                  1..39
                                  mol_type = protein
                                  organism = synthetic construct
SITE                              2
                                  note = D-serine
MOD_RES                           14
                                  note = AminoEthoxyEthoxyAcetic Acyl-AminoEthoxyEthoxyAcetic
                                   Acyl-MaleimidoPropionic Acyl
SEQUENCE: 246
HSQGTFTSDL SKQKESKAAQ DFIEWLKAGG PSSGAPPPS                                     39

SEQ ID NO: 247          moltype = AA   length = 39
FEATURE                 Location/Qualifiers
source                  1..39
                                  mol_type = protein
                                  organism = synthetic construct
SITE                              2
                                  note = D-serine
MOD_RES                           14
                                  note = AminoEthoxyEthoxyAcetic Acyl-8-AminoOctanoic
                                   Acyl-AminoEthoxyEthoxyAcetic Acyl-MaleimidoPropionic Acyl
SEQUENCE: 247
HSQGTFTSDL SKQKESKAAQ DFIEWLKAGG PSSGAPPPS                                     39

SEQ ID NO: 248          moltype = AA   length = 40
FEATURE                 Location/Qualifiers
source                  1..40
                                  mol_type = protein
                                  organism = synthetic construct
SITE                              2
                                  note = D-serine
MOD_RES                           40
                                  note = AminoEthoxyEthoxyAcetic Acyl-MaleimidoPropionic Acyl
SEQUENCE: 248
HSQGTFTSDL SKQLESKAAQ DFIEWLKAGG PSSGAPPPSK                                    40

SEQ ID NO: 249          moltype = AA   length = 40
FEATURE                 Location/Qualifiers
source                  1..40
                                  mol_type = protein
                                  organism = synthetic construct
SITE                              2
                                  note = D-serine
MOD_RES                           40
                                  note = AminoEthoxyEthoxyAcetic Acyl-8-AminoOctanoic
                                   Acyl-MaleimidoPropionic Acyl
SEQUENCE: 249
HSQGTFTSDL SKQLESKAAQ DFIEWLKAGG PSSGAPPPSK                                    40

SEQ ID NO: 250          moltype = AA   length = 31
FEATURE                 Location/Qualifiers
source                  1..31
                                  mol_type = protein
                                  organism = synthetic construct
```

```
MOD_RES              31
                     note = AminoEthoxyEthoxyAcetic
                     Acyl-Bromo-MaleimidoPropionic
                     Acyl//8-amino-3,6-dioxa-octanoic
                     acyl-3-(3-Bromo-2,5-dioxopyrrol-1-yl)propanoic acyl
SEQUENCE: 250
HSQGTFTSDL SEYLDSERAR DFVAWLEAGG K                                       31

SEQ ID NO: 251       moltype = AA  length = 39
FEATURE              Location/Qualifiers
source               1..39
                     mol_type = protein
                     organism = synthetic construct
MOD_RES              2
                     note = Aib
MOD_RES              13
                     note = Alpha-Methyl-Leucine
MOD_RES              17
                     note = AminoEthoxyEthoxyAcetic Acyl-AminoEthoxyEthoxyAcetic
                     Acyl-MaleimidoPropionic Acyl
MOD_RES              20
                     note = Aib
SEQUENCE: 251
YXQGTFTSDY SIXLDKKAQX AFIEYLLEGG PSSGAPPPS                               39

SEQ ID NO: 252       moltype = AA  length = 39
FEATURE              Location/Qualifiers
source               1..39
                     mol_type = protein
                     organism = synthetic construct
MOD_RES              2
                     note = Aib
MOD_RES              20
                     note = Aib
MOD_RES              13
                     note = Alpha-Methyl-Leucine
MOD_RES              17
                     note = AminoEthoxyEthoxyAcetic Acyl-8-AminoOctanoic
                     Acyl-MaleimidoPropionic Acyl
SEQUENCE: 252
YXQGTFTSDY SIXLDKKAQX AFIEYLLEGG PSSGAPPPS                               39

SEQ ID NO: 253       moltype = AA  length = 39
FEATURE              Location/Qualifiers
source               1..39
                     mol_type = protein
                     organism = synthetic construct
MOD_RES              2
                     note = Aib
MOD_RES              20
                     note = Aib
MOD_RES              13
                     note = Alpha-Methyl-Leucine
MOD_RES              17
                     note = AminoEthoxyEthoxyAcetic Acyl-8-AminoOctanoic
                     Acyl-AminoEthoxyEthoxyAcetic Acyl-MaleimidoPropionic Acyl
SEQUENCE: 253
YXQGTFTSDY SIXLDKKAQX AFIEYLLEGG PSSGAPPPS                               39

SEQ ID NO: 254       moltype = AA  length = 40
FEATURE              Location/Qualifiers
source               1..40
                     mol_type = protein
                     organism = synthetic construct
MOD_RES              2
                     note = Aib
MOD_RES              13
                     note = Alpha-Methyl-Leucine
MOD_RES              20
                     note = Aib
MOD_RES              40
                     note = AminoEthoxyEthoxyAcetic Acyl-AminoEthoxyEthoxyAcetic
                     Acyl-MaleimidoPropionic Acyl
SEQUENCE: 254
YXQGTFTSDY SIXLDKIAQX AFIEYLLEGG PSSGAPPPSK                              40

SEQ ID NO: 255       moltype = AA  length = 40
FEATURE              Location/Qualifiers
source               1..40
```

```
                          mol_type = protein
                          organism = synthetic construct
MOD_RES                   2
                          note = Aib
MOD_RES                   20
                          note = Aib
MOD_RES                   13
                          note = Alpha-Methyl-Leucine
MOD_RES                   40
                          note = AminoEthoxyEthoxyAcetic Acyl-8-AminoOctanoic
                           Acyl-MaleimidoPropionic Acyl
SEQUENCE: 255
YXQGTFTSDY SIXLDKIAQX AFIEYLLEGG PSSGAPPPSK                                40

SEQ ID NO: 256            moltype = AA  length = 40
FEATURE                   Location/Qualifiers
source                    1..40
                          mol_type = protein
                          organism = synthetic construct
MOD_RES                   2
                          note = Aib
MOD_RES                   20
                          note = Aib
MOD_RES                   13
                          note = Alpha-Methyl-Leucine
MOD_RES                   40
                          note = AminoEthoxyEthoxyAcetic Acyl-8-AminoOctanoic
                           Acyl-AminoEthoxyEthoxyAcetic Acyl-MaleimidoPropionic Acyl
SEQUENCE: 256
YXQGTFTSDY SIXLDKIAQX AFIEYLLEGG PSSGAPPPSK                                40

SEQ ID NO: 257            moltype = AA  length = 39
FEATURE                   Location/Qualifiers
source                    1..39
                          mol_type = protein
                          organism = synthetic construct
MOD_RES                   10
                          note = AminoEthoxyEthoxyAcetic Acyl-AminoEthoxyEthoxyAcetic
                           Acyl-MaleimidoPropionic Acyl
SEQUENCE: 257
HSQGTFTSDK SKYLDERRAQ DFVQWLLDGG PSSGAPPPS                                 39

SEQ ID NO: 258            moltype = AA  length = 39
FEATURE                   Location/Qualifiers
source                    1..39
                          mol_type = protein
                          organism = synthetic construct
MOD_RES                   10
                          note = AminoEthoxyEthoxyAcetic Acyl-8-AminoOctanoic
                           Acyl-MaleimidoPropionic Acyl
SEQUENCE: 258
HSQGTFTSDK SKYLDERRAQ DFVQWLLDGG PSSGAPPPS                                 39

SEQ ID NO: 259            moltype = AA  length = 40
FEATURE                   Location/Qualifiers
source                    1..40
                          mol_type = protein
                          organism = synthetic construct
MOD_RES                   40
                          note = AminoEthoxyEthoxyAcetic Acyl-MaleimidoPropionic Acyl
SEQUENCE: 259
HSQGTFTSDY SKYLDERRAQ DFVQWLLDGG PSSGAPPPSK                                40

SEQ ID NO: 260            moltype = AA  length = 40
FEATURE                   Location/Qualifiers
source                    1..40
                          mol_type = protein
                          organism = synthetic construct
MOD_RES                   40
                          note = AminoEthoxyEthoxyAcetic
                           Acyl-Bromo-MaleimidoPropionic
                           Acyl//8-amino-3,6-dioxa-octanoic
                           acyl-3-(3-Bromo-2,5-dioxopyrrol-1-yl)propanoic acyl
SEQUENCE: 260
HSQGTFTSDY SKYLDERRAQ DFVQWLLDGG PSSGAPPPSK                                40

SEQ ID NO: 261            moltype = AA  length = 39
FEATURE                   Location/Qualifiers
source                    1..39
```

-continued

```
                         mol_type = protein
                         organism = synthetic construct
MOD_RES                  2
                         note = Aib
MOD_RES                  34
                         note = Aib
MOD_RES                  14
                         note = AminoEthoxyEthoxyAcetic Acyl-AminoEthoxyEthoxyAcetic
                          Acyl-MaleimidoPropionic Acyl
SITE                     29
                         note = D-alanine
MOD_RES                  20
                         note = Aib
SEQUENCE: 261
HXHGTGTSDL SKLKEEQRQX EFIEWLKAAG PPSXKPPPK                                    39

SEQ ID NO: 262           moltype = AA   length = 39
FEATURE                  Location/Qualifiers
source                   1..39
                         mol_type = protein
                         organism = synthetic construct
MOD_RES                  2
                         note = Aib
MOD_RES                  20
                         note = Aib
MOD_RES                  34
                         note = Aib
SITE                     29
                         note = D-alanine
MOD_RES                  39
                         note = AminoEthoxyEthoxyAcetic Acyl-MaleimidoPropionic Acyl
SEQUENCE: 262
HXHGTGTSDL SKLLEEQRQX EFIEWLKAAG PPSXKPPPK                                    39

SEQ ID NO: 263           moltype = AA   length = 40
FEATURE                  Location/Qualifiers
source                   1..40
                         mol_type = protein
                         organism = synthetic construct
MOD_RES                  2
                         note = Aib
MOD_RES                  20
                         note = Aib
MOD_RES                  34
                         note = Aib
SITE                     29
                         note = D-alanine
MOD_RES                  39
                         note = AminoEthoxyEthoxyAcetic Acid //
                          8-amino-3,6-dioxa-octanoic acid
MOD_RES                  40
                         note = AminoEthoxyEthoxyAcetic Acyl-MaleimidoPropionic Acyl
SEQUENCE: 263
HXHGTGTSDL SKLLEEQRQX EFIEWLKAAG PPSXKPPPXK                                   40

SEQ ID NO: 264           moltype = AA   length = 40
FEATURE                  Location/Qualifiers
source                   1..40
                         mol_type = protein
                         organism = synthetic construct
SITE                     2
                         note = D-alanine
MOD_RES                  20
                         note = Aib
MOD_RES                  40
                         note = AminoEthoxyEthoxyAcetic Acyl-MaleimidoPropionic Acyl
SEQUENCE: 264
YAEGTFTSDY AKYLDARRAX EFIAWLVNGG PSSGAPPPSK                                   40

SEQ ID NO: 265           moltype = AA   length = 40
FEATURE                  Location/Qualifiers
source                   1..40
                         mol_type = protein
                         organism = synthetic construct
MOD_RES                  2
                         note = Aib
MOD_RES                  20
                         note = Aib
MOD_RES                  40
```

-continued

```
                          note = AminoEthoxyEthoxyAcetic Acyl-MaleimidoPropionic Acyl
SEQUENCE: 265
YXEGTFTSDY AKYLDARRAX EFIAWLVNGG PSSGAPPPSK                      40

SEQ ID NO: 266         moltype = AA   length = 40
FEATURE                Location/Qualifiers
source                 1..40
                       mol_type = protein
                       organism = synthetic construct
MOD_RES                2
                       note = Aib
MOD_RES                13
                       note = Aib
MOD_RES                20
                       note = Aib
MOD_RES                40
                       note = AminoEthoxyEthoxyAcetic Acyl-MaleimidoPropionic Acyl
SEQUENCE: 266
YXEGTFTSDY SIXLDKRRAX EFIAWLVNGG PSSGAPPPSK                      40

SEQ ID NO: 267         moltype = AA   length = 40
FEATURE                Location/Qualifiers
source                 1..40
                       mol_type = protein
                       organism = synthetic construct
SITE                   2
                       note = D-alanine
MOD_RES                13
                       note = Aib
MOD_RES                20
                       note = Aib
MOD_RES                40
                       note = AminoEthoxyEthoxyAcetic Acyl-MaleimidoPropionic Acyl
SEQUENCE: 267
HAEGTFTSDY SIXLDKRRAX EFIAWLVNGG PSSGAPPPSK                      40

SEQ ID NO: 268         moltype = AA   length = 40
FEATURE                Location/Qualifiers
source                 1..40
                       mol_type = protein
                       organism = synthetic construct
SITE                   2
                       note = D-alanine
MOD_RES                13
                       note = Aib
MOD_RES                20
                       note = Aib
MOD_RES                40
                       note = AminoEthoxyEthoxyAcetic Acyl-MaleimidoPropionic Acyl
SEQUENCE: 268
YAEGTFTSDY SIXLDKRRAX EFIAWLVNGG PSSGAPPPSK                      40

SEQ ID NO: 269         moltype = AA   length = 40
FEATURE                Location/Qualifiers
source                 1..40
                       mol_type = protein
                       organism = synthetic construct
MOD_RES                2
                       note = Aib
MOD_RES                13
                       note = Aib
MOD_RES                20
                       note = Aib
MOD_RES                40
                       note = AminoEthoxyEthoxyAcetic Acyl-MaleimidoPropionic Acyl
SEQUENCE: 269
YXEGTFTSDY SIXLDKIAQX AFIAWLVNGG PSSGAPPPSK                      40

SEQ ID NO: 270         moltype = AA   length = 40
FEATURE                Location/Qualifiers
source                 1..40
                       mol_type = protein
                       organism = synthetic construct
SITE                   2
                       note = D-alanine
MOD_RES                13
                       note = Aib
MOD_RES                20
                       note = Aib
```

-continued

```
MOD_RES                  40
                         note = AminoEthoxyEthoxyAcetic Acyl-MaleimidoPropionic Acyl
SEQUENCE: 270
HAEGTFTSDY SIXLDKIAQX AFIAWLVNGG PSSGAPPPSK                                    40

SEQ ID NO: 271           moltype = AA  length = 40
FEATURE                  Location/Qualifiers
source                   1..40
                         mol_type = protein
                         organism = synthetic construct
SITE                     2
                         note = D-alanine
MOD_RES                  13
                         note = Aib
MOD_RES                  20
                         note = Aib
MOD_RES                  40
                         note = AminoEthoxyEthoxyAcetic Acyl-MaleimidoPropionic Acyl
SEQUENCE: 271
YAEGTFTSDY SIXLDKIAQX AFIAWLVNGG PSSGAPPPSK                                    40

SEQ ID NO: 272           moltype = AA  length = 40
FEATURE                  Location/Qualifiers
source                   1..40
                         mol_type = protein
                         organism = synthetic construct
SITE                     2
                         note = D-alanine
MOD_RES                  13
                         note = Aib
MOD_RES                  20
                         note = Aib
MOD_RES                  40
                         note = AminoEthoxyEthoxyAcetic Acyl-MaleimidoPropionic Acyl
SEQUENCE: 272
HAEGTFTSDY SIXLDKIAQX AFVQWLIAGG PSSGAPPPSK                                    40

SEQ ID NO: 273           moltype = AA  length = 40
FEATURE                  Location/Qualifiers
source                   1..40
                         mol_type = protein
                         organism = synthetic construct
SITE                     2
                         note = D-alanine
MOD_RES                  13
                         note = Aib
MOD_RES                  20
                         note = Aib
MOD_RES                  40
                         note = AminoEthoxyEthoxyAcetic Acyl-MaleimidoPropionic Acyl
SEQUENCE: 273
YAEGTFTSDY SIXLDKIAQX AFVQWLIAGG PSSGAPPPSK                                    40

SEQ ID NO: 274           moltype = AA  length = 41
FEATURE                  Location/Qualifiers
source                   1..41
                         mol_type = protein
                         organism = synthetic construct
MOD_RES                  2
                         note = Aib
MOD_RES                  13
                         note = Aib
MOD_RES                  20
                         note = Aib
MOD_RES                  40
                         note = AminoEthoxyEthoxyAcetic Acid //
                          8-amino-3,6-dioxa-octanoic acid
MOD_RES                  41
                         note = AminoEthoxyEthoxyAcetic Acyl-MaleimidoPropionic Acyl
SEQUENCE: 274
YXEGTFTSDY SIXLDKIAQX AFVQWLIAGG PSSGAPPPSX K                                  41

SEQ ID NO: 275           moltype = AA  length = 40
FEATURE                  Location/Qualifiers
source                   1..40
                         mol_type = protein
                         organism = synthetic construct
SITE                     2
                         note = D-alanine
```

```
MOD_RES              20
                     note = Aib
MOD_RES              40
                     note = AminoEthoxyEthoxyAcetic Acyl-MaleimidoPropionic Acyl
SEQUENCE: 275
HAEGTFTSDY AKYLDARRAX EFVQWLIAGG PSSGAPPPSK                           40

SEQ ID NO: 276       moltype = AA   length = 40
FEATURE              Location/Qualifiers
source               1..40
                     mol_type = protein
                     organism = synthetic construct
SITE                 2
                     note = D-alanine
MOD_RES              20
                     note = Aib
MOD_RES              40
                     note = AminoEthoxyEthoxyAcetic Acyl-MaleimidoPropionic Acyl
SEQUENCE: 276
YAEGTFTSDY AKYLDARRAX EFVQWLIAGG PSSGAPPPSK                           40

SEQ ID NO: 277       moltype = AA   length = 40
FEATURE              Location/Qualifiers
source               1..40
                     mol_type = protein
                     organism = synthetic construct
MOD_RES              2
                     note = Aib
MOD_RES              40
                     note = AminoEthoxyEthoxyAcetic Acyl-MaleimidoPropionic Acyl
MOD_RES              20
                     note = Aib
SEQUENCE: 277
YXEGTFTSDY AKYLDARRAX EFVQWLIAGG PSSGAPPPSK                           40

SEQ ID NO: 278       moltype = AA   length = 40
FEATURE              Location/Qualifiers
source               1..40
                     mol_type = protein
                     organism = synthetic construct
SITE                 2
                     note = D-alanine
MOD_RES              20
                     note = Aib
MOD_RES              40
                     note = AminoEthoxyEthoxyAcetic Acyl-MaleimidoPropionic Acyl
SEQUENCE: 278
HAEGTFTSDY AKYLDKIAQX AFVQWLIAGG PSSGAPPPSK                           40

SEQ ID NO: 279       moltype = AA   length = 40
FEATURE              Location/Qualifiers
source               1..40
                     mol_type = protein
                     organism = synthetic construct
SITE                 2
                     note = D-alanine
MOD_RES              20
                     note = Aib
MOD_RES              40
                     note = AminoEthoxyEthoxyAcetic Acyl-MaleimidoPropionic Acyl
SEQUENCE: 279
YAEGTFTSDY AKYLDKIAQX AFVQWLIAGG PSSGAPPPSK                           40

SEQ ID NO: 280       moltype = AA   length = 40
FEATURE              Location/Qualifiers
source               1..40
                     mol_type = protein
                     organism = synthetic construct
MOD_RES              2
                     note = Aib
MOD_RES              20
                     note = Aib
MOD_RES              40
                     note = AminoEthoxyEthoxyAcetic Acyl-MaleimidoPropionic Acyl
SEQUENCE: 280
YXEGTFTSDY AKYLDKIAQX AFVQWLIAGG PSSGAPPPSK                           40

SEQ ID NO: 281       moltype = AA   length = 40
FEATURE              Location/Qualifiers
```

-continued

```
source                 1..40
                       mol_type = protein
                       organism = synthetic construct
MOD_RES                2
                       note = Aib
MOD_RES                40
                       note = AminoEthoxyEthoxyAcetic Acyl-MaleimidoPropionic Acyl
SEQUENCE: 281
YXQGTFTSDY AKYLDARRAK EFIAWLVNGG PSSGAPPPSK                              40

SEQ ID NO: 282         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 282
YAQGTFTSDY AKYLDARRAK EFIAWLVNGG PSSGAPPPSK                              40

SEQ ID NO: 283         moltype = AA  length = 40
FEATURE                Location/Qualifiers
source                 1..40
                       mol_type = protein
                       organism = synthetic construct
MOD_RES                2
                       note = Aib
MOD_RES                13
                       note = Alpha-Methyl-Leucine
MOD_RES                40
                       note = AminoEthoxyEthoxyAcetic Acyl-MaleimidoPropionic Acyl
SEQUENCE: 283
YXQGTFTSDY SIXLDKRRAK EFIAWLVNGG PSSGAPPPSK                              40

SEQ ID NO: 284         moltype = AA  length = 40
FEATURE                Location/Qualifiers
source                 1..40
                       mol_type = protein
                       organism = synthetic construct
SITE                   2
                       note = D-alanine
MOD_RES                13
                       note = Alpha-Methyl-Leucine
MOD_RES                40
                       note = AminoEthoxyEthoxyAcetic Acyl-MaleimidoPropionic Acyl
SEQUENCE: 284
YAQGTFTSDY SIXLDKRRAK EFIAWLVNGG PSSGAPPPSK                              40

SEQ ID NO: 285         moltype = AA  length = 40
FEATURE                Location/Qualifiers
source                 1..40
                       mol_type = protein
                       organism = synthetic construct
SITE                   2
                       note = D-alanine
MOD_RES                13
                       note = Alpha-Methyl-Leucine
MOD_RES                40
                       note = AminoEthoxyEthoxyAcetic Acyl-MaleimidoPropionic Acyl
SEQUENCE: 285
HAQGTFTSDY SIXLDKRRAK EFIAWLVNGG PSSGAPPPSK                              40

SEQ ID NO: 286         moltype = AA  length = 40
FEATURE                Location/Qualifiers
source                 1..40
                       mol_type = protein
                       organism = synthetic construct
MOD_RES                2
                       note = Aib
MOD_RES                13
                       note = Alpha-Methyl-Leucine
MOD_RES                20
                       note = Aib
MOD_RES                40
                       note = AminoEthoxyEthoxyAcetic Acyl-MaleimidoPropionic Acyl
SEQUENCE: 286
YXQGTFTSDY SIXLDKIAQX AFIAWLVNGG PSSGAPPPSK                              40
```

-continued

```
SEQ ID NO: 287         moltype = AA  length = 40
FEATURE                Location/Qualifiers
source                 1..40
                       mol_type = protein
                       organism = synthetic construct
SITE                   2
                       note = D-alanine
MOD_RES                13
                       note = Alpha-Methyl-Leucine
MOD_RES                20
                       note = Aib
MOD_RES                40
                       note = AminoEthoxyEthoxyAcetic Acyl-MaleimidoPropionic Acyl
SEQUENCE: 287
YAQGTFTSDY SIXLDKIAQX AFIAWLVNGG PSSGAPPPSK                             40

SEQ ID NO: 288         moltype = AA  length = 40
FEATURE                Location/Qualifiers
source                 1..40
                       mol_type = protein
                       organism = synthetic construct
SITE                   2
                       note = D-alanine
MOD_RES                20
                       note = Aib
MOD_RES                40
                       note = AminoEthoxyEthoxyAcetic Acyl-MaleimidoPropionic Acyl
MOD_RES                13
                       note = Alpha-Methyl-Leucine
SEQUENCE: 288
HAQGTFTSDY SIXLDKIAQX AFIAWLVNGG PSSGAPPPSK                             40

SEQ ID NO: 289         moltype = AA  length = 40
FEATURE                Location/Qualifiers
source                 1..40
                       mol_type = protein
                       organism = synthetic construct
SITE                   2
                       note = D-alanine
MOD_RES                20
                       note = Aib
MOD_RES                40
                       note = AminoEthoxyEthoxyAcetic Acyl-MaleimidoPropionic Acyl
MOD_RES                13
                       note = Alpha-Methyl-Leucine
SEQUENCE: 289
YAQGTFTSDY SIXLDKIAQX AFIEYLLEGG PSSGAPPPSK                             40

SEQ ID NO: 290         moltype = AA  length = 40
FEATURE                Location/Qualifiers
source                 1..40
                       mol_type = protein
                       organism = synthetic construct
SITE                   2
                       note = D-alanine
MOD_RES                20
                       note = Aib
MOD_RES                40
                       note = AminoEthoxyEthoxyAcetic Acyl-MaleimidoPropionic Acyl
MOD_RES                13
                       note = Alpha-Methyl-Leucine
SEQUENCE: 290
HAQGTFTSDY SIXLDKIAQX AFIEYLLEGG PSSGAPPPSK                             40

SEQ ID NO: 291         moltype = AA  length = 41
FEATURE                Location/Qualifiers
source                 1..41
                       mol_type = protein
                       organism = synthetic construct
MOD_RES                2
                       note = Aib
MOD_RES                20
                       note = Aib
MOD_RES                13
                       note = Alpha-Methyl-Leucine
MOD_RES                40
                       note = AminoEthoxyEthoxyAcetic Acid //
                        8-amino-3,6-dioxa-octanoic acid
```

-continued

```
MOD_RES                  41
                         note = AminoEthoxyEthoxyAcetic Acyl-MaleimidoPropionic Acyl
SEQUENCE: 291
YXQGTFTSDY SIXLDKIAQX AFIEYLLEGG PSSGAPPPSX K                      41

SEQ ID NO: 292           moltype = AA  length = 40
FEATURE                  Location/Qualifiers
source                   1..40
                         mol_type = protein
                         organism = synthetic construct
SITE                     2
                         note = D-alanine
MOD_RES                  40
                         note = AminoEthoxyEthoxyAcetic Acyl-MaleimidoPropionic Acyl
SEQUENCE: 292
HAQGTFTSDY AKYLDARRAK EFIEYLLEGG PSSGAPPPSK                        40

SEQ ID NO: 293           moltype = AA  length = 40
FEATURE                  Location/Qualifiers
source                   1..40
                         mol_type = protein
                         organism = synthetic construct
MOD_RES                  40
                         note = AminoEthoxyEthoxyAcetic Acyl-MaleimidoPropionic Acyl
MOD_RES                  2
                         note = Aib
SEQUENCE: 293
HXQGTFTSDY AKYLDARRAK EFIEYLLEGG PSSGAPPPSK                        40

SEQ ID NO: 294           moltype = AA  length = 40
FEATURE                  Location/Qualifiers
source                   1..40
                         mol_type = protein
                         organism = synthetic construct
MOD_RES                  2
                         note = Aib
MOD_RES                  40
                         note = AminoEthoxyEthoxyAcetic Acyl-MaleimidoPropionic Acyl
SEQUENCE: 294
YXQGTFTSDY AKYLDARRAK EFIEYLLEGG PSSGAPPPSK                        40

SEQ ID NO: 295           moltype = AA  length = 40
FEATURE                  Location/Qualifiers
source                   1..40
                         mol_type = protein
                         organism = synthetic construct
SITE                     2
                         note = D-alanine
MOD_RES                  40
                         note = AminoEthoxyEthoxyAcetic Acyl-MaleimidoPropionic Acyl
SEQUENCE: 295
YAQGTFTSDY AKYLDARRAK EFIEYLLEGG PSSGAPPPSK                        40

SEQ ID NO: 296           moltype = AA  length = 40
FEATURE                  Location/Qualifiers
source                   1..40
                         mol_type = protein
                         organism = synthetic construct
SITE                     2
                         note = D-alanine
MOD_RES                  20
                         note = Aib
MOD_RES                  40
                         note = AminoEthoxyEthoxyAcetic Acyl-MaleimidoPropionic Acyl
SEQUENCE: 296
HAQGTFTSDY AKYLDKIAQX AFIEYLLEGG PSSGAPPPSK                        40

SEQ ID NO: 297           moltype = AA  length = 40
FEATURE                  Location/Qualifiers
source                   1..40
                         mol_type = protein
                         organism = synthetic construct
MOD_RES                  2
                         note = Aib
MOD_RES                  20
                         note = Aib
MOD_RES                  40
                         note = AminoEthoxyEthoxyAcetic Acyl-MaleimidoPropionic Acyl
SEQUENCE: 297
```

-continued

```
HXQGTFTSDY AKYLDKIAQX AFIEYLLEGG PSSGAPPPSK                          40

SEQ ID NO: 298          moltype = AA  length = 40
FEATURE                 Location/Qualifiers
source                  1..40
                        mol_type = protein
                        organism = synthetic construct
MOD_RES                 2
                        note = Aib
MOD_RES                 20
                        note = Aib
MOD_RES                 40
                        note = AminoEthoxyEthoxyAcetic Acyl-MaleimidoPropionic Acyl
SEQUENCE: 298
YXQGTFTSDY AKYLDKIAQX AFIEYLLEGG PSSGAPPPSK                          40

SEQ ID NO: 299          moltype = AA  length = 40
FEATURE                 Location/Qualifiers
source                  1..40
                        mol_type = protein
                        organism = synthetic construct
SITE                    2
                        note = D-alanine
MOD_RES                 20
                        note = Aib
MOD_RES                 40
                        note = AminoEthoxyEthoxyAcetic Acyl-MaleimidoPropionic Acyl
SEQUENCE: 299
YAQGTFTSDY AKYLDKIAQX AFIEYLLEGG PSSGAPPPSK                          40

SEQ ID NO: 300          moltype = AA  length = 40
FEATURE                 Location/Qualifiers
source                  1..40
                        mol_type = protein
                        organism = synthetic construct
MOD_RES                 2
                        note = Aib
MOD_RES                 20
                        note = Aib
MOD_RES                 40
                        note = AminoEthoxyEthoxyAcetic Acyl-MaleimidoPropionic Acyl
MOD_RES                 13
                        note = Alpha-Methyl-Leucine
SEQUENCE: 300
HXQGTFTSDY SIXLDKIAQX AFIEYLLEGG PSSGAPPPSK                          40

SEQ ID NO: 301          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-8-AminoOctanoic
                         Acyl-AminoEthoxyEthoxyAcetic Acyl-MaleimidoPropionic Acyl
SEQUENCE: 301
HAQGTFTSDY AKYLDARRAK EFIAWLVNGG PSSGAPPPSK                          40

SEQ ID NO: 302          moltype = AA  length = 39
FEATURE                 Location/Qualifiers
source                  1..39
                        mol_type = protein
                        organism = synthetic construct
SITE                    2
                        note = D-alanine
MOD_RES                 17
                        note = AminoEthoxyEthoxyAcetic Acyl-MaleimidoPropionic Acyl
SEQUENCE: 302
HAEGTFTSDY AKYLDAKRAK EFIAWLVNGG PSSGAPPPS                           39

SEQ ID NO: 303          moltype = AA  length = 39
FEATURE                 Location/Qualifiers
source                  1..39
                        mol_type = protein
                        organism = synthetic construct
SITE                    2
                        note = D-alanine
MOD_RES                 17
```

-continued

```
                             note = AminoEthoxyEthoxyAcetic Acyl-AminoEthoxyEthoxyAcetic
                               Acyl-MaleimidoPropionic Acyl
SEQUENCE: 303
HAEGTFTSDY AKYLDAKRAK EFIAWLVNGG PSSGAPPPS                                     39

SEQ ID NO: 304        moltype = AA  length = 39
FEATURE               Location/Qualifiers
source                1..39
                      mol_type = protein
                      organism = synthetic construct
SITE                  2
                      note = D-alanine
MOD_RES               17
                      note = AminoEthoxyEthoxyAcetic Acyl-AminoEthoxyEthoxyAcetic
                        Acyl-8-AminoOctanoic Acyl-MaleimidoPropionic Acyl
SEQUENCE: 304
HAEGTFTSDY AKYLDAKRAK EFIAWLVNGG PSSGAPPPS                                     39

SEQ ID NO: 305        moltype = AA  length = 39
FEATURE               Location/Qualifiers
source                1..39
                      mol_type = protein
                      organism = synthetic construct
SITE                  2
                      note = D-alanine
MOD_RES               17
                      note = AminoEthoxyEthoxyAcetic Acyl-8-AminoOctanoic
                        Acyl-MaleimidoPropionic Acyl
SEQUENCE: 305
HAEGTFTSDY AKYLDAKRAK EFIAWLVNGG PSSGAPPPS                                     39

SEQ ID NO: 306        moltype = AA  length = 39
FEATURE               Location/Qualifiers
source                1..39
                      mol_type = protein
                      organism = synthetic construct
SITE                  2
                      note = D-alanine
MOD_RES               20
                      note = AminoEthoxyEthoxyAcetic Acyl-AminoEthoxyEthoxyAcetic
                        Acyl-MaleimidoPropionic Acyl
SEQUENCE: 306
HAEGTFTSDY AKYLDARRAK EFIAWLVNGG PSSGAPPPS                                     39

SEQ ID NO: 307        moltype = AA  length = 39
FEATURE               Location/Qualifiers
source                1..39
                      mol_type = protein
                      organism = synthetic construct
SITE                  2
                      note = D-alanine
MOD_RES               20
                      note = AminoEthoxyEthoxyAcetic Acyl-AminoEthoxyEthoxyAcetic
                        Acyl-8-AminoOctanoic Acyl-MaleimidoPropionic Acyl
SEQUENCE: 307
HAEGTFTSDY AKYLDARRAK EFIAWLVNGG PSSGAPPPS                                     39

SEQ ID NO: 308        moltype = AA  length = 39
FEATURE               Location/Qualifiers
source                1..39
                      mol_type = protein
                      organism = synthetic construct
SITE                  2
                      note = D-alanine
MOD_RES               20
                      note = AminoEthoxyEthoxyAcetic Acyl-8-AminoOctanoic
                        Acyl-MaleimidoPropionic Acyl
SEQUENCE: 308
HAEGTFTSDY AKYLDARRAK EFIAWLVNGG PSSGAPPPS                                     39

SEQ ID NO: 309        moltype = AA  length = 40
FEATURE               Location/Qualifiers
source                1..40
                      mol_type = protein
                      organism = synthetic construct
SITE                  2
                      note = D-alanine
MOD_RES               40
                      note = AminoEthoxyEthoxyAcetic Acyl-AminoEthoxyEthoxyAcetic
```

```
                        Acyl-gamma-glutamic acid 1-Amido Eicosanedioic acyl //
                        2-[(20-oxoicosanoyl)amino]-5-[2-[2-[2-[2-[2-(carboxymethoxy
                        )ethoxy]ethylamino]-2-oxoethoxy]ethoxy]ethylamino]-5-oxopen
                        tanoic acyl
SEQUENCE: 309
HAQGTFTSDY AKYLDARRAK EFIAWLVNGG PSSGAPPPSK                            40

SEQ ID NO: 310          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-gamma-glutamic acid
                        1-Amido Eicosanedioic acyl //
                        2-[(20-oxoicosanoyl)amino]-5-[2-[2-[2-[2-[2-(carboxymethoxy
                        )ethoxy]ethylamino]-2-oxoethoxy]ethoxy]ethylamino]-5-oxopen
                        tanoic acyl
SEQUENCE: 310
HAQGTFTSDY AKYLDARRAK EFIAWLVNGG PSSGAPPPSK                            40

SEQ ID NO: 311          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-AminoEthoxyEthoxyAcetic
                        Acyl-gamma-glutamic acid 1-Amido 19-Phosphatidyl
                        Nonadecanoic acyl
SEQUENCE: 311
HAQGTFTSDY AKYLDARRAK EFIAWLVNGG PSSGAPPPSK                            40

SEQ ID NO: 312          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = PolyEthylene Glycol
SEQUENCE: 312
HAQGTFTSDY AKYLDARRAK EFIAWLVNGG PSSGAPPPSC                            40

SEQ ID NO: 313          moltype = AA  length = 39
FEATURE                 Location/Qualifiers
source                  1..39
                        mol_type = protein
                        organism = synthetic construct
SITE                    2
                        note = D-alanine
MOD_RES                 17
                        note = AminoEthoxyEthoxyAcetic Acyl-AminoEthoxyEthoxyAcetic
                        Acyl-gamma-glutamic acid 1-Amido Eicosanedioic acyl //
                        2-[(20-oxoicosanoyl)amino]-5-[2-[2-[2-[2-[2-(carboxymethoxy
                        )ethoxy]ethylamino]-2-oxoethoxy]ethoxy]ethylamino]-5-oxopen
                        tanoic acyl
SEQUENCE: 313
HAQGTFTSDY AKYLDAKRAK EFIAWLVNGG PSSGAPPPS                             39

SEQ ID NO: 314          moltype = AA  length = 39
FEATURE                 Location/Qualifiers
source                  1..39
                        mol_type = protein
                        organism = synthetic construct
SITE                    2
                        note = D-alanine
MOD_RES                 17
                        note = AminoEthoxyEthoxyAcetic Acyl-AminoEthoxyEthoxyAcetic
                        Acyl-gamma-glutamic acid 1-Amido Eicosanedioic acyl //
                        2-[(20-oxoicosanoyl)amino]-5-[2-[2-[2-[2-[2-(carboxymethoxy
                        )ethoxy]ethylamino]-2-oxoethoxy]ethoxy]ethylamino]-5-oxopen
                        tanoic acyl
SEQUENCE: 314
```

-continued

```
HAQGTFTSDY AKYLDAKRAK EFIAWLVNGG PSSGAPPPS                                  39

SEQ ID NO: 315          moltype = AA   length = 39
FEATURE                 Location/Qualifiers
source                  1..39
                        mol_type = protein
                        organism = synthetic construct
SITE                    2
                        note = D-alanine
MOD_RES                 17
                        note = AminoEthoxyEthoxyAcetic Acyl-AminoEthoxyEthoxyAcetic
                         Acyl-gamma-glutamic acid 1-Amido 19-Phosphatidyl
                         Nonadecanoic acyl //
SEQUENCE: 315
HAQGTFTSDY AKYLDAKRAK EFIAWLVNGG PSSGAPPPS                                  39

SEQ ID NO: 316          moltype = AA   length = 39
FEATURE                 Location/Qualifiers
source                  1..39
                        mol_type = protein
                        organism = synthetic construct
SITE                    2
                        note = D-alanine
MOD_RES                 17
                        note = N6-[1-O-(17-carboxyheptadecyl)-D-glucopyranuronoyl]
SEQUENCE: 316
HAQGTFTSDY AKYLDAKRAK EFIAWLVNGG PSSGAPPPS                                  39

SEQ ID NO: 317          moltype = AA   length = 39
FEATURE                 Location/Qualifiers
source                  1..39
                        mol_type = protein
                        organism = synthetic construct
MOD_RES                 2
                        note = Aib
MOD_RES                 20
                        note = Aib
MOD_RES                 17
                        note = AminoEthoxyEthoxyAcetic Acyl-AminoEthoxyEthoxyAcetic
                         Acyl-gamma-glutamic acid 1-Amido Eicosanedioic acyl //
                         2-[(20-oxoicosanoyl)amino]-5-[2-[2-[2-[2-[2-(carboxymethoxy
                         )ethoxy]ethylamino]-2-oxoethoxy]ethoxy]ethylamino]-5-oxopen
                         tanoic acyl
MOD_RES                 13
                        note = Alpha-Methyl-Leucine
SEQUENCE: 317
YXQGTFTSDY SIXLDKKAQX AFIEYLLEGG PSSGAPPPS                                  39

SEQ ID NO: 318          moltype = AA   length = 33
FEATURE                 Location/Qualifiers
source                  1..33
                        mol_type = protein
                        organism = synthetic construct
SEQUENCE: 318
HADGSFSDEM NTILDNLAAR DFINWLIQTK ITD                                        33

SEQ ID NO: 319          moltype = AA   length = 28
FEATURE                 Location/Qualifiers
source                  1..28
                        mol_type = protein
                        organism = synthetic construct
SEQUENCE: 319
HSDAVFTDNY TRLRKQMAVK KYLNSILN                                             28

SEQ ID NO: 320          moltype = AA   length = 37
FEATURE                 Location/Qualifiers
source                  1..37
                        mol_type = protein
                        organism = synthetic construct
SEQUENCE: 320
KCNTATCATQ RLANFLVHSS NNFGAILSST NVGSNTY                                    37

SEQ ID NO: 321          moltype = AA   length = 29
FEATURE                 Location/Qualifiers
source                  1..29
                        mol_type = protein
                        organism = synthetic construct
SEQUENCE: 321
YADAIFTNSY RKVLGQLSAR KLLQDIMSR                                             29
```

```
SEQ ID NO: 322        moltype = AA  length = 40
FEATURE               Location/Qualifiers
source                1..40
                      mol_type = protein
                      organism = synthetic construct
VARIANT               1
                      note = X can be H, Y or F
VARIANT               2
                      note = X can be G, D-Alanine, Aib or
                       D-serine,Amino-cyclobutyl-1-carboxylic acid
SITE                  2
                      note = D-alanine or D-serine
VARIANT               3
                      note = X can be
                       A,R,N,D,E,Q,G,H,I,L,K,M,F,P,S,T,W,Y,D-alanine,Aib,D-serine
                       or D-Lysine
SITE                  3
                      note = D-alanine,D-serine or D-Lysine
MOD_RES               2
                      note = Aib or Amino-cyclobutyl-1-carboxylic acid
MOD_RES               3
                      note = Aib
VARIANT               10
                      note = X can be
                       A,R,N,D,E,Q,G,H,I,L,K,M,F,P,S,T,W,Y,D-alanine,Aib,D-serine
                       or D-Lysine
SITE                  10
                      note = D-alanine,D-serine or D-Lysine
MOD_RES               10
                      note = Aib
VARIANT               11
                      note = X can be
                       A,R,N,D,E,Q,G,H,I,L,K,M,F,P,S,T,W,Y,D-alanine,Aib,D-serine
                       or D-Lysine
SITE                  11
                      note = D-alanine,D-serine or D-Lysine
MOD_RES               11
                      note = Aib
VARIANT               12
                      note = X can be
                       A,R,N,D,E,Q,G,H,I,L,K,M,F,P,S,T,W,Y,D-alanine,Aib,D-serine
                       or D-Lysine
SITE                  12
                      note = D-alanine,D-serine or D-Lysine
MOD_RES               12
                      note = Aib
VARIANT               13
                      note = X can be Y, Aib, Q or Alpha-Methyl-Leucine
MOD_RES               13
                      note = Aib or Alpha-Methyl-Leucine
VARIANT               15
                      note = X can be D or E
VARIANT               16
                      note = X can be
                       A,R,N,D,E,Q,G,H,I,L,K,M,F,P,S,T,W,Y,D-alanine,Aib,D-serine
                       or D-Lysine
SITE                  16
                      note = D-alanine,D-serine or D-Lysine
MOD_RES               16
                      note = Aib
VARIANT               17
                      note = X can be
                       A,R,N,D,E,Q,G,H,I,L,K,M,F,P,S,T,W,Y,D-alanine,Aib,D-serine
                       or D-Lysine
SITE                  17
                      note = D-alanine,D-serine or D-Lysine
MOD_RES               17
                      note = Aib
VARIANT               18
                      note = X can be
                       A,R,N,D,E,Q,G,H,I,L,K,M,F,P,S,T,W,Y,D-alanine,Aib,D-serine
                       or D-Lysine
SITE                  18
                      note = D-alanine,D-serine or D-Lysine
MOD_RES               18
                      note = Aib
VARIANT               19
                      note = X can be Q or A
```

-continued

```
VARIANT                20
                       note = X can be Q, K ,R or Aib
MOD_RES                20
                       note = Aib
VARIANT                21
                       note = X can be D, E or A
VARIANT                23
                       note = X can be V or I
VARIANT                24
                       note = X can be Q, A, E or N
VARIANT                28
                       note = X can be
                        A,R,N,D,E,Q,G,H,I,L,K,M,F,P,S,T,W,Y,D-alanine,Aib,D-serine
                        or D-Lysine
SITE                   28
                       note = D-alanine,D-serine or D-Lysine
MOD_RES                28
                       note = Aib
VARIANT                27
                       note = X can be
                        A,R,N,D,E,Q,G,H,I,L,K,M,F,P,S,T,W,Y,D-alanine,Aib,D-serine
                        or D-Lysine
SITE                   27
                       note = D-alanine,D-serine or D-Lysine
MOD_RES                30
                       note = Aib
VARIANT                30
                       note = X can be
                        A,R,N,D,E,Q,G,H,I,L,K,M,F,P,S,T,W,Y,D-alanine,Aib,D-serine
                        or D-Lysine
SITE                   30
                       note = D-alanine,D-serine or D-Lysine
MOD_RES                27
                       note = Aib
VARIANT                40
                       note = X can be K, AminoEthoxyEthoxyAcetic Acid //
                        8-amino-3,6-dioxa-octanoic acid or absent
MOD_RES                40
                       note = AminoEthoxyEthoxyAcetic Acid //
                        8-amino-3,6-dioxa-octanoic acid
SEQUENCE: 322
XXXGTFTSDX XXXLXXXXXX XFXXWLXXGX PSSGAPPPSX                              40

SEQ ID NO: 323         moltype = AA  length = 39
FEATURE                Location/Qualifiers
source                 1..39
                       mol_type = protein
                       organism = synthetic construct
VARIANT                1
                       note = X can be H, Y or F
VARIANT                2
                       note = X can be G, D-Alanine, Aib or
                        D-serine,Amino-cyclobutyl-1-carboxylic acid
SITE                   2
                       note = D-alanine or D-serine
MOD_RES                2
                       note = Aib or Amino-cyclobutyl-1-carboxylic acid
VARIANT                3
                       note = X can be
                        A,R,N,D,E,Q,G,H,I,L,K,M,F,P,S,T,W,Y,D-alanine,Aib,D-serine
                        or D-Lysine
SITE                   3
                       note = D-alanine,D-serine or D-Lysine
MOD_RES                3
                       note = Aib
VARIANT                10
                       note = X can be
                        A,R,N,D,E,Q,G,H,I,L,K,M,F,P,S,T,W,Y,D-alanine,Aib,D-serine
                        or D-Lysine
SITE                   10
                       note = D-alanine,D-serine or D-Lysine
MOD_RES                10
                       note = Aib
VARIANT                11
                       note = X can be
                        A,R,N,D,E,Q,G,H,I,L,K,M,F,P,S,T,W,Y,D-alanine,Aib,D-serine
                        or D-Lysine
SITE                   11
                       note = D-alanine,D-serine or D-Lysine
```

-continued

```
MOD_RES          11
                 note = Aib
VARIANT          12
                 note = X can be
                 A,R,N,D,E,Q,G,H,I,L,K,M,F,P,S,T,W,Y,D-alanine,Aib,D-serine
                 or D-Lysine
SITE             12
                 note = D-alanine,D-serine or D-Lysine
MOD_RES          12
                 note = Aib
VARIANT          13
                 note = X can be Y, Aib, Q or Alpha-Methyl-Leucine
MOD_RES          13
                 note = Aib or Alpha-Methyl-Leucine
VARIANT          15
                 note = X can be D or E
VARIANT          16
                 note = X can be
                 A,R,N,D,E,Q,G,H,I,L,K,M,F,P,S,T,W,Y,D-alanine,Aib,D-serine
                 or D-Lysine
SITE             16
                 note = D-alanine,D-serine or D-Lysine
MOD_RES          2
                 note = Aib
MOD_RES          16
                 note = Aib
VARIANT          17
                 note = X can be
                 A,R,N,D,E,Q,G,H,I,L,K,M,F,P,S,T,W,Y,D-alanine,Aib,D-serine
                 or D-Lysine
SITE             17
                 note = D-alanine,D-serine or D-Lysine
MOD_RES          17
                 note = Aib
VARIANT          18
                 note = X can be
                 A,R,N,D,E,Q,G,H,I,L,K,M,F,P,S,T,W,Y,D-alanine,Aib,D-serine
                 or D-Lysine
SITE             18
                 note = D-alanine,D-serine or D-Lysine
MOD_RES          18
                 note = Aib
VARIANT          19
                 note = X can be Q or A
VARIANT          20
                 note = X can be Q, K ,R or Aib
MOD_RES          20
                 note = Aib
VARIANT          21
                 note = X can be D, E or A
VARIANT          23
                 note = X can be V or I
VARIANT          24
                 note = X can be Q, A, E or N
VARIANT          28
                 note = X can be
                 A,R,N,D,E,Q,G,H,I,L,K,M,F,P,S,T,W,Y,D-alanine,Aib,D-serine
                 or D-Lysine
SITE             28
                 note = D-alanine,D-serine or D-Lysine
MOD_RES          28
                 note = Aib
VARIANT          27
                 note = X can be
                 A,R,N,D,E,Q,G,H,I,L,K,M,F,P,S,T,W,Y,D-alanine,Aib,D-serine
                 or D-Lysine
MOD_RES          30
                 note = Aib
VARIANT          30
                 note = X can be
                 A,R,N,D,E,Q,G,H,I,L,K,M,F,P,S,T,W,Y,D-alanine,Aib,D-serine
                 or D-Lysine
SITE             30
                 note = D-alanine,D-serine or D-Lysine
MOD_RES          27
                 note = Aib
SEQUENCE: 323
XXXGTFTSDX XXXLXXXXXX XFXXWLXXGX PSSGAPPPS                              39
```

-continued

```
SEQ ID NO: 324          moltype = AA  length = 11
FEATURE                 Location/Qualifiers
source                  1..11
                        mol_type = protein
                        organism = synthetic construct
VARIANT                 1
                        note = X can be
                         A,R,N,D,E,Q,G,H,I,L,K,M,F,P,S,T,W,Y,D-alanine,Aib,D-serine
                         or D-Lysine
SITE                    1
                        note = D-alanine,D-serine or D-Lysine
MOD_RES                 1
                        note = Aib
VARIANT                 11
                        note = X can be K, AminoEthoxyEthoxyAcetic Acid //
                         8-amino-3,6-dioxa-octanoic acid or absent
MOD_RES                 11
                        note = AminoEthoxyEthoxyAcetic Acid //
                         8-amino-3,6-dioxa-octanoic acid
SEQUENCE: 324
XPSSGAPPPS X                                                          11

SEQ ID NO: 325          moltype = AA  length = 12
FEATURE                 Location/Qualifiers
source                  1..12
                        mol_type = protein
                        organism = synthetic construct
VARIANT                 1
                        note = X can be
                         A,R,N,D,E,Q,G,H,I,L,K,M,F,P,S,T,W,Y,D-alanine,Aib,D-serine
                         or D-Lysine
SITE                    1
                        note = D-alanine,D-serine or D-Lysine
MOD_RES                 1
                        note = Aib
VARIANT                 2
                        note = X can be Q or A
VARIANT                 3
                        note = X can be Q, K ,R or Aib
MOD_RES                 3
                        note = Aib
VARIANT                 4
                        note = X can be D, E or A
VARIANT                 6
                        note = X can be V or I
VARIANT                 7
                        note = X can be Q, A, E or N
VARIANT                 10
                        note = X can be
                         A,R,N,D,E,Q,G,H,I,L,K,M,F,P,S,T,W,Y,D-alanine,Aib,D-serine
                         or D-Lysine
SITE                    10
                        note = D-alanine,D-serine or D-Lysine
MOD_RES                 10
                        note = Aib
VARIANT                 11
                        note = X can be
                         A,R,N,D,E,Q,G,H,I,L,K,M,F,P,S,T,W,Y,D-alanine,Aib,D-serine
                         or D-Lysine
SITE                    11
                        note = D-alanine,D-serine or D-Lysine
MOD_RES                 11
                        note = Aib
SEQUENCE: 325
XXXXFXXWLX XG                                                        12

SEQ ID NO: 326          moltype = AA  length = 17
FEATURE                 Location/Qualifiers
source                  1..17
                        mol_type = protein
                        organism = synthetic construct
VARIANT                 1
                        note = X can be H, Y or F
VARIANT                 2
                        note = X can be G, D-Alanine, Aib or
                         D-serine,Amino-cyclobutyl-1-carboxylic acid
SITE                    2
                        note = D-alanine or D-serine
MOD_RES                 2
```

-continued

```
                          note = Aib or Amino-cyclobutyl-1-carboxylic acid
VARIANT                   3
                          note = X can be
                           A,R,N,D,E,Q,G,H,I,L,K,M,F,P,S,T,W,Y,D-alanine,Aib,D-serine
                           or D-Lysine
SITE                      3
                          note = D-alanine,D-serine or D-Lysine
MOD_RES                   3
                          note = Aib
VARIANT                   10
                          note = X can be
                           A,R,N,D,E,Q,G,H,I,L,K,M,F,P,S,T,W,Y,D-alanine,Aib,D-serine
                           or D-Lysine
SITE                      10
                          note = D-alanine,D-serine or D-Lysine
MOD_RES                   10
                          note = Aib
VARIANT                   11
                          note = X can be
                           A,R,N,D,E,Q,G,H,I,L,K,M,F,P,S,T,W,Y,D-alanine,Aib,D-serine
                           or D-Lysine
SITE                      11
                          note = D-alanine,D-serine or D-Lysine
MOD_RES                   11
                          note = Aib
VARIANT                   12
                          note = X can be
                           A,R,N,D,E,Q,G,H,I,L,K,M,F,P,S,T,W,Y,D-alanine,Aib,D-serine
                           or D-Lysine
SITE                      12
                          note = D-alanine,D-serine or D-Lysine
MOD_RES                   12
                          note = Aib
VARIANT                   13
                          note = X can be Y, Aib, Q or Alpha-Methyl-Leucine
MOD_RES                   13
                          note = Aib or Alpha-Methyl-Leucine
VARIANT                   15
                          note = X can be D or E
VARIANT                   16
                          note = X can be
                           A,R,N,D,E,Q,G,H,I,L,K,M,F,P,S,T,W,Y,D-alanine,Aib,D-serine
                           or D-Lysine
SITE                      16
                          note = D-alanine,D-serine or D-Lysine
MOD_RES                   16
                          note = Aib
VARIANT                   17
                          note = X can be
                           A,R,N,D,E,Q,G,H,I,L,K,M,F,P,S,T,W,Y,D-alanine,Aib,D-serine
                           or D-Lysine
SITE                      17
                          note = D-alanine,D-serine or D-Lysine
MOD_RES                   17
                          note = Aib
SEQUENCE: 326
XXXGTFTSDX XXXLXXX                                                       17

SEQ ID NO: 327            moltype = AA  length = 11
FEATURE                   Location/Qualifiers
source                    1..11
                          mol_type = protein
                          organism = synthetic construct
VARIANT                   1
                          note = X can be
                           A,R,N,D,E,Q,G,H,I,L,K,M,F,P,S,T,W,Y,D-alanine,Aib,D-serine
                           or D-Lysine
SITE                      1
                          note = D-alanine,D-serine or D-Lysine
MOD_RES                   1
                          note = Aib
SEQUENCE: 327
XPSSGAPPPS K                                                            11

SEQ ID NO: 328            moltype = AA  length = 23
FEATURE                   Location/Qualifiers
source                    1..23
                          mol_type = protein
                          organism = synthetic construct
```

-continued

```
VARIANT           1
                  note = X can be
                   A,R,N,D,E,Q,G,H,I,L,K,M,F,P,S,T,W,Y,D-alanine,Aib,D-serine
                   or D-Lysine
SITE              1
                  note = D-alanine,D-serine or D-Lysine
MOD_RES           1
                  note = Aib
VARIANT           2
                  note = X can be Q or A
VARIANT           3
                  note = X can be Q, K ,R or Aib
MOD_RES           3
                  note = Aib
VARIANT           21
                  note = X can be D, E or A
VARIANT           6
                  note = X can be V or I
VARIANT           7
                  note = X can be Q, A, E or N
VARIANT           10
                  note = X can be
                   A,R,N,D,E,Q,G,H,I,L,K,M,F,P,S,T,W,Y,D-alanine,Aib,D-serine
                   or D-Lysine
SITE              10
                  note = D-alanine,D-serine or D-Lysine
MOD_RES           10
                  note = Aib
VARIANT           11
                  note = X can be
                   A,R,N,D,E,Q,G,H,I,L,K,M,F,P,S,T,W,Y,D-alanine,Aib,D-serine
                   or D-Lysine
SITE              11
                  note = D-alanine,D-serine or D-Lysine
MOD_RES           11
                  note = Aib
VARIANT           13
                  note = X can be
                   A,R,N,D,E,Q,G,H,I,L,K,M,F,P,S,T,W,Y,D-alanine,Aib,D-serine
                   or D-Lysine
SITE              13
                  note = D-alanine,D-serine or D-Lysine
MOD_RES           13
                  note = Aib
VARIANT           23
                  note = X can be K, AminoEthoxyEthoxyAcetic Acid //
                   8-amino-3,6-dioxa-octanoic acid or absent
MOD_RES           23
                  note = AminoEthoxyEthoxyAcetic Acid //
                   8-amino-3,6-dioxa-octanoic acid
VARIANT           4
                  note = X can be D, E or A
SEQUENCE: 328
XXXXFXXWLX XGXPSSGAPP PSX                                          23

SEQ ID NO: 329    moltype = AA  length = 40
FEATURE           Location/Qualifiers
source            1..40
                  mol_type = protein
                  organism = synthetic construct
VARIANT           1
                  note = X can be H, Y or F
VARIANT           2
                  note = X can be G, D-Alanine, Aib or
                   D-serine,Amino-cyclobutyl-1-carboxylic acid
SITE              2
                  note = D-alanine or D-serine
VARIANT           3
                  note = X can be
                   A,R,N,D,E,Q,G,H,I,L,K,M,F,P,S,T,W,Y,D-alanine,Aib,D-serine
                   or D-Lysine
SITE              3
                  note = D-alanine,D-serine or D-Lysine
MOD_RES           2
                  note = Aib or Amino-cyclobutyl-1-carboxylic acid
MOD_RES           3
                  note = Aib
VARIANT           10
                  note = X can be
```

-continued

```
                     A,R,N,D,E,Q,G,H,I,L,K,M,F,P,S,T,W,Y,D-alanine,Aib,D-serine
                     or D-Lysine
SITE                 10
                     note = D-alanine,D-serine or D-Lysine
MOD_RES              10
                     note = Aib
VARIANT              11
                     note = X can be
                     A,R,N,D,E,Q,G,H,I,L,K,M,F,P,S,T,W,Y,D-alanine,Aib,D-serine
                     or D-Lysine
SITE                 11
                     note = D-alanine,D-serine or D-Lysine
MOD_RES              11
                     note = Aib
VARIANT              12
                     note = X can be
                     A,R,N,D,E,Q,G,H,I,L,K,M,F,P,S,T,W,Y,D-alanine,Aib,D-serine
                     or D-Lysine
SITE                 12
                     note = D-alanine,D-serine or D-Lysine
MOD_RES              12
                     note = Aib
VARIANT              13
                     note = X can be Y, Aib, Q or Alpha-Methyl-Leucine
MOD_RES              13
                     note = Aib or Alpha-Methyl-Leucine
VARIANT              15
                     note = X can be D or E
VARIANT              16
                     note = X can be
                     A,R,N,D,E,Q,G,H,I,L,K,M,F,P,S,T,W,Y,D-alanine,Aib,D-serine
                     or D-Lysine
SITE                 16
                     note = D-alanine,D-serine or D-Lysine
MOD_RES              16
                     note = Aib
VARIANT              17
                     note = X can be
                     A,R,N,D,E,Q,G,H,I,L,K,M,F,P,S,T,W,Y,D-alanine,Aib,D-serine
                     or D-Lysine
SITE                 17
                     note = D-alanine,D-serine or D-Lysine
MOD_RES              17
                     note = Aib
VARIANT              18
                     note = X can be
                     A,R,N,D,E,Q,G,H,I,L,K,M,F,P,S,T,W,Y,D-alanine,Aib,D-serine
                     or D-Lysin
SITE                 18
                     note = D-alanine,D-serine or D-Lysine
MOD_RES              18
                     note = Aib
VARIANT              19
                     note = X can be Q or A
VARIANT              20
                     note = X can be Q, K ,R or Aib
MOD_RES              20
                     note = Aib
VARIANT              21
                     note = X can be D, E or A
VARIANT              23
                     note = X can be V or I
VARIANT              24
                     note = X can be Q, A, E or N
VARIANT              28
                     note = X can be
                     A,R,N,D,E,Q,G,H,I,L,K,M,F,P,S,T,W,Y,D-alanine,Aib,D-serine
                     or D-Lysine
SITE                 28
                     note = D-alanine,D-serine or D-Lysine
MOD_RES              28
                     note = Aib
VARIANT              27
                     note = X can be
                     A,R,N,D,E,Q,G,H,I,L,K,M,F,P,S,T,W,Y,D-alanine,Aib,D-serine
                     or D-Lysine
SITE                 27
                     note = D-alanine,D-serine or D-Lysine
MOD_RES              30
```

```
                              note = Aib
VARIANT                       30
                              note = X can be
                               A,R,N,D,E,Q,G,H,I,L,K,M,F,P,S,T,W,Y,D-alanine,Aib,D-serine
                               or D-Lysine
SITE                          30
                              note = D-alanine,D-serine or D-Lysine
MOD_RES                       27
                              note = Aib
VARIANT                       40
                              note = X can be K, AminoEthoxyEthoxyAcetic Acid //
                               8-amino-3,6-dioxa-octanoic acid or absent
MOD_RES                       40
                              note = AminoEthoxyEthoxyAcetic Acid //
                               8-amino-3,6-dioxa-octanoic acid
SEQUENCE: 329
XXXGTFTSDX XXXLXXXXXX XFXXWLXXGX PSSGAPPPSX                          40

SEQ ID NO: 330                moltype = AA  length = 40
FEATURE                       Location/Qualifiers
source                        1..40
                              mol_type = protein
                              organism = synthetic construct
SITE                          2
                              note = D-alanine
MOD_RES                       40
                              note = AminoEthoxyEthoxyAcetic Acyl-MaleimidoPropionic Acyl
SEQUENCE: 330
HAEGTFTSDV SSYLEGQAAK EFIAWLVKGR PSSGAPPPSK                          40

SEQ ID NO: 331                moltype = AA  length = 40
FEATURE                       Location/Qualifiers
source                        1..40
                              mol_type = protein
                              organism = synthetic construct
MOD_RES                       40
                              note = AminoEthoxyEthoxyAcetic Acyl-MaleimidoPropionic Acyl
SEQUENCE: 331
HAEGTFTSDV SSYLEGQAAK EFIAWLVKGR PSSGAPPPSK                          40

SEQ ID NO: 332                moltype = AA  length = 31
FEATURE                       Location/Qualifiers
source                        1..31
                              mol_type = protein
                              organism = synthetic construct
SITE                          2
                              note = D-alanine
MOD_RES                       31
                              note = AminoEthoxyEthoxyAcetic Acyl-MaleimidoPropionic Acyl
SEQUENCE: 332
HAEGTFTSDV SSYLEGQAAK EFIAWLVNGG K                                   31

SEQ ID NO: 333                moltype = AA  length = 31
FEATURE                       Location/Qualifiers
source                        1..31
                              mol_type = protein
                              organism = synthetic construct
SITE                          2
                              note = D-alanine
MOD_RES                       31
                              note = AminoEthoxyEthoxyAcetic Acyl-MaleimidoPropionic Acyl
SEQUENCE: 333
HAEGTFTSDI NKVLDTIAAK EFIAWLVKGR K                                   31

SEQ ID NO: 334                moltype = AA  length = 31
FEATURE                       Location/Qualifiers
source                        1..31
                              mol_type = protein
                              organism = synthetic construct
SITE                          2
                              note = D-alanine
MOD_RES                       31
                              note = AminoEthoxyEthoxyAcetic Acyl-MaleimidoPropionic Acyl
SEQUENCE: 334
HAEGTFTSDA EKAKEAEKAK EFIAWLVKGR K                                   31

SEQ ID NO: 335                moltype = AA  length = 31
FEATURE                       Location/Qualifiers
source                        1..31
```

```
                         mol_type = protein
                         organism = synthetic construct
SITE                     2
                         note = D-alanine
MOD_RES                  31
                         note = AminoEthoxyEthoxyAcetic Acyl-MaleimidoPropionic Acyl
MOD_RES                  10
                         note = Aib
MOD_RES                  13
                         note = Aib
MOD_RES                  16
                         note = Aib
SEQUENCE: 335
HAEGTFTSDX EKXKEXEKAK EFIAWLVKGR K                                              31

SEQ ID NO: 336           moltype = AA   length = 40
FEATURE                  Location/Qualifiers
source                   1..40
                         mol_type = protein
                         organism = synthetic construct
SITE                     2
                         note = D-alanine
MOD_RES                  10
                         note = Aib
MOD_RES                  13
                         note = Aib
MOD_RES                  16
                         note = Aib
MOD_RES                  19
                         note = Aib
MOD_RES                  40
                         note = AminoEthoxyEthoxyAcetic Acyl-MaleimidoPropionic Acyl
SEQUENCE: 336
HAEGTFTSDX ESXKEXEKXK EFIAWLVKGR PSSGAPPPSK                                     40

SEQ ID NO: 337           moltype = AA   length = 40
FEATURE                  Location/Qualifiers
source                   1..40
                         mol_type = protein
                         organism = synthetic construct
SITE                     2
                         note = D-alanine
MOD_RES                  11
                         note = Aib
MOD_RES                  14
                         note = Aib
MOD_RES                  18
                         note = Aib
MOD_RES                  40
                         note = AminoEthoxyEthoxyAcetic Acyl-MaleimidoPropionic Acyl
SEQUENCE: 337
HAEGTFTSDV XSYXEGQXAK EFIAWLVKGR PSSGAPPPSK                                     40

SEQ ID NO: 338           moltype = AA   length = 39
FEATURE                  Location/Qualifiers
source                   1..39
                         mol_type = protein
                         organism = synthetic construct
SITE                     2
                         note = D-alanine
MOD_RES                  17
                         note = AminoEthoxyEthoxyAcetic Acyl-MaleimidoPropionic Acyl
SEQUENCE: 338
HAEGTFTSDV SSYLEGKAAK EFIAWLVKGR PSSGAPPPS                                      39

SEQ ID NO: 339           moltype = AA   length = 40
FEATURE                  Location/Qualifiers
source                   1..40
                         mol_type = protein
                         organism = synthetic construct
SITE                     2
                         note = D-alanine
MOD_RES                  40
                         note = AminoEthoxyEthoxyAcetic Acyl-MaleimidoPropionic Acyl
SEQUENCE: 339
HAEGTFTSDV SSYLEGQAAK EFIAWLVKGR LLLLLLLLLK                                     40

SEQ ID NO: 340           moltype = AA   length = 42
FEATURE                  Location/Qualifiers
```

-continued

```
source                 1..42
                       mol_type = protein
                       organism = synthetic construct
SITE                   2
                       note = D-alanine
SEQUENCE: 340
HAEGTFTSDV SSYLEGQAAK EFIAWLVKGR PEAPTDPEAP TD                    42

SEQ ID NO: 341         moltype = AA  length = 40
FEATURE                Location/Qualifiers
source                 1..40
                       mol_type = protein
                       organism = synthetic construct
MOD_RES                40
                       note = AminoEthoxyEthoxyAcetic Acyl-MaleimidoPropionic Acyl
SEQUENCE: 341
HGEGTFTSDL SKQMEEEAVR LFIEWLKNGG GGGGGGGGGK                       40

SEQ ID NO: 342         moltype = AA  length = 31
FEATURE                Location/Qualifiers
source                 1..31
                       mol_type = protein
                       organism = synthetic construct
SITE                   2
                       note = D-alanine
MOD_RES                31
                       note = (AminoEthoxyEthoxyAcetic Acyl)4-3-MaleimidoPropionic
                        Acyl
SEQUENCE: 342
HAEGTFTSDV SSYLEGQAAK EFIAWLVKGR K                                31

SEQ ID NO: 343         moltype = AA  length = 30
FEATURE                Location/Qualifiers
source                 1..30
                       mol_type = protein
                       organism = synthetic construct
SITE                   2
                       note = D-alanine
MOD_RES                17
                       note = AminoEthoxyEthoxyAcetic Acyl-MaleimidoPropionic Acyl
SEQUENCE: 343
HAEGTFTSDV SSYLEGKAAK EFIAWLVKGR                                  30

SEQ ID NO: 344         moltype = AA  length = 31
FEATURE                Location/Qualifiers
source                 1..31
                       mol_type = protein
                       organism = synthetic construct
SITE                   2
                       note = D-alanine
MOD_RES                31
                       note = 3-MaleimidoPropionic Acid // 3-(2,5-Dioxo-2,5-dihydr
                        o-1H-pyrrol-1-yl)propanoic Acid
SEQUENCE: 344
HAEGTFTSDV SSYLEGQAAK EFIAWLVKGR K                                31

SEQ ID NO: 345         moltype = AA  length = 37
FEATURE                Location/Qualifiers
source                 1..37
                       mol_type = protein
                       organism = synthetic construct
SEQUENCE: 345
HSQGTFTSDY SKYLDSRRAQ DFVQWLMNTK RNKNNIA                          37

SEQ ID NO: 346         moltype = AA  length = 41
FEATURE                Location/Qualifiers
source                 1..41
                       mol_type = protein
                       organism = synthetic construct
SITE                   2
                       note = D-alanine
SEQUENCE: 346
HAEGTFTSDV SSYLEGQAAK EFIAWLVKGP EAPTDPEAPT D                     41

SEQ ID NO: 347         moltype = AA  length = 31
FEATURE                Location/Qualifiers
source                 1..31
                       mol_type = protein
                       organism = synthetic construct
```

-continued

```
SITE                    2
                        note = D-alanine
MOD_RES                 31
                        note = (AminoEthoxyEthoxyAcetic Acyl)4-3-MaleimidoPropionic
                        Acyl
SEQUENCE: 347
HAEGTFTSDV SSYLEGQAAK EFIAWLVKGR K                                       31

SEQ ID NO: 348          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 348
HAEGTFTSDI NKVLDIIAAK EFIAWLVKGR PSSGAPPPSK                              40

SEQ ID NO: 349          moltype = AA  length = 31
FEATURE                 Location/Qualifiers
source                  1..31
                        mol_type = protein
                        organism = synthetic construct
SITE                    2
                        note = D-alanine
MOD_RES                 31
                        note = AminoEthoxyEthoxyAcetic Acyl-MaleimidoPropionic Acyl
SEQUENCE: 349
HAEGTFTSDI NKVLDIIAAK EFIAWLVKGR K                                       31

SEQ ID NO: 350          moltype = AA  length = 40
FEATURE                 Location/Qualifiers
source                  1..40
                        mol_type = protein
                        organism = synthetic construct
MOD_RES                 40
                        note = 3-MaleimidoPropionic Acid //  3-(2,5-Dioxo-2,5-dihydr
                        o-1H-pyrrol-1-yl)propanoic Acid
SEQUENCE: 350
HGEGTFTSDL SKQMEEEAVR LFIEWLKNGG PSSGAPPPSK                              40

SEQ ID NO: 351          moltype = AA  length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 351
HXEGTFTSDY SKYLDKIRAQ EFVAWLMNGG PSSGAPPPSK                              40

SEQ ID NO: 352          moltype = AA  length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 352
HXQGTFTSDY SKYLDKIAAQ DFVAWLLNGG PSSGAPPPSK                              40

SEQ ID NO: 353          moltype = AA  length = 40
FEATURE                 Location/Qualifiers
source                  1..40
                        mol_type = protein
                        organism = synthetic construct
MOD_RES                 40
                        note = AminoEthoxyEthoxyAcetic Acyl-MaleimidoPropionic Acyl
MOD_RES                 2
                        note = Aib
SEQUENCE: 353
HXQGTFTSDY AKYLDKIAAQ DFVAWLLDGG PSSGAPPPSK                              40
```

-continued

```
SEQ ID NO: 354          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 354
HXQGTFTSDY SKYLDKIAAQ DFVAWLLDGG PSSGAPPPSK                      40

SEQ ID NO: 355          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-AminoEthoxyEthoxyAcetic
                        Acyl-MaleimidoPropionic Acyl
SEQUENCE: 355
HXQGTFTSDY SKYLDKIAAQ DFVAYLLDGG PSSGAPPPSK                      40

SEQ ID NO: 356          moltype = AA   length = 40
FEATURE                 Location/Qualifiers
source                  1..40
                        mol_type = protein
                        organism = synthetic construct
MOD_RES                 40
                        note = AminoEthoxyEthoxyAcetic Acyl-AminoEthoxyEthoxyAcetic
                        Acyl-MaleimidoPropionic Acyl
MOD_RES                 2
                        note = Aib
SEQUENCE: 356
HXQGTFTSDL SKYLDEIAVQ DFIEWLLDGG PSSGAPPPSK                      40

SEQ ID NO: 357          moltype = AA   length = 37
FEATURE                 Location/Qualifiers
source                  1..37
                        mol_type = protein
                        organism = synthetic construct
SEQUENCE: 357
HSQGTFTSDY SKYLDSRRAQ DFVQWLMNTK RNRNNIA                         37

SEQ ID NO: 358          moltype = AA   length = 34
FEATURE                 Location/Qualifiers
source                  1..34
                        mol_type = protein
                        organism = synthetic construct
SEQUENCE: 358
IKPEAPGEDA SPEELNRYYA SLRHYLNLVT RQRY                            34

SEQ ID NO: 359          moltype = AA   length = 31
FEATURE                 Location/Qualifiers
source                  1..31
                        mol_type = protein
                        organism = synthetic construct
MOD_RES                 2
                        note = Aib
SEQUENCE: 359
HXEGTFTSDV SSYLEGQALR HYINWLTRQR Y                               31

SEQ ID NO: 360          moltype = AA   length = 45
FEATURE                 Location/Qualifiers
source                  1..45
                        mol_type = protein
                        organism = synthetic construct
SEQUENCE: 360
HGEGTFTSDL SKQMEEEAVR LFIEWLKNGG PSSRHYLNLV TRQRY                45

SEQ ID NO: 361          moltype = AA   length = 51
FEATURE                 Location/Qualifiers
source                  1..51
                        mol_type = protein
                        organism = synthetic construct
SITE                    2
                        note = D-Serine
```

```
SEQUENCE: 361
HXQGTFTSDL SKYLEEEAVR EFIAWLKNGG PSSGAPPPSR HYLNLVTRQR Y          51

SEQ ID NO: 362          moltype = AA  length = 39
FEATURE                 Location/Qualifiers
source                  1..39
                        mol_type = protein
                        organism = synthetic construct
SITE                    2
                        note = D-Serine
SEQUENCE: 362
HXQGTYTNDV SKYXDSRRAQ DFIEWLKNGG PSSGAPPPS              39

SEQ ID NO: 363          moltype = AA  length = 40
FEATURE                 Location/Qualifiers
source                  1..40
                        mol_type = protein
                        organism = synthetic construct
SITE                    2
                        note = D-Serine
SEQUENCE: 363
HXQGTYTNDV SKYKDSRRAQ DFIEWLKNGG PSSGAPPPSC            40

SEQ ID NO: 364          moltype = AA  length = 40
FEATURE                 Location/Qualifiers
source                  1..40
                        mol_type = protein
                        organism = synthetic construct
SITE                    2
                        note = D-Serine
SEQUENCE: 364
HXQGTFTSDL SKQKDSRRAQ DFIEWLKNGG PSSGAPPPSC            40

SEQ ID NO: 365          moltype = AA  length = 40
FEATURE                 Location/Qualifiers
source                  1..40
                        mol_type = protein
                        organism = synthetic construct
SITE                    2
                        note = D-Serine
SEQUENCE: 365
HXQGTYTNDV SKYXDSRRAQ DFIEWLKNGG PSSGAPPPSC            40

SEQ ID NO: 366          moltype = AA  length = 34
FEATURE                 Location/Qualifiers
source                  1..34
                        mol_type = protein
                        organism = synthetic construct
SEQUENCE: 366
PKPEAPGKDA SPEEWNRYYA DLRHYLNWLT RQRY                  34

SEQ ID NO: 367          moltype = AA  length = 34
FEATURE                 Location/Qualifiers
source                  1..34
                        mol_type = protein
                        organism = synthetic construct
SEQUENCE: 367
IKPEAPGEDA SPEELNRYYA SLRHYLNWVT RQXY                  34

SEQ ID NO: 368          moltype = AA  length = 40
FEATURE                 Location/Qualifiers
source                  1..40
                        mol_type = protein
                        organism = synthetic construct
MOD_RES                 2
                        note = Aib
MOD_RES                 20
                        note = Aib
MOD_RES                 40
                        note = AminoEthoxyEthoxyAcetic Acyl-MaleimidoPropionic Acyl
SEQUENCE: 368
YXEGTFTSDY SIYLDKQAAX AFVQWLIAGG PSSGAPPPSK            40

SEQ ID NO: 369          moltype = AA  length = 40
FEATURE                 Location/Qualifiers
source                  1..40
                        mol_type = protein
                        organism = synthetic construct
MOD_RES                 2
```

```
                              note = Aib
MOD_RES                       20
                              note = Aib
MOD_RES                       40
                              note = AminoEthoxyEthoxyAcetic Acyl-MaleimidoPropionic Acyl
SEQUENCE: 369
YXEGTFTSDY SIYLDKQAAX AFVQWLLAGG PSSGAPPPSK                              40

SEQ ID NO: 370                moltype = AA   length = 40
FEATURE                       Location/Qualifiers
source                        1..40
                              mol_type = protein
                              organism = synthetic construct
MOD_RES                       40
                              note = AminoEthoxyEthoxyAcetic Acyl-MaleimidoPropionic Acyl
MOD_RES                       2
                              note = Aib
MOD_RES                       20
                              note = Aib
SEQUENCE: 370
YXEGTFTSDY SIYLDKQAAX EFVQWLIAGG PSSGAPPPSK                              40

SEQ ID NO: 371                moltype = AA   length = 40
FEATURE                       Location/Qualifiers
source                        1..40
                              mol_type = protein
                              organism = synthetic construct
SITE                          2
                              note = D-alanine
MOD_RES                       40
                              note = AminoEthoxyEthoxyAcetic Acyl-MaleimidoPropionic Acyl
MOD_RES                       20
                              note = Aib
SEQUENCE: 371
HAEGTFTSDY SIYLDKQAAX EFVQWLLAGG PSSGAPPPSK                              40

SEQ ID NO: 372                moltype = AA   length = 40
FEATURE                       Location/Qualifiers
source                        1..40
                              mol_type = protein
                              organism = synthetic construct
MOD_RES                       2
                              note = D-alanine
MOD_RES                       40
                              note = AminoEthoxyEthoxyAcetic Acyl-MaleimidoPropionic Acyl
MOD_RES                       20
                              note = Aib
SEQUENCE: 372
YAEGTFTSDY SIYLDKQAAX EFVQWLLAGG PSSGAPPPSK                              40

SEQ ID NO: 373                moltype = AA   length = 40
FEATURE                       Location/Qualifiers
source                        1..40
                              mol_type = protein
                              organism = synthetic construct
MOD_RES                       2
                              note = Aib
MOD_RES                       20
                              note = Aib
MOD_RES                       40
                              note = AminoEthoxyEthoxyAcetic Acyl-MaleimidoPropionic Acyl
SEQUENCE: 373
HXEGTFTSDY SIYLDKQAAX EFVQWLLAGG PSSGAPPPSK                              40

SEQ ID NO: 374                moltype = AA   length = 40
FEATURE                       Location/Qualifiers
source                        1..40
                              mol_type = protein
                              organism = synthetic construct
SITE                          2
                              note = D-alanine
MOD_RES                       20
                              note = Aib
MOD_RES                       40
                              note = AminoEthoxyEthoxyAcetic Acyl-MaleimidoPropionic Acyl
SEQUENCE: 374
HAEGTFTSDY SIYLDKQAAX AFVQWLIAGG PSSGAPPPSK                              40

SEQ ID NO: 375                moltype = AA   length = 40
```

-continued

```
FEATURE                    Location/Qualifiers
source                     1..40
                           mol_type = protein
                           organism = synthetic construct
SITE                       2
                           note = D-alanine
MOD_RES                    20
                           note = Aib
MOD_RES                    40
                           note = AminoEthoxyEthoxyAcetic Acyl-MaleimidoPropionic Acyl
SEQUENCE: 375
HAEGTFTSDY SIYLDKQAAX AFVQWLLAGG PSSGAPPPSK                          40

SEQ ID NO: 376             moltype = AA  length = 40
FEATURE                    Location/Qualifiers
source                     1..40
                           mol_type = protein
                           organism = synthetic construct
SITE                       2
                           note = D-alanine
MOD_RES                    20
                           note = Aib
MOD_RES                    40
                           note = AminoEthoxyEthoxyAcetic Acyl-MaleimidoPropionic Acyl
SEQUENCE: 376
HAEGTFTSDY SIYLDKQAAX EFVQWLIAGG PSSGAPPPSK                          40

SEQ ID NO: 377             moltype = AA  length = 40
FEATURE                    Location/Qualifiers
source                     1..40
                           mol_type = protein
                           organism = synthetic construct
SITE                       2
                           note = D-alanine
MOD_RES                    20
                           note = Aib
MOD_RES                    40
                           note = AminoEthoxyEthoxyAcetic Acyl-MaleimidoPropionic Acyl
SEQUENCE: 377
YAEGTFTSDY SIYLDKQAAX AFVQWLIAGG PSSGAPPPSK                          40

SEQ ID NO: 378             moltype = AA  length = 40
FEATURE                    Location/Qualifiers
source                     1..40
                           mol_type = protein
                           organism = synthetic construct
SITE                       2
                           note = D-alanine
MOD_RES                    20
                           note = Aib
MOD_RES                    40
                           note = AminoEthoxyEthoxyAcetic Acyl-MaleimidoPropionic Acyl
SEQUENCE: 378
YAEGTFTSDY SIYLDKQAAX AFVQWLLAGG PSSGAPPPSK                          40

SEQ ID NO: 379             moltype = AA  length = 40
FEATURE                    Location/Qualifiers
source                     1..40
                           mol_type = protein
                           organism = synthetic construct
MOD_RES                    20
                           note = Aib
SITE                       2
                           note = D-alanine
MOD_RES                    40
                           note = AminoEthoxyEthoxyAcetic Acyl-MaleimidoPropionic Acyl
SEQUENCE: 379
YAEGTFTSDY SIYLDKQAAX EFVQWLIAGG PSSGAPPPSK                          40

SEQ ID NO: 380             moltype = AA  length = 40
FEATURE                    Location/Qualifiers
source                     1..40
                           mol_type = protein
                           organism = synthetic construct
MOD_RES                    2
                           note = Aib
MOD_RES                    40
                           note = AminoEthoxyEthoxyAcetic Acyl-MaleimidoPropionic Acyl
SEQUENCE: 380
```

-continued

```
YXEGTFTSDY AKYLDARRAK EFVQWLLAGG PSSGAPPPSK                    40

SEQ ID NO: 381           moltype = AA   length = 40
FEATURE                  Location/Qualifiers
source                   1..40
                         mol_type = protein
                         organism = synthetic construct
MOD_RES                  2
                         note = Aib
MOD_RES                  40
                         note = AminoEthoxyEthoxyAcetic Acyl-MaleimidoPropionic Acyl
SEQUENCE: 381
YXEGTFTSDY SKYLDARRAK EFVQWLLAGG PSSGAPPPSK                    40

SEQ ID NO: 382           moltype = AA   length = 40
FEATURE                  Location/Qualifiers
source                   1..40
                         mol_type = protein
                         organism = synthetic construct
MOD_RES                  2
                         note = Aib
MOD_RES                  40
                         note = AminoEthoxyEthoxyAcetic Acyl-MaleimidoPropionic Acyl
SEQUENCE: 382
YXEGTFTSDY SKYLDKRRAK EFVQWLLAGG PSSGAPPPSK                    40

SEQ ID NO: 383           moltype = AA   length = 40
FEATURE                  Location/Qualifiers
source                   1..40
                         mol_type = protein
                         organism = synthetic construct
SITE                     2
                         note = D-alanine
MOD_RES                  40
                         note = AminoEthoxyEthoxyAcetic Acyl-MaleimidoPropionic Acyl
SEQUENCE: 383
HAEGTFTSDY AKYLDARRAK EFVQWLLAGG PSSGAPPPSK                    40

SEQ ID NO: 384           moltype = AA   length = 40
FEATURE                  Location/Qualifiers
source                   1..40
                         mol_type = protein
                         organism = synthetic construct
SITE                     2
                         note = D-alanine
MOD_RES                  40
                         note = AminoEthoxyEthoxyAcetic Acyl-MaleimidoPropionic Acyl
SEQUENCE: 384
HAEGTFTSDY SKYLDARRAK EFVQWLLAGG PSSGAPPPSK                    40

SEQ ID NO: 385           moltype = AA   length = 40
FEATURE                  Location/Qualifiers
source                   1..40
                         mol_type = protein
                         organism = synthetic construct
SITE                     2
                         note = D-alanine
MOD_RES                  40
                         note = AminoEthoxyEthoxyAcetic Acyl-MaleimidoPropionic Acyl
SEQUENCE: 385
HAEGTFTSDY SKYLDKRRAK EFVQWLLAGG PSSGAPPPSK                    40

SEQ ID NO: 386           moltype = AA   length = 40
FEATURE                  Location/Qualifiers
source                   1..40
                         mol_type = protein
                         organism = synthetic construct
SITE                     2
                         note = D-alanine
MOD_RES                  40
                         note = AminoEthoxyEthoxyAcetic Acyl-MaleimidoPropionic Acyl
SEQUENCE: 386
YAEGTFTSDY AKYLDARRAK EFVQWLLAGG PSSGAPPPSK                    40

SEQ ID NO: 387           moltype = AA   length = 40
FEATURE                  Location/Qualifiers
source                   1..40
                         mol_type = protein
                         organism = synthetic construct
```

-continued

```
SITE                    2
                        note = D-alanine
MOD_RES                 40
                        note = AminoEthoxyEthoxyAcetic Acyl-MaleimidoPropionic Acyl
SEQUENCE: 387
YAEGTFTSDY SKYLDARRAK EFVQWLLAGG PSSGAPPPSK                              40

SEQ ID NO: 388          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 388
YAEGTFTSDY SKYLDKRRAK EFVQWLLAGG PSSGAPPPSK                              40

SEQ ID NO: 389          moltype = AA  length = 40
FEATURE                 Location/Qualifiers
source                  1..40
                        mol_type = protein
                        organism = synthetic construct
MOD_RES                 40
                        note = AminoEthoxyEthoxyAcetic Acyl-MaleimidoPropionic Acyl
MOD_RES                 2
                        note = Aib
SEQUENCE: 389
HXEGTFTSDY AKYLDARRAK EFVQWLLAGG PSSGAPPPSK                              40

SEQ ID NO: 390          moltype = AA  length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 390
HXEGTFTSDY SKYLDARRAK EFVQWLLAGG PSSGAPPPSK                              40

SEQ ID NO: 391          moltype = AA  length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 391
HXEGTFTSDY SKYLDKRRAK EFVQWLLAGG PSSGAPPPSK                              40

SEQ ID NO: 392          moltype = AA  length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 392
YXEGTFTSDY AKYLDARRAK AFVQWLIAGG PSSGAPPPSK                              40

SEQ ID NO: 393          moltype = AA  length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 393
YXEGTFTSDY SKYLDARRAK AFVQWLIAGG PSSGAPPPSK                              40
```

-continued

```
SEQ ID NO: 394          moltype = AA  length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 394
YXEGTFTSDY SKYLDKRRAK AFVQWLIAGG PSSGAPPPSK                              40

SEQ ID NO: 395          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 395
HAEGTFTSDY AKYLDARRAK AFVQWLIAGG PSSGAPPPSK                              40

SEQ ID NO: 396          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 396
HAEGTFTSDY SKYLDARRAK AFVQWLIAGG PSSGAPPPSK                              40

SEQ ID NO: 397          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 397
HAEGTFTSDY SKYLDKRRAK AFVQWLIAGG PSSGAPPPSK                              40

SEQ ID NO: 398          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 398
YAEGTFTSDY AKYLDARRAK AFVQWLIAGG PSSGAPPPSK                              40

SEQ ID NO: 399          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 399
YAEGTFTSDY SKYLDARRAK AFVQWLIAGG PSSGAPPPSK                              40

SEQ ID NO: 400          moltype = AA  length = 40
FEATURE                 Location/Qualifiers
source                  1..40
                        mol_type = protein
                        organism = synthetic construct
SITE                    2
                        note = D-alanine
```

-continued

```
MOD_RES                     40
                            note = AminoEthoxyEthoxyAcetic Acyl-MaleimidoPropionic Acyl
SEQUENCE: 400
YAEGTFTSDY SKYLDKRRAK AFVQWLIAGG PSSGAPPPSK                              40

SEQ ID NO: 401              moltype = AA  length = 40
FEATURE                     Location/Qualifiers
source                      1..40
                            mol_type = protein
                            organism = synthetic construct
MOD_RES                     2
                            note = Aib
MOD_RES                     40
                            note = AminoEthoxyEthoxyAcetic Acyl-MaleimidoPropionic Acyl
SEQUENCE: 401
HXEGTFTSDY AKYLDARRAK AFVQWLIAGG PSSGAPPPSK                              40

SEQ ID NO: 402              moltype = AA  length = 40
FEATURE                     Location/Qualifiers
source                      1..40
                            mol_type = protein
                            organism = synthetic construct
MOD_RES                     2
                            note = Aib
MOD_RES                     40
                            note = AminoEthoxyEthoxyAcetic Acyl-MaleimidoPropionic Acyl
SEQUENCE: 402
HXEGTFTSDY SKYLDARRAK AFVQWLIAGG PSSGAPPPSK                              40

SEQ ID NO: 403              moltype = AA  length = 40
FEATURE                     Location/Qualifiers
source                      1..40
                            mol_type = protein
                            organism = synthetic construct
MOD_RES                     2
                            note = Aib
MOD_RES                     40
                            note = AminoEthoxyEthoxyAcetic Acyl-MaleimidoPropionic Acyl
SEQUENCE: 403
HXEGTFTSDY SKYLDKRRAK AFVQWLIAGG PSSGAPPPSK                              40

SEQ ID NO: 404              moltype = AA  length = 40
FEATURE                     Location/Qualifiers
source                      1..40
                            mol_type = protein
                            organism = synthetic construct
SITE                        2
                            note = D-alanine
MOD_RES                     40
                            note = AminoEthoxyEthoxyAcetic Acyl-MaleimidoPropionic Acyl
SEQUENCE: 404
HAQGTFTSDL SKQLESKAAQ DFIEWLKAGG PSSGAPPPSK                              40

SEQ ID NO: 405              moltype = AA  length = 40
FEATURE                     Location/Qualifiers
source                      1..40
                            mol_type = protein
                            organism = synthetic construct
SITE                        2
                            note = D-serine
MOD_RES                     40
                            note = AminoEthoxyEthoxyAcetic Acyl-MaleimidoPropionic Acyl
SEQUENCE: 405
HSQGTFTSDY AKYLDARRAK EFIEWLKAGG PSSGAPPPSK                              40

SEQ ID NO: 406              moltype = AA  length = 40
FEATURE                     Location/Qualifiers
source                      1..40
                            mol_type = protein
                            organism = synthetic construct
SITE                        2
                            note = D-serine
MOD_RES                     40
                            note = AminoEthoxyEthoxyAcetic Acyl-MaleimidoPropionic Acyl
SEQUENCE: 406
HSQGTFTSDY SKYLDARRAK EFIEWLKAGG PSSGAPPPSK                              40

SEQ ID NO: 407              moltype = AA  length = 40
FEATURE                     Location/Qualifiers
```

-continued

```
source                  1..40
                        mol_type = protein
                        organism = synthetic construct
SITE                    2
                        note = D-serine
MOD_RES                 40
                        note = AminoEthoxyEthoxyAcetic Acyl-MaleimidoPropionic Acyl
SEQUENCE: 407
HSQGTFTSDY AKYLDSRRAK EFIEWLKAGG PSSGAPPPSK                             40

SEQ ID NO: 408          moltype = AA   length = 40
FEATURE                 Location/Qualifiers
source                  1..40
                        mol_type = protein
                        organism = synthetic construct
SITE                    2
                        note = D-serine
MOD_RES                 40
                        note = AminoEthoxyEthoxyAcetic Acyl-MaleimidoPropionic Acyl
SEQUENCE: 408
HSQGTFTSDY SKYLDSRRAK EFIEWLKAGG PSSGAPPPSK                             40

SEQ ID NO: 409          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 409
HAQGTFTSDY SKYLDSRRAK EFIEWLKAGG PSSGAPPPSK                             40

SEQ ID NO: 410          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 410
HAQGTFTSDY AKYLDARRAK EFIEWLKAGG PSSGAPPPSK                             40

SEQ ID NO: 411          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 411
HAQGTFTSDL SKQLESKAAQ DFIAWLVNGG PSSGAPPPSK                             40

SEQ ID NO: 412          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 412
HAQGTFTSDY AKYLDARRAK DFIEWLKAGG PSSGAPPPSK                             40

SEQ ID NO: 413          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
```

-continued

```
SEQUENCE: 413
HAQGTFTSDY SKYLDARRAQ EFIEWLKAGG PSSGAPPPSK                              40

SEQ ID NO: 414          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 414
HAQGTFTSDY AKYLDSRAAK EFIEWLKAGG PSSGAPPPSK                              40

SEQ ID NO: 415          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 415
HAQGTFTSDY SKYLDSKRAK EFIEWLKAGG PSSGAPPPSK                              40

SEQ ID NO: 416          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 416
HAQGTFTSDY AKYLEARRAK EFIEWLKAGG PSSGAPPPSK                              40

SEQ ID NO: 417          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 417
HAQGTFTSDY AKQLEARRAK EFIEWLKAGG PSSGAPPPSK                              40

SEQ ID NO: 418          moltype = AA  length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 418
HXQGTFTSDY SKYLDERAAQ AFIEYLLEGG PSSGAPPPSK                              40

SEQ ID NO: 419          moltype = AA  length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 419
HAQGTFTSDY SKYLDERAAQ DFVQWLLDGG PSSGAPPPSK                              40

SEQ ID NO: 420          moltype = AA  length = 40
FEATURE                 Location/Qualifiers
source                  1..40
                        mol_type = protein
```

-continued

```
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 420
HAQGTFTSDY SKYLDERAAQ AFIEYLLEGG PSSGAPPPSK                          40

SEQ ID NO: 421          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 421
HXQGTFTSDY SKYLDARRAK EFVQWLLDGG PSSGAPPPSK                          40

SEQ ID NO: 422          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 422
HXQGTFTSDY SKYLDARRAK EFIEYLLEGG PSSGAPPPSK                          40

SEQ ID NO: 423          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 423
HXQGTFTSDY AKYLDARRAK EFVQWLLDGG PSSGAPPPSK                          40

SEQ ID NO: 424          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 424
HAQGTFTSDY SKYLDARRAK EFVQWLLDGG PSSGAPPPSK                          40

SEQ ID NO: 425          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 425
HAQGTFTSDY AKYLDARRAK EFVQWLLDGG PSSGAPPPSK                          40

SEQ ID NO: 426          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 426
HAQGTFTSDY SKYLDARRAK EFIEYLLEGG PSSGAPPPSK                          40
```

-continued

```
SEQ ID NO: 427          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 427
HXQGTFTSDY SKYLDERAAQ AFIEYLLDGG PSSGAPPPSK                                    40

SEQ ID NO: 428          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 428
HAQGTFTSDY SKYLDERAAQ DFVQWLLEGG PSSGAPPPSK                                    40

SEQ ID NO: 429          moltype = AA   length = 40
FEATURE                 Location/Qualifiers
source                  1..40
                        mol_type = protein
                        organism = synthetic construct
SITE                    2
                        note = D-alanine
MOD_RES                 40
                        note = AminoEthoxyEthoxyAcetic Acyl-MaleimidoPropionic Acyl
SEQUENCE: 429
HAQGTFTSDY SKYLDERAAQ AFIEYLLDGG PSSGAPPPSK                                    40

SEQ ID NO: 430          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 430
HXQGTFTSDY SKYLDARRAK EFVQWLLEGG PSSGAPPPSK                                    40

SEQ ID NO: 431          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 431
HXQGTFTSDY SKYLDARRAK EFIEYLLDGG PSSGAPPPSK                                    40

SEQ ID NO: 432          moltype = AA   length = 40
FEATURE                 Location/Qualifiers
source                  1..40
                        mol_type = protein
                        organism = synthetic construct
MOD_RES                 2
                        note = Aib
MOD_RES                 40
                        note = AminoEthoxyEthoxyAcetic Acyl-MaleimidoPropionic Acyl
SEQUENCE: 432
HXQGTFTSDY AKYLDARRAK EFVQWLLEGG PSSGAPPPSK                                    40

SEQ ID NO: 433          moltype = AA   length = 40
FEATURE                 Location/Qualifiers
source                  1..40
                        mol_type = protein
                        organism = synthetic construct
MOD_RES                 2
```

-continued

```
                              note = Aib
MOD_RES                       40
                              note = AminoEthoxyEthoxyAcetic Acyl-MaleimidoPropionic Acyl
SEQUENCE: 433
HXQGTFTSDY AKYLDARRAK EFIEYLLDGG PSSGAPPPSK                            40

SEQ ID NO: 434             moltype = AA  length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-MaleimidoPropionic Acyl
SEQUENCE: 434
HAQGTFTSDY SKYLDARRAK EFVQWLLEGG PSSGAPPPSK                            40

SEQ ID NO: 435             moltype = AA  length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-MaleimidoPropionic Acyl
SEQUENCE: 435
HAQGTFTSDY AKYLDARRAK EFVQWLLEGG PSSGAPPPSK                            40

SEQ ID NO: 436             moltype = AA  length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-MaleimidoPropionic Acyl
SEQUENCE: 436
HAQGTFTSDY SKYLDARRAK EFIEYLLDGG PSSGAPPPSK                            40

SEQ ID NO: 437             moltype = AA  length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-MaleimidoPropionic Acyl
SEQUENCE: 437
HAQGTFTSDY AKYLDARRAK EFIEYLLDGG PSSGAPPPSK                            40

SEQ ID NO: 438             moltype = AA  length = 40
FEATURE                    Location/Qualifiers
source                     1..40
                           mol_type = protein
                           organism = synthetic construct
MOD_RES                    2
                           note = Aib
MOD_RES                    40
                           note = AminoEthoxyEthoxyAcetic Acyl-MaleimidoPropionic Acyl
SEQUENCE: 438
HXQGTFTSDY SKYLDERAAQ AFIEWLLEGG PSSGAPPPSK                            40

SEQ ID NO: 439             moltype = AA  length = 40
FEATURE                    Location/Qualifiers
source                     1..40
                           mol_type = protein
                           organism = synthetic construct
SITE                       2
                           note = D-alanine
MOD_RES                    40
                           note = AminoEthoxyEthoxyAcetic Acyl-MaleimidoPropionic Acyl
SEQUENCE: 439
HAQGTFTSDY SKYLDERAAQ DFVQYLLDGG PSSGAPPPSK                            40

SEQ ID NO: 440             moltype = AA  length = 40
```

-continued

```
FEATURE               Location/Qualifiers
source                1..40
                      mol_type = protein
                      organism = synthetic construct
SITE                  2
                      note = D-alanine
MOD_RES               40
                      note = AminoEthoxyEthoxyAcetic Acyl-MaleimidoPropionic Acyl
SEQUENCE: 440
HAQGTFTSDY SKYLDERAAQ AFIEWLLEGG PSSGAPPPSK                                40

SEQ ID NO: 441        moltype = AA  length = 40
FEATURE               Location/Qualifiers
source                1..40
                      mol_type = protein
                      organism = synthetic construct
MOD_RES               2
                      note = Aib
MOD_RES               40
                      note = AminoEthoxyEthoxyAcetic Acyl-MaleimidoPropionic Acyl
SEQUENCE: 441
HXQGTFTSDY SKYLDARRAK EFVQYLLDGG PSSGAPPPSK                                40

SEQ ID NO: 442        moltype = AA  length = 40
FEATURE               Location/Qualifiers
source                1..40
                      mol_type = protein
                      organism = synthetic construct
MOD_RES               2
                      note = Aib
MOD_RES               40
                      note = AminoEthoxyEthoxyAcetic Acyl-MaleimidoPropionic Acyl
SEQUENCE: 442
HXQGTFTSDY SKYLDARRAK EFIEWLLEGG PSSGAPPPSK                                40

SEQ ID NO: 443        moltype = AA  length = 40
FEATURE               Location/Qualifiers
source                1..40
                      mol_type = protein
                      organism = synthetic construct
MOD_RES               2
                      note = Aib
MOD_RES               40
                      note = AminoEthoxyEthoxyAcetic Acyl-MaleimidoPropionic Acyl
SEQUENCE: 443
HXQGTFTSDY AKYLDARRAK EFVQYLLDGG PSSGAPPPSK                                40

SEQ ID NO: 444        moltype = AA  length = 40
FEATURE               Location/Qualifiers
source                1..40
                      mol_type = protein
                      organism = synthetic construct
MOD_RES               2
                      note = Aib
MOD_RES               40
                      note = AminoEthoxyEthoxyAcetic Acyl-MaleimidoPropionic Acyl
SEQUENCE: 444
HXQGTFTSDY AKYLDARRAK EFIEWLLEGG PSSGAPPPSK                                40

SEQ ID NO: 445        moltype = AA  length = 40
FEATURE               Location/Qualifiers
source                1..40
                      mol_type = protein
                      organism = synthetic construct
SITE                  2
                      note = D-alanine
MOD_RES               40
                      note = AminoEthoxyEthoxyAcetic Acyl-MaleimidoPropionic Acyl
SEQUENCE: 445
HAQGTFTSDY SKYLDARRAK EFVQYLLDGG PSSGAPPPSK                                40

SEQ ID NO: 446        moltype = AA  length = 40
FEATURE               Location/Qualifiers
source                1..40
                      mol_type = protein
                      organism = synthetic construct
SITE                  2
                      note = D-alanine
MOD_RES               40
```

```
                              note = AminoEthoxyEthoxyAcetic Acyl-MaleimidoPropionic Acyl
SEQUENCE: 446
HAQGTFTSDY AKYLDARRAK EFVQYLLDGG PSSGAPPPSK                              40

SEQ ID NO: 447         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 447
HAQGTFTSDY SKYLDARRAK EFIEWLLEGG PSSGAPPPSK                              40

SEQ ID NO: 448         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 448
HAQGTFTSDY AKYLDARRAK EFIEWLLEGG PSSGAPPPSK                              40

SEQ ID NO: 449         moltype = AA  length = 40
FEATURE                Location/Qualifiers
source                 1..40
                       mol_type = protein
                       organism = synthetic construct
MOD_RES                2
                       note = Aib
MOD_RES                40
                       note = AminoEthoxyEthoxyAcetic Acyl-MaleimidoPropionic Acyl
SEQUENCE: 449
HXQGTFTSDY SKYLDERAAQ AFVQYLLEGG PSSGAPPPSK                              40

SEQ ID NO: 450         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 450
HAQGTFTSDY SKYLDERAAQ DFIEWLLDGG PSSGAPPPSK                              40

SEQ ID NO: 451         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 451
HAQGTFTSDY SKYLDERAAQ AFVQYLLEGG PSSGAPPPSK                              40

SEQ ID NO: 452         moltype = AA  length = 40
FEATURE                Location/Qualifiers
source                 1..40
                       mol_type = protein
                       organism = synthetic construct
MOD_RES                2
                       note = Aib
MOD_RES                40
                       note = AminoEthoxyEthoxyAcetic Acyl-MaleimidoPropionic Acyl
SEQUENCE: 452
HXQGTFTSDY SKYLDARRAK EFIEWLLDGG PSSGAPPPSK                              40

SEQ ID NO: 453         moltype = AA  length = 40
FEATURE                Location/Qualifiers
source                 1..40
```

-continued

```
                            mol_type = protein
                            organism = synthetic construct
MOD_RES                     2
                            note = Aib
MOD_RES                     40
                            note = AminoEthoxyEthoxyAcetic Acyl-MaleimidoPropionic Acyl
SEQUENCE: 453
HXQGTFTSDY SKYLDARRAK EFVQYLLEGG PSSGAPPPSK                              40

SEQ ID NO: 454             moltype = AA   length = 40
FEATURE                    Location/Qualifiers
source                     1..40
                            mol_type = protein
                            organism = synthetic construct
MOD_RES                     2
                            note = Aib
MOD_RES                     40
                            note = AminoEthoxyEthoxyAcetic Acyl-MaleimidoPropionic Acyl
SEQUENCE: 454
HXQGTFTSDY AKYLDARRAK EFIEWLLDGG PSSGAPPPSK                              40

SEQ ID NO: 455             moltype = AA   length = 40
FEATURE                    Location/Qualifiers
source                     1..40
                            mol_type = protein
                            organism = synthetic construct
MOD_RES                     2
                            note = Aib
MOD_RES                     40
                            note = AminoEthoxyEthoxyAcetic Acyl-MaleimidoPropionic Acyl
SEQUENCE: 455
HXQGTFTSDY AKYLDARRAK EFVQYLLEGG PSSGAPPPSK                              40

SEQ ID NO: 456             moltype = AA   length = 40
FEATURE                    Location/Qualifiers
source                     1..40
                            mol_type = protein
                            organism = synthetic construct
SITE                        2
                            note = D-alanine
MOD_RES                     40
                            note = AminoEthoxyEthoxyAcetic Acyl-MaleimidoPropionic Acyl
SEQUENCE: 456
HAQGTFTSDY SKYLDARRAK EFIEWLLDGG PSSGAPPPSK                              40

SEQ ID NO: 457             moltype = AA   length = 40
FEATURE                    Location/Qualifiers
source                     1..40
                            mol_type = protein
                            organism = synthetic construct
SITE                        2
                            note = D-alanine
MOD_RES                     40
                            note = AminoEthoxyEthoxyAcetic Acyl-MaleimidoPropionic Acyl
SEQUENCE: 457
HAQGTFTSDY AKYLDARRAK EFIEWLLDGG PSSGAPPPSK                              40

SEQ ID NO: 458             moltype = AA   length = 40
FEATURE                    Location/Qualifiers
source                     1..40
                            mol_type = protein
                            organism = synthetic construct
SITE                        2
                            note = D-alanine
MOD_RES                     40
                            note = AminoEthoxyEthoxyAcetic Acyl-MaleimidoPropionic Acyl
SEQUENCE: 458
HAQGTFTSDY SKYLDARRAK EFVQYLLEGG PSSGAPPPSK                              40

SEQ ID NO: 459             moltype = AA   length = 40
FEATURE                    Location/Qualifiers
source                     1..40
                            mol_type = protein
                            organism = synthetic construct
SITE                        2
                            note = D-alanine
MOD_RES                     40
                            note = AminoEthoxyEthoxyAcetic Acyl-MaleimidoPropionic Acyl
SEQUENCE: 459
```

-continued

```
HAQGTFTSDY AKYLDARRAK EFVQYLLEGG PSSGAPPPSK                                40

SEQ ID NO: 460         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 460
HAEGTFTSDY AKYLDARRAK EFVQWLVNGG PSSGAPPPSK                                40

SEQ ID NO: 461         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 461
HAEGTFTSDY AKYLDARRAK EFIAWLLDGG PSSGAPPPSK                                40

SEQ ID NO: 462         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 462
HAEGTFTSDY AKYLDARRAK EFIEYLVNGG PSSGAPPPSK                                40

SEQ ID NO: 463         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 463
HAEGTFTSDY AKYLDARRAK EFIAYLLEGG PSSGAPPPSK                                40

SEQ ID NO: 464         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 464
HAEGTFTSDY AKYLDARRAK EFIEWLVNGG PSSGAPPPSK                                40

SEQ ID NO: 465         moltype = AA  length = 40
FEATURE                Location/Qualifiers
source                 1..40
                       mol_type = protein
                       organism = synthetic construct
SITE                   2
                       note = D-alanine
MOD_RES                40
                       note = AminoEthoxyEthoxyAcetic Acyl-MaleimidoPropionic Acyl
SEQUENCE: 465
HAEGTFTSDY AKYLDARRAK EFVQWLKAGG PSSGAPPPSK                                40

SEQ ID NO: 466         moltype = AA  length = 40
FEATURE                Location/Qualifiers
source                 1..40
                       mol_type = protein
                       organism = synthetic construct
```

-continued

```
SITE                      2
                          note = D-alanine
MOD_RES                   40
                          note = AminoEthoxyEthoxyAcetic Acyl-AminoEthoxyEthoxyAcetic
                          Acyl-MaleimidoPropionic Acyl
SEQUENCE: 466
YAEGTFTSDY AIYLDAQAQQ DFVQWLLAGG PSSGAPPPSK                              40

SEQ ID NO: 467            moltype = AA  length = 40
FEATURE                   Location/Qualifiers
source                    1..40
                          mol_type = protein
                          organism = synthetic construct
SITE                      2
                          note = D-alanine
MOD_RES                   40
                          note = AminoEthoxyEthoxyAcetic Acyl-AminoEthoxyEthoxyAcetic
                          Acyl-MaleimidoPropionic Acyl
SEQUENCE: 467
YAEGTFTSDY SIYLDKIAQQ DFVQWLLAGG PSSGAPPPSK                              40

SEQ ID NO: 468            moltype = AA  length = 40
FEATURE                   Location/Qualifiers
source                    1..40
                          mol_type = protein
                          organism = synthetic construct
MOD_RES                   2
                          note = Aib
MOD_RES                   40
                          note = AminoEthoxyEthoxyAcetic Acyl-MaleimidoPropionic Acyl
SEQUENCE: 468
HXQGTFTSDY SKYLDERAAQ DFVQWLLDGG PSSGAPPPSK                              40

SEQ ID NO: 469            moltype = AA  length = 40
FEATURE                   Location/Qualifiers
source                    1..40
                          mol_type = protein
                          organism = synthetic construct
MOD_RES                   2
                          note = Aib
MOD_RES                   40
                          note = AminoEthoxyEthoxyAcetic Acyl-AminoEthoxyEthoxyAcetic
                          Acyl-MaleimidoPropionic Acyl
SEQUENCE: 469
HXQGTFTSDY SKYLDKIAAQ DFVAYLLDGG PSSGAPPPSK                              40

SEQ ID NO: 470            moltype = AA  length = 40
FEATURE                   Location/Qualifiers
source                    1..40
                          mol_type = protein
                          organism = synthetic construct
SITE                      2
                          note = D-alanine
MOD_RES                   40
                          note = AminoEthoxyEthoxyAcetic Acyl-MaleimidoPropionic Acyl
SEQUENCE: 470
YAEGTFTSDY SIYLDKIAQQ DFVQWLLAGG PSSGAPPPSK                              40

SEQ ID NO: 471            moltype = AA  length = 39
FEATURE                   Location/Qualifiers
source                    1..39
                          mol_type = protein
                          organism = synthetic construct
MOD_RES                   2
                          note = Aib
MOD_RES                   13
                          note = Aib
MOD_RES                   20
                          note = AminoEthoxyEthoxyAcetic Acyl-AminoEthoxyEthoxyAcetic
                          Acyl-MaleimidoPropionic Acyl
SEQUENCE: 471
YXEGTFTSDY SIXLDKIAQK AFVQWLIAGG PSSGAPPPS                               39
```